(12) United States Patent
Messick et al.

(10) Patent No.: US 11,242,317 B2
(45) Date of Patent: Feb. 8, 2022

(54) EBNA1 INHIBITORS AND THEIR METHOD OF USE

(71) Applicant: THE WISTAR INSTITUTE OF ANATOMY AND BIOLOGY, Philadelphia, PA (US)

(72) Inventors: Troy E. Messick, Upper Darby, PA (US); Garry R. Smith, Royersford, PA (US); Allen B. Reitz, Lansdale, PA (US); Paul M. Lieberman, Wynnewood, PA (US); Mark E. McDonnell, Lansdale, PA (US); Yan Zhang, Fort Washington, PA (US); Venkata Velvadapu, Ankeny, IA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 16/519,590

(22) Filed: Jul. 23, 2019

(65) Prior Publication Data

US 2020/0181078 A1 Jun. 11, 2020

Related U.S. Application Data

(63) Continuation of application No. 15/814,600, filed on Nov. 16, 2017, now Pat. No. 10,421,718, which is a
(Continued)

(51) Int. Cl.
| | |
|---|---|
| *A61K 31/405* | (2006.01) |
| *A61K 31/41* | (2006.01) |
| *A61K 31/42* | (2006.01) |
| *A61K 31/415* | (2006.01) |
| *A61K 31/40* | (2006.01) |
| *C07D 515/02* | (2006.01) |
| *C07D 209/44* | (2006.01) |
| *C07D 295/04* | (2006.01) |
| *C07D 261/06* | (2006.01) |
| *C07D 233/02* | (2006.01) |

(Continued)

(52) U.S. Cl.
CPC ........ *C07D 207/327* (2013.01); *A61K 31/192* (2013.01); *A61K 31/404* (2013.01); *A61K 31/44* (2013.01); *A61K 31/4439* (2013.01); *A61K 31/496* (2013.01); *C07C 53/18* (2013.01); *C07C 63/66* (2013.01); *C07C 65/19* (2013.01); *C07C 65/28* (2013.01); *C07C 211/27* (2013.01); *C07C 217/84* (2013.01); *C07C 229/56* (2013.01); *C07C 229/64* (2013.01); *C07C 233/11* (2013.01); *C07C 233/64* (2013.01); *C07C 233/65* (2013.01); *C07C 235/58* (2013.01); *C07C 255/55* (2013.01); *C07C 311/08* (2013.01); *C07C 311/16* (2013.01); *C07C 311/17* (2013.01); *C07C 317/14* (2013.01); *C07C 317/44* (2013.01); *C07D 207/08* (2013.01); *C07D 207/12* (2013.01); *C07D 207/14* (2013.01); *C07D 207/16* (2013.01); *C07D 209/08* (2013.01); *C07D 211/70* (2013.01); *C07D 213/55* (2013.01); *C07D 213/64* (2013.01); *C07D 213/74* (2013.01); *C07D 215/14* (2013.01); *C07D 231/12* (2013.01); *C07D 235/06* (2013.01); *C07D 239/26* (2013.01); *C07D 249/06* (2013.01); *C07D 277/30* (2013.01); *C07D 295/155* (2013.01); *C07D 307/79* (2013.01); *C07D 333/54* (2013.01); *C07D 401/04* (2013.01); *C07D 401/10* (2013.01); *C07D 403/10* (2013.01); *C07D 409/10* (2013.01); *C07D 417/10* (2013.01); *C07D 471/04* (2013.01); *C07D 487/04* (2013.01); *C07C 2601/02* (2017.05)

(58) Field of Classification Search
CPC .. A61K 31/192; A61K 31/235; A61K 31/404; A61K 31/415; A61K 31/42
USPC ............... 514/415, 359, 378, 406, 429, 568; 546/119; 548/470, 578, 247, 300.1, 311.1
See application file for complete search history.

(56) References Cited

U.S. PATENT DOCUMENTS

| | | |
|---|---|---|
| 4,638,002 A | 1/1987 | Szekely et al. |
| 5,155,248 A | 10/1992 | Ullrich et al. |

(Continued)

FOREIGN PATENT DOCUMENTS

| | | |
|---|---|---|
| CN | 1634810 A | 7/2005 |
| DE | 3936297 A1 | 5/1991 |

(Continued)

OTHER PUBLICATIONS

PubChem CID 299282 (Year: 2005).*
(Continued)

*Primary Examiner* — Shengjun Wang
(74) *Attorney, Agent, or Firm* — Saul Ewing Arnstein & Lehr LLP; Kathryn Doyle; Domingos Silva

(57) ABSTRACT

Pharmaceutical compositions of the invention comprise EBNA1 inhibitors useful for the treatment of diseases caused by EBNA1 activity such as cancer, infectious mononucleosis, chronic fatigue syndrome, multiple sclerosis, systemic lupus erythematosus and rheumatoid arthritis. Pharmaceutical compositions of the invention also comprise EBNA1 inhibitors useful for the treatment of diseases caused by latent Epstein-Barr Virus (EBV) infection. Pharmaceutical compositions of the invention also comprise EBNA1 inhibitors useful for the treatment of diseases caused by lytic Epstein-Barr Virus (EBV) infection.

17 Claims, No Drawings

Specification includes a Sequence Listing.

Related U.S. Application Data continuation of application No. 15/036,211, filed as application No. PCT/US2014/065765 on Nov. 14, 2014, now Pat. No. 9,856,214.

(60) Provisional application No. 61/904,555, filed on Nov. 15, 2013.

(51) Int. Cl.

| | | |
|---|---|---|
| C07D 233/00 | (2006.01) | |
| C07D 207/327 | (2006.01) | |
| A61K 31/404 | (2006.01) | |
| A61K 31/4439 | (2006.01) | |
| A61K 31/496 | (2006.01) | |
| A61K 31/192 | (2006.01) | |
| A61K 31/44 | (2006.01) | |
| C07C 229/56 | (2006.01) | |
| C07C 255/54 | (2006.01) | |
| C07C 255/55 | (2006.01) | |
| C07C 211/27 | (2006.01) | |
| C07C 217/84 | (2006.01) | |
| C07C 233/11 | (2006.01) | |
| C07C 233/64 | (2006.01) | |
| C07C 233/65 | (2006.01) | |
| C07C 235/58 | (2006.01) | |
| C07C 311/08 | (2006.01) | |
| C07C 311/16 | (2006.01) | |
| C07C 311/17 | (2006.01) | |
| C07C 317/14 | (2006.01) | |
| C07D 235/06 | (2006.01) | |
| C07D 403/10 | (2006.01) | |
| C07D 239/26 | (2006.01) | |
| C07D 409/10 | (2006.01) | |
| C07D 417/10 | (2006.01) | |
| C07D 471/04 | (2006.01) | |
| C07D 487/04 | (2006.01) | |
| C07D 209/08 | (2006.01) | |
| C07D 295/155 | (2006.01) | |
| C07D 213/55 | (2006.01) | |
| C07C 53/18 | (2006.01) | |
| C07C 63/66 | (2006.01) | |
| C07C 65/19 | (2006.01) | |
| C07C 65/28 | (2006.01) | |
| C07C 229/64 | (2006.01) | |
| C07C 317/44 | (2006.01) | |
| C07D 207/08 | (2006.01) | |
| C07D 207/12 | (2006.01) | |
| C07D 207/14 | (2006.01) | |
| C07D 207/16 | (2006.01) | |
| C07D 211/70 | (2006.01) | |
| C07D 213/64 | (2006.01) | |
| C07D 213/74 | (2006.01) | |
| C07D 215/14 | (2006.01) | |
| C07D 231/12 | (2006.01) | |
| C07D 249/06 | (2006.01) | |
| C07D 277/30 | (2006.01) | |
| C07D 307/79 | (2006.01) | |
| C07D 333/54 | (2006.01) | |
| C07D 401/04 | (2006.01) | |
| C07D 401/10 | (2006.01) | |

(56) References Cited

U.S. PATENT DOCUMENTS

| | | |
|---|---|---|
| 5,185,454 A | 2/1993 | Bader et al. |
| 5,356,919 A | 10/1994 | Djuric et al. |
| 6,166,028 A | 12/2000 | Bloom et al. |
| 2003/0032623 A1 | 2/2003 | Ban et al. |
| 2003/0199511 A1 | 10/2003 | Li et al. |
| 2004/0044041 A1 | 3/2004 | Kuduk et al. |
| 2006/0030613 A1 | 2/2006 | Conte-Mayweg et al. |
| 2006/0258645 A1 | 11/2006 | Failli et al. |
| 2008/0153802 A1 | 6/2008 | Lessene et al. |
| 2009/0171091 A1 | 7/2009 | Thombare et al. |
| 2011/0009447 A1 | 1/2011 | Huth et al. |
| 2013/0040949 A1 | 2/2013 | Gray et al. |
| 2014/0113897 A1 | 4/2014 | Lieberman et al. |

FOREIGN PATENT DOCUMENTS

| | | |
|---|---|---|
| DE | 10021246 A1 | 10/2001 |
| JP | 2004510697 A | 4/2004 |
| JP | 2004512259 A | 4/2004 |
| JP | 2008506702 A | 3/2008 |
| JP | 2008520662 A | 6/2008 |
| WO | 0153274 A1 | 7/2001 |
| WO | 0190101 A1 | 11/2001 |
| WO | 2006002474 A1 | 1/2006 |
| WO | 2006019831 A1 | 2/2006 |
| WO | 2006055070 A2 | 5/2006 |
| WO | 2007002433 A1 | 1/2007 |
| WO | 2007002587 A2 | 1/2007 |
| WO | 2007023242 A1 | 3/2007 |
| WO | 2010048332 A2 | 4/2010 |
| WO | 2010092043 A1 | 8/2010 |
| WO | 2010100475 A1 | 9/2010 |
| WO | 2010118009 A1 | 10/2010 |
| WO | 2010124047 A1 | 10/2010 |
| WO | 2010127440 A1 | 11/2010 |
| WO | 2011082098 A1 | 7/2011 |
| WO | 2011090911 A1 | 7/2011 |
| WO | 2012098416 A1 | 7/2012 |
| WO | 2012162291 A1 | 11/2012 |
| WO | 2014145022 A1 | 9/2014 |
| WO | 2015073864 A1 | 5/2015 |

OTHER PUBLICATIONS

PubChem CID 22140186 (Year: 2007).*
PubChem. Compound Summary for: CID 1962039. Create Date: Dec. 5, 2007 [retrieved on Mar. 31, 2015], Retrieved from the Internet: <URL: https//pubchem.ncbi.nlm.nih.gov/compound/19612039>. entire document.
STN registration file RN 1244017-13-7, 2010.
STN registration file RN 873330-62.2, 2006.
STN Registry 178742-95-5, 1996.
STN Registry RN 10601-99-7, 1984.
STN Registry RN 1244017-13-7, 2010.
STN Registry RN 87330-62, 2006.
Bochkarev, et al.,Crystal Structure of the DNA-Binding Domain of the Epstein-Barr Virus Origin-Binding Protein, EBNA1, Bound to DNA, 1996, Cell 84:791-800.
Crawford, et al.,The Preparation of Some Alkyl-substituted Benxoic Acids, Jan. 1, 1952—Retrieved from the Internet: URL:http://pubs.rsc.org/en/content/articlepdf/1952/jr/jr9520004443 [retrieved on Apr. 7, 2017].
Faigl, et al.,Organometallic Approach to the Functionalization of Alkyl Groups Containing 1-Phenylpyrroles., 2006, Synthetic Communications 36:2841-2849 Abstract.
Gao, et al.,Discovery and Optimization of 3-(2-(Pyrazolo[1,5-a]pyrimidin-6-yl) ethynyl)benzamides as Novel Selective and Orally Bioavailable Discoidin Domain Receptor 1 (DDR1) Inhibitors, J. Med. Chem., 2013, 56 (8), pp. 3281-3295 (Abstract).
Ghosh, et al.,Histone deacetylase inhibitors are potent inducers of gene expression in latent EBV and sensitize lymphoma cells to nucleoside antiviral agents., 2012, Blood 119(4):1008-1017.
Kim, et al.,Palladium-Catalyzed Domino Cyclization (5-exo/3-exo), Ring-Expansion by Palladium Rearrangement, and Aromatization: An Expedient Synthesis of 4-Arylnicotinates from Morita-Baylis-Hillman Adducts., 2013, Advanced Synthesis & Catalysis 355:1977-1983 Abstract.

(56) References Cited

OTHER PUBLICATIONS

Li, et al.,Discover of selective inhibitors agains EBNA1 via high throughput in silico virtual screening., PLoS ONE, Apr. 12, 2010, vol. 5, No. 4, pp. e10126.
Liu, et al.,Studies of Phenylethynyl-pyrrolo[1,2-a]pyrazine as mGluR5 Antagonists Using 3D-QSAR Method, Asian Journal of Chemistry; vol. 24, No. 1 (2012), 238-248.
Newman, et al.,The Synthesis of 6,6'-Diethynyldiphenic Anhydride., 1971, J Org Chem 36(10:1398-1401.
Shimakage, et al.,Significant role of macrophages in human cancers associate with Epstein-Barr virus (Review)., Oncology Reports 32:1763-1771, 2014.
Thompson, et al.,Development of a High-Throughput Screen for Inhibitors of Epstein-Barr Virus EBNA1, Journal of Biomolecular Screening 15(9); 2010 pp. 1107-1115.
STN Registry RN 1259291-73-0, Jan. 13, 2011 [retrieved online Aug. 10, 2021].

\* cited by examiner

SEQUENCE LISTING

<160> NUMBER OF SEQ ID NOS: 1

<210> SEQ ID NO 1
<211> LENGTH: 36
<212> TYPE: DNA
<213> ORGANISM: Artificial Sequence
<220> FEATURE:
<223> OTHER INFORMATION: Oligonucleotide (including 5'-bt tag)

<400> SEQUENCE: 1
gggtagcata tgctatctag atagcatatg ctaccc          36

EBNA1 INHIBITORS AND THEIR METHOD OF USE

CROSS-REFERENCE TO RELATED APPLICATION

This application is a continuation of, and claims priority to, U.S. patent application Ser. No. 15/814,600, filed Nov. 16, 2017, issued as U.S. Pat. No. 10,421,718, which is a continuation of, and claims priority to, U.S. patent application Ser. No. 15/036,211, filed May 12, 2016, issued as U.S. Pat. No. 9,856,214, a 35 U.S.C. § 371 national phase application from, and claims priority to, International Application No. PCT/US2014/065765, filed Nov. 14, 2014, and published under PCT Article 21(2) in English, which claims priority under 35 U.S.C. § 119(e) to U.S. Provisional Application No. 61/904,555, filed Nov. 15, 2013, all of which applications are incorporated by reference herein in their entireties.

STATEMENT OF FEDERALLY SPONSORED RESEARCH

This invention was made with government support under grant number 5R43AI079928, awarded by the National Institutes of Health (NIAID) to Vironika, LLC; and grant number 1R21NS063906, awarded by the National Institutes of Health (NINDS) to The Wistar Institute. The government has certain rights in the invention.

BACKGROUND OF THE INVENTION

Field of the Invention

The present invention describes compounds and methods useful as EBNA1 inhibitors, e.g., useful for the treatment of diseases caused by EBNA1 activity. The present invention also describes compounds and methods useful as EBNA1 inhibitors, e.g., useful for the treatment of diseases caused by the Epstein-Barr Virus (EBV).

Related Art

EBV is a human gamma-herpesvirus that infects over 90% of the adult population worldwide [Young, L. S. and A. B. Rickinson, *Epstein-Barr virus: 40 years on*, Nat. Rev. Cancer, 2004, 4:757-68; Rickinson, A. B. and E. Kieff, *Epstein-Barr Virus, in Fields Virology, Third Edition*, 1996, Lippincott-Raven Publishers, pp. 2397-446]. In combination with known and unknown cofactors, especially immunosuppression, EBV infection constitutes a high carcinogenic risk. EBV has been classified by the World Health Organization as a class I human carcinogen because of its causal association with Burkitt's lymphoma, nasopharyngeal carcinoma, ~50% of all Hodgkin's lymphoma, gastric carcinoma, angiocentric T/NK lymphoma, and lymphoproliferative disorders of the immunosuppressed. It has been estimated that EBV is responsible for ~1% of all human cancers worldwide [Parkin, D. M., F. Bray, J. Ferlay, and P. Pisani (2005) *Global Cancer Statistics*, 2002, Cancer J. Clin. 55:75-108]. The oncogenic potential of EBV is readily demonstrated in vitro by its capacity to immortalize primary B-lymphocytes in culture and in vivo by its ability to drive infected B-cells into aggressive lymphoblastic lymphomas in immunocompromised hosts.

EBV, like other herpesviruses, has a latent and lytic replication cycle. While the EBV lytic cycle is essential for viral transmission and increases risk of EBV-associated malignancy, it is the latent viral infection that is oncogenic [Thorley-Lawson, D. A. and A. Gross, *Persistence of the Epstein-Barr virus and the origins of associated lymphomas*, N. Engl. J. Med., 2004. 350:1328-37]. The latent virus expresses a limited set of viral genes that stimulate cellular proliferation and survival. Clinically available inhibitors of herpesvirus DNA polymerases, including variants of acyclovir (e.g. ganciclovir) and phosphonoacetic acid (e.g. foscamet), have at least partial inhibitory activity against EBV lytic replication. However, none of the available herpesvirus antivirals are effective at blocking the virus from progressing to a latent infection or eliminating latent infection. Primary infections with EBV can evoke a robust, sometimes debilitating, immune response referred to as infectious mononucleosis (IM) [Vetsika, E. K. and M. Callan, *Infectious mononucleosis and Epstein-Barr virus*, Expert Rev. Mol. Med., 2004. 6:1-16]. Despite this robust immune reaction, the virus efficiently establishes latent infection in B-lymphocytes, where the virus can reside in long-lived memory B-cells [Babcock, G. J., L. L. Decker, M. Volk, and D. A. Thorley-Lawson, EBV persistence in memory B cells in vivo, *Immunity*, 1998, 9:395-404]. In some circumstances, latent infection can also be established in T-lymphocytes and epithelial cells. During latency, the virus does not produce infectious particles, and viral gene expression is limited to a subset of transcripts with growth-transforming and anti-apoptotic functions that contribute to EBV carcinogenesis. Thus, no existing anti-viral drug or immunological response can block the establishment of an EBV latent infection, which has the potential to drive lymphoid and epithelial cell oncogenic growth transformation.

Numerous studies have demonstrated that Epstein-Barr Nuclear Antigen 1 (EBNA1) is an ideal target for elimination of latent infection and treatment of EBV-associated disease. First, EBNA1 is expressed in all EBV-positive tumors [Leight, E. R. and B. Sugden, EBNA-1: a protein pivotal to latent infection by Epstein-Barr virus, *Rev. Med. Virol.*, 2000, 10:83-100; Altmann, M., D. Pich, R. Ruiss, J. Wang, B. Sugden, and W. Hammerschmidt, Transcriptional activation by EBV nuclear antigen 1 is essential for the expression of EBV's transforming genes, *Proc. Natl. Acad. Sci. USA*, 2006, 103:14188-93]. Second, EBNA1 is required for immortalization of primary B-lymphocytes and for the stable maintenance of the EBV genome in latently infected cells [Humme, S., G. Reisbach, R. Feederle, H. J. Delecluse, K. Bousset, W. Hammerschmidt, and A. Schepers, *The EBV nuclear antigen 1 (EBNA1) enhances B cell immortalization several thousand-fold*, Proc. Natl. Acad. Sci. USA, 2003, 100:10989-94]. Third, genetic disruption of EBNA1 blocks the ability of EBV to immortalize primary human B-lymphocytes and causes loss of cell viability in previously established EBV-positive cell lines [Lee, M. A., M. E. Diamond, and J. L. Yates, *Genetic evidence that EBNA-1 is needed for efficient, stable latent infection by Epstein-Barr virus*, J. Virol., 1999. 73:2974-82]. Fourth, biochemical disruption of EBNA1 folding blocks the establishment of EBV latent infection. HSP90 inhibitors cause the selective killing of EBV$^+$ B-cells and block lymphomagenesis in mouse models [Sun, X., E. A. Barlow, S. Ma S. R. Hagemeier, S. J. Duellman, R. R. Burgess, J. Tellam, R. Khanna, and S. C. Kenney, 2010, Hsp90 inhibitors block outgrowth of EBV-infected malignant cells in vitro and in vivo through an EBNA1-dependent mechanism, *Proc. Natl. Acad. Sci. USA*, 107:3146-51]. Fifth, EBNA1 is a noncellular viral oncoprotein that is functionally and structurally well characterized. The three-dimensional structure of EBNA1 bound to its cognate DNA sequence has been solved by X-ray crystallography [Bochkarev, A., J. A. Barwell, R. A. Pfuetzner, E. Bochkareva, L. Frappier, and A. M. Edwards, Crystal structure of the DNA-binding domain of the Epstein-Barr virus origin-binding protein, EBNA1, bound to DNA, *Cell,* 1996, 84:791-800; Bochkarev, A., J. A. Barwell, R. A. Pfuetzner, W. Furey, A. M. Edwards, and L. Frappier, *Crystal structure of the DNA binding domain of the Epstein-Barr virus origin binding protein EBNA-1*, Cell, 1995, 83:39-46; Bochkarev A, Bochkareva E, Frappier L, Edwards A M. *The 2.2 Å structure of a permanganate-sensitive DNA site bound by the Epstein-Barr virus origin binding protein, EBNA*1. J Mol Biol, 1998. 284:1273-78]. Analysis of the DNA binding domain reveals that EBNA1 protein is druggable, with several deep pockets and channels within the DNA binding domain that are predicted to disrupt DNA binding when bound to small molecules. Sixth, targeting a non-self viral-encoded protein for inhibition mitigates the potential risk of inherent toxicity. EBNA1 has a unique structural fold that is distinct from all known cellular DNA binding and replication proteins [Sun X, Barlow E A, Ma S, Hagemeier S R, Duellman S J, Burgess R R, Tellam J, Khanna R, Kenney S C. (2010) Hsp90 inhibitors block outgrowth of EBV-infected malignant cells in vitro and in vivo through an EBNA1-dependent mechanism. *Proc Natl Acad Sci USA* 107:3146-51; Bochkarev A, Barwell J A, Pfuetzner R A, Bochkareva E, Frappier L, Edwards A M. Crystal structure of the DNA-binding domain of the Epstein-Barr virus origin-binding protein, EBNA1, bound to DNA. *Cell,* 1996. 84:791-800; Bochkarev A, Barwell J A, Pfuetzner R A, Furey W, Edwards A M, Frappier L. Crystal structure of the DNA binding domain of the Epstein-Barr virus origin binding protein EBNA-1. Cell, 1995. 83:39-46]. Finally, the EBNA1 DNA binding function is essential for all known EBNA1 functions, including genome maintenance, DNA replication, transcription regulation, and host-cell survival [Leight, E. R. and B. Sugden, EBNA-1: a protein pivotal to latent infection by Epstein-Barr virus. *Rev Med Virol,* 2000. 10:83-100. Altmann M, Pich D, Ruiss R, Wang J, Sugden B, Hammerschmidt W. Transcriptional activation by EBV nuclear antigen 1 is essential for the expression of EBV's transforming genes. *Proc Natl Acad Sci USA,* 2006. 103:14188-93; Rawlins D R, Milman G, Hayward S D, Hayward G S. Sequence-specific DNA binding of the Epstein-Barr virus nuclear antigen (EBNA-1) to clustered sites in the plasmid maintenance region. Cell, 1985. 42:859-68; Ritzi M, Tillack K, Gerhardt J, Ott E, Humme S, Kremmer E, Hammerschmidt W, Schepers A. Complex protein-DNA dynamics at the latent origin of DNA replication of Epstein-Barr virus. *J Cell Sci,* 2003. 116:3971-84; Schepers A, Ritzi M, Bousset K, Kremmer E, Yates J L, Harwood J, Diffley J F, Hammerschmidt W. Human origin recognition complex binds to the region of the latent origin of DNA replication of Epstein-Barr virus. *EMBO J,* 2001. 20:4588-602]. Collectively, these studies demonstrate that EBNA1-DNA binding domain is an ideal and validated target for inhibition of EBV-latent infection and treatment of EBV-associated malignancies.

EBV plays a causative role in the tumorigenesis for a number of cancers including nasopharyngeal carcinoma, gastric carcinomas, non-hodgkin lymphoma (anaplastic large-cell lymphoma, angioimmunoblastic T-cell lymphoma, hepatosplenic T-cell lymphoma, B-cell lymphoma, Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma, B-cell chronic lymphocytic leukemia, mantle cell lymphoma, mediastinal large B cell lymphoma, lymphoplasmactic lymphoma, nodal marginal zone B cell lymphoma, splenic marginal zone lymphoma, intravascular large B-cell lymphoma, primary effusion lymphoma, lyphomatoid granulomatosis, angioimmunoblastic lymphadenopathy), leiomyosarcomas, X-linked lymphoproliferative disease, post-transplant lymphoproliferative disorders, Hodgkin's lymphoma and breast cancer. EBV has been classified as a class I human carcinogen responsible for at least 1% of all human cancer by the World Health Organization. EBV-associated malignancies account for more than 100,000 new cancer cases each year in the United States. An inhibitor of EBNA1 would change current clinical practice and be valuable for therapeutic treatment of EBV-associated diseases. Currently, nucleoside analogues (aciclovir, ganciclovir, foscamet) can be used to treat lytic EBV infection and pathologies related to lytic EBV infection. However, these general anti-viral drugs are not specific for lytic EBV infection, and carry the risk of severe adverse effects. To date, no effective treatments exist for latent EBV infection, no treatment exists for pathologies related to latent EBV infection, and no treatments exist for the treatment of diseases associated with EBNA1.

EBV infection and EBNA1 have also been implicated in infectious mononucleosis [Henle W, Henle G. Epstein-Barr virus and infectious mononucleosis, *N Engl J Med.* 1973. 288:263-64; Vetsika E K, Callan M. Infectious mononucleosis and Epstein-Barr virus, *Expert Rev Mol Med.* 2004 6:1-16], chronic fatigue syndrome (CFS) [Watt T, Oberfoell S, Balise R, Lunn M R, Kar A K, Merrihew L, Bhangoo M S, Montoya J G. Response to valganciclovir in chronic fatigue syndrome patients with human herpesvirus 6 and Epstein-Barr virus IgG antibody titers. J Med Virol. 2012, 84:1967-74; Natelson B H, Ye N, Moul D E, Jenkins F J, Oren D A, Tapp W N, Cheng Y C. High titers of anti-Epstein-Barr virus DNA polymerase are found in patients with severe fatiguing illness. J Med Virol. 1994. 42:42-6; Wallace H L 2nd, Natelson B, Gause W, Hay J. Human herpesviruses in chronic fatigue syndrome. Clin Diagn Lab Immunol. 1999 6:216-23], multiple sclerosis [Tselis A. Epstein-Barr virus cause of multiple sclerosis, *Curr Opin Rheumatol.* 2012. 24:424-28; Lucas R M, Hughes A M, Lay M L, Ponsonby A L, Dwyer D E, Taylor B V, Pender M P. Epstein-Barr virus and multiple sclerosis, *J Neurol Neurosurg Psychiatry.* 2011. 82:1142-48; Ascherio A, Munger K L. Epstein-barr virus infection and multiple sclerosis: a review, J Neuroimmune Pharmacol. 2010. 3:271-77], systemic lupus erythematosus [Draborg A H, Duus K, Houen G. Epstein-Barr virus and systemic lupus erythematosus, *Clin Dev Immunol.* 2012: 370516; Doria A, Canova M, Tonon M, Zen M, Rampudda E, Bassi N, Atzeni F, Zampieri S, Ghirardello A. Infections as triggers and complications of systemic lupus erythematosus, *Autoimmun Rev.* 2008. 8:24-28; Poole B D, Scofield R H, Harley J B, James J A. Epstein-Barr virus and molecular mimicry in systemic lupus erythematosus. Autoimmunity. 2006 39:63-70], and rheumatoid arthritis [Lossius A, Johansen J N, Torkildsen Ø, Vartdal F, Holmoy T. Epstein-Barr virus in systemic lupus erythematosus, rheumatoid arthritis and multiple sclerosis-association and causation. *Viruses.* 2012. 4:3701-30; Balandraud N, Roudier J, Roudier C. Epstein-Barr virus and rheumatoid arthritis, *Autoimmun Rev.* 2004 3:362-67; Oliver J E, Silman A J. Risk factors for the development of rheumatoid arthritis. *Scand J Rheumatol.* 2006. 35:169-74]. Treatment with compounds that prevent EBV infection would provide therapeutic relief to patients suffering from infectious mononucleosis, multiple sclerosis, systemic lupus erythematosus, and rheumatoid arthritis. Further, treatment with compounds that prevent lytic EBV infection would provide therapeutic relief to patients suffering from infectious mononucleosis, multiple sclerosis, systemic lupus erythematosus, and rheumatoid arthritis. Further, treatment with compounds that prevent latent EBV infection would provide therapeutic relief to patients suffering from infectious mononucleosis, chronic fatigue syndrome, multiple sclerosis, systemic lupus erythematosus, and rheumatoid arthritis. Treatment with compounds that inhibit EBNA1 would provide therapeutic relief for suffering from infectious mononucleosis, chronic fatigue syndrome, multiple sclerosis, systemic lupus erythematosus, and rheumatoid arthritis. To date, however, no effective specific treatments exist for lytic EBV infection and no specific treatment exists for pathologies related to lytic EBV infection. In addition, to date, however, no effective treatments exist for latent EBV infection, no treatment exists for pathologies related to latent EBV infection, and no treatments exist for the treatment of diseases associated with EBNA1.

There is a long felt need for new treatments that are both disease-modifying and effective in treating patients that are refractory to current treatments for diseases and conditions associated with EBV infection such as nasopharyngeal carcinoma, gastric carcinomas, non-hodgkin lymphoma, anaplastic large-cell lymphoma, angioimmunoblastic T-cell lymphoma, hepatosplenic T-cell lymphoma, B-cell lymphoma, Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma, B-cell chronic lymphocytic leukemia, mantle cell lymphoma, mediastinal large B cell lymphoma, lymphoplasmactic lymphoma, nodal marginal zone B cell lymphoma, splenic marginal zone lymphoma, intravascular large B-cell lymphoma, primary effusion lymphoma, lyphomatoid granulomatosis, angioimmunoblastic lymphadenopathy, leiomyosarcomas, X-linked lymphoproliferative disease, post-transplant lymphoproliferative disorders, Hodgkin's lymphoma and breast cancer. There is also a long felt need for new treatments that are both disease-modifying and effective in treating patients that are refractory to current treatments for infectious mononucleosis. There is also a long felt need for new treatments that are both disease-modifying and effective in treating patients that are refractory to current treatments for chronic fatigues syndrome. There is also a long felt need for new treatments that are both disease-modifying and effective in treating patients that are refractory to current treatments for multiple sclerosis. There is also a long felt need for new treatments that are both disease-modifying and effective in treating patients that are refractory to current treatments for systemic lupus erythematosus. There is also a long felt need for new treatments that are both disease-modifying and effective in treating patients that are refractory to current treatments for rheumatoid arthritis. There is also a clear and present need for the treatment of EBV infection, and there is a long felt need for treatments that can specifically block lytic EBV infection. There is a long felt need for treatments that can block latent EBV infection. There is also a clear and present need for new treatments that are both disease-modifying and effective in treating diseases associated with EBNA1.

The present invention addresses the need to identify new treatments for diseases and conditions associated with EBV infection such as infectious mononucleosis, chronic fatigue syndrome, multiple sclerosis, systemic lupus erythematosus, and rheumatoid arthritis, and cancer, including nasopharyngeal carcinoma, gastric carcinomas, non-hodgkin lymphoma (anaplastic large-cell lymphoma, angioimmunoblastic T-cell lymphoma, hepatosplenic T-cell lymphoma, B-cell lymphoma, Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma, B-cell chronic lymphocytic leukemia, mantle cell lymphoma, mediastinal large B cell lymphoma, lymphoplasmactic lymphoma, nodal marginal zone B cell lymphoma, splenic marginal zone lymphoma, intravascular large B-cell lymphoma, primary effusion lymphoma, lyphomatoid granulomatosis, angioimmunoblastic lymphadenopathy), leiomyosarcomas, X-linked lymphoproliferative disease, post-transplant lymphoproliferative disorders, Hodgkin's lymphoma, and breast cancer by identifying novel EBNA1 inhibitors useful as therapeutic agents and in therapeutic compositions.

BRIEF SUMMARY OF THE INVENTION

The present invention is directed toward EBNA1 inhibitors of the formula (I),

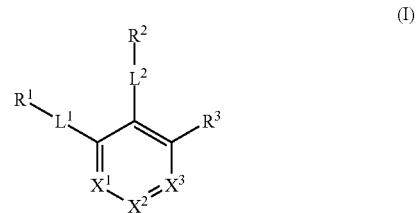

including hydrates, solvates, polymorphs, pharmaceutically acceptable salts, prodrugs, and complexes thereof, wherein:
$X^1$ is selected from the group consisting of $CR^{4a}$ and N;
$X^2$ is selected from the group consisting of $CR^{4b}$ and N;
$X^3$ is selected from the group consisting of $CR^{4c}$ and N;
$R^1$ is selected from the group consisting of optionally substituted $C_{1-6}$ linear alkyl, optionally substituted $C_{3-6}$ branched alkyl, optionally substituted $C_{3-6}$ cyclic alkyl, optionally substituted phenyl, optionally substituted heteroaryl, optionally substituted benzyl, optionally substituted heteroaryl methyl,

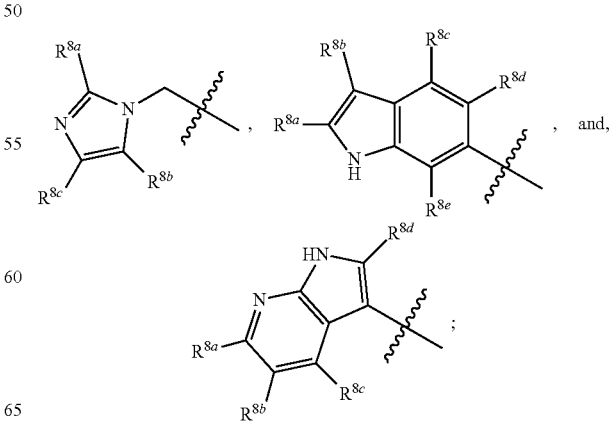

$R^2$ is selected from the group consisting of hydrogen, $NR^{10a}R^{10b}$, fluorine, optionally substituted phenyl, optionally substituted heteroaryl,

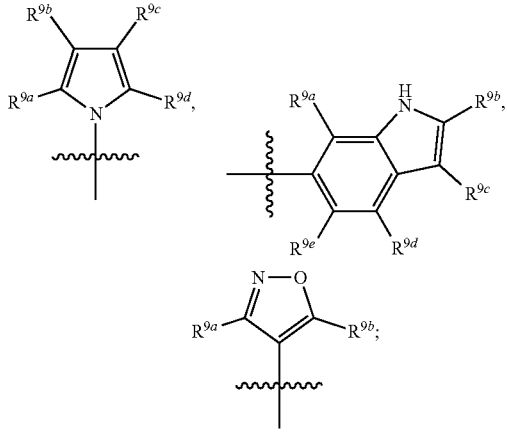

$R^3$ is selected from the group consisting of

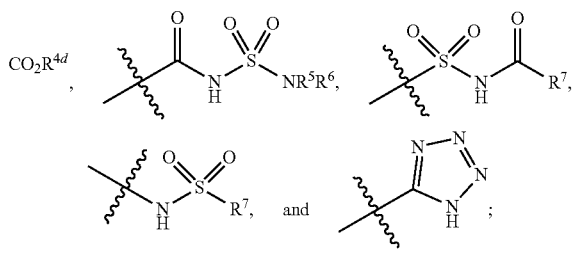

$R^{4a}$, $R^{4b}$, and $R^{4c}$ are each independently selected from the group consisting of fluorine, chlorine, bromine, iodine, and hydrogen;

$R^{4d}$ is selected from the group consisting of hydrogen, optionally substituted $C_{1-6}$ linear alkyl, and optionally substituted $C_{3-6}$ branched alkyl;

$R^5$ is selected from the group consisting of hydrogen, optionally substituted $C_{1-6}$ linear alkyl, and optionally substituted $C_{3-6}$ branched alkyl;

$R^6$ is selected from the group consisting of hydrogen, optionally substituted $C_{1-6}$ linear alkyl, and optionally substituted $C_{3-6}$ branched alkyl;

$R^7$ is selected from the group consisting of hydrogen, optionally substituted $C_{1-6}$ linear alkyl, and optionally substituted $C_{3-6}$ branched alkyl;

$R^{8a}$, $R^{8b}$, $R^{8c}$, $R^{8d}$, and $R^{8e}$ are each independently selected from the group consisting of hydrogen, optionally substituted $C_{1-6}$ linear alkyl, and optionally substituted $C_{3-6}$ branched alkyl;

$R^{9a}$, $R^{9b}$, $R^{9c}$, $R^{9d}$, and $R^{9e}$ are each independently selected from the group consisting of hydrogen, optionally substituted $C_{1-6}$ linear alkyl, and optionally substituted $C_{3-6}$ branched alkyl;

$R^{10a}$, and $R^{10b}$ are each independently selected from the group consisting of hydrogen, optionally substituted $C_{1-6}$ linear alkyl, and optionally substituted $C_{1-6}$ branched alkyl;

$L^1$ is selected from the group consisting of

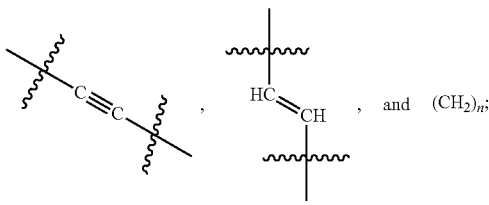

$L^2$ is selected from a group consisting of NH, $(CH_2)_m$, and

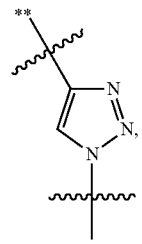

wherein "**" indicates the point of attachment for $R^2$;

n is 0, 1, 2, or 3; and m is 0, 1, 2, or 3.

The compounds of the present invention include compounds having formula (II):

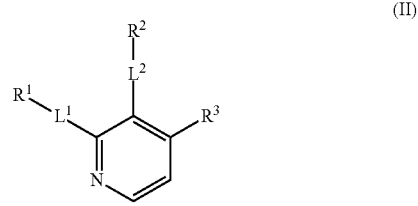

including hydrates, solvates, polymorphs, pharmaceutically acceptable salts, prodrugs, and complexes thereof. Substituents for this formula and subsequent formulas are as noted above for formula (I), unless otherwise specified.

The compounds of the present invention include compounds having formula (III):

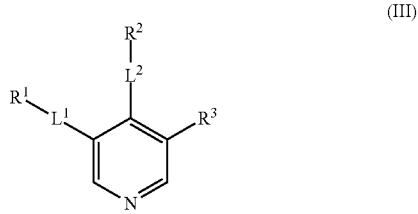

including hydrates, solvates, polymorphs, pharmaceutically acceptable salts, prodrugs, and complexes thereof.

The compounds of the present invention include compounds having formula (IV):

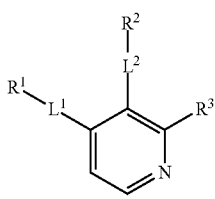

(IV)

including hydrates, solvates, polymorphs, pharmaceutically acceptable salts, prodrugs, and complexes thereof.

The compounds of the present invention include compounds having formula (V):

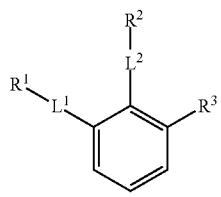

(V)

including hydrates, solvates, polymorphs, pharmaceutically acceptable salts, prodrugs, and complexes thereof.

The compounds of the present invention include compounds having formula (VI):

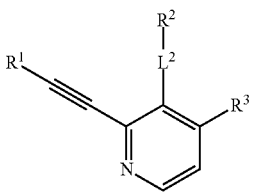

(VI)

including hydrates, solvates, polymorphs, pharmaceutically acceptable salts, prodrugs, and complexes thereof.

The compounds of the present invention include compounds having formula (VII):

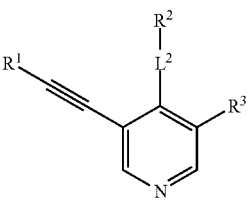

(VII)

including hydrates, solvates, polymorphs, pharmaceutically acceptable salts, prodrugs, and complexes thereof.

The compounds of the present invention include compounds having formula (VIII):

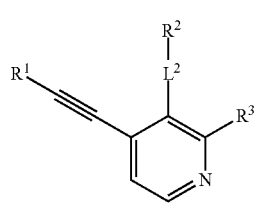

(VIII)

including hydrates, solvates, polymorphs, pharmaceutically acceptable salts, prodrugs, and complexes thereof.

The compounds of the present invention include compounds having formula (IX):

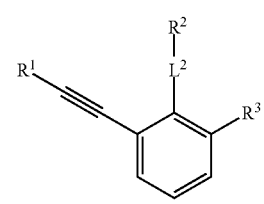

(IX)

including hydrates, solvates, polymorphs, pharmaceutically acceptable salts, prodrugs, and complexes thereof.

The compounds of the present invention include compounds having formula (X):

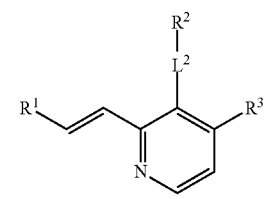

(X)

including hydrates, solvates, polymorphs, pharmaceutically acceptable salts, prodrugs, and complexes thereof.

The compounds of the present invention include compounds having formula (XI):

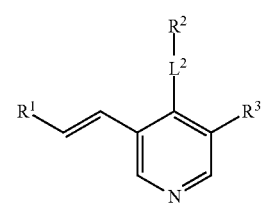

(XI)

including hydrates, solvates, polymorphs, pharmaceutically acceptable salts, prodrugs, and complexes thereof.

The compounds of the present invention include compounds having formula (XII):

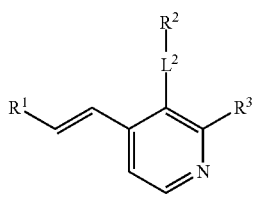

(XII)

including hydrates, solvates, polymorphs, pharmaceutically acceptable salts, prodrugs, and complexes thereof.

The compounds of the present invention include compounds having formula (XIII):

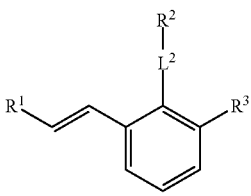

(XIII)

including hydrates, solvates, polymorphs, pharmaceutically acceptable salts, prodrugs, and complexes thereof.

The compounds of the present invention include compounds having formula (XIV):

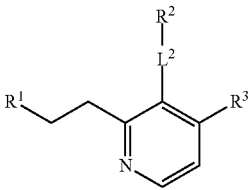

(XIV)

including hydrates, solvates, polymorphs, pharmaceutically acceptable salts, prodrugs, and complexes thereof.

The compounds of the present invention include compounds having formula (XV):

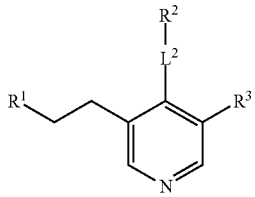

(XV)

including hydrates, solvates, polymorphs, pharmaceutically acceptable salts, prodrugs, and complexes thereof.

The compounds of the present invention include compounds having formula (XVI):

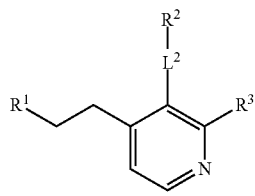

(XVI)

including hydrates, solvates, polymorphs, pharmaceutically acceptable salts, prodrugs, and complexes thereof.

The compounds of the present invention include compounds having formula (XVII):

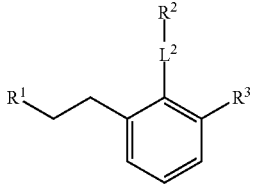

(XVII)

including hydrates, solvates, polymorphs, pharmaceutically acceptable salts, prodrugs, and complexes thereof.

The present invention further relates to compositions comprising an effective amount of one or more compounds according to the present invention and an excipient.

The present invention also relates to a method for treating or preventing diseases or conditions caused by EBNA1 activity, the method comprising administering to a subject an effective amount of a compound or composition according to the present invention.

The present invention yet further relates to a method for treating or preventing diseases or conditions caused by EBNA1 activity, wherein the method comprises administering to a subject a composition comprising an effective amount of one or more compounds according to the present invention and an excipient.

The present invention also relates to methods for treating or preventing disease or conditions associated with EBNA1 activity. The methods comprise administering to a subject an effective amount of a compound or composition according to the present invention.

The present invention yet further relates to a method for treating or preventing disease or conditions associated with EBNA1 activity, wherein the method comprises administering to a subject a composition comprising an effective amount of one or more compounds according to the present invention and an excipient.

The present invention also relates to a method for treating or preventing EBV infection, the method comprising administering to a subject an effective amount of a compound or composition according to the present invention.

The present invention yet further relates to a method for treating or preventing EBV infection, wherein the method comprises administering to a subject a composition comprising an effective amount of one or more compounds according to the present invention and an excipient.

The present invention also relates to methods for treating or preventing disease or conditions associated with EBV infection. The methods comprise administering to a subject an effective amount of a compound or composition according to the present invention.

The present invention yet further relates to a method for treating or preventing disease or conditions associated with EBV infection, wherein the method comprises administering to a subject a composition comprising an effective amount of one or more compounds according to the present invention and an excipient.

The present invention also relates to a method for treating or preventing lytic EBV infection, the method comprising administering to a subject an effective amount of a compound or composition according to the present invention.

The present invention yet further relates to a method for treating or preventing lytic EBV infection, wherein the method comprises administering to a subject a composition comprising an effective amount of one or more compounds according to the present invention and an excipient.

The present invention also relates to methods for treating or preventing disease or conditions associated with lytic EBV infection. The methods comprise administering to a subject an effective amount of a compound or composition according to the present invention.

The present invention yet further relates to a method for treating or preventing disease or conditions associated with lytic EBV infection, wherein the method comprises administering to a subject a composition comprising an effective amount of one or more compounds according to the present invention and an excipient.

The present invention also relates to a method for treating or preventing latent EBV infection, the method comprising administering to a subject an effective amount of a compound or composition according to the present invention.

The present invention yet further relates to a method for treating or preventing latent EBV infection, wherein the method comprises administering to a subject a composition comprising an effective amount of one or more compounds according to the present invention and an excipient.

The present invention also relates to methods for treating or preventing disease or conditions associated with latent EBV infection. The methods comprise administering to a subject an effective amount of a compound or composition according to the present invention.

The present invention yet further relates to a method for treating or preventing disease or conditions associated with latent EBV infection, wherein the method comprises administering to a subject a composition comprising an effective amount of one or more compounds according to the present invention and an excipient.

The present invention yet further relates to a method for treating or preventing cancer, particularly nasopharyngeal carcinoma, gastric carcinomas, non-Hodgkin lymphoma, anaplastic large-cell lymphoma, angioimmunoblastic T-cell lymphoma, hepatosplenic T-cell lymphoma, B-cell lymphoma, Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma, B-cell chronic lymphocytic leukemia, mantle cell lymphoma, mediastinal large B cell lymphoma, lymphoplasmactic lymphoma, nodal marginal zone B cell lymphoma, splenic marginal zone lymphoma, intravascular large B-cell lymphoma, primary effusion lymphoma, lyphomatoid granulomatosis, angioimmunoblastic lymphadenopathy, leiomyosarcomas, X-linked lymphoproliferative disease, post-transplant lymphoproliferative disorders, Hodgkin's lymphoma and breast cancer.

The present invention yet further relates to a method for treating of preventing cancer, particularly nasopharyngeal carcinoma, gastric carcinomas, non-hodgkin lymphoma, anaplastic large-cell lymphoma, angioimmunoblastic T-cell lymphoma, hepatosplenic T-cell lymphoma, B-cell lymphoma, Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma, B-cell chronic lymphocytic leukemia, mantle cell lymphoma, mediastinal large B cell lymphoma, lymphoplasmactic lymphoma, nodal marginal zone B cell lymphoma, splenic marginal zone lymphoma, intravascular large B-cell lymphoma, primary effusion lymphoma, lyphomatoid granulomatosis, angioimmunoblastic lymphadenopathy, leiomyosarcomas, X-linked lymphoproliferative disease, post-transplant lymphoproliferative disorders, Hodgkin's lymphoma and breast cancer wherein the method comprising administering to a subject an effective amount of a compound or composition according to the present invention.

The present invention yet further relates to a method for treating of preventing cancer particularly nasopharyngeal carcinoma, gastric carcinomas, non-hodgkin lymphoma, anaplastic large-cell lymphoma, angioimmunoblastic T-cell lymphoma, hepatosplenic T-cell lymphoma, B-cell lymphoma, Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma, B-cell chronic lymphocytic leukemia, mantle cell lymphoma, mediastinal large B cell lymphoma, lymphoplasmactic lymphoma, nodal marginal zone B cell lymphoma, splenic marginal zone lymphoma, intravascular large B-cell lymphoma, primary effusion lymphoma, lyphomatoid granulomatosis, angioimmunoblastic lymphadenopathy, leiomyosarcomas, X-linked lymphoproliferative disease, post-transplant lymphoproliferative disorders, Hodgkin's lymphoma and breast cancer wherein the method comprising administering to a subject an effective amount of a compound or composition according to the present invention and an excipient.

The present invention yet further relates to a method for treating or preventing infectious mononucleosis.

The present invention yet further relates to a method for treating of infectious mononucleosis wherein the method comprising administering to a subject an effective amount of a compound or composition according to the present invention.

The present invention yet further relates to a method for treating of preventing infectious mononucleosis wherein the method comprising administering to a subject an effective amount of a compound or composition according to the present invention and an excipient.

The present invention yet further relates to a method for treating or preventing chronic fatigue syndrome.

The present invention yet further relates to a method for treating of chronic fatigue syndrome wherein the method comprising administering to a subject an effective amount of a compound or composition according to the present invention.

The present invention yet further relates to a method for treating of preventing chronic fatigue syndrome wherein the method comprising administering to a subject an effective amount of a compound or composition according to the present invention and an excipient.

The present invention yet further relates to a method for treating or preventing multiple sclerosis.

The present invention yet further relates to a method for treating of multiple sclerosis wherein the method comprising administering to a subject an effective amount of a compound or composition according to the present invention.

The present invention yet further relates to a method for treating of preventing multiple sclerosis wherein the method comprising administering to a subject an effective amount of a compound or composition according to the present invention and an excipient.

The present invention yet further relates to a method for treating or preventing systemic lupus erythematosus.

The present invention yet further relates to a method for treating of systemic lupus erythematosus wherein the method comprising administering to a subject an effective amount of a compound or composition according to the present invention.

The present invention yet further relates to a method for treating of preventing systemic lupus erythematosus wherein the method comprising administering to a subject an effective amount of a compound or composition according to the present invention and an excipient.

The present invention yet further relates to a method for treating or preventing rheumatoid arthritis.

The present invention yet further relates to a method for treating of rheumatoid arthritis wherein the method comprising administering to a subject an effective amount of a compound or composition according to the present invention.

The present invention yet further relates to a method for treating of preventing rheumatoid arthritis wherein the method comprising administering to a subject an effective amount of a compound or composition according to the present invention and an excipient.

The present invention further relates to a process for preparing the EBNA1-inhibitors of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The EBNA1-inhibitors of the present invention are capable of treating and preventing diseases or conditions caused by EBNA1 activity. In addition, compounds of the disclosure are capable of treating and preventing disease or conditions associated with EBNA1 activity. Further, compounds of the disclosure are also capable of treating or preventing EBV infection. In addition, compounds of the disclosure are capable of treating or preventing disease or conditions associated with EBV infection. Further, compounds of the disclosure are also capable of treating or preventing lytic EBV infection. Compounds of the disclosure are also capable of treating or preventing latent EBV infection. In addition, compounds of the disclosure are also capable of treating or preventing disease or conditions associated with lytic EBV infection. Further, compounds of the disclosure are also capable of treating or preventing disease or conditions associated with latent EBV infection. Without wishing to be limited by theory, it is believed that the EBNA1-inhibitors of the present invention can ameliorate, abate, prevent, reverse, or otherwise cause to be controlled, cancer, particularly nasopharyngeal carcinoma, gastric carcinomas, non-hodgkin lymphoma, anaplastic large-cell lymphoma, angioimmunoblastic T-cell lymphoma, hepatosplenic T-cell lymphoma, B-cell lymphoma, Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma, B-cell chronic lymphocytic leukemia, mantle cell lymphoma, mediastinal large B cell lymphoma, lymphoplasmactic lymphoma, nodal marginal zone B cell lymphoma, splenic marginal zone lymphoma, intravascular large B-cell lymphoma, primary effusion lymphoma, lyphomatoid granulomatosis, angioimmunoblastic lymphadenopathy, leiomyosarcomas, X-linked lymphoproliferative disease, post-transplant lymphoproliferative disorders, Hodgkin's lymphoma and breast cancer. Further, without wishing to be limited by theory, it is believed that the EBNA1-inhibitors of the present invention can ameliorate, abate, prevent, reverse, or otherwise cause to be controlled infectious mononucleosis. Further, without wishing to be limited by theory, it is believed that the EBNA1-inhibitors of the present invention can ameliorate, abate, prevent, reverse, or otherwise cause to be controlled infectious mononucleosis. Further, without wishing to be limited by theory, it is believed that the EBNA1-inhibitors of the present invention can ameliorate, abate, prevent, reverse, or otherwise cause to be controlled chronic fatigue syndrome. Further, without wishing to be limited by theory, it is believed that the EBNA1-inhibitors of the present invention can ameliorate, abate, prevent, reverse, or otherwise cause to be controlled multiple sclerosis. In addition, without wishing to be limited by theory, it is believed that the EBNA1-inhibitors of the present invention can ameliorate, abate, prevent, reverse, or otherwise cause to be controlled systemic lupus erythematosus. In addition, without wishing to be limited by theory, it is believed that the EBNA1-inhibitors of the present invention can ameliorate, abate, prevent, reverse, or otherwise cause to be controlled and rheumatoid arthritis.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, the term "halogen" shall mean chlorine, bromine, fluorine and iodine.

As used herein, unless otherwise noted, "alkyl" and "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, isobutyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2$amino, the alkyl groups may be the same or different.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2. 1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, $CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino)phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted. Non-limiting examples of heterocyclic units having a single ring include: diazirinyl, aziridinyl, urazolyl, azetidinyl, pyrrolyl, thiophenyl, furanyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, benzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxyquinolinyl, and isoquinolinyl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposes of the present invention, fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

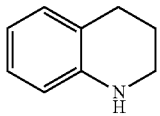

is, for the purposes of the present invention, considered a heterocyclic unit. 6,7-Dihydro-5H-cyclopentapyrimidine having the formula:

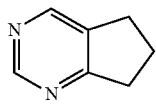

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

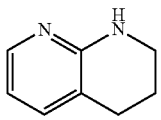

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^{10}$, —SR$^{10}$, —N(R$^{10}$)$_2$, —NR$^{10}$C(O)R$^{10}$, —SO$_2$R$^{10}$, —SO$_2$OR$^{10}$, —SO$_2$N(R$^{10}$)$_2$, —C(O)R$^{10}$, —C(O)OR$^{10}$, —C(O)N(R$^{10}$)$_2$, C$_{1-6}$ alkyl, C$_{1-6}$ haloalkyl, C$_{1-6}$ alkoxy, C$_{2-8}$ alkenyl, C$_{2-8}$ alkynyl, C$_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^{10}$; wherein R10, at each occurrence, independently is hydrogen, —OR$^{11}$, —SR$^{11}$, —C(O)R$^{11}$, —C(O)OR$^{11}$, —C(O)N(R$^{11}$)$_2$, —SO$_2$R$^{11}$, —S(O)$_2$OR$^{11}$, —N(R$^{11}$)$_2$, —NR$^{11}$C(O)R$^{11}$, C$_{1-6}$ alkyl, C$_{1-6}$ haloalkyl, C$_{2-8}$ alkenyl, C$_{2-8}$ alkynyl, cycloalkyl (e.g., C$_{3-6}$ cycloalkyl), aryl, heterocycle, or heteroaryl, or two R$^{10}$ units taken together with the atom(s) to which they are bound form an optionally substituted carbocycle or heterocycle wherein said carbocycle or heterocycle has 3 to 7 ring atoms; wherein R$^{11}$, at each occurrence, independently is hydrogen, C$_{1-6}$ alkyl, C$_{1-6}$ haloalkyl, C$_{2-8}$ alkenyl, C$_{2-8}$ alkynyl, cycloalkyl (e.g., C$_{3-6}$ cycloalkyl), aryl, heterocycle, or heteroaryl, or two R$^{11}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —OR$^{12}$; for example, —OH, —OCH$_3$, —OCH$_2$CH$_3$, —OCH$_2$CH$_2$CH$_3$;
ii) —C(O)R$^{12}$; for example, —COCH$_3$, —COCH$_2$CH$_3$, —COCH$_2$CH$_2$CH$_3$;
iii) —C(O)OR$^{12}$; for example, —CO$_2$CH$_3$, —CO$_2$CH$_2$CH$_3$, —CO$_2$CH$_2$CH$_2$CH$_3$;
iv) —C(O)N(R$^{12}$)$_2$; for example, —CONH$_2$, —CONHCH$_3$, —CON(CH$_3$)$_2$;
v) —N(R$^{12}$)$_2$; for example, —NH$_2$, —NHCH$_3$, —N(CH$_3$)$_2$, —NH(CH$_2$CH$_3$);
vi) halogen: —F, —Cl, —Br, and —I;
vii) —CH$_e$X$_g$; wherein X is halogen, m is from 0 to 2, e+g=3; for example, —CH$_2$F, —CHF$_2$, —CF$_3$, —CCl$_3$, or —CBr$_3$;

viii) —SO$_2$R$^{12}$; for example, —SO$_2$H; —SO$_2$CH$_3$; —SO$_2$C$_6$H$_5$;
ix) C$_1$-C$_6$ linear, branched, or cyclic alkyl;
x) Cyano
xi) Nitro;
xii) N(R$^{12}$)C(O)R$^{12}$;
xiii) Oxo (=O);
xiv) Heterocycle; and
xv) Heteroaryl.

wherein each R$^{12}$ is independently hydrogen, optionally substituted C$_1$-C$_6$ linear or branched alkyl (e.g., optionally substituted C$_1$-C$_4$ linear or branched alkyl), or optionally substituted C$_3$-C$_6$ cycloalkyl (e.g optionally substituted C$_3$-C$_4$ cycloalkyl); or two R$^{12}$ units can be taken together to form a ring comprising 3-7 ring atoms. In certain aspects, each R$^{12}$ is independently hydrogen, C$_1$-C$_6$ linear or branched alkyl optionally substituted with halogen or C$_3$-C$_6$ cycloalkyl or C$_3$-C$_6$ cycloalkyl.

At various places in the present specification, substituents of compounds are disclosed in groups or in ranges. It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$, alkyl.

For the purposes of the present invention the terms "compound," "analog," and "composition of matter" stand equally well for the prodrug agent described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include NaHCO$_3$, Na$_2$CO$_3$, KHCO$_3$, K$_2$CO$_3$, Cs$_2$CO$_3$, LiOH, NaOH, KOH, NaH$_2$PO$_4$, Na$_2$HPO$_4$, and Na$_3$PO$_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in N(R$^{10}$)$_2$, each R$^{10}$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

As used herein, the term "EBNA1 inhibitor" shall mean a compound that inhibits EBNA1.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The EBNA1 Inhibitors:

The EBNA1 inhibitors of the present invention include all enantiomeric and diastereomeric forms and pharmaceutically accepted salts thereof having the formula (I):

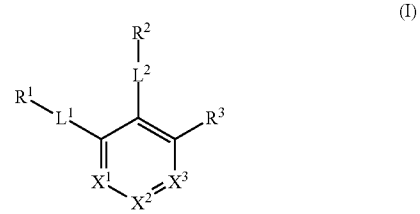

including hydrates, solvates, polymorphs, pharmaceutically acceptable salts, prodrugs, and complexes thereof, wherein:

$X^1$ is selected from the group consisting of $CR^{4a}$ and N;
$X^2$ is selected from the group consisting of $CR^{4b}$ and N;
$X^3$ is selected from the group consisting of $CR^{4c}$ and N;
$R^1$ is selected from the group consisting of optionally substituted $C_{1-6}$ linear alkyl, optionally substituted $C_{3-6}$ branched alkyl, optionally substituted $C_{3-6}$ cyclic alkyl, optionally substituted phenyl, optionally substituted heteroaryl, optionally substituted benzyl, optionally substituted heteroaryl methyl,

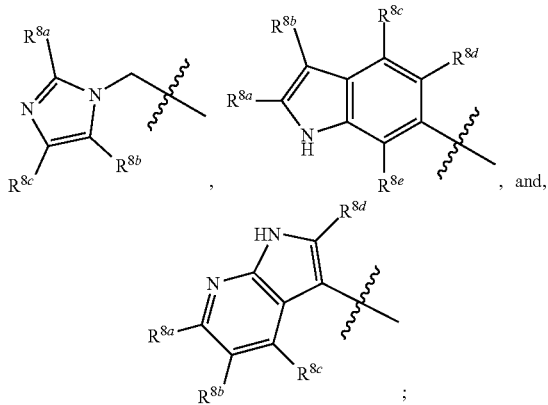

$R^2$ is selected from the group consisting of hydrogen, $NR^{10a}R^{10b}$, fluorine, optionally substituted phenyl, optionally substituted heteroaryl,

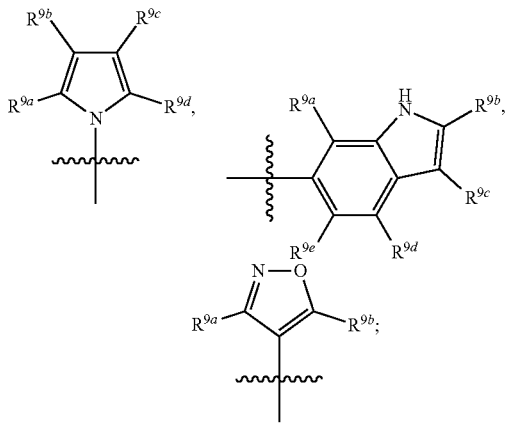

$R^3$ is selected from the group consisting of

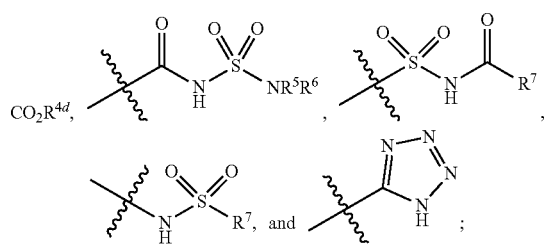

$R^{4a}$, $R^{4b}$, and $R^{4c}$ are each independently selected from the group consisting of fluorine, chlorine, bromine, iodine, and hydrogen;
$R^{4d}$ is selected from the group consisting of hydrogen, optionally substituted $C_{1-6}$ linear alkyl, and optionally substituted $C_{3-6}$ branched alkyl;
$R^5$ is selected from the group consisting of hydrogen, optionally substituted $C_{1-6}$ linear alkyl, and optionally substituted $C_{3-6}$ branched alkyl;
$R^6$ is selected from the group consisting of hydrogen, optionally substituted $C_{1-6}$ linear alkyl, and optionally substituted $C_{3-6}$ branched alkyl;
$R^7$ is selected from the group consisting of hydrogen, optionally substituted $C_{1-6}$ linear alkyl, and optionally substituted $C_{3-6}$ branched alkyl;
$R^{8a}$, $R^{8b}$, $R^{8c}$, $R^{8d}$, and $R^{8e}$ are each independently selected from the group consisting of hydrogen, optionally substituted $C_{1-6}$ linear alkyl, and optionally substituted $C_{3-6}$ branched alkyl;
$R^{9a}$, $R^{9b}$, $R^{9c}$, $R^{9d}$, and $R^{9e}$ are each independently selected from the group consisting of hydrogen, optionally substituted $C_{1-6}$ linear alkyl, and optionally substituted $C_{3-6}$ branched alkyl;
$R^{10a}$, and $R^{10b}$ are each independently selected from the group consisting of hydrogen, optionally substituted $C_{1-6}$ linear alkyl, and optionally substituted $C_{1-6}$ branched alkyl;
$L^1$ is selected from the group consisting of

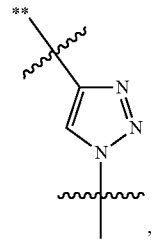

$L^2$ is selected from a group consisting of NH, $(CH_2)_m$, and

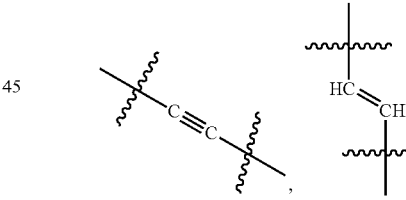

, and $(CH_2)_n$;

wherein "**" indicates the point of attachment for $R^2$;
n is 0, 1, 2, or 3; and
m is 0, 1, 2, or 3.

The compounds of the present invention include compounds having formula (II):

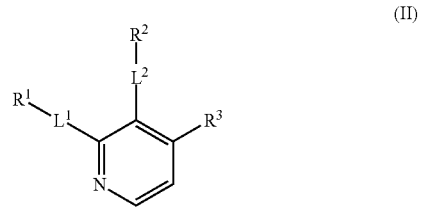

including hydrates, solvates, polymorphs, pharmaceutically acceptable salts, prodrugs, and complexes thereof. Substituents for this formula and subsequent formulas are as noted above for formula (I), unless otherwise specified.

The compounds of the present invention include compounds having formula (III):

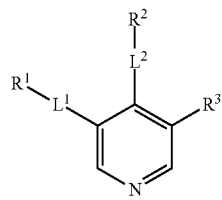

(III)

including hydrates, solvates, polymorphs, pharmaceutically acceptable salts, prodrugs, and complexes thereof.

The compounds of the present invention include compounds having formula (IV):

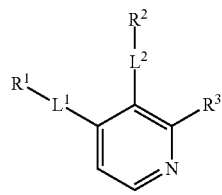

(IV)

including hydrates, solvates, polymorphs, pharmaceutically acceptable salts, prodrugs, and complexes thereof.

The compounds of the present invention include compounds having formula (V):

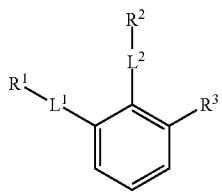

(V)

including hydrates, solvates, polymorphs, pharmaceutically acceptable salts, prodrugs, and complexes thereof.

The compounds of the present invention include compounds having formula (VI):

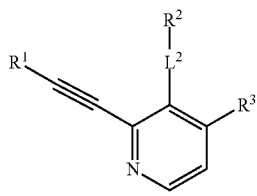

(VI)

including hydrates, solvates, polymorphs, pharmaceutically acceptable salts, prodrugs, and complexes thereof.

The compounds of the present invention include compounds having formula (VII):

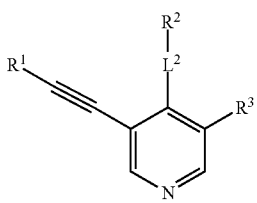

(VII)

including hydrates, solvates, polymorphs, pharmaceutically acceptable salts, prodrugs, and complexes thereof.

The compounds of the present invention include compounds having formula (VIII):

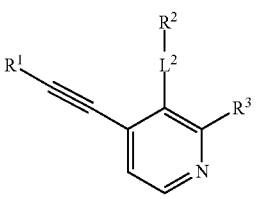

(VIII)

including hydrates, solvates, polymorphs, pharmaceutically acceptable salts, prodrugs, and complexes thereof.

The compounds of the present invention include compounds having formula (IX):

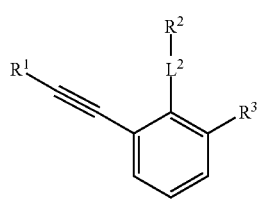

(IX)

including hydrates, solvates, polymorphs, pharmaceutically acceptable salts, prodrugs, and complexes thereof.

The compounds of the present invention include compounds having formula (X):

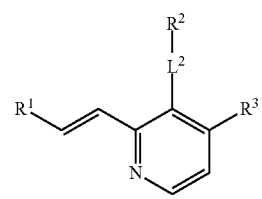

(X)

including hydrates, solvates, polymorphs, pharmaceutically acceptable salts, prodrugs, and complexes thereof.

The compounds of the present invention include compounds having formula (XI):

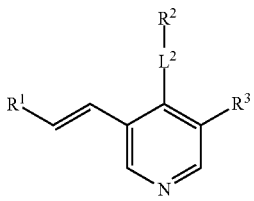

(XI)

including hydrates, solvates, polymorphs, pharmaceutically acceptable salts, prodrugs, and complexes thereof.

The compounds of the present invention include compounds having formula (XII):

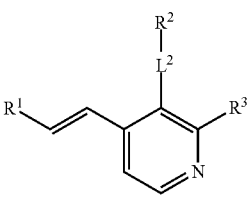

(XII)

including hydrates, solvates, polymorphs, pharmaceutically acceptable salts, prodrugs, and complexes thereof.

The compounds of the present invention include compounds having formula (XIII):

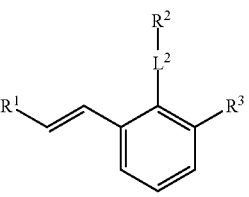

(XIII)

including hydrates, solvates, polymorphs, pharmaceutically acceptable salts, prodrugs, and complexes thereof.

The compounds of the present invention include compounds having formula (XIV):

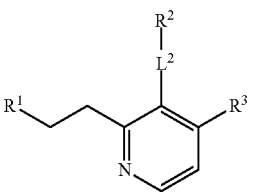

(XIV)

including hydrates, solvates, polymorphs, pharmaceutically acceptable salts, prodrugs, and complexes thereof.

The compounds of the present invention include compounds having formula (XV):

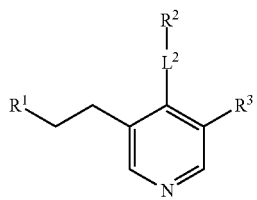

(XV)

including hydrates, solvates, polymorphs, pharmaceutically acceptable salts, prodrugs, and complexes thereof.

The compounds of the present invention include compounds having formula (XVI):

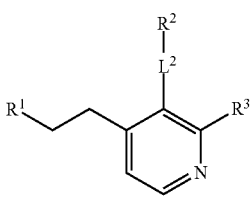

(XVI)

including hydrates, solvates, polymorphs, pharmaceutically acceptable salts, prodrugs, and complexes thereof.

The compounds of the present invention include compounds having formula (XVII):

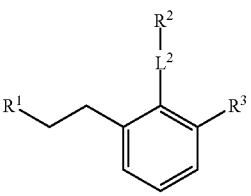

(XVII)

including hydrates, solvates, polymorphs, pharmaceutically acceptable salts, prodrugs, and complexes thereof.

In some embodiments $X^1$ is $CR^{4a}$.

In some embodiments $X^1$ is N.

In some embodiments $X^2$ is $CR^{4a}$.

In some embodiments $X^2$ is N.

In some embodiments $X^3$ is $CR^{4a}$.

In some embodiments $X^3$ is N.

In some embodiments $R^1$ is optionally substituted $C_{1-6}$ linear alkyl.

In some embodiments $R^1$ is optionally substituted $C_{3-6}$ branched alkyl.

In some embodiments $R^1$ is optionally substituted $C_{3-6}$ cyclic alkyl.

In some embodiments $R^1$ is optionally substituted heteroaryl methyl.

In some embodiments $R^1$ is optionally substituted phenyl.

In some embodiments $R^1$ is optionally substituted heteroaryl.

In some embodiments $R^1$ is optionally substituted benzyl.

In some embodiments $R^1$ is

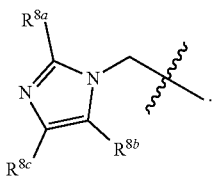

In some embodiments $R^1$ is

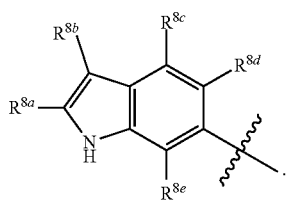

In some embodiments $R^1$ is

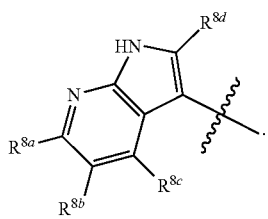

In some embodiments $R^2$ is hydrogen.
In some embodiments $R^2$ is $NR^{10a}R^{10b}$.
In some embodiments $R^2$ is fluorine.
In some embodiments $R^2$ is optionally substituted phenyl.
In some embodiments $R^2$ is optionally substituted heteroaryl.
In some embodiments $R^2$ is

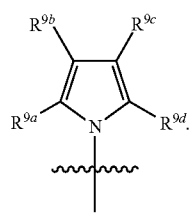

In some embodiments $R^2$ is

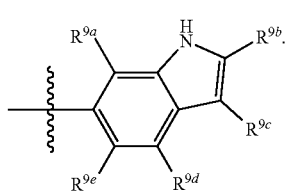

In some embodiments $R^2$ is

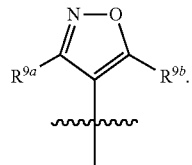

In some embodiments $R^3$ is $CO_2R^{4d}$.
In some embodiments $R^3$ is

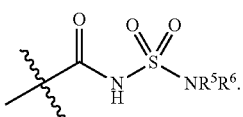

In some embodiments $R^3$ is

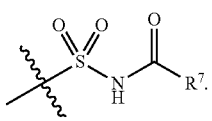

In some embodiments $R^3$ is

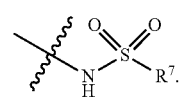

In some embodiments $R^3$ is

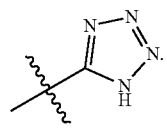 [SMILES: *c1nnn[nH]1]

In some embodiments $R^{4a}$ is fluorine.
In some embodiments $R^{4a}$ is chlorine.
In some embodiments $R^{4a}$ is bromine.
In some embodiments $R^{4a}$ is iodine.
In some embodiments $R^{4a}$ is hydrogen.
In some embodiments $R^{4b}$ is fluorine.
In some embodiments $R^{4b}$ is chlorine.
In some embodiments $R^{4b}$ is bromine.
In some embodiments $R^{4b}$ is iodine.
In some embodiments $R^{4b}$ is hydrogen.
In some embodiments $R^{4c}$ is fluorine.
In some embodiments $R^{4c}$ is chlorine.
In some embodiments $R^{4c}$ is bromine.
In some embodiments $R^{4c}$ is iodine.
In some embodiments $R^{4c}$ is hydrogen.
In some embodiments $R^{4d}$ is hydrogen.
In some embodiments $R^{4d}$ is optionally substituted $C_{1-6}$ linear alkyl.
In some embodiments $R^{4d}$ is optionally substituted $C_{3-6}$ branched alkyl.
In some embodiments $R^5$ is hydrogen.

In some embodiments $R^5$ is optionally substituted $C_{1-6}$ linear alkyl.
In some embodiments $R^5$ is optionally substituted $C_{3-6}$ branched alkyl.
In some embodiments $R^6$ is hydrogen.
In some embodiments $R^6$ is optionally substituted $C_{1-6}$ linear alkyl.
In some embodiments $R^6$ is optionally substituted $C_{3-6}$ branched alkyl.
In some embodiments $R^7$ is hydrogen.
In some embodiments $R^7$ is optionally substituted $C_{1-6}$ linear alkyl.
In some embodiments $R^7$ is optionally substituted $C_{3-6}$ branched alkyl.
In some embodiments $R^{8a}$ is hydrogen.
In some embodiments $R^{8a}$ is optionally substituted $C_{1-6}$ linear alkyl.
In some embodiments $R^{8a}$ is optionally substituted $C_{3-6}$ branched alkyl.
In some embodiments $R^{8b}$ is hydrogen.
In some embodiments $R^{8b}$ is optionally substituted $C_{1-6}$ linear alkyl.
In some embodiments $R^{8b}$ is optionally substituted $C_{3-6}$ branched alkyl.
In some embodiments $R^{8c}$ is hydrogen.
In some embodiments $R^{8c}$ is optionally substituted $C_{1-6}$ linear alkyl.
In some embodiments $R^{8c}$ is optionally substituted $C_{3-6}$ branched alkyl.
In some embodiments $R^{8d}$ is hydrogen.
In some embodiments $R^{8d}$ is optionally substituted $C_{1-6}$ linear alkyl.
In some embodiments $R^{8d}$ is optionally substituted $C_{3-6}$ branched alkyl.
In some embodiments $R^{9a}$ is hydrogen.
In some embodiments $R^{9a}$ is optionally substituted $C_{1-6}$ linear alkyl.
In some embodiments $R^{9a}$ is optionally substituted $C_{3-6}$ branched alkyl.
In some embodiments $R^{9b}$ is hydrogen.
In some embodiments $R^{9b}$ is optionally substituted $C_{1-6}$ linear alkyl.
In some embodiments $R^{9b}$ is optionally substituted $C_{3-6}$ branched alkyl.
In some embodiments $R^{9c}$ is hydrogen.
In some embodiments $R^{9c}$ is optionally substituted $C_{1-6}$ linear alkyl.
In some embodiments $R^{9c}$ is optionally substituted $C_{3-6}$ branched alkyl.
In some embodiments $R^{9d}$ is hydrogen.
In some embodiments $R^{9d}$ is optionally substituted $C_{1-6}$ linear alkyl.
In some embodiments $R^{9d}$ is optionally substituted $C_{3-6}$ branched alkyl.
In some embodiments $R^{10a}$ is hydrogen.
In some embodiments $R^{10a}$ is optionally substituted $C_{1-6}$ linear alkyl.
In some embodiments $R^{10a}$ is optionally substituted $C_{3-6}$ branched alkyl.
In some embodiments $R^{10b}$ is hydrogen.
In some embodiments $R^{10b}$ is optionally substituted $C_{1-6}$ linear alkyl.
In some embodiments $R^{10b}$ is optionally substituted $C_{3-6}$ branched alkyl.

In some embodiments $L^1$ is

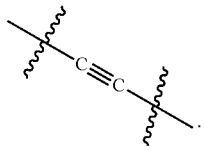 [SMILES: *C#C*]

In some embodiments $L^1$ is

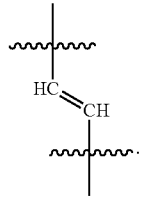

In some embodiments $L^1$ is $(CH_2)_n$.
In some embodiments $L^2$ is NH.
In some embodiments $L^2$ is $(CH_2)_m$.
In some embodiments $L^2$ is

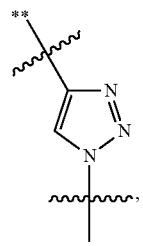

wherein "**" indicates the point of attachment for $R^2$.
In some embodiments m is 0.
In some embodiments m is 1.
In some embodiments m is 2.
In some embodiments m is 3.
In some embodiments n is 0.
In some embodiments n is 1.
In some embodiments n is 2.
In some embodiments n is 3.

Exemplary embodiments include compounds having the formula (XVIII) or a pharmaceutically acceptable salt form thereof:

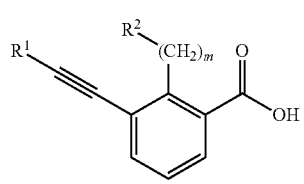

(XVIII)

wherein non-limiting examples of $R^1$, $R^2$, and m are defined herein below in Table 1.

TABLE 1

| Entry | R¹ | R² | m |
|---|---|---|---|
| 1 | phenyl | N-pyrrolyl | 0 |
| 2 | 2-fluorophenyl | N-pyrrolyl | 0 |
| 3 | 3-fluorophenyl | N-pyrrolyl | 0 |
| 4 | 4-fluorophenyl | N-pyrrolyl | 0 |
| 5 | 2,3-difluorophenyl | N-pyrrolyl | 0 |
| 6 | 2,4-difluorophenyl | N-pyrrolyl | 0 |
| 7 | 3,4-difluorophenyl | N-pyrrolyl | 0 |
| 8 | 3,5-difluorophenyl | N-pyrrolyl | 0 |
| 9 | 2,6-difluorophenyl | N-pyrrolyl | 0 |
| 10 | 2,4,6-trifluorophenyl | N-pyrrolyl | 0 |
| 11 | 2-chlorophenyl | N-pyrrolyl | 0 |
| 12 | 3-chlorophenyl | N-pyrrolyl | 0 |
| 13 | 4-chlorophenyl | N-pyrrolyl | 0 |
| 14 | 2,3-dichlorophenyl | N-pyrrolyl | 0 |
| 15 | 2,4-dichlorophenyl | N-pyrrolyl | 0 |
| 16 | 3,4-dichlorophenyl | N-pyrrolyl | 0 |
| 17 | 3,5-dichlorophenyl | N-pyrrolyl | 0 |
| 18 | 2,6-dichlorophenyl | N-pyrrolyl | 0 |
| 19 | 3-chloro-5-fluorophenyl | N-pyrrolyl | 0 |
| 20 | 2-hydroxyphenyl | N-pyrrolyl | 0 |
| 21 | 3-hydroxyphenyl | N-pyrrolyl | 0 |
| 22 | 4-hydroxyphenyl | N-pyrrolyl | 0 |
| 23 | 3-fluoro-4-hydroxyphenyl | N-pyrrolyl | 0 |
| 24 | 3-fluoro-5-hydroxyphenyl | N-pyrrolyl | 0 |
| 25 | 3-chloro-4-hydroxyphenyl | N-pyrrolyl | 0 |
| 26 | 3-chloro-5-hydroxyphenyl | N-pyrrolyl | 0 |
| 27 | 2-methoxyphenyl | N-pyrrolyl | 0 |
| 28 | 3-methoxyphenyl | N-pyrrolyl | 0 |
| 29 | 4-methoxyphenyl | N-pyrrolyl | 0 |
| 30 | 2-methoxy-4-fluorophenyl | N-pyrrolyl | 0 |
| 31 | 2-methoxy-5-fluorophenyl | N-pyrrolyl | 0 |
| 32 | 3-methoxy-5-fluorophenyl | N-pyrrolyl | 0 |
| 33 | 2-methoxy-4-chlorophenyl | N-pyrrolyl | 0 |
| 34 | 2-methoxy-5-chlorophenyl | N-pyrrolyl | 0 |
| 35 | 3-methoxy-5-chlorophenyl | N-pyrrolyl | 0 |
| 36 | 3-hydroxy-5-methoxyphenyl | N-pyrrolyl | 0 |
| 37 | 3-carboxamidophenyl | N-pyrrolyl | 0 |
| 38 | 3-carboxamido-4-fluorophenyl | N-pyrrolyl | 0 |
| 39 | 3-carboxamido-5-fluorophenyl | N-pyrrolyl | 0 |
| 40 | 3-carboxamido-4-hydroxyphenyl | N-pyrrolyl | 0 |
| 41 | 3-carboxamido-5-hydroxyphenyl | N-pyrrolyl | 0 |
| 42 | 3-carboxamido-4-methoxyphenyl | N-pyrrolyl | 0 |
| 43 | 3-carboxamido-5-methoxyphenyl | N-pyrrolyl | 0 |
| 44 | 4-carboxamidophenyl | N-pyrrolyl | 0 |
| 45 | 3-fluoro-4-carboxamidephenyl | N-pyrrolyl | 0 |
| 46 | 3-chloro-4-carboxamidephenyl | N-pyrrolyl | 0 |
| 47 | 3-hydroxy-4-carboxamidephenyl | N-pyrrolyl | 0 |
| 48 | 3-methoxy-4-carboxamidephenyl | N-pyrrolyl | 0 |
| 49 | 2-trifluoromethylphenyl | N-pyrrolyl | 0 |
| 50 | 3-trifluoromethylphenyl | N-pyrrolyl | 0 |
| 51 | 4-trifluoromethylphenyl | N-pyrrolyl | 0 |
| 52 | 2-trifluoromethoxyphenyl | N-pyrrolyl | 0 |
| 53 | 3-trifluoromethoxyphenyl | N-pyrrolyl | 0 |
| 54 | 4-trifluoromethoxyphenyl | N-pyrrolyl | 0 |
| 55 | 2-difluoromethoxyphenyl | N-pyrrolyl | 0 |
| 56 | 3-difluoromethoxyphenyl | N-pyrrolyl | 0 |
| 57 | 4-difluoromethoxyphenyl | N-pyrrolyl | 0 |
| 58 | 2-methylphenyl | N-pyrrolyl | 0 |
| 59 | 3-methylphenyl | N-pyrrolyl | 0 |
| 60 | 4-methylphenyl | N-pyrrolyl | 0 |
| 61 | 2,4-dimethylphenyl | N-pyrrolyl | 0 |
| 62 | 3,4-dimethylphenyl | N-pyrrolyl | 0 |
| 63 | 3,5-dimethylphenyl | N-pyrrolyl | 0 |
| 64 | 2-hydroxymethylphenyl | N-pyrrolyl | 0 |
| 65 | 3-hydroxymethylphenyl | N-pyrrolyl | 0 |
| 66 | 3-(2-hydroxyprop-2-yl)phenyl | N-pyrrolyl | 0 |
| 67 | 4-hydroxymethylphenyl | N-pyrrolyl | 0 |
| 68 | 2-carboxyphenyl | N-pyrrolyl | 0 |
| 69 | 3-carboxyphenyl | N-pyrrolyl | 0 |
| 70 | 4-carboxyphenyl | N-pyrrolyl | 0 |
| 71 | 3-aminomethylphenyl | N-pyrrolyl | 0 |
| 72 | 4-aminomethylphenyl | N-pyrrolyl | 0 |
| 73 | 3-cyclopropanesulfonamido-methylphenyl | N-pyrrolyl | 0 |
| 74 | 3-benzenesulfonamidomethyl | N-pyrrolyl | 0 |
| 75 | 3-(3,5-difluoro-benzenesulfonamidomethyl)phenyl | N-pyrrolyl | 0 |
| 76 | 4-cyclopropanesulfonamido-methylphenyl | N-pyrrolyl | 0 |
| 77 | 4-benzenesulfonamido-methylphenyl | N-pyrrolyl | 0 |
| 78 | 4-(3,5-difluoro-benzenesulfonamidomethyl)phenyl | N-pyrrolyl | 0 |
| 79 | 4-(1,2-dimethyl-1H-imidazole-5-sulfonamidomethyl)phenyl | N-pyrrolyl | 0 |
| 80 | 3-dimethylsulfamoylphenyl | N-pyrrolyl | 0 |
| 81 | 3-methylsulfamoylphenyl | N-pyrrolyl | 0 |
| 82 | 3-sulfamoylphenyl | N-pyrrolyl | 0 |
| 83 | 3-methanesulfonamidophenyl | N-pyrrolyl | 0 |
| 84 | 4-dimethylsulfamoylphenyl | N-pyrrolyl | 0 |
| 85 | 4-methylsulfamoylphenyl | N-pyrrolyl | 0 |
| 86 | 4-sulfamoylphenyl | N-pyrrolyl | 0 |
| 87 | 4-methanesulfonamidophenyl | N-pyrrolyl | 0 |
| 88 | 3-(3,3-dimethyl-2-oxoazetidin-1-yl)phenyl | N-pyrrolyl | 0 |
| 89 | 3-[(2-carboxy-2,2-dimethylethy)amino]phenyl | N-pyrrolyl | 0 |
| 90 | 4-acetylamidophenyl | N-pyrrolyl | 0 |
| 91 | 3-acetylamidophenyl | N-pyrrolyl | 0 |
| 92 | phenyl | 1H-indol-5-yl | 0 |
| 93 | 2-fluorophenyl | 1H-indol-5-yl | 0 |
| 94 | 3-fluorophenyl | 1H-indol-5-yl | 0 |
| 95 | 4-fluorophenyl | 1H-indol-5-yl | 0 |
| 96 | 2,3-difluorophenyl | 1H-indol-5-yl | 0 |
| 97 | 2,4-difluorophenyl | 1H-indol-5-yl | 0 |
| 98 | 3,4-difluorophenyl | 1H-indol-5-yl | 0 |
| 99 | 3,5-difluorophenyl | 1H-indol-5-yl | 0 |
| 100 | 2,6-difluorophenyl | 1H-indol-5-yl | 0 |
| 101 | 2,4,6-trifluorophenyl | 1H-indol-5-yl | 0 |
| 102 | 2-chlorophenyl | 1H-indol-5-yl | 0 |
| 103 | 3-chlorophenyl | 1H-indol-5-yl | 0 |
| 104 | 4-chlorophenyl | 1H-indol-5-yl | 0 |
| 105 | 2,3-dichlorophenyl | 1H-indol-5-yl | 0 |
| 106 | 2,4-dichlorophenyl | 1H-indol-5-yl | 0 |
| 107 | 3,4-dichlorophenyl | 1H-indol-5-yl | 0 |
| 108 | 3,5-dichlorophenyl | 1H-indol-5-yl | 0 |
| 109 | 2,6-dichlorophenyl | 1H-indol-5-yl | 0 |
| 110 | 3-chloro-5-fluorophenyl | 1H-indol-5-yl | 0 |
| 111 | 2-hydroxyphenyl | 1H-indol-5-yl | 0 |
| 112 | 3-hydroxyphenyl | 1H-indol-5-yl | 0 |
| 113 | 4-hydroxyphenyl | 1H-indol-5-yl | 0 |
| 114 | 3-fluoro-4-hydroxyphenyl | 1H-indol-5-yl | 0 |
| 115 | 3-fluoro-5-hydroxyphenyl | 1H-indol-5-yl | 0 |
| 116 | 3-chloro-4-hydroxyphenyl | 1H-indol-5-yl | 0 |
| 117 | 3-chloro-5-hydroxyphenyl | 1H-indol-5-yl | 0 |
| 118 | 2-methoxyphenyl | 1H-indol-5-yl | 0 |
| 119 | 3-methoxyphenyl | 1H-indol-5-yl | 0 |
| 120 | 4-methoxyphenyl | 1H-indol-5-yl | 0 |
| 121 | 2-methoxy-4-fluorophenyl | 1H-indol-5-yl | 0 |
| 122 | 2-methoxy-5-fluorophenyl | 1H-indol-5-yl | 0 |
| 123 | 3-methoxy-5-fluorophenyl | 1H-indol-5-yl | 0 |
| 124 | 2-methoxy-4-chlorophenyl | 1H-indol-5-yl | 0 |
| 125 | 2-methoxy-5-chlorophenyl | 1H-indol-5-yl | 0 |
| 126 | 3-methoxy-5-chlorophenyl | 1H-indol-5-yl | 0 |
| 127 | 3-hydroxy-5-methoxyphenyl | 1H-indol-5-yl | 0 |
| 128 | 3-carboxamidophenyl | 1H-indol-5-yl | 0 |
| 129 | 3-carboxamido-4-fluorophenyl | 1H-indol-5-yl | 0 |
| 130 | 3-carboxamido-5-fluorophenyl | 1H-indol-5-yl | 0 |
| 131 | 3-carboxamido-4-hydroxyphenyl | 1H-indol-5-yl | 0 |
| 132 | 3-carboxamido-5-hydroxyphenyl | 1H-indol-5-yl | 0 |
| 133 | 3-carboxamido-4-methoxyphenyl | 1H-indol-5-yl | 0 |
| 134 | 3-carboxamido-5-methoxyphenyl | 1H-indol-5-yl | 0 |
| 135 | 4-carboxamidophenyl | 1H-indol-5-yl | 0 |
| 136 | 3-fluoro-4-carboxamidephenyl | 1H-indol-5-yl | 0 |
| 137 | 3-chloro-4-carboxamidephenyl | 1H-indol-5-yl | 0 |
| 138 | 3-hydroxy-4-carboxamidephenyl | 1H-indol-5-yl | 0 |
| 139 | 3-methoxy-4-carboxamidephenyl | 1H-indol-5-yl | 0 |
| 140 | 2-trifluoromethylphenyl | 1H-indol-5-yl | 0 |
| 141 | 3-trifluoromethylphenyl | 1H-indol-5-yl | 0 |
| 142 | 4-trifluoromethylphenyl | 1H-indol-5-yl | 0 |

TABLE 1-continued

| Entry | R¹ | R² | m |
|---|---|---|---|
| 143 | 2-trifluoromethoxyphenyl | 1H-indol-5-yl | 0 |
| 144 | 3-trifluoromethoxyphenyl | 1H-indol-5-yl | 0 |
| 145 | 4-trifluoromethoxyphenyl | 1H-indol-5-yl | 0 |
| 146 | 2-difluoromethoxyphenyl | 1H-indol-5-yl | 0 |
| 147 | 3-difluoromethoxyphenyl | 1H-indol-5-yl | 0 |
| 148 | 4-difluoromethoxyphenyl | 1H-indol-5-yl | 0 |
| 149 | 2-methylphenyl | 1H-indol-5-yl | 0 |
| 150 | 3-methylphenyl | 1H-indol-5-yl | 0 |
| 151 | 4-methylphenyl | 1H-indol-5-yl | 0 |
| 152 | 2,4-dimethylphenyl | 1H-indol-5-yl | 0 |
| 153 | 3,4-dimethylphenyl | 1H-indol-5-yl | 0 |
| 154 | 3,5-dimethylphenyl | 1H-indol-5-yl | 0 |
| 155 | 2-hydroxymethylphenyl | 1H-indol-5-yl | 0 |
| 156 | 3-hydroxymethylphenyl | 1H-indol-5-yl | 0 |
| 157 | 3-(2-hydroxyprop-2-yl)phenyl | 1H-indol-5-yl | 0 |
| 158 | 4-hydroxymethylphenyl | 1H-indol-5-yl | 0 |
| 159 | 2-carboxyphenyl | 1H-indol-5-yl | 0 |
| 160 | 3-carboxyphenyl | 1H-indol-5-yl | 0 |
| 161 | 4-carboxyphenyl | 1H-indol-5-yl | 0 |
| 162 | 3-aminomethylphenyl | 1H-indol-5-yl | 0 |
| 163 | 4-aminomethylphenyl | 1H-indol-5-yl | 0 |
| 164 | 3-cyclopropanesulfonamido-methylphenyl | 1H-indol-5-yl | 0 |
| 165 | 3-benzenesulfonamido-methylphenyl | 1H-indol-5-yl | 0 |
| 166 | 3-(3,5-difluoro-benzenesulfon-amidomethyl)phenyl | 1H-indol-5-yl | 0 |
| 167 | 4-cyclopropanesulfonamido-methylphenyl | 1H-indol-5-yl | 0 |
| 168 | 4-benzenesulfonamido-methylphenyl | 1H-indol-5-yl | 0 |
| 169 | 4-(3,5-difluoro-benzenesulfon-amidomethyl)phenyl | 1H-indol-5-yl | 0 |
| 170 | 4-(1,2-dimethyl-1H-imidazole-5-sulfonamidomethyl)phenyl | 1H-indol-5-yl | 0 |
| 171 | 3-dimethylsulfamoylphenyl | 1H-indol-5-yl | 0 |
| 172 | 3-methylsulfamoylphenyl | 1H-indol-5-yl | 0 |
| 173 | 3-sulfamoylphenyl | 1H-indol-5-yl | 0 |
| 174 | 3-methanesulfonamidophenyl | 1H-indol-5-yl | 0 |
| 175 | 4-dimethylsulfamoylphenyl | 1H-indol-5-yl | 0 |
| 176 | 4-methylsulfamoylphenyl | 1H-indol-5-yl | 0 |
| 177 | 4-sulfamoylphenyl | 1H-indol-5-yl | 0 |
| 178 | 4-methanesulfonamidophenyl | 1H-indol-5-yl | 0 |
| 179 | 3-(3,3-dimethyl-2-oxoazetidin-1-yl)phenyl | 1H-indol-5-yl | 0 |
| 180 | 3-[(2-carboxy-2,2-dimethylethy)amino]phenyl | 1H-indol-5-yl | 0 |
| 181 | 4-acetylamidophenyl | 1H-indol-5-yl | 0 |
| 182 | 3-acetylamidophenyl | 1H-indol-5-yl | 0 |
| 183 | phenyl | 3-hydroxyphenyl | 0 |
| 184 | 2-fluorophenyl | 3-hydroxyphenyl | 0 |
| 185 | 3-fluorophenyl | 3-hydroxyphenyl | 0 |
| 186 | 4-fluorophenyl | 3-hydroxyphenyl | 0 |
| 187 | 2,3-difluorophenyl | 3-hydroxyphenyl | 0 |
| 188 | 2,4-difluorophenyl | 3-hydroxyphenyl | 0 |
| 189 | 3,4-difluorophenyl | 3-hydroxyphenyl | 0 |
| 190 | 3,5-difluorophenyl | 3-hydroxyphenyl | 0 |
| 191 | 2,6-difluorophenyl | 3-hydroxyphenyl | 0 |
| 192 | 2,4,6-trifluorophenyl | 3-hydroxyphenyl | 0 |
| 193 | 2-chlorophenyl | 3-hydroxyphenyl | 0 |
| 194 | 3-chlorophenyl | 3-hydroxyphenyl | 0 |
| 195 | 4-chlorophenyl | 3-hydroxyphenyl | 0 |
| 196 | 2,3-dichlorophenyl | 3-hydroxyphenyl | 0 |
| 197 | 2,4-dichlorophenyl | 3-hydroxyphenyl | 0 |
| 198 | 3,4-dichlorophenyl | 3-hydroxyphenyl | 0 |
| 199 | 3,5-dichlorophenyl | 3-hydroxyphenyl | 0 |
| 200 | 2,6-dichlorophenyl | 3-hydroxyphenyl | 0 |
| 201 | 3-chloro-5-fluorophenyl | 3-hydroxyphenyl | 0 |
| 202 | 2-hydroxyphenyl | 3-hydroxyphenyl | 0 |
| 203 | 3-hydroxyphenyl | 3-hydroxyphenyl | 0 |
| 204 | 4-hydroxyphenyl | 3-hydroxyphenyl | 0 |
| 205 | 3-fluoro-4-hydroxyphenyl | 3-hydroxyphenyl | 0 |
| 206 | 3-fluoro-5-hydroxyphenyl | 3-hydroxyphenyl | 0 |
| 207 | 3-chloro-4-hydroxyphenyl | 3-hydroxyphenyl | 0 |
| 208 | 3-chloro-5-hydroxyphenyl | 3-hydroxyphenyl | 0 |
| 209 | 2-methoxyphenyl | 3-hydroxyphenyl | 0 |
| 210 | 3-methoxyphenyl | 3-hydroxyphenyl | 0 |
| 211 | 4-methoxyphenyl | 3-hydroxyphenyl | 0 |
| 212 | 2-methoxy-4-fluorophenyl | 3-hydroxyphenyl | 0 |
| 213 | 2-methoxy-5-fluorophenyl | 3-hydroxyphenyl | 0 |
| 214 | 3-methoxy-5-fluorophenyl | 3-hydroxyphenyl | 0 |
| 215 | 2-methoxy-4-chlorophenyl | 3-hydroxyphenyl | 0 |
| 216 | 2-methoxy-5-chlorophenyl | 3-hydroxyphenyl | 0 |
| 217 | 3-methoxy-5-chlorophenyl | 3-hydroxyphenyl | 0 |
| 218 | 3-hydroxy-5-methoxyphenyl | 3-hydroxyphenyl | 0 |
| 219 | 3-carboxamidophenyl | 3-hydroxyphenyl | 0 |
| 220 | 3-carboxamido-4-fluorophenyl | 3-hydroxyphenyl | 0 |
| 221 | 3-carboxamido-5-fluorophenyl | 3-hydroxyphenyl | 0 |
| 222 | 3-carboxamido-4-hydroxyphenyl | 3-hydroxyphenyl | 0 |
| 223 | 3-carboxamido-5-hydroxyphenyl | 3-hydroxyphenyl | 0 |
| 224 | 3-carboxamido-4-methoxyphenyl | 3-hydroxyphenyl | 0 |
| 225 | 3-carboxamido-5-methoxyphenyl | 3-hydroxyphenyl | 0 |
| 226 | 4-carboxamidophenyl | 3-hydroxyphenyl | 0 |
| 227 | 3-fluoro-4-carboxamidephenyl | 3-hydroxyphenyl | 0 |
| 228 | 3-chloro-4-carboxamidephenyl | 3-hydroxyphenyl | 0 |
| 229 | 3-hydroxy-4-carboxamidephenyl | 3-hydroxyphenyl | 0 |
| 230 | 3-methoxy-4-carboxamidephenyl | 3-hydroxyphenyl | 0 |
| 231 | 2-trifluoromethylphenyl | 3-hydroxyphenyl | 0 |
| 232 | 3-trifluoromethylphenyl | 3-hydroxyphenyl | 0 |
| 233 | 4-trifluoromethylphenyl | 3-hydroxyphenyl | 0 |
| 234 | 2-trifluoromethoxyphenyl | 3-hydroxyphenyl | 0 |
| 235 | 3-trifluoromethoxyphenyl | 3-hydroxyphenyl | 0 |
| 236 | 4-trifluoromethoxyphenyl | 3-hydroxyphenyl | 0 |
| 237 | 2-difluoromethoxyphenyl | 3-hydroxyphenyl | 0 |
| 238 | 3-difluoromethoxyphenyl | 3-hydroxyphenyl | 0 |
| 239 | 4-difluoromethoxyphenyl | 3-hydroxyphenyl | 0 |
| 240 | 2-methylphenyl | 3-hydroxyphenyl | 0 |
| 241 | 3-methylphenyl | 3-hydroxyphenyl | 0 |
| 242 | 4-methylphenyl | 3-hydroxyphenyl | 0 |
| 243 | 2,4-dimethylphenyl | 3-hydroxyphenyl | 0 |
| 244 | 3,4-dimethylphenyl | 3-hydroxyphenyl | 0 |
| 245 | 3,5-dimethylphenyl | 3-hydroxyphenyl | 0 |
| 246 | 2-hydroxymethylphenyl | 3-hydroxyphenyl | 0 |
| 247 | 3-hydroxymethylphenyl | 3-hydroxyphenyl | 0 |
| 248 | 3-(2-hydroxyprop-2-yl)phenyl | 3-hydroxyphenyl | 0 |
| 249 | 4-hydroxymethylphenyl | 3-hydroxyphenyl | 0 |
| 250 | 2-carboxyphenyl | 3-hydroxyphenyl | 0 |
| 251 | 3-carboxyphenyl | 3-hydroxyphenyl | 0 |
| 252 | 4-carboxyphenyl | 3-hydroxyphenyl | 0 |
| 253 | 3-aminomethylphenyl | 3-hydroxyphenyl | 0 |
| 254 | 4-aminomethylphenyl | 3-hydroxyphenyl | 0 |
| 255 | 3-cyclopropanesulfonamido-methylphenyl | 3-hydroxyphenyl | 0 |
| 256 | 3-benzenesulfon-amidomethylphenyl | 3-hydroxyphenyl | 0 |
| 257 | 3-(3,5-difluoro-benzenesulfon-amidomethyl)phenyl | 3-hydroxyphenyl | 0 |
| 258 | 4-cyclopropanesulfon-amidomethylphenyl | 3-hydroxyphenyl | 0 |
| 259 | 4-benzenesulfon-amidomethylphenyl | 3-hydroxyphenyl | 0 |
| 260 | 4-(3,5-difluoro-benzenesulfon-amidomethyl)phenyl | 3-hydroxyphenyl | 0 |
| 261 | 4-(1,2-dimethyl-1H-imidazole-5-sulfonamidomethyl)phenyl | 3-hydroxyphenyl | 0 |
| 262 | 3-dimethylsulfamoylphenyl | 3-hydroxyphenyl | 0 |
| 263 | 3-methylsulfamoylphenyl | 3-hydroxyphenyl | 0 |
| 264 | 3-sulfamoylphenyl | 3-hydroxyphenyl | 0 |
| 265 | 3-methanesulfonamidophenyl | 3-hydroxyphenyl | 0 |
| 266 | 4-dimethylsulfamoylphenyl | 3-hydroxyphenyl | 0 |
| 267 | 4-methylsulfamoylphenyl | 3-hydroxyphenyl | 0 |
| 268 | 4-sulfamoylphenyl | 3-hydroxyphenyl | 0 |
| 269 | 4-methanesulfonamidophenyl | 3-hydroxyphenyl | 0 |
| 270 | 3-(3,3-dimethyl-2-oxoazetidin-1-yl)phenyl | 3-hydroxyphenyl | 0 |
| 271 | 3-[(2-carboxy-2,2-dimethylethy)amino]phenyl | 3-hydroxyphenyl | 0 |
| 272 | 4-acetylamidophenyl | 3-hydroxyphenyl | 0 |
| 273 | 3-acetylamidophenyl | 3-hydroxyphenyl | 0 |
| 274 | phenyl | F | 0 |

TABLE 1-continued

| Entry | R¹ | R² | m |
|---|---|---|---|
| 275 | 2-fluorophenyl | F | 0 |
| 276 | 3-fluorophenyl | F | 0 |
| 277 | 4-fluorophenyl | F | 0 |
| 278 | 2,3-difluorophenyl | F | 0 |
| 279 | 2,4-difluorophenyl | F | 0 |
| 280 | 3,4-difluorophenyl | F | 0 |
| 281 | 3,5-difluorophenyl | F | 0 |
| 282 | 2,6-difluorophenyl | F | 0 |
| 283 | 2,4,6-trifluorophenyl | F | 0 |
| 284 | 2-chlorophenyl | F | 0 |
| 285 | 3-chlorophenyl | F | 0 |
| 286 | 4-chlorophenyl | F | 0 |
| 287 | 2,3-dichlorophenyl | F | 0 |
| 288 | 2,4-dichlorophenyl | F | 0 |
| 289 | 3,4-dichlorophenyl | F | 0 |
| 290 | 3,5-dichlorophenyl | F | 0 |
| 291 | 2,6-dichlorophenyl | F | 0 |
| 292 | 3-chloro-5-fluorophenyl | F | 0 |
| 293 | 2-hydroxyphenyl | F | 0 |
| 294 | 3-hydroxyphenyl | F | 0 |
| 295 | 4-hydroxyphenyl | F | 0 |
| 296 | 3-fluoro-4-hydroxyphenyl | F | 0 |
| 297 | 3-fluoro-5-hydroxyphenyl | F | 0 |
| 298 | 3-chloro-4-hydroxyphenyl | F | 0 |
| 299 | 3-chloro-5-hydroxyphenyl | F | 0 |
| 300 | 2-methoxyphenyl | F | 0 |
| 301 | 3-methoxyphenyl | F | 0 |
| 302 | 4-methoxyphenyl | F | 0 |
| 303 | 2-methoxy-4-fluorophenyl | F | 0 |
| 304 | 2-methoxy-5-fluorophenyl | F | 0 |
| 305 | 3-methoxy-5-fluorophenyl | F | 0 |
| 306 | 2-methoxy-4-chlorophenyl | F | 0 |
| 307 | 2-methoxy-5-chlorophenyl | F | 0 |
| 308 | 3-methoxy-5-chlorophenyl | F | 0 |
| 309 | 3-hydroxy-5-methoxyphenyl | F | 0 |
| 310 | 3-carboxamidophenyl | F | 0 |
| 311 | 3-carboxamido-4-fluorophenyl | F | 0 |
| 312 | 3-carboxamido-5-fluorophenyl | F | 0 |
| 313 | 3-carboxamido-4-hydroxyphenyl | F | 0 |
| 314 | 3-carboxamido-5-hydroxyphenyl | F | 0 |
| 315 | 3-carboxamido-4-methoxyphenyl | F | 0 |
| 316 | 3-carboxamido-5-methoxyphenyl | F | 0 |
| 317 | 4-carboxamidophenyl | F | 0 |
| 318 | 3-fluoro-4-carboxamidephenyl | F | 0 |
| 319 | 3-chloro-4-carboxamidephenyl | F | 0 |
| 320 | 3-hydroxy-4-carboxamidephenyl | F | 0 |
| 321 | 3-methoxy-4-carboxamidephenyl | F | 0 |
| 322 | 2-trifluoromethylphenyl | F | 0 |
| 323 | 3-trifluoromethylphenyl | F | 0 |
| 324 | 4-trifluoromethylphenyl | F | 0 |
| 325 | 2-trifluoromethoxyphenyl | F | 0 |
| 326 | 3-trifluoromethoxyphenyl | F | 0 |
| 327 | 4-trifluoromethoxyphenyl | F | 0 |
| 328 | 2-difluoromethoxyphenyl | F | 0 |
| 329 | 3-difluoromethoxyphenyl | F | 0 |
| 330 | 4-difluoromethoxyphenyl | F | 0 |
| 331 | 2-methylphenyl | F | 0 |
| 332 | 3-methylphenyl | F | 0 |
| 333 | 4-methylphenyl | F | 0 |
| 334 | 2,4-dimethylphenyl | F | 0 |
| 335 | 3,4-dimethylphenyl | F | 0 |
| 336 | 3,5-dimethylphenyl | F | 0 |
| 337 | 2-hydroxymethylphenyl | F | 0 |
| 338 | 3-hydroxymethylphenyl | F | 0 |
| 339 | 3-(2-hydroxyprop-2-yl)phenyl | F | 0 |
| 340 | 4-hydroxymethylphenyl | F | 0 |
| 341 | 2-carboxyphenyl | F | 0 |
| 342 | 3-carboxyphenyl | F | 0 |
| 343 | 4-carboxyphenyl | F | 0 |
| 344 | 3-aminomethylphenyl | F | 0 |
| 345 | 4-aminomethylphenyl | F | 0 |
| 346 | 3-cyclopropanesulfonamidomethylphenyl | F | 0 |
| 347 | 3-benzenesulfonamidomethyl | F | 0 |
| 348 | 3-(3,5-difluorobenzenesulfonamidomethyl)phenyl | F | 0 |
| 349 | 4-cyclopropanesulfonamidomethylphenyl | F | 0 |
| 350 | 4-benzenesulfonamidomethylphenyl | F | 0 |
| 351 | 4-(3,5-difluorobenzenesulfonamidomethyl)phenyl | F | 0 |
| 352 | 4-(1,2-dimethyl-1H-imidazole-5-sulfonamidomethyl)phenyl | F | 0 |
| 353 | 3-dimethylsulfamoylphenyl | F | 0 |
| 354 | 3-methylsulfamoylphenyl | F | 0 |
| 355 | 3-sulfamoylphenyl | F | 0 |
| 356 | 3-methanesulfonamidophenyl | F | 0 |
| 357 | 4-dimethylsulfamoylphenyl | F | 0 |
| 358 | 4-methylsulfamoylphenyl | F | 0 |
| 359 | 4-sulfamoylphenyl | F | 0 |
| 360 | 4-methanesulfonamidophenyl | F | 0 |
| 361 | 3-(3,3-dimethyl-2-oxoazetidin-1-yl)phenyl | F | 0 |
| 362 | 3-[(2-carboxy-2,2-dimethylethy)amino]phenyl | F | 0 |
| 363 | 4-acetylamidophenyl | F | 0 |
| 364 | 3-acetylamidophenyl | F | 0 |
| 365 | phenyl | NH₂ | 0 |
| 366 | 2-fluorophenyl | NH₂ | 0 |
| 367 | 3-fluorophenyl | NH₂ | 0 |
| 368 | 4-fluorophenyl | NH₂ | 0 |
| 369 | 2,3-difluorophenyl | NH₂ | 0 |
| 370 | 2,4-difluorophenyl | NH₂ | 0 |
| 371 | 3,4-difluorophenyl | NH₂ | 0 |
| 372 | 3,5-difluorophenyl | NH₂ | 0 |
| 373 | 2,6-difluorophenyl | NH₂ | 0 |
| 374 | 2,4,6-trifluorophenyl | NH₂ | 0 |
| 375 | 2-chlorophenyl | NH₂ | 0 |
| 376 | 3-chlorophenyl | NH₂ | 0 |
| 377 | 4-chlorophenyl | NH₂ | 0 |
| 378 | 2,3-dichlorophenyl | NH₂ | 0 |
| 379 | 2,4-dichlorophenyl | NH₂ | 0 |
| 380 | 3,4-dichlorophenyl | NH₂ | 0 |
| 381 | 3,5-dichlorophenyl | NH₂ | 0 |
| 382 | 2,6-dichlorophenyl | NH₂ | 0 |
| 383 | 3-chloro-5-fluorophenyl | NH₂ | 0 |
| 384 | 2-hydroxyphenyl | NH₂ | 0 |
| 385 | 3-hydroxyphenyl | NH₂ | 0 |
| 386 | 4-hydroxyphenyl | NH₂ | 0 |
| 387 | 3-fluoro-4-hydroxyphenyl | NH₂ | 0 |
| 388 | 3-fluoro-5-hydroxyphenyl | NH₂ | 0 |
| 389 | 3-chloro-4-hydroxyphenyl | NH₂ | 0 |
| 390 | 3-chloro-5-hydroxyphenyl | NH₂ | 0 |
| 391 | 2-methoxyphenyl | NH₂ | 0 |
| 392 | 3-methoxyphenyl | NH₂ | 0 |
| 393 | 4-methoxyphenyl | NH₂ | 0 |
| 394 | 2-methoxy-4-fluorophenyl | NH₂ | 0 |
| 395 | 2-methoxy-5-fluorophenyl | NH₂ | 0 |
| 396 | 3-methoxy-5-fluorophenyl | NH₂ | 0 |
| 397 | 2-methoxy-4-chlorophenyl | NH₂ | 0 |
| 398 | 2-methoxy-5-chlorophenyl | NH₂ | 0 |
| 399 | 3-methoxy-5-chlorophenyl | NH₂ | 0 |
| 400 | 3-hydroxy-5-methoxyphenyl | NH₂ | 0 |
| 401 | 3-carboxamidophenyl | NH₂ | 0 |
| 402 | 3-carboxamido-4-fluorophenyl | NH₂ | 0 |
| 403 | 3-carboxamido-5-fluorophenyl | NH₂ | 0 |
| 404 | 3-carboxamido-4-hydroxyphenyl | NH₂ | 0 |
| 405 | 3-carboxamido-5-hydroxyphenyl | NH₂ | 0 |
| 406 | 3-carboxamido-4-methoxyphenyl | NH₂ | 0 |
| 407 | 3-carboxamido-5-methoxyphenyl | NH₂ | 0 |
| 408 | 4-carboxamidophenyl | NH₂ | 0 |
| 409 | 3-fluoro-4-carboxamidephenyl | NH₂ | 0 |
| 410 | 3-chloro-4-carboxamidephenyl | NH₂ | 0 |
| 411 | 3-hydroxy-4-carboxamidephenyl | NH₂ | 0 |
| 412 | 3-methoxy-4-carboxamidephenyl | NH₂ | 0 |
| 413 | 2-trifluoromethylphenyl | NH₂ | 0 |
| 414 | 3-trifluoromethylphenyl | NH₂ | 0 |
| 415 | 4-trifluoromethylphenyl | NH₂ | 0 |
| 416 | 2-trifluoromethoxyphenyl | NH₂ | 0 |
| 417 | 3-trifluoromethoxyphenyl | NH₂ | 0 |
| 418 | 4-trifluoromethoxyphenyl | NH₂ | 0 |

TABLE 1-continued

| Entry | R¹ | R² | m |
|---|---|---|---|
| 419 | 2-difluoromethoxyphenyl | NH₂ | 0 |
| 420 | 3-difluoromethoxyphenyl | NH₂ | 0 |
| 421 | 4-difluoromethoxyphenyl | NH₂ | 0 |
| 422 | 2-methylphenyl | NH₂ | 0 |
| 423 | 3-methylphenyl | NH₂ | 0 |
| 424 | 4-methylphenyl | NH₂ | 0 |
| 425 | 2,4-dimethylphenyl | NH₂ | 0 |
| 426 | 3,4-dimethylphenyl | NH₂ | 0 |
| 427 | 3,5-dimethylphenyl | NH₂ | 0 |
| 428 | 2-hydroxymethylphenyl | NH₂ | 0 |
| 429 | 3-hydroxymethylphenyl | NH₂ | 0 |
| 430 | 3-(2-hydroxyprop-2-yl)phenyl | NH₂ | 0 |
| 431 | 4-hydroxymethylphenyl | NH₂ | 0 |
| 432 | 2-carboxyphenyl | NH₂ | 0 |
| 433 | 3-carboxyphenyl | NH₂ | 0 |
| 434 | 4-carboxyphenyl | NH₂ | 0 |
| 435 | 3-aminomethylphenyl | NH₂ | 0 |
| 436 | 4-aminomethylphenyl | NH₂ | 0 |
| 437 | 3-cyclopropanesulfonamidomethylphenyl | NH₂ | 0 |
| 438 | 3-benzenesulfonamidomethyl | NH₂ | 0 |
| 439 | 3-(3,5-difluoro-benzenesulfonamidomethyl)phenyl | NH₂ | 0 |
| 440 | 4-cyclopropanesulfonamidomethylphenyl | NH₂ | 0 |
| 441 | 4-benzenesulfonamidomethylphenyl | NH₂ | 0 |
| 442 | 4-(3,5-difluoro-benzenesulfonamidomethyl)phenyl | NH₂ | 0 |
| 443 | 4-(1,2-dimethyl-1H-imidazole-5-sulfonamidomethyl)phenyl | NH₂ | 0 |
| 444 | 3-dimethylsulfamoylphenyl | NH₂ | 0 |
| 445 | 3-methylsulfamoylphenyl | NH₂ | 0 |
| 446 | 3-sulfamoylphenyl | NH₂ | 0 |
| 447 | 3-methanesulfonamidophenyl | NH₂ | 0 |
| 448 | 4-dimethylsulfamoylphenyl | NH₂ | 0 |
| 449 | 4-methylsulfamoylphenyl | NH₂ | 0 |
| 450 | 4-sulfamoylphenyl | NH₂ | 0 |
| 451 | 4-methanesulfonamidophenyl | NH₂ | 0 |
| 452 | 3-(3,3-dimethyl-2-oxoazetidin-1-yl)phenyl | NH₂ | 0 |
| 453 | 3-[(2-carboxy-2,2-dimethylethy)amino]phenyl | NH₂ | 0 |
| 454 | 4-acetylamidophenyl | NH₂ | 0 |
| 455 | 3-acetylamidophenyl | NH₂ | 0 |
| 456 | Phenyl | 2,5-dimethylpyrrol-1-yl | 0 |
| 457 | 4-methylphenyl | 2,5-dimethylpyrrol-1-yl | 0 |
| 458 | Phenyl | 4,5-dimethyl-1,2oxazol-4-yl | 0 |
| 459 | Phenyl | 1H-pyrazol-4-yl | 0 |
| 460 | Phenyl | 1-methyl-1H-pyrazol-4-yl | 0 |
| 461 | Phenyl | pyrimidin-5-yl | 0 |
| 462 | Phenyl | pyrimidin-2-yl | 0 |
| 463 | Phenyl | pyrimidin-4-yl | 0 |
| 464 | Phenyl | pyridin-2-yl | 0 |
| 465 | Phenyl | pyridin-3-yl | 0 |
| 466 | Phenyl | pyridin-4-yl | 0 |
| 467 | Phenyl | 5-hydroxy-pyridin-3-yl | 0 |
| 468 | Phenyl | 5-methoxy-pyridin-3-yl | 0 |
| 469 | Phenyl | 3-hydroxy-pyridin-4-yl | 0 |
| 470 | Phenyl | 3-methoxy-pyridin-4-yl | 0 |
| 471 | Phenyl | 2-methoxy-pyridin-5-yl | 0 |
| 472 | Phenyl | N,N-dimethylamino-pyridin-5-yl | 0 |
| 473 | Phenyl | 4-methanesulfonylphenyl | 0 |
| 474 | Phenyl | 3-methanesulfonylphenyl | 0 |
| 475 | Phenyl | N,N-dimethylamino-methylphenyl | 0 |
| 476 | Phenyl | 2-methoxyphenyl | 0 |
| 477 | Phenyl | 3-methoxyphenyl | 0 |
| 478 | Phenyl | 4-methoxyphenyl | 0 |
| 479 | Phenyl | 3,5-dimethoxyphenyl | 0 |
| 480 | Phenyl | 3,4-dimethoxyphenyl | 0 |
| 481 | Phenyl | 3-hydroxy-4-methoxyphenyl | 0 |
| 482 | Phenyl | 3-hydroxy-5-methoxyphenyl | 0 |
| 483 | Phenyl | quinolin-3-yl | 0 |
| 484 | Phenyl | cyclopropyl | 0 |
| 485 | Phenyl | 3-hydroxymethylphenyl | 0 |
| 486 | Phenyl | 4-hydroxymethylphenyl | 0 |
| 487 | Phenyl | 1-benzofuran-5-yl | 0 |
| 488 | Phenyl | 1-benzothiophen-5-yl | 0 |
| 489 | Phenyl | 1H-indol-6-yl | 0 |
| 490 | Phenyl | 1H-indol-3-yl | 0 |
| 491 | Phenyl | 1-methyl-1H-indol-5-yl | 0 |
| 492 | Phenyl | 1-methyl-1H-indol-6-yl | 0 |
| 493 | Phenyl | 1H-indazol-5-yl | 0 |
| 494 | Phenyl | 1H-indazol-6-yl | 0 |
| 495 | Phenyl | 1-methyl-1H-indazol-5-yl | 0 |
| 496 | Phenyl | 1-methyl-1H-indazol-6-yl | 0 |
| 497 | Phenyl | 2-methyl-1,3-benzothiazol-5-yl | 0 |
| 498 | Phenyl | N,N-dimethylaminophen-4-yl | 0 |
| 499 | Phenyl | 4-methyl-3,4-dihydro-2H-1,4-benzoxazin-7-yl | 0 |
| 500 | Phenyl | benzimidazol-5-yl | 0 |
| 501 | Phenyl | 3-acetyl-1H-indol-6-yl | 0 |
| 502 | Phenyl | phenyl | 0 |
| 503 | Phenyl | 4-hydroxphenyl | 0 |
| 504 | Phenyl | 3-fluoro-5-hydroxyphenyl | 0 |
| 505 | Phenyl | 3-chloro-5-hydroxyphenyl | 0 |
| 506 | Phenyl | 2-phenoxyphenyl | 0 |
| 507 | Phenyl | 3-phenoxyphenyl | 0 |
| 508 | Phenyl | 4-phenoxyphenyl | 0 |
| 509 | Phenyl | 4-phenyl-1H-1,2,3-triazol-1-yl | 0 |
| 510 | Phenyl | 3-methoxyphenyl)-1H-1,2,3-triazol-1-yl | 0 |
| 511 | Phenyl | 4-(pyridin-3-yl)-1H-1,2,3-triazol-1-yl | 0 |
| 512 | Phenyl | 3-hydroxypropyl)-1H-1,2,3-triazol-1-yl | 0 |
| 513 | Phenyl | benzylamino | 0 |
| 514 | Phenyl | benzyloxy | 0 |
| 515 | Phenyl | piperazin-1-yl | 0 |
| 516 | Phenyl | pyrrolidin-l-yl | 0 |
| 517 | Phenyl | 3-hydroxypyrrolidin-1-yl | 0 |
| 518 | Phenyl | 3-carboxypyrrolidin-1-yl | 0 |
| 519 | Phenyl | 3-(dimethylamino)pyrrolidin-1-yl | 0 |
| 520 | Phenyl | 2-phenylpyrrolidin-1-yl | 0 |
| 521 | Phenyl | 1,2,3,6-tetrahydropyridin-4-yl | 0 |
| 522 | Phenyl | 3-(methoxycarbonyl)-1H-indol-6-yl] | 0 |
| 523 | Phenyl | 4-(cyclopropylcarbamoyl)phenyl | 0 |
| 524 | Phenyl | 2-[(2-hydroxyethyl)sulfamoyl]phenynaphthalen-2-yl | 0 |
| 525 | Phenyl | 4-methylphenyl | 0 |
| 526 | Phenyl | 3-methanesulfonamido-phenyl | 0 |
| 527 | Phenyl | | |
| 528 | 3-hydroxyphenyl | 2,5-dimethylpyrrol-1-yl | 0 |
| 529 | 3-hydroxyphenyl | 4,5-dimethyl-1,2oxazol-4-yl | 0 |
| 530 | 3-hydroxyphenyl | 1H-pyrazol-4-yl | 0 |
| 531 | 3-hydroxyphenyl | 1-methyl-1H-pyrazol-4-yl | 0 |
| 532 | 3-hydroxyphenyl | pyrimidin-5-yl | 0 |
| 533 | 3-hydroxyphenyl | pyrimidin-2-yl | 0 |
| 534 | 3-hydroxyphenyl | pyrimidin-4-yl | 0 |
| 535 | 3-hydroxyphenyl | pyridin-2-yl | 0 |
| 536 | 3-hydroxyphenyl | pyridin-3-yl | 0 |
| 537 | 3-hydroxyphenyl | pyridin-4-yl | 0 |
| 538 | 3-hydroxyphenyl | 5-hydroxy-pyridin-3-yl | 0 |
| 539 | 3-hydroxyphenyl | 5-methoxy-pyridin-3-yl | 0 |
| 540 | 3-hydroxyphenyl | 3-hydroxy-pyridin-4-yl | 0 |
| 541 | 3-hydroxyphenyl | 3-methoxy-pyridin-4-yl | 0 |
| 542 | 3-hydroxyphenyl | N,N-dimethylamino-pyridin-5-yl | 0 |

TABLE 1-continued

| Entry | R¹ | R² | m |
|---|---|---|---|
| 543 | 3-hydroxyphenyl | 4-methanesulfonylphenyl | 0 |
| 544 | 3-hydroxyphenyl | 3-methanesulfonylphenyl | 0 |
| 545 | 3-hydroxyphenyl | N,N-dimethylamino-methylphenyl | 0 |
| 546 | 3-hydroxyphenyl | 2-methoxyphenyl | 0 |
| 547 | 3-hydroxyphenyl | 3-methoxyphenyl | 0 |
| 548 | 3-hydroxyphenyl | 4-methoxyphenyl | 0 |
| 549 | 3-hydroxyphenyl | 3,5-dimethoxyphenyl | 0 |
| 550 | 3-hydroxyphenyl | 3,4-dimethoxyphenyl | 0 |
| 551 | 3-hydroxyphenyl | 3-hydroxy-4-methoxyphenyl | 0 |
| 552 | 3-hydroxyphenyl | 3-hydroxy-5-methoxyphenyl | 0 |
| 553 | 3-hydroxyphenyl | quinolin-3-yl | 0 |
| 554 | 3-hydroxyphenyl | cyclopropyl | 0 |
| 555 | 3-hydroxyphenyl | 3-hydroxymethylphenyl | 0 |
| 556 | 3-hydroxyphenyl | 4-hydroxymethylphenyl | 0 |
| 557 | 3-hydroxyphenyl | 1-benzofuran-5-yl | 0 |
| 558 | 3-hydroxyphenyl | 1-benzothiophen-5-yl | 0 |
| 559 | 3-hydroxyphenyl | 1H-indol-6-yl | 0 |
| 560 | 3-hydroxyphenyl | 1H-indol-3-yl | 0 |
| 561 | 3-hydroxyphenyl | 1-methyl-1H-indol-5-yl | 0 |
| 562 | 3-hydroxyphenyl | 1-methyl-1H-indol-6-yl | 0 |
| 563 | 3-hydroxyphenyl | 1H-indazol-5-yl | 0 |
| 564 | 3-hydroxyphenyl | 1H-indazol-6-yl | 0 |
| 565 | 3-hydroxyphenyl | 1-methyl-1H-indazol-5-yl | 0 |
| 566 | 3-hydroxyphenyl | 1-methyl-1H-indazol-6-yl | 0 |
| 567 | 3-hydroxyphenyl | 2-methyl-1,3-benzothiazol-5-yl | 0 |
| 568 | 3-hydroxyphenyl | N,N-dimethyl-aminophen-4-yl | 0 |
| 569 | 3-hydroxyphenyl | 4-methyl-3,4-dihydro-2H-1,4-benzoxazin-7-yl | 0 |
| 570 | 3-hydroxyphenyl | benzimidazol-5-yl | 0 |
| 571 | 3-hydroxyphenyl | 3-acetyl-1H-indol-6-yl | 0 |
| 572 | 3-hydroxyphenyl | phenyl | 0 |
| 573 | 3-hydroxyphenyl | 4-hydroxphenyl | 0 |
| 574 | 3-hydroxyphenyl | 3-fluoro-5-hydroxyphenyl | 0 |
| 575 | 3-hydroxyphenyl | 3-chloro-5-hydroxyphenyl | 0 |
| 576 | 3-hydroxyphenyl | 2-phenoxyphenyl | 0 |
| 577 | 3-hydroxyphenyl | 3-phenoxyphenyl | 0 |
| 578 | 3-hydroxyphenyl | 4-phenoxyphenyl | 0 |
| 579 | 3-fluorophenyl | 2,5-dimethylpyrrol-1-yl | 0 |
| 580 | 3-fluorophenyl | 4,5-dimethyl-1,2oxazol-4-yl | 0 |
| 581 | 3-fluorophenyl | 1H-pyrazol-4-yl | 0 |
| 582 | 3-fluorophenyl | 1-methyl-1H-pyrazol-4-yl | 0 |
| 583 | 3-fluorophenyl | pyrimidin-5-yl | 0 |
| 584 | 3-fluorophenyl | pyrimidin-2-yl | 0 |
| 585 | 3-fluorophenyl | pyrimidin-4-yl | 0 |
| 586 | 3-fluorophenyl | pyridin-2-yl | 0 |
| 587 | 3-fluorophenyl | pyridin-3-yl | 0 |
| 588 | 3-fluorophenyl | pyridin-4-yl | 0 |
| 589 | 3-fluorophenyl | 5-hydroxy-pyridin-3-yl | 0 |
| 590 | 3-fluorophenyl | 5-methoxy-pyridin-3-yl | 0 |
| 591 | 3-fluorophenyl | 3-hydroxy-pyridin-4-yl | 0 |
| 592 | 3-fluorophenyl | 3-methoxy-pyridin-4-yl | 0 |
| 593 | 3-fluorophenyl | N,N-dimethyl-aminopyridin-5-yl | 0 |
| 594 | 3-fluorophenyl | 4-methanesulfonylphenyl | 0 |
| 595 | 3-fluorophenyl | 3-methanesulfonylphenyl | 0 |
| 596 | 3-fluorophenyl | N,N-dimethylamino-methylphenyl | 0 |
| 597 | 3-fluorophenyl | 2-methoxyphenyl | 0 |
| 598 | 3-fluorophenyl | 3-methoxyphenyl | 0 |
| 599 | 3-fluorophenyl | 4-methoxyphenyl | 0 |
| 600 | 3-fluorophenyl | 3,5-dimethoxyphenyl | 0 |
| 601 | 3-fluorophenyl | 3,4-dimethoxyphenyl | 0 |
| 602 | 3-fluorophenyl | 3-hydroxy-4-methoxyphenyl | 0 |
| 603 | 3-fluorophenyl | 3-hydroxy-5-methoxyphenyl | 0 |
| 604 | 3-fluorophenyl | quinolin-3-yl | 0 |
| 605 | 3-fluorophenyl | cyclopropyl | 0 |
| 606 | 3-fluorophenyl | 3-hydroxymethylphenyl | 0 |
| 607 | 3-fluorophenyl | 4-hydroxymethylphenyl | 0 |
| 608 | 3-fluorophenyl | 1-benzofuran-5-yl | 0 |
| 609 | 3-fluorophenyl | 1-benzothiophen-5-yl | 0 |
| 610 | 3-fluorophenyl | 1H-indol-6-yl | 0 |
| 611 | 3-fluorophenyl | 1H-indol-3-yl | 0 |
| 612 | 3-fluorophenyl | 1-methyl-1H-indol-5-yl | 0 |
| 613 | 3-fluorophenyl | 1-methyl-1H-indol-6-yl | 0 |
| 614 | 3-fluorophenyl | 1H-indazol-5-yl | 0 |
| 615 | 3-fluorophenyl | 1H-indazol-6-yl | 0 |
| 616 | 3-fluorophenyl | 1-methyl-1H-indazol-5-yl | 0 |
| 617 | 3-fluorophenyl | 1-methyl-1H-indazol-6-yl | 0 |
| 618 | 3-fluorophenyl | 2-methyl-1,3-benzothiazol-5-yl | 0 |
| 619 | 3-fluorophenyl | N,N-dimethyl-aminophen-4-yl | 0 |
| 620 | 3-fluorophenyl | 4-methyl-3,4-dihydro-2H-1,4-benzoxazin-7-yl | 0 |
| 621 | 3-fluorophenyl | benzimidazol-5-yl | 0 |
| 622 | 3-fluorophenyl | 3-acetyl-1H-indol-6-yl | 0 |
| 623 | 3-fluorophenyl | phenyl | 0 |
| 624 | 3-fluorophenyl | 4-hydroxphenyl | 0 |
| 625 | 3-fluorophenyl | 3-fluoro-5-hydroxyphenyl | 0 |
| 626 | 3-fluorophenyl | 3-chloro-5-hydroxyphenyl | 0 |
| 627 | 3-fluorophenyl | 2-phenoxyphenyl | 0 |
| 628 | 3-fluorophenyl | 3-phenoxyphenyl | 0 |
| 629 | 3-fluorophenyl | 4-phenoxyphenyl | 0 |
| 630 | 3-fluorophenyl | 4-(cyclopropylcarbamoyl)-phenyl | 0 |
| 631 | pyridin-2-yl | N-pyrrolyl | 0 |
| 632 | pyridin-3-yl | N-pyrrolyl | 0 |
| 633 | 5-hydroxy-pyridin-3-yl | N-pyrrolyl | 0 |
| 634 | 5-methoxy-pyridin-3-yl | N-pyrrolyl | 0 |
| 635 | pyridin-4-yl | N-pyrrolyl | 0 |
| 636 | 2-hydroxy-pyridin-4-yl | N-pyrrolyl | 0 |
| 637 | 2-methoxy-pyridin-4-yl | N-pyrrolyl | 0 |
| 638 | pyrimid-2-yl | N-pyrrolyl | 0 |
| 639 | pyrimid-4-yl | N-pyrrolyl | 0 |
| 640 | pyrimid-5-yl | N-pyrrolyl | 0 |
| 641 | indol-3-yl | N-pyrrolyl | 0 |
| 642 | indol-4-yl | N-pyrrolyl | 0 |
| 643 | indol-5-yl | N-pyrrolyl | 0 |
| 644 | indol-6-yl | N-pyrrolyl | 0 |
| 645 | indol-7-yl | N-pyrrolyl | 0 |
| 646 | indazol-3-yl | N-pyrrolyl | 0 |
| 647 | indazol-4-yl | N-pyrrolyl | 0 |
| 648 | indazol-5-yl | N-pyrrolyl | 0 |
| 649 | indazol-6-yl | N-pyrrolyl | 0 |
| 650 | indazol-7-yl | N-pyrrolyl | 0 |
| 651 | benzimidazol-4-yl | N-pyrrolyl | 0 |
| 652 | benzimidazol-5-yl | N-pyrrolyl | 0 |
| 653 | 7-azaindol-3-yl | N-pyrrolyl | 0 |
| 654 | 7-azaindol-4-yl | N-pyrrolyl | 0 |
| 655 | 7-azaindol-5-yl | N-pyrrolyl | 0 |
| 656 | 7-azaindol-6-yl | N-pyrrolyl | 0 |
| 657 | N-methyl-indolin-4-yl | N-pyrrolyl | 0 |
| 658 | N-methyl-indolin-5-yl | N-pyrrolyl | 0 |
| 659 | N-methyl-indolin-6-yl | N-pyrrolyl | 0 |
| 660 | N-methyl-indolin-7-yl | N-pyrrolyl | 0 |
| 661 | 1-benzothiophene-5-yl | N-pyrrolyl | 0 |
| 662 | 1-benzothiophene-6-yl | N-pyrrolyl | 0 |
| 663 | imidazo[1,2a]pyridin-6-yl | N-pyrrolyl | 0 |
| 664 | imidazo[1,2a]pyridin-5-yl | N-pyrrolyl | 0 |
| 665 | imidazo[1,2a]pyridin-3-yl | N-pyrrolyl | 0 |
| 666 | imidazo[1,2a]pyrazin-3-yl | N-pyrrolyl | 0 |
| 667 | [1,2,4]triazolo[1,5a]pyridin-7-yl | N-pyrrolyl | 0 |
| 668 | benzyl | N-pyrrolyl | 0 |
| 669 | phenethyl | N-pyrrolyl | 0 |
| 670 | phenylmethanol | N-pyrrolyl | 0 |
| 671 | 2-hydroxy-prop-2-yl | N-pyrrolyl | 0 |
| 672 | 3-hydroxy-prop-1-yl | N-pyrrolyl | 0 |
| 673 | 2-hydroxy-3-methyl-prop-2-yl | N-pyrrolyl | 0 |
| 674 | 2-amino-prop-2-yl | N-pyrrolyl | 0 |
| 675 | 2-methyl-prop-2-yl | N-pyrrolyl | 0 |
| 676 | 1-hydroxy-cyclohex-1-yl | N-pyrrolyl | 0 |
| 677 | 1-amino-cyclohex-1-yl | N-pyrrolyl | 0 |
| 678 | thiazol-4-yl | N-pyrrolyl | 0 |
| 679 | thiazol-5-yl | N-pyrrolyl | 0 |
| 680 | 1-methyl-imidazol-2-yl | N-pyrrolyl | 0 |
| 681 | 1-methyl-imidazol-5-yl | N-pyrrolyl | 0 |
| 682 | 1,2-dimethyl-imidazol-4-yl | N-pyrrolyl | 0 |
| 683 | 1-methyl-pyrazol-4-yl | N-pyrrolyl | 0 |

TABLE 1-continued

| Entry | R¹ | R² | m |
|---|---|---|---|
| 684 | 1-imidazol-methyl | N-pyrrolyl | 0 |
| 685 | N-benzyl-N-methyl-aminomethyl | N-pyrrolyl | 0 |
| 686 | 2,3-dihydro-1H-indol-6-yl | N-pyrrolyl | 0 |
| 687 | cyclopropyl | N-pyrrolyl | 0 |
| 688 | dimethylaminomethyl | N-pyrrolyl | 0 |
| 689 | pyridin-2-yl | 1H-indol-5-yl | 0 |
| 690 | pyridin-3-yl | 1H-indol-5-yl | 0 |
| 691 | 5-hydroxy-pyridin-3-yl | 1H-indol-5-yl | 0 |
| 692 | 5-methoxy-pyridin-3-yl | 1H-indol-5-yl | 0 |
| 693 | pyridin-4-yl | 1H-indol-5-yl | 0 |
| 694 | 2-hydroxy-pyridin-4-yl | 1H-indol-5-yl | 0 |
| 695 | 2-methoxy-pyridin-4-yl | 1H-indol-5-yl | 0 |
| 696 | pyrimid-2-yl | 1H-indol-5-yl | 0 |
| 697 | pyrimid-4-yl | 1H-indol-5-yl | 0 |
| 698 | pyrimid-5-yl | 1H-indol-5-yl | 0 |
| 699 | indol-3-yl | 1H-indol-5-yl | 0 |
| 700 | indol-4-yl | 1H-indol-5-yl | 0 |
| 701 | indol-5-yl | 1H-indol-5-yl | 0 |
| 702 | indol-6-yl | 1H-indol-5-yl | 0 |
| 703 | indol-7-yl | 1H-indol-5-yl | 0 |
| 704 | indazol-3-yl | 1H-indol-5-yl | 0 |
| 705 | indazol-4-yl | 1H-indol-5-yl | 0 |
| 706 | indazol-5-yl | 1H-indol-5-yl | 0 |
| 707 | indazol-6-yl | 1H-indol-5-yl | 0 |
| 708 | indazol-7-yl | 1H-indol-5-yl | 0 |
| 709 | benzimidazol-4-yl | 1H-indol-5-yl | 0 |
| 710 | benzimidazol-5-yl | 1H-indol-5-yl | 0 |
| 711 | 7-azaindol-3-yl | 1H-indol-5-yl | 0 |
| 712 | 7-azaindol-4-yl | 1H-indol-5-yl | 0 |
| 713 | 7-azaindol-5-yl | 1H-indol-5-yl | 0 |
| 714 | 7-azaindol-6-yl | 1H-indol-5-yl | 0 |
| 715 | N-methyl-indolin-4-yl | 1H-indol-5-yl | 0 |
| 716 | N-methyl-indolin-5-yl | 1H-indol-5-yl | 0 |
| 717 | N-methyl-indolin-6-yl | 1H-indol-5-yl | 0 |
| 718 | N-methyl-indolin-7-yl | 1H-indol-5-yl | 0 |
| 719 | 1-benzothiophene-5-yl | 1H-indol-5-yl | 0 |
| 720 | 1-benzothiophene-6-yl | 1H-indol-5-yl | 0 |
| 721 | imidazo[1,2a]pyridin-6-yl | 1H-indol-5-yl | 0 |
| 722 | imidazo[1,2a]pyridin-5-yl | 1H-indol-5-yl | 0 |
| 723 | imidazo[1,2a]pyridin-3-yl | 1H-indol-5-yl | 0 |
| 724 | imidazo[1,2a]pyrazin-3-yl | 1H-indol-5-yl | 0 |
| 725 | [1,2,4]triazolo[1,5a]pyridin-7-yl | 1H-indol-5-yl | 0 |
| 726 | benzyl | 1H-indol-5-yl | 0 |
| 727 | phenethyl | 1H-indol-5-yl | 0 |
| 728 | 2-hydroxy-prop-2-yl | 1H-indol-5-yl | 0 |
| 729 | 3-hydroxy-prop-1-yl | 1H-indol-5-yl | 0 |
| 730 | 2-hydroxy-3-methyl-prop-2-yl | 1H-indol-5-yl | 0 |
| 731 | 2-amino-prop-2-yl | 1H-indol-5-yl | 0 |
| 732 | 2-methyl-prop-2-yl | 1H-indol-5-yl | 0 |
| 733 | 1-hydroxy-cyclohex-1-yl | 1H-indol-5-yl | 0 |
| 734 | 1-amino-cyclohex-1-yl | 1H-indol-5-yl | 0 |
| 735 | thiazol-4-yl | 1H-indol-5-yl | 0 |
| 736 | thiazol-5-yl | 1H-indol-5-yl | 0 |
| 737 | 1-methyl-imidazol-2-yl | 1H-indol-5-yl | 0 |
| 738 | 1-methyl-imidazol-5-yl | 1H-indol-5-yl | 0 |
| 739 | 1,2-dimethyl-imidazol-4-yl | 1H-indol-5-yl | 0 |
| 740 | 1-methyl-pyrazol-4-yl | 1H-indol-5-yl | 0 |
| 741 | 1-imidazol-methyl | 1H-indol-5-yl | 0 |
| 742 | N-benzyl-N-methyl-aminomethyl | 1H-indol-5-yl | 0 |
| 743 | 2,3-dihydro-1H-indol-6-yl | 1H-indol-5-yl | 0 |
| 744 | cyclopropyl | 1H-indol-5-yl | 0 |
| 745 | dimethylaminomethyl | 1H-indol-5-yl | 0 |
| 746 | pyridin-2-yl | 3-hydroxphenyl | 0 |
| 747 | pyridin-3-yl | 3-hydroxphenyl | 0 |
| 748 | 5-hydroxy-pyridin-3-yl | 3-hydroxphenyl | 0 |
| 749 | 5-methoxy-pyridin-3-yl | 3-hydroxphenyl | 0 |
| 750 | pyridin-4-yl | 3-hydroxphenyl | 0 |
| 751 | 2-hydroxy-pyridin-4-yl | 3-hydroxphenyl | 0 |
| 752 | 2-methoxy-pyridin-4-yl | 3-hydroxphenyl | 0 |
| 753 | pyrimid-2-yl | 3-hydroxphenyl | 0 |
| 754 | pyrimid-4-yl | 3-hydroxphenyl | 0 |
| 755 | pyrimid-5-yl | 3-hydroxphenyl | 0 |
| 756 | indol-3-yl | 3-hydroxphenyl | 0 |
| 757 | indol-4-yl | 3-hydroxphenyl | 0 |
| 758 | indol-5-yl | 3-hydroxphenyl | 0 |
| 759 | indol-6-yl | 3-hydroxphenyl | 0 |
| 760 | indol-7-yl | 3-hydroxphenyl | 0 |
| 761 | indazol-3-yl | 3-hydroxphenyl | 0 |
| 762 | indazol-4-yl | 3-hydroxphenyl | 0 |
| 763 | indazol-5-yl | 3-hydroxphenyl | 0 |
| 764 | indazol-6-yl | 3-hydroxphenyl | 0 |
| 765 | indazol-7-yl | 3-hydroxphenyl | 0 |
| 766 | benzimidazol-4-yl | 3-hydroxphenyl | 0 |
| 767 | benzimidazol-5-yl | 3-hydroxphenyl | 0 |
| 768 | 7-azaindol-3-yl | 3-hydroxphenyl | 0 |
| 769 | 7-azaindol-4-yl | 3-hydroxphenyl | 0 |
| 770 | 7-azaindol-5-yl | 3-hydroxphenyl | 0 |
| 771 | 7-azaindol-6-yl | 3-hydroxphenyl | 0 |
| 772 | N-methyl-indolin-4-yl | 3-hydroxphenyl | 0 |
| 773 | N-methyl-indolin-5-yl | 3-hydroxphenyl | 0 |
| 774 | N-methyl-indolin-6-yl | 3-hydroxphenyl | 0 |
| 775 | N-methyl-indolin-7-yl | 3-hydroxphenyl | 0 |
| 776 | 1-benzothiophene-5-yl | 3-hydroxphenyl | 0 |
| 777 | 1-benzothiophene-6-yl | 3-hydroxphenyl | 0 |
| 778 | imidazo[1,2a]pyridin-6-yl | 3-hydroxphenyl | 0 |
| 779 | imidazo[1,2a]pyridin-5-yl | 3-hydroxphenyl | 0 |
| 780 | imidazo[1,2a]pyridin-3-yl | 3-hydroxphenyl | 0 |
| 781 | imidazo[1,2a]pyrazin-3-yl | 3-hydroxphenyl | 0 |
| 782 | benzyl | 3-hydroxphenyl | 0 |
| 783 | phenethyl | 3-hydroxphenyl | 0 |
| 784 | 2-hydroxy-prop-2-yl | 3-hydroxphenyl | 0 |
| 785 | 3-hydroxy-prop-1-yl | 3-hydroxphenyl | 0 |
| 786 | 2-hydroxy-3-methyl-prop-2-yl | 3-hydroxphenyl | 0 |
| 787 | 2-amino-prop-2-yl | 3-hydroxphenyl | 0 |
| 788 | 2-methyl-prop-2-yl | 3-hydroxphenyl | 0 |
| 789 | 1-hydroxy-cyclohex-1-yl | 3-hydroxphenyl | 0 |
| 790 | 1-amino-cyclohex-1-yl | 3-hydroxphenyl | 0 |
| 791 | thiazol-4-yl | 3-hydroxphenyl | 0 |
| 792 | thiazol-5-yl | 3-hydroxphenyl | 0 |
| 793 | 1-methyl-imidazol-2-yl | 3-hydroxphenyl | 0 |
| 794 | 1-methyl-imidazol-5-yl | 3-hydroxphenyl | 0 |
| 795 | 1,2-dimethyl-imidazol-4-yl | 3-hydroxphenyl | 0 |
| 796 | 1-methyl-pyrazol-4-yl | 3-hydroxphenyl | 0 |
| 797 | 1-imidazol-methyl | 3-hydroxphenyl | 0 |
| 798 | N-benzyl-N-methyl-aminomethyl | 3-hydroxphenyl | 0 |
| 799 | 2,3-dihydro-1H-indol-6-yl | 3-hydroxphenyl | 0 |
| 800 | cyclopropyl | 3-hydroxphenyl | 0 |
| 801 | dimethylaminomethyl | 3-hydroxphenyl | 0 |
| 802 | pyridin-2-yl | F | 0 |
| 803 | pyridin-3-yl | F | 0 |
| 804 | 5-hydroxy-pyridin-3-yl | F | 0 |
| 805 | 5-methoxy-pyridin-3-yl | F | 0 |
| 806 | pyridin-4-yl | F | 0 |
| 807 | 2-hydroxy-pyridin-4-yl | F | 0 |
| 808 | 2-methoxy-pyridin-4-yl | F | 0 |
| 809 | pyrimid-2-yl | F | 0 |
| 810 | pyrimid-4-yl | F | 0 |
| 811 | pyrimid-5-yl | F | 0 |
| 812 | indol-3-yl | F | 0 |
| 813 | indol-4-yl | F | 0 |
| 814 | indol-5-yl | F | 0 |
| 815 | indol-6-yl | F | 0 |
| 816 | indol-7-yl | F | 0 |
| 817 | indazol-3-yl | F | 0 |
| 818 | indazol-4-yl | F | 0 |
| 819 | indazol-5-yl | F | 0 |
| 820 | indazol-6-yl | F | 0 |
| 821 | indazol-7-yl | F | 0 |
| 822 | benzimidazol-4-yl | F | 0 |
| 823 | benzimidazol-5-yl | F | 0 |
| 824 | 7-azaindol-3-yl | F | 0 |
| 825 | 7-azaindol-4-yl | F | 0 |
| 826 | 7-azaindol-5-yl | F | 0 |
| 827 | 7-azaindol-6-yl | F | 0 |
| 828 | N-methyl-indolin-4-yl | F | 0 |
| 829 | N-methyl-indolin-5-yl | F | 0 |
| 830 | N-methyl-indolin-6-yl | F | 0 |
| 831 | N-methyl-indolin-7-yl | F | 0 |
| 832 | 1-benzothiophene-5-yl | F | 0 |
| 833 | 1-benzothiophene-6-yl | F | 0 |
| 834 | imidazo[1,2a]pyridin-6-yl | F | 0 |
| 835 | imidazo[1,2a]pyridin-5-yl | F | 0 |
| 836 | imidazo[1,2a]pyridin-3-yl | F | 0 |
| 837 | imidazo[1,2a]pyrazin-3-yl | F | 0 |

TABLE 1-continued

| Entry | R¹ | R² | m |
|---|---|---|---|
| 838 | benzyl | F | 0 |
| 839 | phenethyl | F | 0 |
| 840 | 2-hydroxy-prop-2-yl | F | 0 |
| 841 | 3-hydroxy-prop-1-yl | F | 0 |
| 842 | 2-hydroxy-3-methyl-prop-2-yl | F | 0 |
| 843 | 2-amino-prop-2-yl | F | 0 |
| 844 | 2-methyl-prop-2-yl | F | 0 |
| 845 | 1-hydroxy-cyclohex-1-yl | F | 0 |
| 846 | 1-amino-cyclohex-1-yl | F | 0 |
| 847 | thiazol-4-yl | F | 0 |
| 848 | thiazol-5-yl | F | 0 |
| 849 | 1-methyl-imidazol-2-yl | F | 0 |
| 850 | 1-methyl-imidazol-5-yl | F | 0 |
| 851 | 1,2-dimethyl-imidazol-4-yl | F | 0 |
| 852 | 1-methyl-pyrazol-4-yl | F | 0 |
| 853 | 1-imidazol-methyl | F | 0 |
| 854 | N-benzyl-N-methyl-aminomethyl | F | 0 |
| 856 | cyclopropyl | F | 0 |
| 857 | dimethylaminomethyl | F | 0 |
| 858 | pyridin-2-yl | NH₂ | 0 |
| 859 | pyridin-3-yl | NH₂ | 0 |
| 860 | 5-hydroxy-pyridin-3-yl | NH₂ | 0 |
| 861 | 5-methoxy-pyridin-3-yl | NH₂ | 0 |
| 862 | pyridin-4-yl | NH₂ | 0 |
| 863 | 2-hydroxy-pyridin-4-yl | NH₂ | 0 |
| 864 | 2-methoxy-pyridin-4-yl | NH₂ | 0 |
| 865 | pyrimid-2-yl | NH₂ | 0 |
| 866 | pyrimid-4-yl | NH₂ | 0 |
| 867 | pyrimid-5-yl | NH₂ | 0 |
| 868 | indol-3-yl | NH₂ | 0 |
| 869 | indol-4-yl | NH₂ | 0 |
| 870 | indol-5-yl | NH₂ | 0 |
| 871 | indol-6-yl | NH₂ | 0 |
| 872 | indol-7-yl | NH₂ | 0 |
| 873 | indazol-3-yl | NH₂ | 0 |
| 874 | indazol-4-yl | NH₂ | 0 |
| 875 | indazol-5-yl | NH₂ | 0 |
| 876 | indazol-6-yl | NH₂ | 0 |
| 877 | indazol-7-yl | NH₂ | 0 |
| 878 | benzimidazol-4-yl | NH₂ | 0 |
| 879 | benzimidazol-5-yl | NH₂ | 0 |
| 880 | 7-azaindol-3-yl | NH₂ | 0 |
| 881 | 7-azaindol-4-yl | NH₂ | 0 |
| 882 | 7-azaindol-5-yl | NH₂ | 0 |
| 883 | 7-azaindol-6-yl | NH₂ | 0 |
| 884 | N-methyl-indolin-4-yl | NH₂ | 0 |
| 885 | N-methyl-indolin-5-yl | NH₂ | 0 |
| 886 | N-methyl-indolin-6-yl | NH₂ | 0 |
| 887 | N-methyl-indolin-7-yl | NH₂ | 0 |
| 888 | 1-benzothiophene-5-yl | NH₂ | 0 |
| 889 | 1-benzothiophene-6-yl | NH₂ | 0 |
| 890 | imidazo[1,2a]pyridin-6-yl | NH₂ | 0 |
| 891 | imidazo[1,2a]pyridin-5-yl | NH₂ | 0 |
| 892 | imidazo[1,2a]pyridin-3-yl | NH₂ | 0 |
| 893 | imidazo[1,2a]pyrazin-3-yl | NH₂ | 0 |
| 894 | benzyl | NH₂ | 0 |
| 895 | phenethyl | NH₂ | 0 |
| 896 | 2-hydroxy-prop-2-yl | NH₂ | 0 |
| 897 | 3-hydroxy-prop-1-yl | NH₂ | 0 |
| 898 | 2-hydroxy-3-methyl-prop-2-yl | NH₂ | 0 |
| 899 | 2-amino-prop-2-yl | NH₂ | 0 |
| 900 | 2-methyl-prop-2-yl | NH₂ | 0 |
| 901 | 1-hydroxy-cyclohex-1-yl | NH₂ | 0 |
| 902 | 1-amino-cyclohex-1-yl | NH₂ | 0 |
| 903 | thiazol-4-yl | NH₂ | 0 |
| 904 | thiazol-5-yl | NH₂ | 0 |
| 905 | 1-methyl-imidazol-2-yl | NH₂ | 0 |
| 906 | 1-methyl-imidazol-5-yl | NH₂ | 0 |
| 907 | 1,2-dimethyl-imidazol-4-yl | NH₂ | 0 |
| 908 | 1-methyl-pyrazol-4-yl | NH₂ | 0 |
| 909 | 1-imidazol-methyl | NH₂ | 0 |
| 910 | N-benzyl-N-methyl-aminomethyl | NH₂ | 0 |
| 911 | 2,3-dihydro-1H-indol-6-yl | NH₂ | 0 |
| 912 | cyclopropyl | NH₂ | 0 |
| 913 | dimethylaminomethyl | NH₂ | 0 |
| 914 | 4-pyridyl | 2,5-dimethylpyrrol-1-yl | 0 |
| 915 | 4-pyridyl | 4,5-dimethyl-1,2oxazol-4-yl | 0 |
| 916 | 4-pyridyl | 1H-pyrazol-4-yl | 0 |
| 917 | 4-pyridyl | 1-methyl-1H-pyrazol-4-yl | 0 |
| 918 | 4-pyridyl | pyrimidin-5-yl | 0 |
| 919 | 4-pyridyl | pyrimidin-2-yl | 0 |
| 920 | 4-pyridyl | pyrimidin-4-yl | 0 |
| 921 | 4-pyridyl | pyridin-2-yl | 0 |
| 922 | 4-pyridyl | pyridin-3-yl | 0 |
| 923 | 4-pyridyl | pyridin-4-yl | 0 |
| 924 | 4-pyridyl | 5-hydroxy-pyridin-3-yl | 0 |
| 925 | 4-pyridyl | 5-methoxy-pyridin-3-yl | 0 |
| 926 | 4-pyridyl | 3-hydroxy-pyridin-4-yl | 0 |
| 927 | 4-pyridyl | 3-methoxy-pyridin-4-yl | 0 |
| 928 | 4-pyridyl | N,N-dimethyl-aminopyridin-5-yl | 0 |
| 929 | 4-pyridyl | 4-methanesulfonylphenyl | 0 |
| 930 | 4-pyridyl | 3-methanesulfonylphenyl | 0 |
| 931 | 4-pyridyl | N,N-dimethylamino-methylphenyl | 0 |
| 932 | 4-pyridyl | 2-methoxyphenyl | 0 |
| 933 | 4-pyridyl | 3-methoxyphenyl | 0 |
| 934 | 4-pyridyl | 4-methoxyphenyl | 0 |
| 935 | 4-pyridyl | 3,5-dimethoxyphenyl | 0 |
| 936 | 4-pyridyl | 3,4-dimethoxyphenyl | 0 |
| 937 | 4-pyridyl | 3-hydroxy-4-methoxyphenyl | 0 |
| 938 | 4-pyridyl | 3-hydroxy-5-methoxyphenyl | 0 |
| 939 | 4-pyridyl | quinolin-3-yl | 0 |
| 940 | 4-pyridyl | cyclopropyl | 0 |
| 941 | 4-pyridyl | 3-hydroxymethylphenyl | 0 |
| 942 | 4-pyridyl | 4-hydroxymethylphenyl | 0 |
| 943 | 4-pyridyl | 1-benzofuran-5-yl | 0 |
| 944 | 4-pyridyl | 1-benzothiophen-5-yl | 0 |
| 945 | 4-pyridyl | 1H-indol-6-yl | 0 |
| 946 | 4-pyridyl | 1H-indol-3-yl | 0 |
| 947 | 4-pyridyl | 1-methyl-1H-indol-5-yl | 0 |
| 948 | 4-pyridyl | 1-methyl-1H-indol-6-yl | 0 |
| 949 | 4-pyridyl | 1H-indazol-5-yl | 0 |
| 950 | 4-pyridyl | 1H-indazol-6-yl | 0 |
| 951 | 4-pyridyl | 1-methyl-1H-indazol-5-yl | 0 |
| 952 | 4-pyridyl | 1-methyl-1H-indazol-6-yl | 0 |
| 953 | 4-pyridyl | 2-methyl-1,3-benzothiazol-5-yl | 0 |
| 954 | 4-pyridyl | N,N-dimethyl-aminophen-4-yl | 0 |
| 955 | 4-pyridyl | 4-methyl-3,4-dihydro-2H-1,4-benzoxazin-7-yl | 0 |
| 956 | 4-pyridyl | benzimidazol-5-yl | 0 |
| 957 | 4-pyridyl | 3-acetyl-1H-indol-6-yl | 0 |
| 958 | 4-pyridyl | phenyl | 0 |
| 959 | 4-pyridyl | 4-hydroxphenyl | 0 |
| 960 | 4-pyridyl | 3-fluoro-5-hydroxyphenyl | 0 |
| 961 | 4-pyridyl | 3-chloro-5-hydroxyphenyl | 0 |
| 962 | 4-pyridyl | 2-phenoxyphenyl | 0 |
| 963 | 4-pyridyl | 3-phenoxyphenyl | 0 |
| 964 | 4-pyridyl | 4-phenoxyphenyl | 0 |
| 965 | 7-azaindol-3-yl | 2,5-dimethylpyrrol-1-yl | 0 |
| 966 | 7-azaindol-3-yl | 4,5-dimethyl-1,2oxazol-4-yl | 0 |
| 967 | 7-azaindol-3-yl | 1H-pyrazol-4-yl | 0 |
| 968 | 7-azaindol-3-yl | 1-methyl-1H-pyrazol-4-yl | 0 |
| 969 | 7-azaindol-3-yl | pyrimidin-5-yl | 0 |
| 970 | 7-azaindol-3-yl | pyrimidin-2-yl | 0 |
| 971 | 7-azaindol-3-yl | pyrimidin-4-yl | 0 |
| 972 | 7-azaindol-3-yl | pyridin-2-yl | 0 |
| 973 | 7-azaindol-3-yl | pyridin-3-yl | 0 |
| 974 | 7-azaindol-3-yl | pyridin-4-yl | 0 |
| 975 | 7-azaindol-3-yl | 5-hydroxy-pyridin-3-yl | 0 |
| 976 | 7-azaindol-3-yl | 5-methoxy-pyridin-3-yl | 0 |
| 977 | 7-azaindol-3-yl | 3-hydroxy-pyridin-4-yl | 0 |
| 978 | 7-azaindol-3-yl | 3-methoxy-pyridin-4-yl | 0 |
| 979 | 7-azaindol-3-yl | N,N-dimethylamino-pyridin-5-yl | 0 |
| 980 | 7-azaindol-3-yl | 4-methanesulfonylphenyl | 0 |
| 981 | 7-azaindol-3-yl | 3-methanesulfonylphenyl | 0 |
| 982 | 7-azaindol-3-yl | N,N-dimethylamino-methylphenyl | 0 |
| 983 | 7-azaindol-3-yl | 2-methoxyphenyl | 0 |

TABLE 1-continued

| Entry | R¹ | R² | m |
|---|---|---|---|
| 984 | 7-azaindol-3-yl | 3-methoxyphenyl | 0 |
| 985 | 7-azaindol-3-yl | 4-methoxyphenyl | 0 |
| 986 | 7-azaindol-3-yl | 3,5-dimethoxyphenyl | 0 |
| 987 | 7-azaindol-3-yl | 3,4-dimethoxyphenyl | 0 |
| 988 | 7-azaindol-3-yl | 3-hydroxy-4-methoxyphenyl | 0 |
| 989 | 7-azaindol-3-yl | 3-hydroxy-5-methoxyphenyl | 0 |
| 990 | 7-azaindol-3-yl | quinolin-3-yl | 0 |
| 991 | 7-azaindol-3-yl | cyclopropyl | 0 |
| 992 | 7-azaindol-3-yl | 3-hydroxymethylphenyl | 0 |
| 993 | 7-azaindol-3-yl | 4-hydroxymethylphenyl | 0 |
| 994 | 7-azaindol-3-yl | 1-benzofuran-5-yl | 0 |
| 995 | 7-azaindol-3-yl | 1-benzothiophen-5-yl | 0 |
| 996 | 7-azaindol-3-yl | 1H-indol-6-yl | 0 |
| 997 | 7-azaindol-3-yl | 1H-indol-3-yl | 0 |
| 998 | 7-azaindol-3-yl | 1-methyl-1H-indol-5-yl | 0 |
| 999 | 7-azaindol-3-yl | 1-methyl-1H-indol-6-yl | 0 |
| 1000 | 7-azaindol-3-yl | 1H-indazol-5-yl | 0 |
| 1001 | 7-azaindol-3-yl | 1H-indazol-6-yl | 0 |
| 1002 | 7-azaindol-3-yl | 1-methyl-1H-indazol-5-yl | 0 |
| 1003 | 7-azaindol-3-yl | 1-methyl-1H-indazol-6-yl | 0 |
| 1004 | 7-azaindol-3-yl | 2-methyl-1,3-benzothiazol-5-yl | 0 |
| 1005 | 7-azaindol-3-yl | N,N-dimethyl-aminophen-4-yl | 0 |
| 1006 | 7-azaindol-3-yl | 4-methyl-3,4-dihydro-2H-1,4-benzoxazin-7-yl | 0 |
| 1007 | 7-azaindol-3-yl | benzimidazol-5-yl | 0 |
| 1008 | 7-azaindol-3-yl | 3-acetyl-1H-indol-6-yl | 0 |
| 1009 | 7-azaindol-3-yl | phenyl | 0 |
| 1010 | 7-azaindol-3-yl | 4-hydroxphenyl | 0 |
| 1011 | 7-azaindol-3-yl | 3-fluoro-5-hydroxyphenyl | 0 |
| 1012 | 7-azaindol-3-yl | 3-chloro-5-hydroxyphenyl | 0 |
| 1013 | 7-azaindol-3-yl | 2-phenoxyphenyl | 0 |
| 1014 | 7-azaindol-3-yl | 3-phenoxyphenyl | 0 |
| 1015 | 7-azaindol-3-yl | 4-phenoxyphenyl | 0 |
| 1016 | thiazol-4-yl | 2,5-dimethylpyrrol-1-yl | 0 |
| 1017 | thiazol-4-yl | 4,5-dimethyl-1,2oxazol-4-yl | 0 |
| 1018 | thiazol-4-yl | 1H-pyrazol-4-yl | 0 |
| 1019 | thiazol-4-yl | 1-methyl-1H-pyrazol-4-yl | 0 |
| 1020 | thiazol-4-yl | pyrimidin-5-yl | 0 |
| 1021 | thiazol-4-yl | pyrimidin-2-yl | 0 |
| 1022 | thiazol-4-yl | pyrimidin-4-yl | 0 |
| 1023 | thiazol-4-yl | pyridin-2-yl | 0 |
| 1024 | thiazol-4-yl | pyridin-3-yl | 0 |
| 1025 | thiazol-4-yl | pyridin-4-yl | 0 |
| 1026 | thiazol-4-yl | 5-hydroxy-pyridin-3-yl | 0 |
| 1027 | thiazol-4-yl | 5-methoxy-pyridin-3-yl | 0 |
| 1028 | thiazol-4-yl | 3-hydroxy-pyridin-4-yl | 0 |
| 1029 | thiazol-4-yl | 3-methoxy-pyridin-4-yl | 0 |
| 1030 | thiazol-4-yl | N,N-dimethylamino-pyridin-5-yl | 0 |
| 1031 | thiazol-4-yl | 4-methanesulfonylphenyl | 0 |
| 1032 | thiazol-4-yl | 3-methanesulfonylphenyl | 0 |
| 1033 | thiazol-4-yl | N,N-dimethylamino-methylphenyl | 0 |
| 1034 | thiazol-4-yl | 2-methoxyphenyl | 0 |
| 1035 | thiazol-4-yl | 3-methoxyphenyl | 0 |
| 1036 | thiazol-4-yl | 4-methoxyphenyl | 0 |
| 1037 | thiazol-4-yl | 3,5-dimethoxyphenyl | 0 |
| 1038 | thiazol-4-yl | 3,4-dimethoxyphenyl | 0 |
| 1039 | thiazol-4-yl | 3-hydroxy-4-methoxyphenyl | 0 |
| 1040 | thiazol-4-yl | 3-hydroxy-5-methoxyphenyl | 0 |
| 1041 | thiazol-4-yl | quinolin-3-yl | 0 |
| 1042 | thiazol-4-yl | cyclopropyl | 0 |
| 1043 | thiazol-4-yl | 3-hydroxymethylphenyl | 0 |
| 1044 | thiazol-4-yl | 4-hydroxymethylphenyl | 0 |
| 1045 | thiazol-4-yl | 1-benzofuran-5-yl | 0 |
| 1046 | thiazol-4-yl | 1-benzothiophen-5-yl | 0 |
| 1047 | thiazol-4-yl | 1H-indol-6-yl | 0 |
| 1048 | thiazol-4-yl | 1H-indol-3-yl | 0 |
| 1049 | thiazol-4-yl | 1-methyl-1H-indol-5-yl | 0 |
| 1050 | thiazol-4-yl | 1-methyl-1H-indol-6-yl | 0 |
| 1051 | thiazol-4-yl | 1H-indazol-5-yl | 0 |
| 1052 | thiazol-4-yl | 1H-indazol-6-yl | 0 |
| 1053 | thiazol-4-yl | 1-methyl-1H-indazol-5-yl | 0 |
| 1054 | thiazol-4-yl | 1-methyl-1H-indazol-6-yl | 0 |
| 1055 | thiazol-4-yl | 2-methyl-1,3-benzothiazol-5-yl | 0 |
| 1056 | thiazol-4-yl | N,N-dimethylamino-phen-4-yl | 0 |
| 1057 | thiazol-4-yl | 4-methyl-3,4-dihydro-2H-1,4-benzoxazin-7-yl | 0 |
| 1058 | thiazol-4-yl | benzimidazol-5-yl | 0 |
| 1059 | thiazol-4-yl | 3-acetyl-1H-indol-6-yl | 0 |
| 1060 | thiazol-4-yl | phenyl | 0 |
| 1061 | thiazol-4-yl | 4-hydroxphenyl | 0 |
| 1062 | thiazol-4-yl | 3-fluoro-5-hydroxyphenyl | 0 |
| 1063 | thiazol-4-yl | 3-chloro-5-hydroxyphenyl | 0 |
| 1064 | thiazol-4-yl | 2-phenoxyphenyl | 0 |
| 1065 | thiazol-4-yl | 3-phenoxyphenyl | 0 |
| 1066 | thiazol-4-yl | 4-phenoxyphenyl | 0 |
| 1067 | indol-6-yl | 2,5-dimethylpyrrol-1-yl | 0 |
| 1068 | indol-6-yl | 4,5-dimethyl-1,2oxazol-4-yl | 0 |
| 1069 | indol-6-yl | 1H-pyrazol-4-yl | 0 |
| 1070 | indol-6-yl | 1-methyl-1H-pyrazol-4-yl | 0 |
| 1071 | indol-6-yl | pyrimidin-5-yl | 0 |
| 1072 | indol-6-yl | pyrimidin-2-yl | 0 |
| 1073 | indol-6-yl | pyrimidin-4-yl | 0 |
| 1074 | indol-6-yl | pyridin-2-yl | 0 |
| 1075 | indol-6-yl | pyridin-3-yl | 0 |
| 1076 | indol-6-yl | pyridin-4-yl | 0 |
| 1077 | indol-6-yl | 5-hydroxy-pyridin-3-yl | 0 |
| 1078 | indol-6-yl | 5-methoxy-pyridin-3-yl | 0 |
| 1079 | indol-6-yl | 3-hydroxy-pyridin-4-yl | 0 |
| 1080 | indol-6-yl | 3-methoxy-pyridin-4-yl | 0 |
| 1081 | indol-6-yl | N,N-dimethylamino-pyridin-5-yl | 0 |
| 1082 | indol-6-yl | 4-methanesulfonylphenyl | 0 |
| 1083 | indol-6-yl | 3-methanesulfonylphenyl | 0 |
| 1084 | indol-6-yl | N,N-dimethylamino-methylphenyl | 0 |
| 1085 | indol-6-yl | 2-methoxyphenyl | 0 |
| 1086 | indol-6-yl | 3-methoxyphenyl | 0 |
| 1087 | indol-6-yl | 4-methoxyphenyl | 0 |
| 1088 | indol-6-yl | 3,5-dimethoxyphenyl | 0 |
| 1089 | indol-6-yl | 3,4-dimethoxyphenyl | 0 |
| 1090 | indol-6-yl | 3-hydroxy-4-methoxyphenyl | 0 |
| 1091 | indol-6-yl | 3-hydroxy-5-methoxyphenyl | 0 |
| 1092 | indol-6-yl | quinolin-3-yl | 0 |
| 1093 | indol-6-yl | cyclopropyl | 0 |
| 1094 | indol-6-yl | 3-hydroxymethylphenyl | 0 |
| 1095 | indol-6-yl | 4-hydroxymethylphenyl | 0 |
| 1096 | indol-6-yl | 1-benzofuran-5-yl | 0 |
| 1097 | indol-6-yl | 1-benzothiophen-5-yl | 0 |
| 1098 | indol-6-yl | 1H-indol-6-yl | 0 |
| 1099 | indol-6-yl | 1H-indol-3-yl | 0 |
| 1100 | indol-6-yl | 1-methyl-1H-indol-5-yl | 0 |
| 1101 | indol-6-yl | 1-methyl-1H-indol-6-yl | 0 |
| 1102 | indol-6-yl | 1H-indazol-5-yl | 0 |
| 1103 | indol-6-yl | 1H-indazol-6-yl | 0 |
| 1104 | indol-6-yl | 1-methyl-1H-indazol-5-yl | 0 |
| 1105 | indol-6-yl | 1-methyl-1H-indazol-6-yl | 0 |
| 1106 | indol-6-yl | 2-methyl-1,3-benzothiazol-5-yl | 0 |
| 1107 | indol-6-yl | N,N-dimethylamino-phen-4-yl | 0 |
| 1108 | indol-6-yl | 4-methyl-3,4-dihydro-2H-1,4-benzoxazin-7-yl | 0 |
| 1109 | indol-6-yl | benzimidazol-5-yl | 0 |
| 1110 | indol-6-yl | 3-acetyl-1H-indol-6-yl | 0 |
| 1111 | indol-6-yl | phenyl | 0 |
| 1112 | indol-6-yl | 4-hydroxphenyl | 0 |
| 1113 | indol-6-yl | 3-fluoro-5-hydroxyphenyl | 0 |
| 1114 | indol-6-yl | 3-chloro-5-hydroxyphenyl | 0 |
| 1115 | indol-6-yl | 2-phenoxyphenyl | 0 |
| 1116 | indol-6-yl | 3-phenoxyphenyl | 0 |
| 1117 | indol-6-yl | 4-phenoxyphenyl | 0 |
| 1118 | pyrrolidin-1-yl-methyl | phenyl | 0 |
| 1119 | 4-phenylpiperazin-1-yl-methyl | phenyl | 0 |
| 1120 | 3-(1H-imidazol-1- | phenyl | 0 |

TABLE 1-continued

| Entry | R¹ | R² | m |
|---|---|---|---|
| 1121 | benzylaminomethyl | yl)propylaminomethyl phenyl | 0 |
| 1122 | hydroxymethyl | phenyl | 0 |
| 1123 | imidazo[1,2-a]pyrazin-3-yl | quinolin-3-yl | 0 |
| 1124 | 3-hydroxy-prop-1-yl | quinolin-3-yl | 0 |
| 1125 | 4-carboxy-1H-indol-6-yl | Hydrogen | 0 |
| 1126 | 4-carboxamide-1H-indol-6-yl | Hydrogen | 0 |
| 1127 | 3-benzamidyl | Hydrogen | 0 |
| 1128 | 1-benzenesulfonyl-1H-indol-3-yl | Hydrogen | 0 |
| 1129 | 1H-indol-3-yl | Hydrogen | 0 |
| 1130 | 3-carbomethoxy-phenyl | Hydrogen | 0 |
| 1131 | 3-carbamoyl-5-methoxy-phenyl | Hydrogen | 0 |
| 1132 | 4-pyridyl | 1H-pyrazol-3-yl | 0 |
| 1133 | Phenyl | 1,3,5-trimethyl-1H-pyrazol-4-yl | 0 |
| 1134 | 1-hydroxy-1-methyl-ethyl | 2,5-dimethyl-pyrrol-1-yl | 0 |
| 1135 | 3-carbamoyl-phenyl | 2,5-dimethyl-pyrrol-1-yl | 0 |
| 1136 | 3-carboxy-phenyl | 2,5-dimethyl-pyrrol-1-yl | 0 |
| 1137 | 3-hydroxymethyl-phenyl | 2,5-dimethyl-pyrrol-1-yl | 0 |
| 1138 | Phenyl-hydroxymethyl | 2,5-dimethyl-pyrrol-1-yl | 0 |
| 1139 | 3-acetylamino-phenyl | 2,5-dimethyl-pyrrol-1-yl | 0 |
| 1140 | Cyclopropyl | 2,5-dimethyl-pyrrol-1-yl | 0 |
| 1141 | 3-methoxy-phenyl | 2,5-dimethyl-pyrrol-1-yl | 0 |
| 1142 | Phenyl | Benzo[1,3]dioxol-5-yl-3-phenyl | 0 |
| 1143 | Phenyl | Isoquinolin-6-yl | 0 |
| 1144 | Phenyl | Benzofuran-2-yl | 0 |
| 1145 | Phenyl | Quinolin-8-yl | 0 |
| 1146 | Phenyl | 2-amino-pyrimidin-5-yl | 0 |
| 1147 | 4-amino-phenyl | 1H-indol-6-yl | 0 |
| 1148 | 4-carboxy-phenyl | 1H-indol-6-yl | 0 |
| 1149 | 4-methoxy-phenyl | 1H-indol-6-yl | 0 |
| 1150 | 4-carbamoyl-phenyl | 1H-indol-6-yl | 0 |
| 1151 | 4-(piperazine-1-carbonyl)-phenyl | 1H-indol-6-yl | 0 |
| 1152 | 4-acetylamino-phenyl | 1H-indol-6-yl | 0 |
| 1153 | 4-[(pyridine-3-carbonyl)-amino]-phenyl | 1H-indol-6-yl | 0 |
| 1154 | 4-methanesulfonylamino-phenyl | 1H-indol-6-yl | 0 |
| 1155 | 4-(thiophene-2-sulfonylamino)-phenyl | 1H-indol-6-yl | 0 |
| 1156 | thiazol-4-yl | 3-(Methoxycarbonyl)-1H-indol-6-yl | 0 |
| 1157 | 3-hydroxyphenyl | 3-chloro-1H-indol-6-yl | 0 |
| 1158 | 3-hydroxyphenyl | 3-(2-acetamidoethyl)-1H-indol-6-yl | 0 |
| 1159 | 3-(N,N-dimethylsulfamoyl)phenyl | Fluoro | 0 |
| 1160 | 4-(tetrahydro-2H-pyran-4-yloxy)phenyl | 1H-indol-6-yl | 0 |
| 1161 | 4-morpholinophenyl | 1H-indol-6-yl | 0 |
| 1162 | 3-carbamoylphenyl | 1H-indol-6-yl | 0 |
| 1163 | 4-Fluorophenyl | 1H-indol-6-yl | 0 |
| 1164 | 2,4-Difluorophenyl | 1H-indol-6-yl | 0 |
| 1165 | 3-Acetamidophenyl | 1H-indol-6-yl | 0 |
| 1166 | 3-(nicotinamido)phenyl | 1H-indol-6-yl | 0 |
| 1167 | 3-(3-chloro-4-fluorophenyl-sulfonamido)phenyl | 1H-indol-6-yl | 0 |
| 1168 | 3-aminophenyl | 1H-indol-6-yl | 0 |
| 1169 | 3-(methylsulfonamido)phenyl | 1H-indol-6-yl | 0 |
| 1170 | 3-(thiophene-2-sulfonamido)phenyl | 1H-indol-6-yl | 0 |
| 1171 | 3-acetamido-5-fluorophenyl | 1H-indol-6-yl | 0 |
| 1172 | Phenyl | indolin-6-yl | 0 |
| 1173 | 3-hydroxyphenyl | indolin-6-yl | 0 |
| 1174 | 6-aminopyridin-2-yl | 1H-indol-6-yl | 0 |
| 1175 | 2-aminopyridin-4-yl | 1H-indol-6-yl | 0 |
| 1176 | 3-hydroxyphenyl | benzo[d][1,3]dioxol-5-yl | 0 |
| 1177 | 3-hydroxyphenyl | 4-amino-3-methoxyphenyl | 0 |
| 1178 | 2-hydroxyethyl | 1H-indol-6-yl | 0 |
| 1179 | 1-amino-1-methyl-ethyl | 1H-indol-6-yl | 0 |
| 1180 | phenyl-C(OH)(CH₃)- (1-hydroxy-1-phenyl-ethyl attachment) | 1H-indol-6-yl | 0 |
| 1181 | 1-hydroxy-1-methyl-ethyl | 1H-indol-6-yl | 0 |
| 1182 | 3-(hydroxymethyl)phenyl | 1H-indol-6-yl | 0 |
| 1183 | Phenyl | 2-carboxy-1H-indol-6-yl | 0 |
| 1184 | Phenyl | 2-(ethylcarboxy)-1H-indol-6-yl | 0 |
| 1185 | 3-carbamoyl-5-methoxyphenyl | 1H-indol-6-yl | 0 |
| 1186 | 3-hydroxyphenyl | 2-carboxy-1H-indol-6-yl | 0 |
| 1187 | 4-methoxyphenyl | 2-carboxy-1H-indol-6-yl | 0 |
| 1188 | 4-fluoro-3-(tetrahydro-2H-pyran-4-yloxy)phenyl | 1H-indol-6-yl | 0 |
| 1189 | Phenyl | 3-acetamidophenyl | 0 |
| 1190 | 5-amino-1H-1,3-benzodiazol-1-ylmethyl | Phenyl | 0 |
| 1191 | pyridin-4-yl | 4-methylphenyl | 0 |
| 1192 | 3-hydroxyphenyl | 4-methylphenyl | 0 |
| 1193 | 1H-benzimidazol-5-ylaminoethyl | Phenyl | 0 |
| 1194 | 3-hydroxyphenyl | 3-methanesulfonamidophenyl | 0 |
| 1195 | 3-hydroxyphenyl | 3-carbamoylphenyl | 0 |
| 1196 | 3-hydroxyphenyl | 1-(benzenesulfonyl)-1H-indol-3-yl | 0 |
| 1197 | (4-fluorophenyl)(hydroxy)methyl | 3-hydroxyphenyl | 0 |
| 1198 | 3-carbamoylphenyl | NH₂ | 0 |
| 1190 | 3-carboxyphenyl | NH₂ | 0 |
| 1191 | 3-(morpholine-4-carbonyl)-phenyl | H | 0 |
| 1192 | 3-methylcarbamoyl-phenyl | H | 0 |
| 1193 | 3-dimethylcarbamoyl-phenyl | H | 0 |
| 1194 | 3-(4-methyl-piperazine-1-carbonyl)-phenyl | H | 0 |
| 1195 | 3-(4-phenyl-piperazine-1-carbonyl)-phenyl | H | 0 |
| 1196 | 4-pyridyl | indol-1-yl | 0 |
| 1197 | 4-pyridyl | imidazol-1-yl | 0 |
| 1198 | 4-pyridyl | [1,2,4]triazol-1-yl | 0 |
| 1199 | Phenyl | Imidazol-1-yl | 0 |
| 1200 | Phenyl | Pyrazol-1-yl | 0 |
| 1201 | Phenyl | [1,2,4]triazol-1-yl | 0 |
| 1202 | Phenyl | Benzoimidazol-1-yl | 0 |
| 1203 | Phenyl | Indazol-1-yl | 0 |
| 1204 | Phenyl | Indol-1-yl | 0 |
| 1205 | 4-pyridyl | benzoimidazol-1-yl | 0 |

Exemplary embodiments include compounds having the formula (XIX) or a pharmaceutically acceptable salt form thereof:

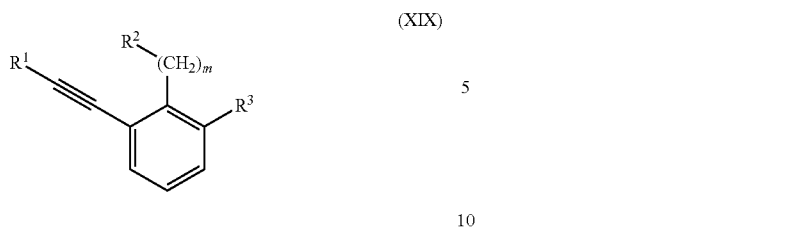

(XIX)

wherein non-limiting examples of $R^1$, $R^2$, $R^3$ and m are defined herein below in Table 2.

TABLE 2

| Entry | $R^1$ | $R^2$ | $R^3$ | m |
|---|---|---|---|---|
| 1 | Phenyl | N-pyrrolyl | 1H-tetrazol-5-yl | 0 |
| 2 | 3-hydroxyphenyl | N-pyrrolyl | 1H-tetrazol-5-yl | 0 |
| 3 | 3-fluorophenyl | N-pyrrolyl | 1H-tetrazol-5-yl | 0 |
| 4 | indol-6-yl | N-pyrrolyl | 1H-tetrazol-5-yl | 0 |
| 5 | pyridin-4-yl | N-pyrrolyl | 1H-tetrazol-5-yl | 0 |
| 6 | 7-azaindol-3-yl | N-pyrrolyl | 1H-tetrazol-5-yl | 0 |
| 7 | thiazol-4-yl | N-pyrrolyl | 1H-tetrazol-5-yl | 0 |
| 8 | Phenyl | indol-6-yl | 1H-tetrazol-5-yl | 0 |
| 9 | 3-hydroxyphenyl | indol-6-yl | 1H-tetrazol-5-yl | 0 |
| 10 | 3-fluorophenyl | indol-6-yl | 1H-tetrazol-5-yl | 0 |
| 11 | indol-6-yl | indol-6-yl | 1H-tetrazol-5-yl | 0 |
| 12 | pyridin-4-yl | indol-6-yl | 1H-tetrazol-5-yl | 0 |
| 13 | 7-azaindol-3-yl | indol-6-yl | 1H-tetrazol-5-yl | 0 |
| 14 | thiazol-4-yl | indol-6-yl | 1H-tetrazol-5-yl | 0 |
| 15 | Phenyl | 3-hydroxyphenyl | 1H-tetrazol-5-yl | 0 |
| 16 | 3-hydroxyphenyl | 3-hydroxyphenyl | 1H-tetrazol-5-yl | 0 |
| 17 | 3-fluorophenyl | 3-hydroxyphenyl | 1H-tetrazol-5-yl | 0 |
| 18 | indol-6-yl | 3-hydroxyphenyl | 1H-tetrazol-5-yl | 0 |
| 19 | pyridin-4-yl | 3-hydroxyphenyl | 1H-tetrazol-5-yl | 0 |
| 20 | 7-azaindol-3-yl | 3-hydroxyphenyl | 1H-tetrazol-5-yl | 0 |
| 21 | thiazol-4-yl | 3-hydroxyphenyl | 1H-tetrazol-5-yl | 0 |
| 22 | Phenyl | N-pyrrolyl | methanesulfonamidocarbonyl | 0 |
| 23 | 3-hydroxyphenyl | N-pyrrolyl | methanesulfonamidocarbonyl | 0 |
| 24 | 3-fluorophenyl | N-pyrrolyl | methanesulfonamidocarbonyl | 0 |
| 25 | indol-6-yl | N-pyrrolyl | methanesulfonamidocarbonyl | 0 |
| 26 | pyridin-4-yl | N-pyrrolyl | methanesulfonamidocarbonyl | 0 |
| 27 | 7-azaindol-3-yl | N-pyrrolyl | methanesulfonamidocarbonyl | 0 |
| 28 | thiazol-4-yl | N-pyrrolyl | methanesulfonamidocarbonyl | 0 |
| 29 | Phenyl | indol-6-yl | methanesulfonamidocarbonyl | 0 |
| 30 | 3-hydroxyphenyl | indol-6-yl | methanesulfonamidocarbonyl | 0 |
| 31 | 3-fluorophenyl | indol-6-yl | methanesulfonamidocarbonyl | 0 |
| 32 | indol-6-yl | indol-6-yl | methanesulfonamidocarbonyl | 0 |
| 33 | pyridin-4-yl | indol-6-yl | methanesulfonamidocarbonyl | 0 |
| 34 | 7-azaindol-3-yl | indol-6-yl | methanesulfonamidocarbonyl | 0 |
| 35 | thiazol-4-yl | indol-6-yl | methanesulfonamidocarbonyl | 0 |
| 36 | Phenyl | 3-hydroxyphenyl | methanesulfonamidocarbonyl | 0 |
| 37 | 3-hydroxyphenyl | 3-hydroxyphenyl | methanesulfonamidocarbonyl | 0 |
| 38 | 3-fluorophenyl | 3-hydroxyphenyl | methanesulfonamidocarbonyl | 0 |
| 39 | indol-6-yl | 3-hydroxyphenyl | methanesulfonamidocarbonyl | 0 |
| 40 | pyridin-4-yl | 3-hydroxyphenyl | methanesulfonamidocarbonyl | 0 |
| 41 | 7-azaindol-3-yl | 3-hydroxyphenyl | methanesulfonamidocarbonyl | 0 |
| 42 | thiazol-4-yl | 3-hydroxyphenyl | methanesulfonamidocarbonyl | 0 |
| 43 | Phenyl | N-pyrrolyl | aminosulfonamidocarbonyl | 0 |
| 44 | 3-hydroxyphenyl | N-pyrrolyl | aminosulfonamidocarbonyl | 0 |
| 45 | 3-fluorophenyl | N-pyrrolyl | aminosulfonamidocarbonyl | 0 |
| 46 | indol-6-yl | N-pyrrolyl | aminosulfonamidocarbonyl | 0 |
| 47 | pyridin-4-yl | N-pyrrolyl | aminosulfonamidocarbonyl | 0 |
| 48 | 7-azaindol-3-yl | N-pyrrolyl | aminosulfonamidocarbonyl | 0 |
| 49 | thiazol-4-yl | N-pyrrolyl | aminosulfonamidocarbonyl | 0 |
| 50 | Phenyl | indol-6-yl | aminosulfonamidocarbonyl | 0 |
| 51 | 3-hydroxyphenyl | indol-6-yl | aminosulfonamidocarbonyl | 0 |
| 52 | 3-fluorophenyl | indol-6-yl | aminosulfonamidocarbonyl | 0 |
| 53 | indol-6-yl | indol-6-yl | aminosulfonamidocarbonyl | 0 |
| 54 | pyridin-4-yl | indol-6-yl | aminosulfonamidocarbonyl | 0 |
| 55 | 7-azaindol-3-yl | indol-6-yl | aminosulfonamidocarbonyl | 0 |
| 56 | thiazol-4-yl | indol-6-yl | aminosulfonamidocarbonyl | 0 |
| 57 | Phenyl | 3-hydroxyphenyl | aminosulfonamidocarbonyl | 0 |
| 58 | 3-hydroxyphenyl | 3-hydroxyphenyl | aminosulfonamidocarbonyl | 0 |
| 59 | 3-fluorophenyl | 3-hydroxyphenyl | aminosulfonamidocarbonyl | 0 |
| 60 | indol-6-yl | 3-hydroxyphenyl | aminosulfonamidocarbonyl | 0 |

TABLE 2-continued

| Entry | R¹ | R² | R³ | m |
|---|---|---|---|---|
| 61 | pyridin-4-yl | 3-hydroxyphenyl | aminosulfonamidocarbonyl | 0 |
| 62 | 7-azaindol-3-yl | 3-hydroxyphenyl | aminosulfonamidocarbonyl | 0 |
| 63 | thiazol-4-yl | 3-hydroxyphenyl | aminosulfonamidocarbonyl | 0 |
| 64 | Phenyl | N-pyrrolyl | morpholin-4-yl-sulfonamidocarbonyl | 0 |
| 65 | 3-hydroxyphenyl | N-pyrrolyl | morpholin-4-yl-sulfonamidocarbonyl | 0 |
| 66 | 3-fluorophenyl | N-pyrrolyl | morpholin-4-yl-sulfonamidocarbonyl | 0 |
| 67 | indol-6-yl | N-pyrrolyl | morpholin-4-yl-sulfonamidocarbonyl | 0 |
| 68 | pyridin-4-yl | N-pyrrolyl | morpholin-4-yl-sulfonamidocarbonyl | 0 |
| 69 | 7-azaindol-3-yl | N-pyrrolyl | morpholin-4-yl-sulfonamidocarbonyl | 0 |
| 70 | thiazol-4-yl | N-pyrrolyl | morpholin-4-yl-sulfonamidocarbonyl | 0 |
| 71 | Phenyl | indol-6-yl | morpholin-4-yl-sulfonamidocarbonyl | 0 |
| 72 | 3-hydroxyphenyl | indol-6-yl | morpholin-4-yl-sulfonamidocarbonyl | 0 |
| 73 | 3-fluorophenyl | indol-6-yl | morpholin-4-yl-sulfonamidocarbonyl | 0 |
| 74 | indol-6-yl | indol-6-yl | morpholin-4-yl-sulfonamidocarbonyl | 0 |
| 75 | pyridin-4-yl | indol-6-yl | morpholin-4-yl-sulfonamidocarbonyl | 0 |
| 76 | 7-azaindol-3-yl | indol-6-yl | morpholin-4-yl-sulfonamidocarbonyl | 0 |
| 77 | thiazol-4-yl | indol-6-yl | morpholin-4-yl-sulfonamidocarbonyl | 0 |
| 78 | Phenyl | 3-hydroxyphenyl | morpholin-4-yl-sulfonamidocarbonyl | 0 |
| 79 | 3-hydroxyphenyl | 3-hydroxyphenyl | morpholin-4-yl-sulfonamidocarbonyl | 0 |
| 80 | 3-fluorophenyl | 3-hydroxyphenyl | morpholin-4-yl-sulfonamidocarbonyl | 0 |
| 81 | indol-6-yl | 3-hydroxyphenyl | morpholin-4-yl-sulfonamidocarbonyl | 0 |
| 82 | pyridin-4-yl | 3-hydroxyphenyl | morpholin-4-yl-sulfonamidocarbonyl | 0 |
| 83 | 7-azaindol-3-yl | 3-hydroxyphenyl | morpholin-4-yl-sulfonamidocarbonyl | 0 |
| 84 | thiazol-4-yl | 3-hydroxyphenyl | morpholin-4-yl-sulfonamidocarbonyl | 0 |
| 85 | Phenyl | N-pyrrolyl | 1,1-dioxo-4-thiomorpholin-4-yl-sulfonamidocarbonyl | 0 |
| 86 | 3-hydroxyphenyl | N-pyrrolyl | 1,1-dioxo-4-thiomorpholin-4-yl-sulfonamidocarbonyl | 0 |
| 87 | 3-fluorophenyl | N-pyrrolyl | 1,1-dioxo-4-thiomorpholin-4-yl-sulfonamidocarbonyl | 0 |
| 88 | indol-6-yl | N-pyrrolyl | 1,1-dioxo-4-thiomorpholin-4-yl-sulfonamidocarbonyl | 0 |
| 89 | pyridin-4-yl | N-pyrrolyl | 1,1-dioxo-4-thiomorpholin-4-yl-sulfonamidocarbonyl | 0 |
| 90 | 7-azaindol-3-yl | N-pyrrolyl | 1,1-dioxo-4-thiomorpholin-4-yl-sulfonamidocarbonyl | 0 |
| 91 | thiazol-4-yl | N-pyrrolyl | 1,1-dioxo-4-thiomorpholin-4-yl-sulfonamidocarbonyl | 0 |
| 92 | Phenyl | indol-6-yl | 1,1-dioxo-4-thiomorpholin-4-yl-sulfonamidocarbonyl | 0 |
| 93 | 3-hydroxyphenyl | indol-6-yl | 1,1-dioxo-4-thiomorpholin-4-yl-sulfonamidocarbonyl | 0 |
| 94 | 3-fluorophenyl | indol-6-yl | 1,1-dioxo-4-thiomorpholin-4-yl-sulfonamidocarbonyl | 0 |
| 95 | indol-6-yl | indol-6-yl | 1,1-dioxo-4-thiomorpholin-4-yl-sulfonamidocarbonyl | 0 |
| 96 | pyridin-4-yl | indol-6-yl | 1,1-dioxo-4-thiomorpholin-4-yl-sulfonamidocarbonyl | 0 |
| 97 | 7-azaindol-3-yl | indol-6-yl | 1,1-dioxo-4-thiomorpholin-4-yl-sulfonamidocarbonyl | 0 |
| 98 | thiazol-4-yl | indol-6-yl | 1,1-dioxo-4-thiomorpholin-4-yl-sulfonamidocarbonyl | 0 |
| 99 | Phenyl | 3-hydroxyphenyl | 1,1-dioxo-4-thiomorpholin-4-yl-sulfonamidocarbonyl | 0 |
| 100 | 3-hydroxyphenyl | 3-hydroxyphenyl | 1,1-dioxo-4-thiomorpholin-4-yl-sulfonamidocarbonyl | 0 |

TABLE 2-continued

| Entry | R¹ | R² | R³ | m |
|---|---|---|---|---|
| 101 | 3-fluorophenyl | 3-hydroxyphenyl | 1,1-dioxo-4-thiomorpholin-4-yl-sulfonamidocarbonyl | 0 |
| 102 | indol-6-yl | 3-hydroxyphenyl | 1,1-dioxo-4-thiomorpholin-4-yl-sulfonamidocarbonyl | 0 |
| 103 | pyridin-4-yl | 3-hydroxyphenyl | 1,1-dioxo-4-thiomorpholin-4-yl-sulfonamidocarbonyl | 0 |
| 104 | 7-azaindol-3-yl | 3-hydroxyphenyl | 1,1-dioxo-4-thiomorpholin-4-yl-sulfonamidocarbonyl | 0 |
| 105 | thiazol-4-yl | 3-hydroxyphenyl | 1,1-dioxo-4-thiomorpholin-4-yl-sulfonamidocarbonyl | 0 |
| 106 | Phenyl | N-pyrrolyl | sulfonamide | 0 |
| 107 | 3-hydroxyphenyl | N-pyrrolyl | sulfonamide | 0 |
| 108 | 3-fluorophenyl | N-pyrrolyl | sulfonamide | 0 |
| 109 | indol-6-yl | N-pyrrolyl | sulfonamide | 0 |
| 110 | pyridin-4-yl | N-pyrrolyl | sulfonamide | 0 |
| 111 | 7-azaindol-3-yl | N-pyrrolyl | sulfonamide | 0 |
| 112 | thiazol-4-yl | N-pyrrolyl | sulfonamide | 0 |
| 113 | Phenyl | indol-6-yl | sulfonamide | 0 |
| 114 | 3-hydroxyphenyl | indol-6-yl | sulfonamide | 0 |
| 115 | 3-fluorophenyl | indol-6-yl | sulfonamide | 0 |
| 116 | indol-6-yl | indol-6-yl | sulfonamide | 0 |
| 117 | pyridin-4-yl | indol-6-yl | sulfonamide | 0 |
| 118 | 7-azaindol-3-yl | indol-6-yl | sulfonamide | 0 |
| 119 | thiazol-4-yl | indol-6-yl | sulfonamide | 0 |
| 120 | Phenyl | 3-hydroxyphenyl | sulfonamide | 0 |
| 121 | 3-hydroxyphenyl | 3-hydroxyphenyl | sulfonamide | 0 |
| 122 | 3-fluorophenyl | 3-hydroxyphenyl | sulfonamide | 0 |
| 123 | indol-6-yl | 3-hydroxyphenyl | sulfonamide | 0 |
| 124 | pyridin-4-yl | 3-hydroxyphenyl | sulfonamide | 0 |
| 125 | 7-azaindol-3-yl | 3-hydroxyphenyl | sulfonamide | 0 |
| 126 | thiazol-4-yl | 3-hydroxyphenyl | sulfonamide | 0 |
| 127 | Phenyl | N-pyrrolyl | N-acetyl-sulfonamido | 0 |
| 128 | 3-hydroxyphenyl | N-pyrrolyl | N-acetyl-sulfonamido | 0 |
| 129 | 3-fluorophenyl | N-pyrrolyl | N-acetyl-sulfonamido | 0 |
| 130 | indol-6-yl | N-pyrrolyl | N-acetyl-sulfonamido | 0 |
| 131 | pyridin-4-yl | N-pyrrolyl | N-acetyl-sulfonamido | 0 |
| 132 | 7-azaindol-3-yl | N-pyrrolyl | N-acetyl-sulfonamido | 0 |
| 133 | thiazol-4-yl | N-pyrrolyl | N-acetyl-sulfonamido | 0 |
| 134 | Phenyl | indol-6-yl | N-acetyl-sulfonamido | 0 |
| 135 | 3-hydroxyphenyl | indol-6-yl | N-acetyl-sulfonamido | 0 |
| 136 | 3-fluorophenyl | indol-6-yl | N-acetyl-sulfonamido | 0 |
| 137 | indol-6-yl | indol-6-yl | N-acetyl-sulfonamido | 0 |
| 138 | pyridin-4-yl | indol-6-yl | N-acetyl-sulfonamido | 0 |
| 139 | 7-azaindol-3-yl | indol-6-yl | N-acetyl-sulfonamido | 0 |
| 140 | thiazol-4-yl | indol-6-yl | N-acetyl-sulfonamido | 0 |
| 141 | Phenyl | 3-hydroxyphenyl | N-acetyl-sulfonamido | 0 |
| 142 | 3-hydroxyphenyl | 3-hydroxyphenyl | N-acetyl-sulfonamido | 0 |
| 143 | 3-fluorophenyl | 3-hydroxyphenyl | N-acetyl-sulfonamido | 0 |
| 144 | indol-6-yl | 3-hydroxyphenyl | N-acetyl-sulfonamido | 0 |
| 145 | pyridin-4-yl | 3-hydroxyphenyl | N-acetyl-sulfonamido | 0 |
| 146 | 7-azaindol-3-yl | 3-hydroxyphenyl | N-acetyl-sulfonamido | 0 |
| 147 | thiazol-4-yl | 3-hydroxyphenyl | N-acetyl-sulfonamido | 0 |
| 148 | 5-1H-indolyl | H | 1H-tetrazol-5-yl | 0 |
| 149 | 3-1H-pyrrolo[2,3-b]pyridine | H | 1H-tetrazol-5-yl | 0 |
| 150 | 6-1H-indolyl | H | 1H-tetrazol-5-yl | 0 |
| 151 | 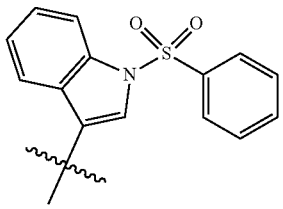 [SMILES: *c1cn(S(=O)(=O)c2ccccc2)c2ccccc12] | H | 1H-tetrazol-5-yl | 0 |
| 152 | 3-1H-indolyl | H | 1H-tetrazol-5-yl | 0 |
| 153 | 2-hydroxymethylphenyl | H | 1H-tetrazol-5-yl | 0 |

Exemplary embodiments include compounds having the formula (XX) or a pharmaceutically acceptable salt form thereof:

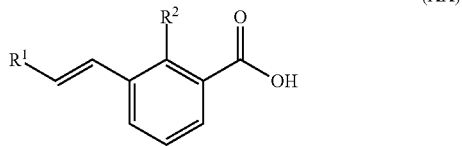

(XX)

wherein non-limiting examples of $R^1$ and $R^2$ are defined herein below in Table 3.

TABLE 3

| Entry | $R^1$ | $R^2$ |
|---|---|---|
| 1 | phenyl | N-pyrrolyl |
| 2 | 4-fluorophenyl | N-pyrrolyl |
| 3 | methoxymethyl | N-pyrrolyl |
| 4 | indol-6-yl | N-pyrrolyl |
| 5 | phenyl | indol-6-yl |
| 6 | 4-fluorophenyl | indol-6-yl |
| 7 | methoxymethyl | indol-6-yl |
| 8 | indol-6-yl | indol-6-yl |
| 9 | phenyl | 3-hydroxyphenyl |
| 10 | 4-fluorophenyl | 3-hydroxyphenyl |
| 11 | methoxymethyl | 3-hydroxyphenyl |
| 12 | indol-6-yl | 3-hydroxyphenyl |
| 13 | phenyl | N-pyrrolidinyl |
| 14 | 4-fluorophenyl | N-pyrrolidinyl |
| 15 | methoxymethyl | N-pyrrolidinyl |
| 16 | indol-6-yl | N-pyrrolidinyl |

Exemplary embodiments include compounds having the formula (XXI) or a pharmaceutically acceptable salt form thereof:

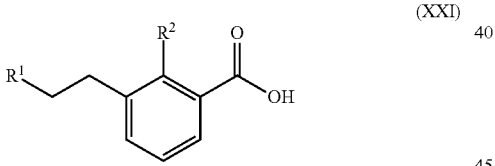

(XXI)

wherein non-limiting examples of $R^1$ and $R^2$ are defined herein below in Table 4.

TABLE 4

| Entry | $R^1$ | $R^2$ |
|---|---|---|
| 1 | phenyl | N-pyrrolyl |
| 2 | 4-fluorophenyl | N-pyrrolyl |
| 3 | methoxymethyl | N-pyrrolyl |
| 4 | indol-6-yl | N-pyrrolyl |
| 5 | phenyl | indol-6-yl |
| 6 | 4-fluorophenyl | indol-6-yl |
| 7 | methoxymethyl | indol-6-yl |
| 8 | indol-6-yl | indol-6-yl |
| 9 | phenyl | 3-hydroxyphenyl |
| 10 | 4-fluorophenyl | 3-hydroxyphenyl |
| 11 | methoxymethyl | 3-hydroxyphenyl |
| 12 | indol-6-yl | 3-hydroxyphenyl |
| 13 | phenyl | N-pyrrolidinyl |
| 14 | 4-fluorophenyl | N-pyrrolidinyl |
| 15 | methoxymethyl | N-pyrrolidinyl |
| 16 | indol-6-yl | N-pyrrolidinyl |

Exemplary embodiments include compounds having the formula (XXII) or a pharmaceutically acceptable salt form thereof:

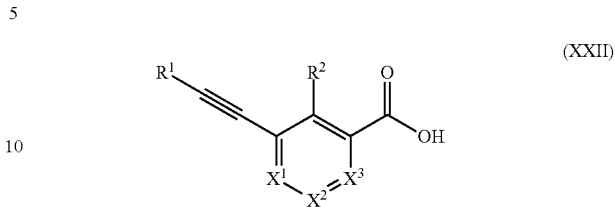

(XXII)

wherein non-limiting examples of $R^1$, $R^2$, $X^1$, $X^2$, and $X^3$ are defined herein below in Table 5.

TABLE 5

| Entry | $R^1$ | $R^2$ | $X^1$ | $X^2$ | $X^3$ |
|---|---|---|---|---|---|
| 1 | phenyl | N-pyrrolyl | CH | N | CH |
| 2 | 4-fluorophenyl | N-pyrrolyl | CH | N | CH |
| 3 | 3-methoxyphenyl | N-pyrrolyl | CH | N | CH |
| 4 | indol-6-yl | N-pyrrolyl | CH | N | CH |
| 5 | 2-hydroxy-prop-2-yl | N-pyrrolyl | CH | N | CH |
| 6 | phenyl | indol-6-yl | CH | N | CH |
| 7 | 4-fluorophenyl | indol-6-yl | CH | N | CH |
| 8 | 3-methoxyphenyl | indol-6-yl | CH | N | CH |
| 9 | indol-6-yl | indol-6-yl | CH | N | CH |
| 10 | 2-hydroxy-prop-2-yl | indol-6-yl | CH | N | CH |
| 11 | phenyl | N-pyrrolyl | CF | CH | CH |
| 12 | 4-fluorophenyl | N-pyrrolyl | CF | CH | CH |
| 13 | 3-methoxyphenyl | N-pyrrolyl | CF | CH | CH |
| 14 | indol-6-yl | N-pyrrolyl | CF | CH | CH |
| 15 | 2-hydroxy-prop-2-yl | N-pyrrolyl | CF | CH | CH |
| 16 | phenyl | indol-6-yl | CF | CH | CH |
| 17 | 4-fluorophenyl | indol-6-yl | CF | CH | CH |
| 18 | 3-methoxyphenyl | indol-6-yl | CF | CH | CH |
| 19 | indol-6-yl | indol-6-yl | CF | CH | CH |
| 20 | 2-hydroxy-prop-2-yl | indol-6-yl | CF | CH | CH |
| 21 | phenyl | N-pyrrolyl | CH | CF | CH |
| 22 | 4-fluorophenyl | N-pyrrolyl | CH | CF | CH |
| 23 | 3-methoxyphenyl | N-pyrrolyl | CH | CF | CH |
| 24 | indol-6-yl | N-pyrrolyl | CH | CF | CH |
| 25 | 2-hydroxy-prop-2-yl | N-pyrrolyl | CH | CF | CH |
| 26 | phenyl | indol-6-yl | CH | CF | CH |
| 27 | 4-fluorophenyl | indol-6-yl | CH | CF | CH |
| 28 | 3-methoxyphenyl | indol-6-yl | CH | CF | CH |
| 29 | indol-6-yl | indol-6-yl | CH | CF | CH |
| 30 | 2-hydroxy-prop-2-yl | indol-6-yl | CH | CF | CH |
| 31 | phenyl | N-pyrrolyl | CH | CCl | CH |
| 32 | 4-fluorophenyl | N-pyrrolyl | CH | CCl | CH |
| 33 | 3-methoxyphenyl | N-pyrrolyl | CH | CCl | CH |
| 34 | indol-6-yl | N-pyrrolyl | CH | CCl | CH |
| 35 | 2-hydroxy-prop-2-yl | N-pyrrolyl | CH | CCl | CH |
| 36 | phenyl | indol-6-yl | CH | CCl | CH |
| 37 | 4-fluorophenyl | indol-6-yl | CH | CCl | CH |
| 38 | 3-methoxyphenyl | indol-6-yl | CH | CCl | CH |
| 39 | indol-6-yl | indol-6-yl | CH | CCl | CH |
| 40 | 2-hydroxy-prop-2-yl | indol-6-yl | CH | CCl | CH |

For the purposes of the present invention, a compound depicted by the racemic formula will stand equally well for either of the two enantiomers or mixtures thereof, or in the case where a second chiral center is present, all diastereomers.

For the purposes of demonstrating the manner in which the compounds of the present invention are named and referred to herein, the compound having the formula:

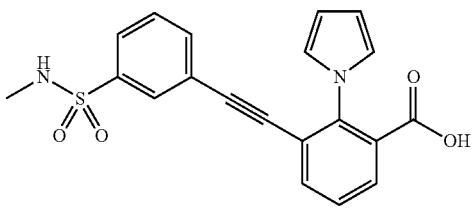 [SMILES: CNS(=O)(=O)c1cccc(C#Cc2cccc(C(=O)O)c2-n2cccc2)c1]

has the chemical name 3-(3-Methylsulfamoyl-phenylethynyl)-2-pyrrol-1-yl-benzoic acid.

For the purposes of demonstrating the manner in which the compounds of the present invention are named and referred to herein, the compound having the formula:

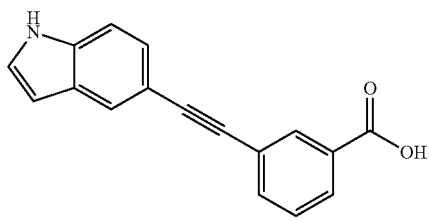 [SMILES: O=C(O)c1cccc(C#Cc2ccc3[nH]ccc3c2)c1]

has the chemical name 3-[2-(1H-indol-5-yl)ethynyl]benzoic acid.

For the purposes of demonstrating the manner in which the compounds of the present invention are named and referred to herein, the compound having the formula:

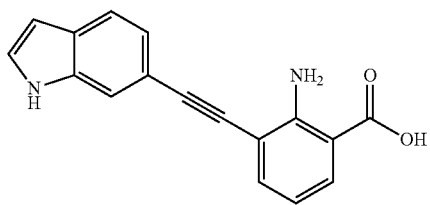 [SMILES: Nc1c(C#Cc2ccc3cc[nH]c3c2)cccc1C(=O)O]

has the chemical name 2-amino-3-[2-(1H-indol-6-yl)ethynyl]benzoic acid.

For the purposes of demonstrating the manner in which the compounds of the present invention are named and referred to herein, the compound having the formula:

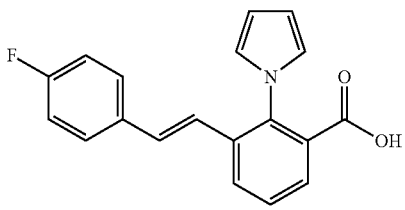 [SMILES: O=C(O)c1cccc(/C=C/c2ccc(F)cc2)c1-n1cccc1]

has the chemical name 3-[(E)-2-(4-fluorophenyl)ethenyl]-2-(1H-pyrrol-1-yl)benzoic acid.

For the purposes of demonstrating the manner in which the compounds of the present invention are named and referred to herein, the compound having the formula:

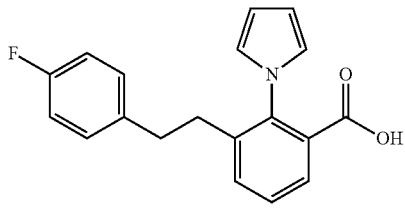 [SMILES: O=C(O)c1cccc(CCc2ccc(F)cc2)c1-n1cccc1]

has the chemical name 3-[2-(4-fluorophenyl)ethyl]-2-(1H-pyrrol-1-yl)benzoic acid.

For the purposes of the present invention, a compound depicted by the racemic formula will stand equally well for either of the two enantiomers having the formula or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Process

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), and subsequent editions, the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of formula (I) may be prepared according to the process outlined in schemes 1-21.

Accordingly, a suitably substituted compound of the formula (1), a known compound or compound prepared by known methods, is reacted with a suitably substituted compound of the formula (2), a known compound or compound prepared by known methods, in the presence of an acid such as hydrochloric acid, sulfuric acid, trifluoroacetic acid, and the like, in an organic solvent such as methanol, ethanol, N, N-dimethylformamide, tetrahydrofuran, 1,4-dioxane, methylene chloride and the like, optionally heated, optionally heated with microwave irradiation to provide a compound of the formula (3). Alternatively, a compound of the formula (1) may be reacted with trimethylsilyldiazomethane in an organic solvent such as methylene chloride, 1,2-dichloroethane, tetrahydrofuran, 1,4-dioxane, N, N-dimethylformamide, and the like to provide a compound of the formula (3). A compound of the formula (3) is then reacted with a compound of the formula (4), a known compound or compound prepared by known methods, in the presence of a catalyst, such as 4-chloropyridine hydrochloride, in an organic solvent such as methylene chloride, 1,2-dichloroethane, tetrahydrofuran, 1,4-dioxane, N, N-dimethylformamide, and the like optionally heated, optionally heated with microwave irradiation to provide a compound of the formula (5). Alternatively, a compound of the formula (3) reacted with a compound of the formula (6), a known compound or compound prepared by known methods, in the presence of an acid such as hydrochloric acid, sulfuric acid, trifluoroacetic acid, acetic acid, and the like, in an organic solvent such as methanol, ethanol, N, N-dimethylformamide, tetrahydrofuran, 1,4-dioxane, methylene chloride, 1,2-dichloroethane, and the like, optionally heated, optionally heated with microwave irradiation to provide a compound of the formula (5).

Scheme 1

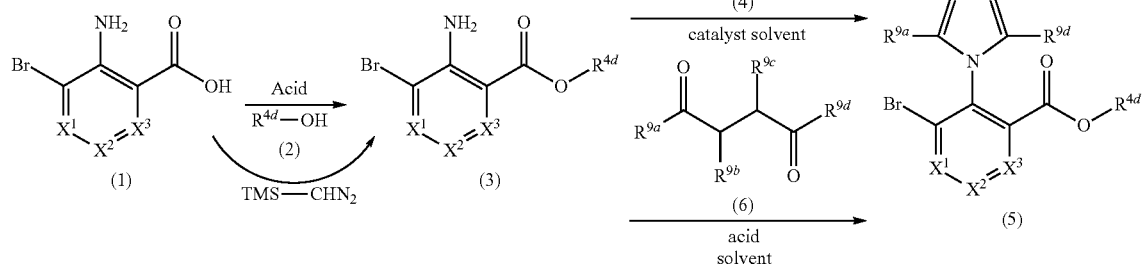

Scheme 2

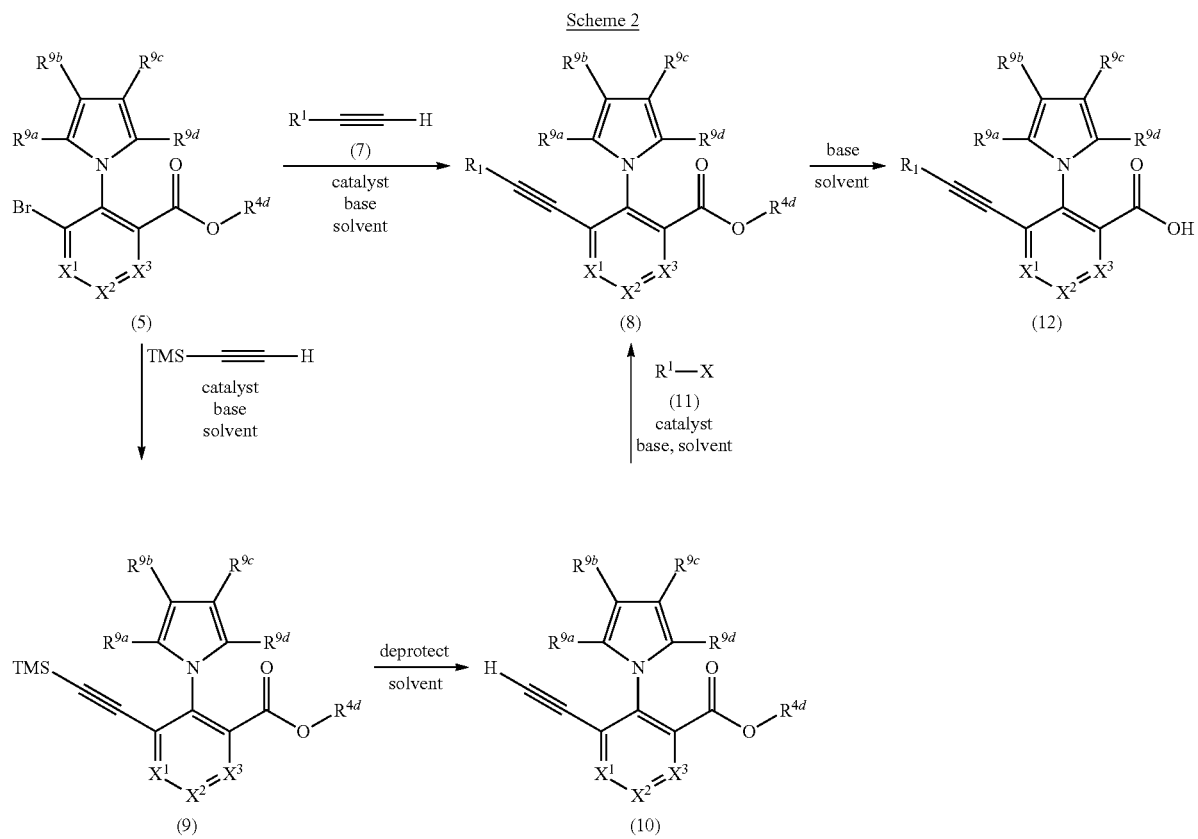

A compound of the formula (5) is reacted with a compound of the formula (7), a known compound or compound prepared by known methods, in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile) dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (8). Alternatively, a compound of the formula (5) is reacted with trimethylsilyl acetylene in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile) dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (9). A compound of the formula (9) is then deprotected by removal of the trimethylsily moiety by reacting a compound of the formula (9) with a fluoride source such as tetrabutylammonium fluoride, and the like in an organic solvent such as tetrahydrofuran, 1,4-dioxane, methylene chloride, 1,2-dichloroethane, and the like to provide a compound of the formula (10). A compound of the formula (10) is reacted with a compound of the formula (11), a known compound or compound prepared by known methods wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile) dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (8). A compound of the formula (8) is reacted with a base such as sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, and the like optionally heated, optionally heated with microwave irradiation to provide a compound of the formula (12).

Scheme 3

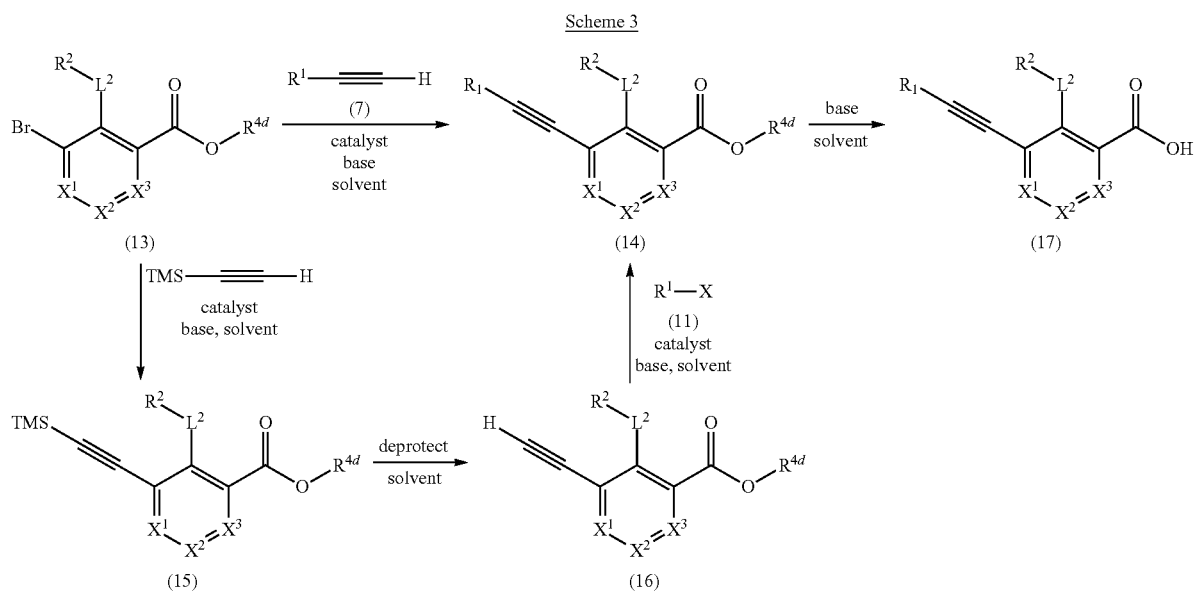

A compound of the formula (13) is reacted with a compound of the formula (7), a known compound or compound prepared by known methods, in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile) dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (14). Alternatively, a compound of the formula (13) is reacted with trimethylsilyl acetylene in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile) dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (15). A compound of the formula (15) is then deprotected by removal of the trimethylsily moiety by reacting a compound of the formula (15) with a fluoride source such as tetrabutylammonium fluoride, the like in an organic solvent such as tetrahydrofuran, 1,4-dioxane, methylene chloride, 1,2-dichloroethane, and the like to provide a compound of the formula (16). A compound of the formula (16) is reacted with a compound of the formula (11), a known compound or compound prepared by known methods wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile) dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (14). A compound of the formula (14) is reacted with a base such as sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, and the like optionally heated, optionally heated with microwave irradiation to provide a compound of the formula (17).

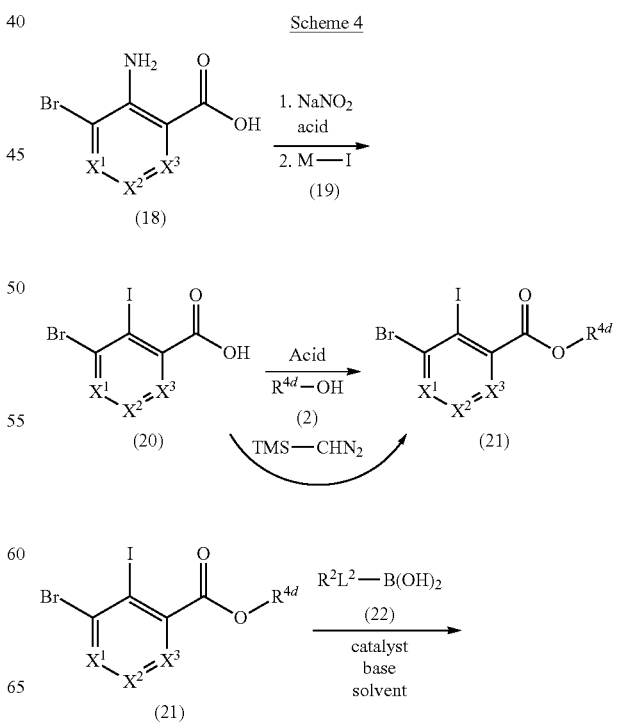

Scheme 4

-continued

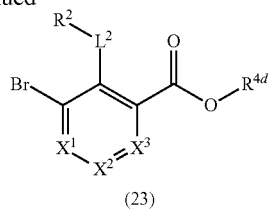

(23)

A compound of the formula (18) a known compound or compound prepared by known methods, is reacted with sodium nitrite in the presence of an acid such as hydrochloric acid, sulfuric acid, acetic acid, trifluoroacetic acid, and the like, in an organic solvent such as methanol, ethanol, N,N-dimethylformamide, tetrahydrofuran, 1,4-dioxane, and the like optionally heated, optionally heated with microwave irradiation. Further reaction with a compound of the formula (19) wherein M is a metal such as sodium, potassium, and the like in an organic solvent such as methanol, ethanol, N, N-dimethylformamide, tetrahydrofuran, 1,4-dioxane, and the like optionally heated, optionally heated with microwave irradiation to provide a compound of the formula (20). A compound of the formula (20) is reacted with a suitably substituted compound of the formula (2), a known compound or compound prepared by known methods, in the presence of an acid such as hydrochloric acid, sulfuric acid, trifluoroacetic acid, and the like, in an organic solvent such as methanol, ethanol, N, N-dimethylformamide, tetrahydrofuran, 1,4-dioxane, methylene chloride and the like, optionally heated, optionally heated with microwave irradiation to provide a compound of the formula (21). Alternatively, a compound of the formula (20) may be reacted with trimethylsilyldiazomethane in an organic solvent such as methylene chloride, 1,2-dichloroethane, tetrahydrofuran, 1,4-dioxane, N, N-dimethylformamide, and the like to provide a compound of the formula (21). A compound of the formula (21) is reacted with a compound of the formula (22), a known compound or compound prepared by known methods, in the presence of a palladium catalyst such as palladium (II) acetate, tetrakis(triphenylphosphine)palladium(0), dichlorobis (triphenylphosphine)palladium(II), palladium on carbon, bis(acetonitrile)dichloropalladium(II), and the like, in the presence of a base such as triethylamine, diisopropylethylamine, pyridine, 2,6-dimethylpyridine, sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, 1,2-dimethoxyethane and the like optionally heated, optionally heated with microwave irradiation to provide a compound of the formula (23).

Scheme 5

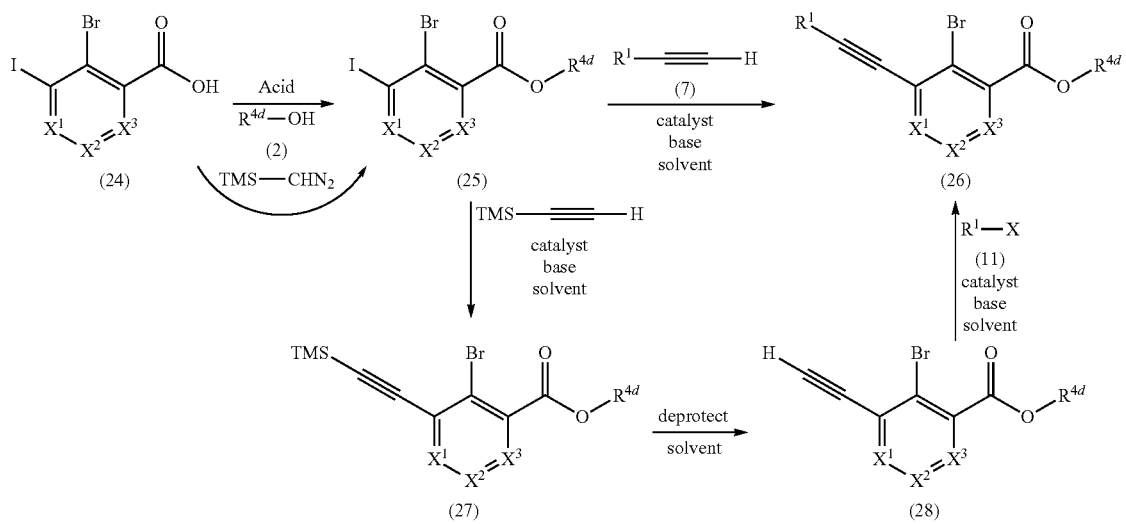

A compound of the formula (24), a known compound or compound prepared by known methods, is reacted with a suitably substituted compound of the formula (2), a known compound or compound prepared by known methods, in the presence of an acid such as hydrochloric acid, sulfuric acid, trifluoroacetic acid, and the like, in an organic solvent such as methanol, ethanol, N, N-dimethylformamide, tetrahydrofuran, 1,4-dioxane, methylene chloride and the like, optionally heated, optionally heated with microwave irradiation to provide a compound of the formula (25). Alternatively, a compound of the formula (24) may be reacted with trimethylsilyldiazomethane in an organic solvent such as methylene chloride, 1,2-dichloroethane, tetrahydrofuran, 1,4-dioxane, N, N-dimethylformamide, and the like to provide a compound of the formula (25). A compound of the formula (25) is reacted with a compound of the formula (7), a known compound or compound prepared by known methods, in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine) palladium(II), palladium on carbon, bis(acetonitrile)dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (26). Alternatively, a compound of the formula (25)

is reacted with trimethylsilyl acetylene in the presence of a base such as triethylamine, diisopropylethylamine, pyridine, 2,6-dimethylpyridine, and the like in the presence of a palladium catalyst such as palladium (II) acetate, tetrakis (triphenylphosphine)palladium(0), dichlorobis (triphenylphosphine)palladium(II), palladium on carbon, bis(acetonitrile)dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (27). A compound of the formula (27) is then deprotected by removal of the trimethylsily moiety by reacting a compound of the formula (27) with a fluoride source such as tetrabutylammonium fluoride, and the like in an organic solvent such as tetrahydrofuran, 1,4-dioxane, methylene chloride, 1,2-dichloroethane, and the like to provide a compound of the formula (28). A compound of the formula (28) is reacted with a compound of the formula (11), a known compound or compound prepared by known methods wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile) dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (26).

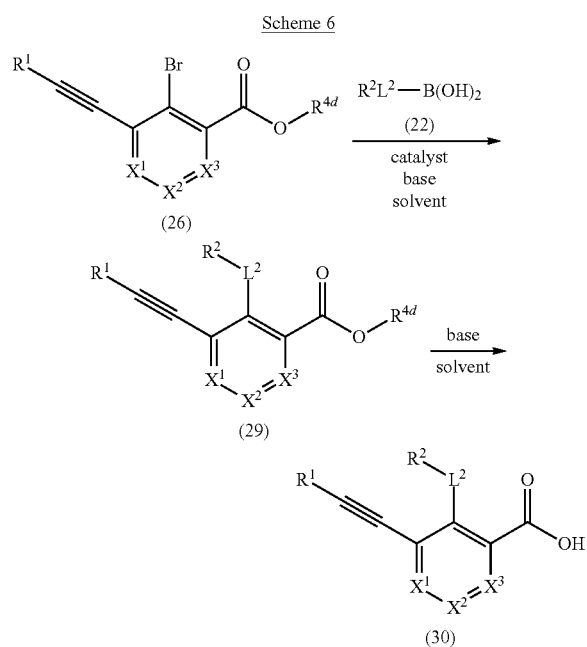

A compound of the formula (26), is reacted with a compound of the formula (22), a known compound or compound prepared by known methods, in the presence of a palladium catalyst such as palladium (II) acetate, tetrakis (triphenylphosphine)palladium(0), dichlorobis (triphenylphosphine)palladium(II), palladium on carbon, bis(acetonitrile)dichloropalladium(II), and the like, in the presence of a base such as triethylamine, diisopropylethylamine, pyridine, 2,6-dimethylpyridine, sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, 1,2-dimethoxyethane and the like optionally heated, optionally heated with microwave irradiation to provide a compound of the formula (29). A compound of the formula (29) is reacted with a base such as sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, and the like optionally heated, optionally heated with microwave irradiation to provide a compound of the formula (30).

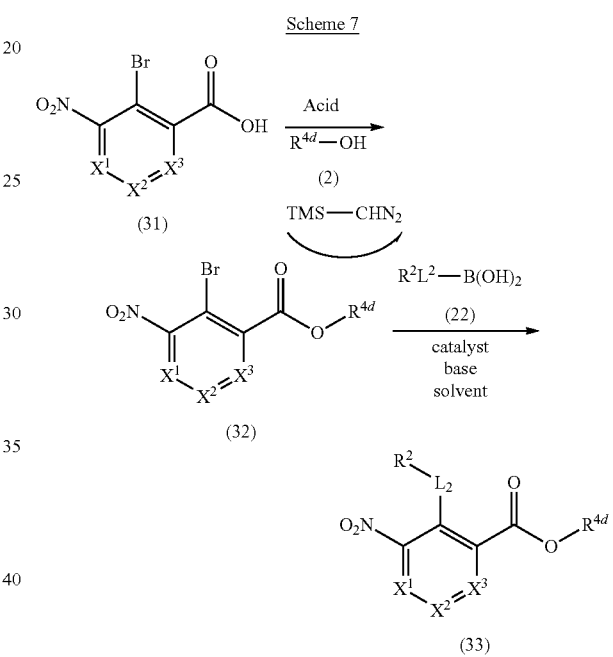

A compound of the formula (31), a known compound or compound prepared by known methods, is reacted with a suitably substituted compound of the formula (2), a known compound or compound prepared by known methods, in the presence of an acid such as hydrochloric acid, sulfuric acid, trifluoroacetic acid, and the like, in an organic solvent such as methanol, ethanol, N, N-dimethylformamide, tetrahydrofuran, 1,4-dioxane, methylene chloride and the like, optionally heated, optionally heated with microwave irradiation to provide a compound of the formula (32). Alternatively, a compound of the formula (31) may be reacted with trimethylsilyldiazomethane in an organic solvent such as methylene chloride, 1,2-dichloroethane, tetrahydrofuran, 1,4-dioxane, N, N-dimethylformamide, and the like to provide a compound of the formula (32). A compound of the formula (32) is reacted with a compound of the formula (22), a known compound or compound prepared by known methods, in the presence of a palladium catalyst such as palladium (II) acetate, tetrakis(triphenylphosphine)palladium(0), dichlorobis (triphenylphosphine)palladium(II), palladium on carbon, bis(acetonitrile)dichloropalladium(II), and the like, in the presence of a base such as triethylamine, diisopropylethylamine, pyridine, 2,6-dimethylpyridine, sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, 1,2-dimethoxyethane and the like, optionally heated, optionally heated with microwave irradiation to provide a compound of the formula (33).

dine, 2,6-dimethylpyridine, and the like in the presence of a palladium catalyst such as palladium (II) acetate, tetrakis (triphenylphosphine)palladium(0), dichlorobis (triphenylphosphine)palladium(II), palladium on carbon, bis(acetonitrile)dichloropalladium(II), and the like, in an organic solvent such as N, N-dimethylformamide, tetrahydrofuran, 1,4-dioxane, methylene chloride, 1,2-dichloroethane, and

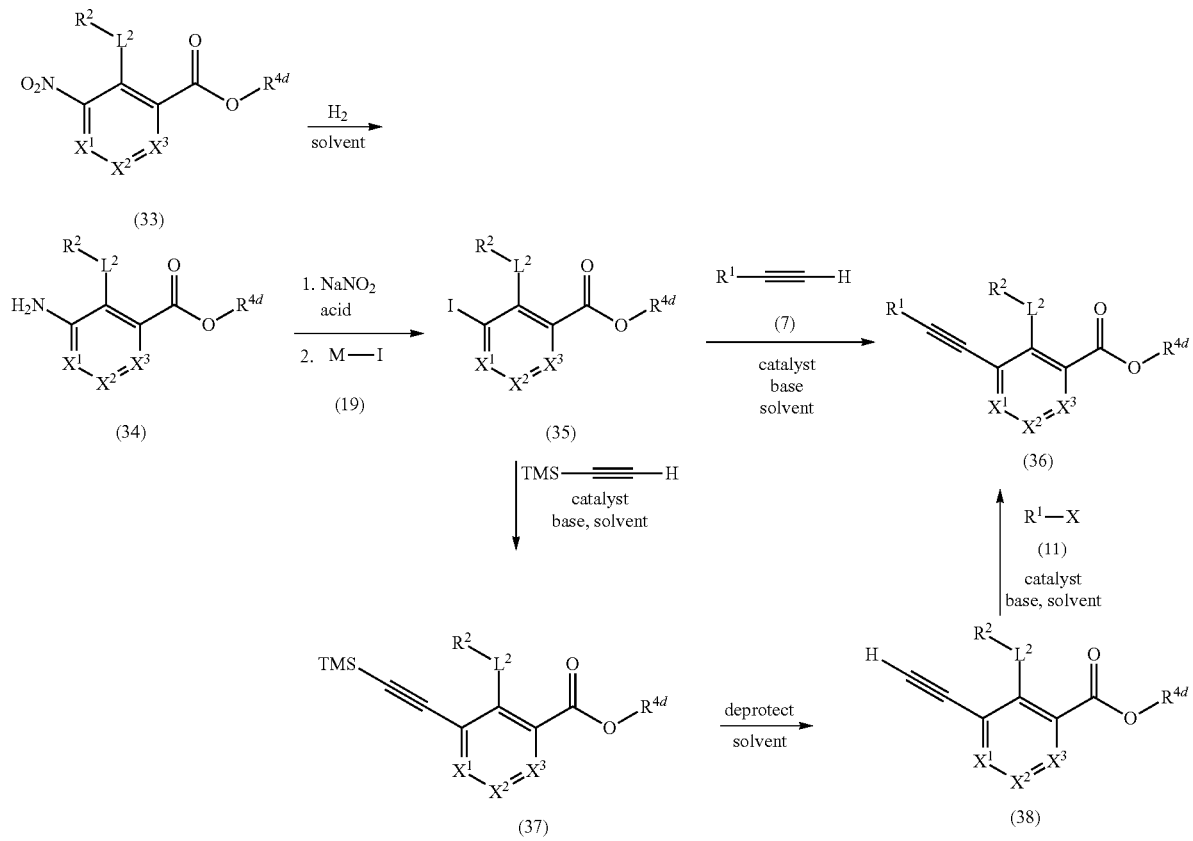

Scheme 8

A compound of the formula (33) is reacted with hydrogen in the presence of a catalyst such as palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as methanol, ethanol, N, N-dimethylformamide, tetrahydrofuran, 1,4-dioxane, and the like to provide a compound of the formula (34). A compound of the formula (34) is reacted with sodium nitrite in the presence of an acid such as hydrochloric acid, sulfuric acid, acetic acid, trifluoroacetic acid, and the like in an organic solvent such as methanol, ethanol, N, N-dimethylformamide, tetrahydrofuran, 1,4-dioxane, and the like optionally heated, optionally heated with microwave irradiation. Further reaction with a compound of the formula (19) wherein M is a metal such as sodium, potassium, and the like in an organic solvent such as methanol, ethanol, N, N-dimethylformamide, tetrahydrofuran, 1,4-dioxane, and the like optionally heated, optionally heated with microwave irradiation to provide a compound of the formula (35). A compound of the formula (35) is reacted with a compound of the formula (7), a known compound or compound prepared by known methods, in the presence of a base such as triethylamine, diisopropylethylamine, pyri- the like, optionally heated, optionally heated with microwave irradiation to provide a compound of the formula (36). Alternatively, a compound of the formula (35) is reacted with trimethylsilyl acetylene in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile) dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (37). A compound of the formula (37) is then deprotected by removal of the trimethylsily moiety by reacting a compound of the formula (37) with a fluoride source such as tetrabutylammonium fluoride, and the like in an organic solvent such as tetrahydrofuran, 1,4-dioxane, methylene chloride, 1,2-dichloroethane, and the like to provide a compound of the formula (38). A compound of the formula (38) is reacted with a compound of the formula (11), a known compound or compound prepared by known methods wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (36).

Scheme 9

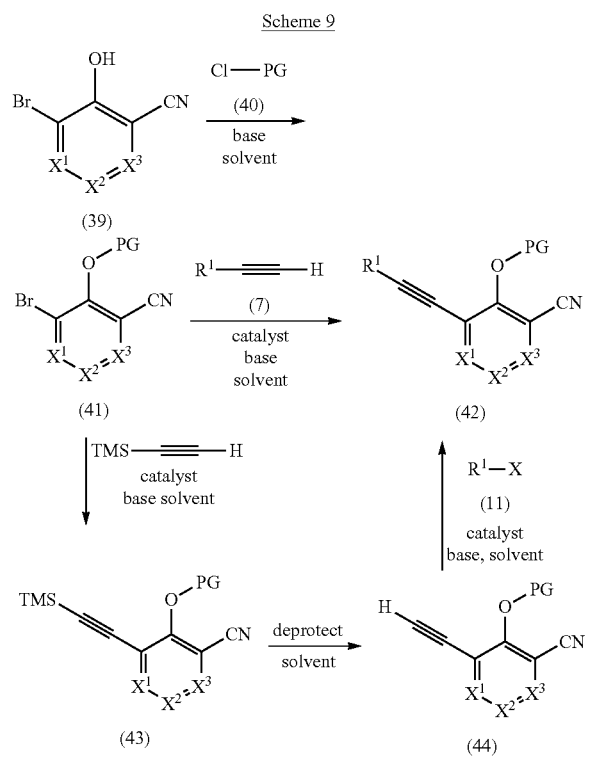

A compound of the formula (39), a known compound or compound prepared by known methods, is reacted with a compound of the formula (40) wherein PG is tert-butyldimethylsilyl, tert-butyldiphenylsilyl, acetyl, benzoyl and the like, in the presence of a base such as triethylamine, diisopropylethylamine, pyridine, 2,6-dimethylpyridine, and the like, in an organic solvent such as N, N-dimethylformamide, tetrahydrofuran, 1,4-dioxane, methylene chloride, 1,2-dichloroethane, and the like, to provide a compound of the formula (41). A compound of the formula (41) is reacted with a compound of the formula (7), a known compound or compound prepared by known methods, in the presence of a base such as triethylamine, diisopropylethylamine, pyridine, 2,6-dimethylpyridine, and the like in the presence of a palladium catalyst such as palladium (II) acetate, tetrakis (triphenylphosphine)palladium(0), dichlorobis (triphenylphosphine)palladium(II), palladium on carbon, bis(acetonitrile)dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (42). Alternatively, a compound of the formula (41) is reacted with trimethylsilyl acetylene in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (43). A compound of the formula (43) is then deprotected by removal of the trimethylsily moiety by reacting a compound of the formula (43) with an fluoride source such as tetrabutylammonium fluoride, and the like in an organic solvent such as tetrahydrofuran, 1,4-dioxane, methylene chloride, 1,2-dichloroethane, and the like to provide a compound of the formula (44). A compound of the formula (44) is reacted with a compound of the formula (11), a known compound or compound prepared by known methods wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (42).

Scheme 10

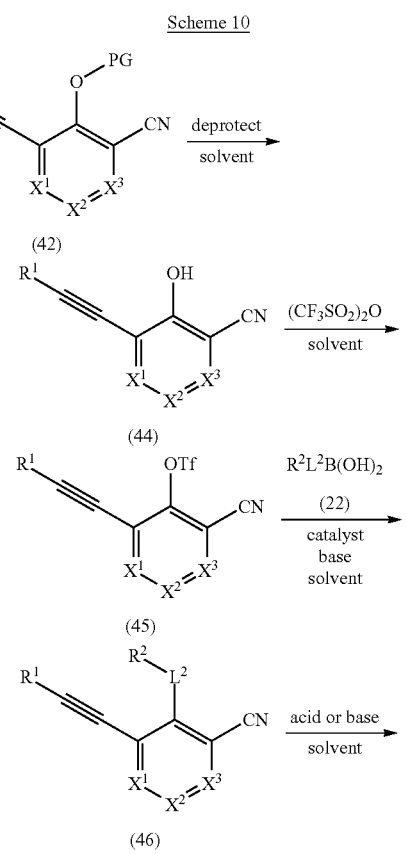

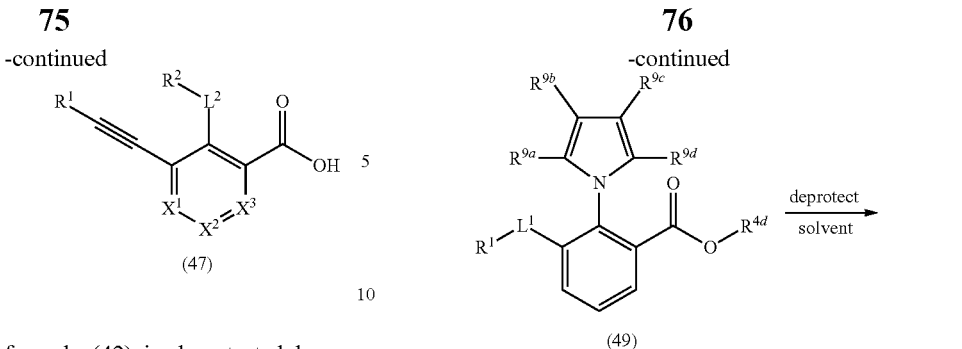

(47)

A compound of the formula (42) is deprotected by a fluoride source such as tetrabutylammounim fluoride and the like or a base such as aqueous sodium carbonate, potassium carbonate, cesium carbonate and the like, in an organic solvent such as methanol, ethanol, in an organic solvent such as tetrahydrofuran, 1,4-dioxane, and the like to provide a compound of the formula (44). A compound of the formula (44) is reacted with trifluoromethanesulfonic anhydride, in an organic solvent such as tetrahydrofuran, 1,4-dioxane, methylene chloride, 1,2-dichloroethane, N, N-dimethylformamide, and the like, optionally in the presence of a base such as triethylamine, diisopropylethylamine, pyridine, 2,6-dimethylpyridine, and the like, to provide a compound of the formula (45). A compound of the formula (45) is reacted with a compound of the formula (22), a known compound or compound prepared by known methods, in the presence of a palladium catalyst such as palladium (II) acetate, tetrakis (triphenylphosphine)palladium(0), dichlorobis (triphenylphosphine)palladium(II), palladium on carbon, bis(acetonitrile)dichloropalladium(II), and the like, in the presence of a base such as triethylamine, diisopropylethylamine, pyridine, 2,6-dimethylpyridine, sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, 1,2-dimethoxyethane and the like optionally heated, optionally heated with microwave irradiation to provide a compound of the formula (46). A compound of the formula (46) is then reacted with an acid such as hydrochloric acid, sulfuric acid, and the like, in a solvent such as water, N, N-dimethylformamide, tetrahydrofuran, 1,4-dioxane, and the like optionally heated, optionally heated with microwave irradiation to provide a compound of the formula (47). Alternatively, a compound of the formula (46) is reacted with a base such as sodium hydroxide, lithium hydroxide, potassium hydroxide, and the like, in a solvent such as water, methanol, ethanol, N, N-dimethylformamide, tetrahydrofuran, 1,4-dioxane, and the like optionally heated, optionally heated with microwave irradiation to provide a compound of the formula (47).

Scheme 11

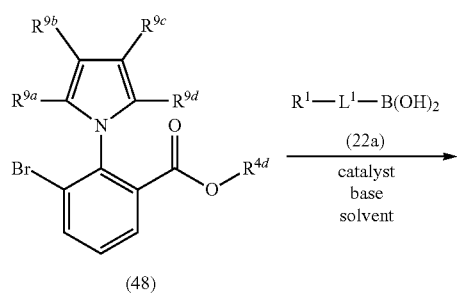

(48)

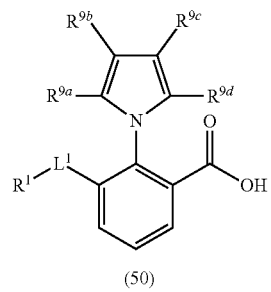

(49)

(50)

A compound of the formula (48) is reacted with a compound of the formula (22a), a known compound or compound prepared by known methods, in the presence of a palladium catalyst such as palladium (II) acetate, tetrakis (triphenylphosphine)palladium(0), dichlorobis (triphenylphosphine)palladium(II), palladium on carbon, bis(acetonitrile)dichloropalladium(II), and the like, in the presence of a base such as triethylamine, diisopropylethylamine, pyridine, 2,6-dimethylpyridine, sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, and the like optionally heated, optionally heated with microwave irradiation to provide a compound of the formula (49). A compound of the formula (49) is reacted with a base such as sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, and the like optionally heated, optionally heated with microwave irradiation to provide a compound of the formula (50).

Scheme 12

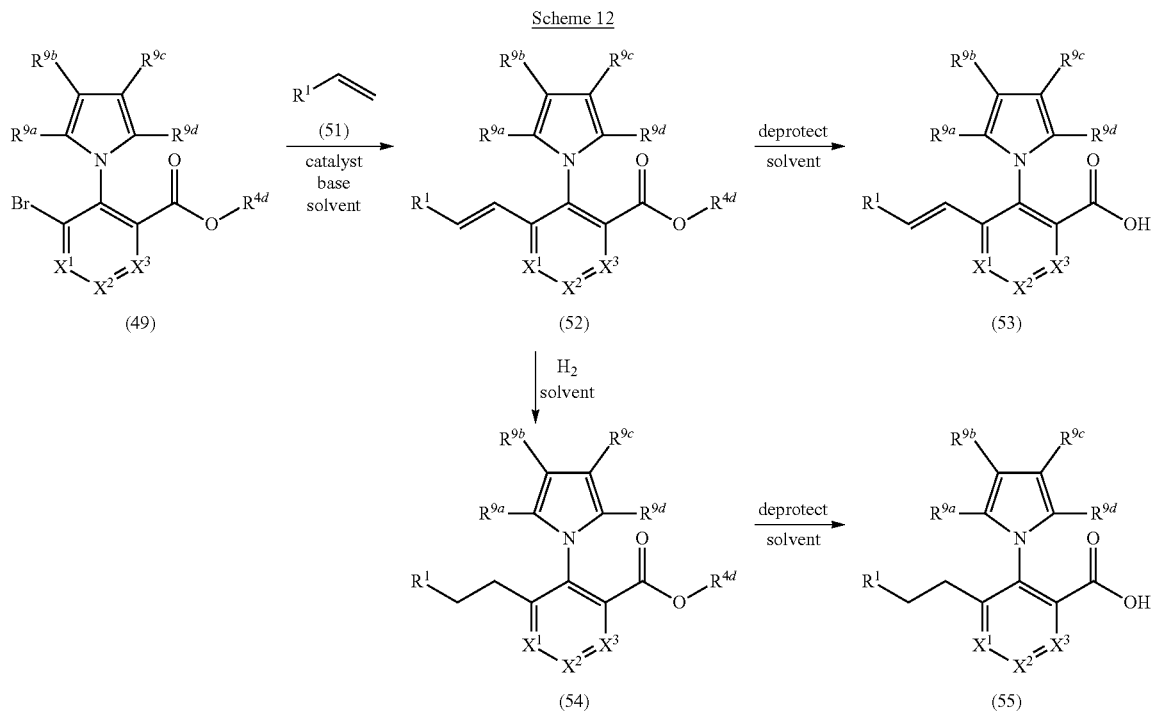

A compound of the formula (49) is reacted with a compound of the formula (51), a known compound or compound prepared by known methods, in the presence of a palladium catalyst such as palladium (II) acetate, tetrakis(triphenylphosphine)palladium(0), dichlorobis (triphenylphosphine)palladium(II), palladium on carbon, bis(acetonitrile) dichloropalladium(II), and the like, in the presence of a base such as triethylamine, diisopropylethylamine, pyridine, 2,6-dimethylpyridine, sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, and the like optionally heated, optionally heated with microwave irradiation to provide a compound of the formula (52). A compound of the formula (52) is reacted with a base such as sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, and the like optionally heated, optionally heated with microwave irradiation to provide a compound of the formula (53). Alternatively, a compound of the formula (52) is reacted with hydrogen in the presence of a catalyst such as palladium (II) acetate, tetrakis(triphenylphosphine) palladium(0), dichlorobis (triphenylphosphine)palladium (II), palladium on carbon, bis(acetonitrile)dichloropalladium(II), and the like, in an organic solvent such as methanol, ethanol, N, N-dimethylformamide, tetrahydrofuran, 1,4-dioxane, and the like to provide a compound of the formula (54). A compound of the formula (54) is reacted with a base such as sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, and the like optionally heated, optionally heated with microwave irradiation to provide a compound of the formula (55).

Scheme 13

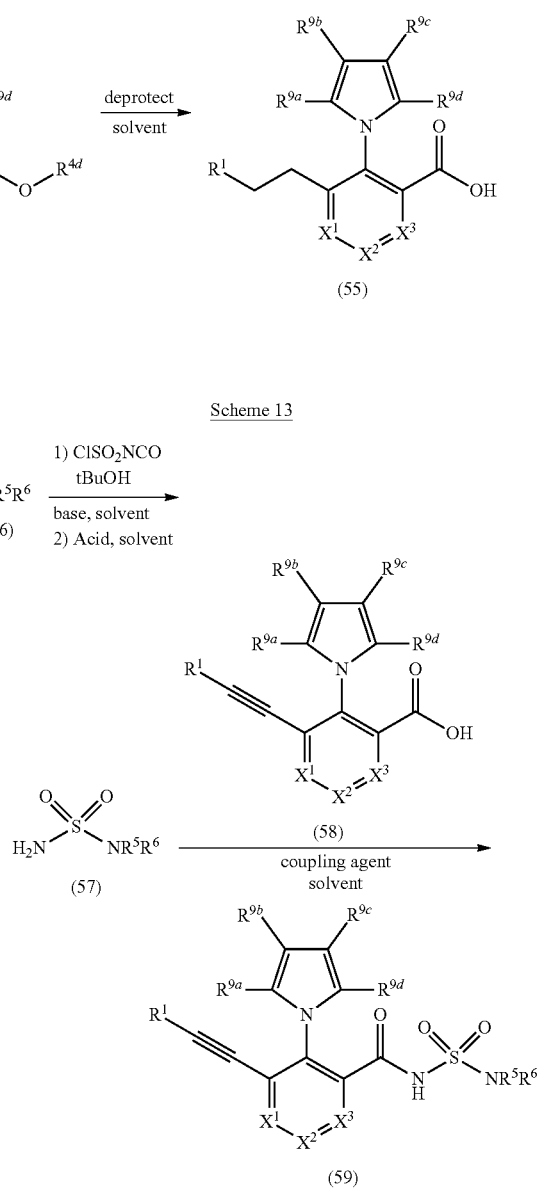

A compound of the formula (56), a known compound or compound prepared by known methods, is first, reacted with chlorosulfonylisocyanate and tert-butanol in the presence of a base such as triethylamine, diisopropylethylamine, pyridine, 2,6-dimethylpyridine, and the like in a solvent such as methylene chloride, 1,2-dichloroethane, N, N-dimethylformamide, tetrahydrofuran, 1,4-dioxane, and the like, and second, is deprotected by treatment with an acid such as hydrogen chloride, trifluoroacetic acid, and the like in an organic solvent such as ethyl acetate, methylene chloride and the like to provide a compound of the formula (57). A compound of the formula (57) is reacted with a compound of the formula (58) in the presence of coupling agent such as such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydronfuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide a compound of the formula (59).

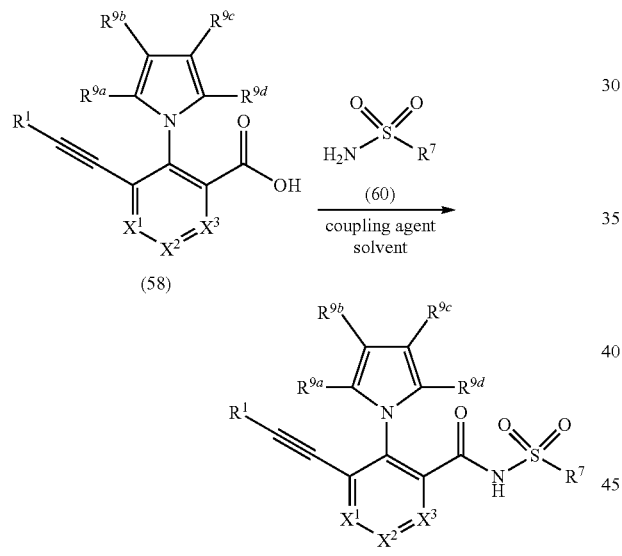

Alternatively, a compound of the formula (58) is reacted with a compound of the formula (60) in the presence of coupling agent such as such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydronfuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide a compound of the formula (61).

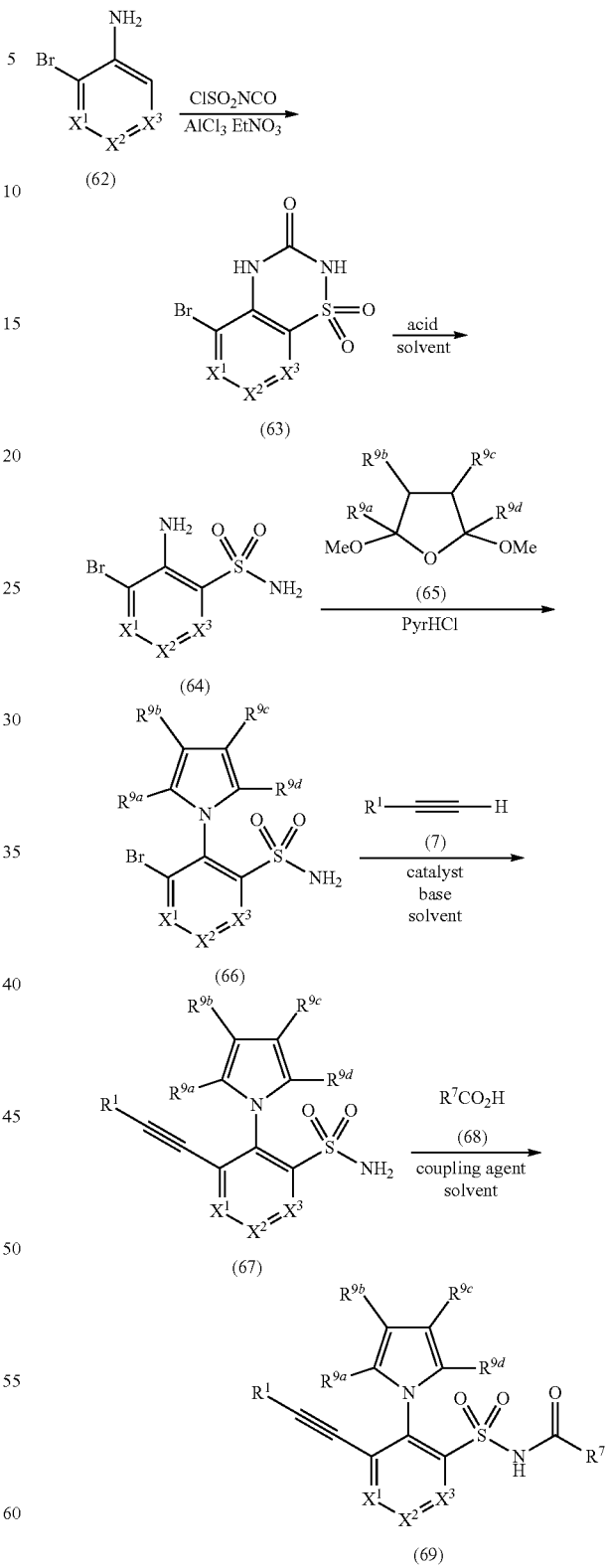

A compound of the formula (62), a known compound or compound prepared by known methods, is reacted with chlorosulfonylisocyanate in the presence of aluminum trichloride in nitroethane to provide a compound of the formula (63). A compound of the formula (63) is reacted with an acid such as hydrochloric acid, sulfuric acid, trifluoroacetic acid, acetic acid, and the like, optionally in an organic solvent such as tetrahydronfuran, 1,4-dioxane, dimethylformamide, methylene chloride, dichloroethane, methanol, ethanol, and the like, to provide a compound of the formula (64). A compound of the formula (64) is reacted with a compound of the formula (65) in the presence of pyridine hydrochloride, optionally in an organic solvent such as tetrahydronfuran, 1,4-dioxane, dimethylformamide, methylene chloride, 1,2-dichloroethane, methanol, ethanol, and the like, optionally heated, optionally heated with microwave irradiation to provide a compound of the formula (66). A compound of the formula (66) is reacted with a compound of the formula (7) a known compound or compound prepared by known methods, in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile) dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (67). A compound of the formula (67) is reacted with a compound of the formula (68), a known compound or compound prepared by known methods, in the presence of coupling agent such as such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyl-uronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydronfuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide a compound of the formula (69).

Scheme 16

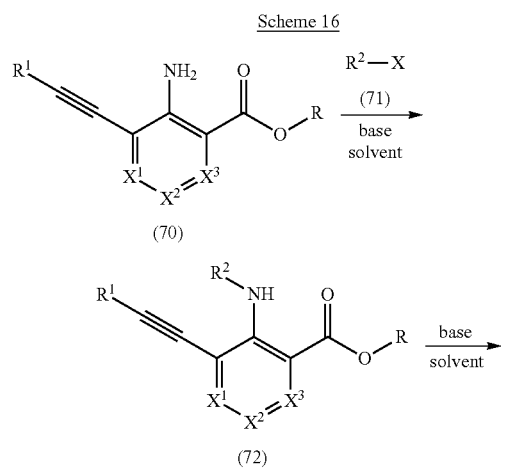

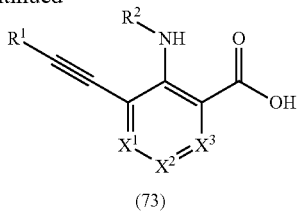

(73)

A compound of the formula (70) is reacted with a compound of the formula (71), a known compound or compound prepared by known methods wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like, in an organic solvent such as tetrahydronfuran, 1,4-dioxane, dimethylformamide, methylene chloride, 1,2-dichloroethane, and the like, to provide a compound of the formula (72). A compound of the formula (72) is reacted with a base such as sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, and the like optionally heated, optionally heated with microwave irradiation to provide a compound of the formula (73).

Scheme 17

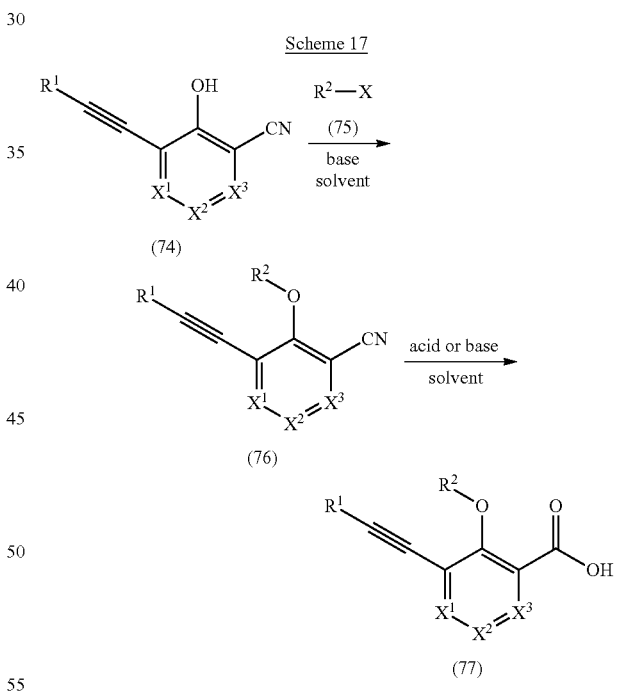

A compound of the formula (74) is reacted with a compound of the formula (75), a known compound or compound prepared by known methods wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like, in an organic solvent such as tetrahydronfuran, 1,4-dioxane, dimethylformamide, methylene chloride, 1,2-dichloroethane, and the like, to provide a compound of the formula (76). A compound of the formula (76) is then reacted with an acid such as hydrochloric acid, sulfuric acids, and the like, in a solvent such as water, methanol, ethanol, N, N-dimethylformamide, tetrahydrofuran, 1,4-dioxane, and the like optionally heated, optionally heated with microwave irradiation to provide a compound of the formula (77). Alternatively, a compound of the formula (76) is reacted with a base such as sodium hydroxide, lithium hydroxide, potassium hydroxide, and the like, in a solvent such as water, methanol, ethanol, N, N-dimethylformamide, tetrahydrofuran, 1,4-dioxane, and the like optionally heated, optionally heated with microwave irradiation to provide a compound of the formula (77).

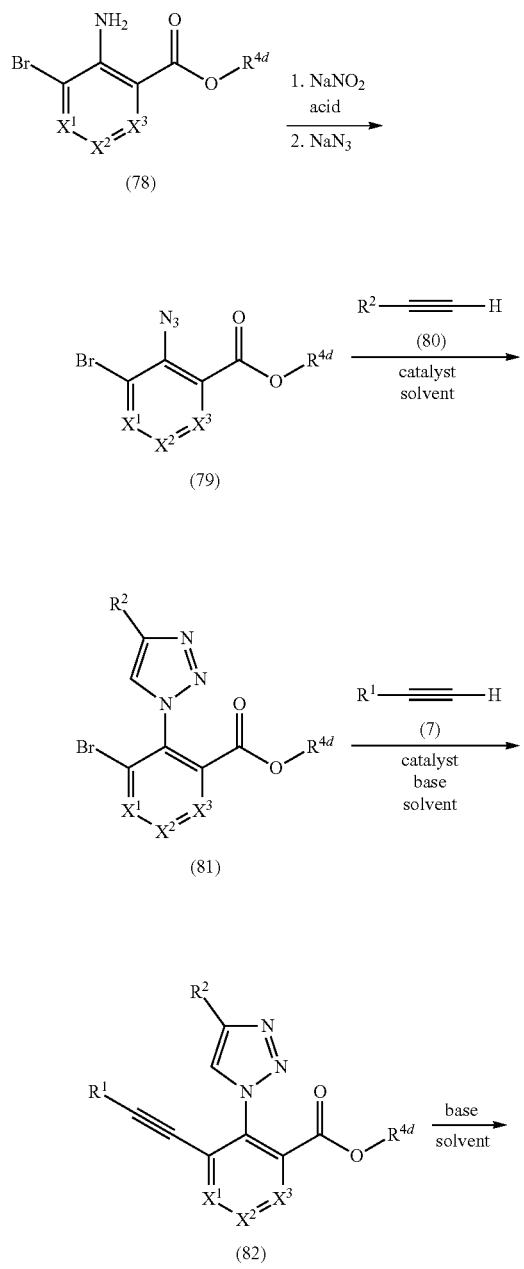

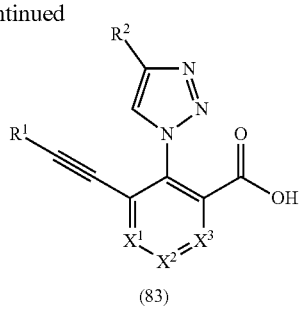

A compound of the formula (78), a known compound or compound prepared by known methods, is reacted with sodium nitrite in the presence of an acid such as hydrochloric acid, sulfuric acid, tetrafluoroboric acid, and the like, optionally in a solvent such as water, methanol, ethanol, N, N-dimethylformamide, tetrahydrofuran, 1,4-dioxane, and the like, followed by reaction with sodium azide in a solvent such as water, methanol, ethanol, N, N-dimethylformamide, tetrahydrofuran, 1,4-dioxane, and the like to provide a compound of the formula (79). A compound of the formula (79) is reacted with a compound of the formula (80), a known compound or compound prepared by known methods, in the presence of a catalyst such as sodium ascorbate and copper sulfate and the like, in an organic solvent such as methanol, ethanol, N, N-dimethylformamide, tetrahydrofuran, 1,4-dioxane, and the like, optionally heated, optionally heated with microwave irradiation to provide a compound of the formula (81). A compound of the formula (81) is reacted with a compound of the formula (7), a known compound or compound prepared by known methods, in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (82). A compound of the formula (82) is reacted with a base such as sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, and the like optionally heated, optionally heated with microwave irradiation to provide a compound of the formula (83).

Scheme 19

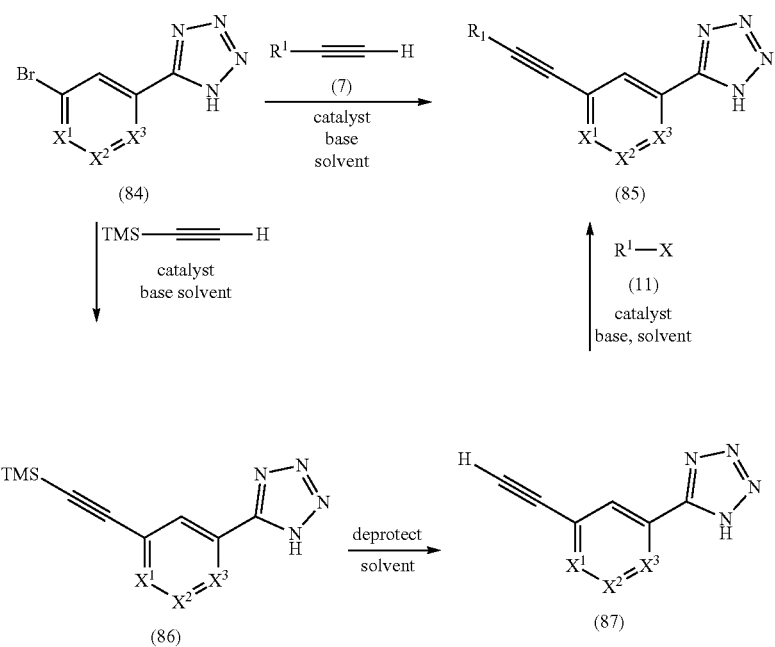

A compound of the formula (84), a known compound or a compound prepared by known methods, is reacted with a compound of the formula (7), a known compound or a compound prepared by known methods, in the presence of a base such as triethylamine, diisopropylethylamine, pyridine, 2,6-dimethylpyridine, and the like, in the presence of a palladium catalyst such as palladium (II) acetate, tetrakis (triphenylphosphine)palladium(0), dichlorobis (triphenylphosphine)palladium(II), palladium on carbon, bis(acetonitrile)dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (85). Alternatively, a compound of the formula (84) is reacted with trimethylsilyl acetylene in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile) dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (86). A compound of the formula (86) is then deprotected by removal of the trimethylsily moiety by reacting a compound of the formula (86) with an fluoride source such as tetrabutylammonium fluoride, and the like in an organic solvent such as tetrahydrofuran, 1,4-dioxane, methylene chloride, 1,2-dichloroethane, N, N-dimethylformamide, and the like to provide a compound of the formula (87). Alternatively, a compound of the formula (86) is reacted with hydrogen fluoride in the presence of a base such as pyridine, 2,6-dimethylpyridine, triethyl amine, and the like, optionally in a solvent such as tetrahydrofuran, 1,4-dioxane, methylene chloride, 1,2-dichloroethane, N, N-dimethylformamide, and the like to provide a compound of the formula (87). Alternatively, a compound of the formula (86) is reacted with a base such as aqueous sodium hydroxide, potassium hydroxide, lithium hydroxide and the like, in a solvent such as tetrahydrofuran, 1,4-dioxane, methylene chloride, 1,2-dichloroethane, N, N-dimethylformamide, and the like, optionally heated, optionally heated with microwave irradiation to provide a compound of the formula (87). A compound of the formula (87) is reacted with a compound of the formula (11), a known compound or compound prepared by known methods wherein X is a leaving group such as chloride, bromide, iodide, methanesulfonate, trifluoromethanesulfonate, tosylate, and the like in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis (acetonitrile)dichloropalladium(II), and the like, in an organic solvent such as N, N-dimethylformamide, tetrahydrofuran, 1,4-dioxane, methylene chloride, 1,2-dichloroethane, and the like, optionally heated, optionally heated with microwave irradiation to provide a compound of the formula (85).

Scheme 20

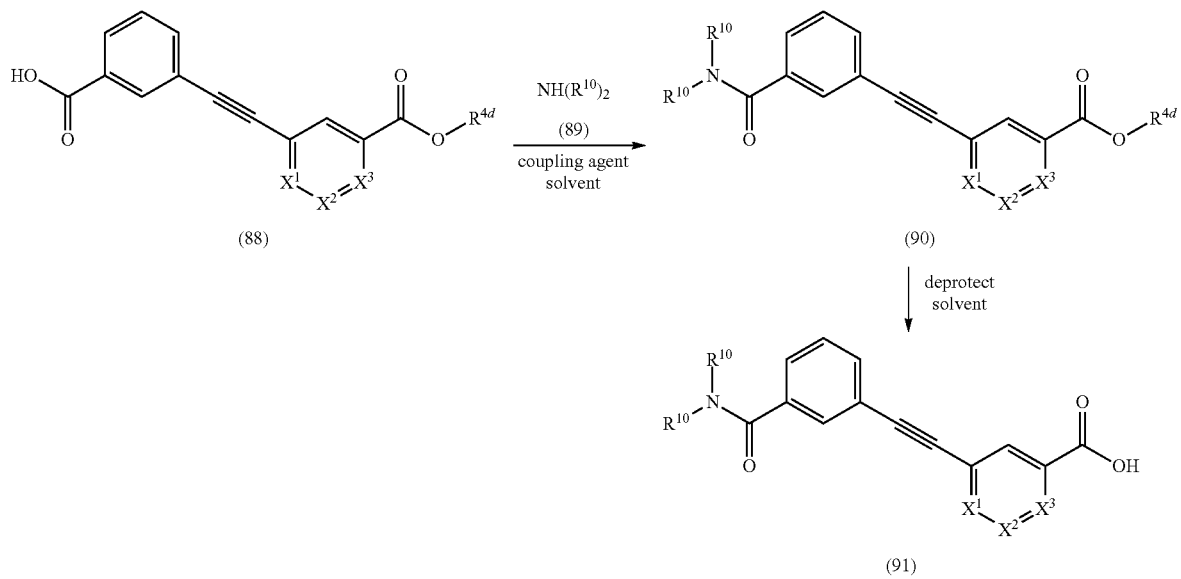

A compound of the formula (88), a known compound or compound prepared by known methods, is reacted with a compound of the formula (89), a known compound or compound prepared by known means, in the presence of coupling agent such as such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidino-phosphonium hexafluorophosphate, and the like, in an organic solvent such as tetrahydronfuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide a compound of the formula (90). A compound of the formula (90) is reacted with a base such as sodium hydroxide, lithium hydroxide, potassium hydroxide, sodium carbonate, lithium carbonate, potassium carbonate, and the like, in an organic solvent such as methanol, ethanol, N, N-dimethylformamide, tetrahydrofuran, 1,4-dioxane, and the like optionally heated, optionally heated with microwave irradiation to provide a compound of the formula (91). Alternatively, a compound of the formula (90) is reacted with an acid such as trifluoroacetic acid, hydrochloric acid, sulfuric acid, and the like, optionally in the presence of a solvent such as methanol, ethanol, N, N-dimethylformamide, tetrahydrofuran, 1,4-dioxane, methylene chloride and the like optionally heated, optionally heated with microwave irradiation to provide a compound of the formula (91).

Scheme 21

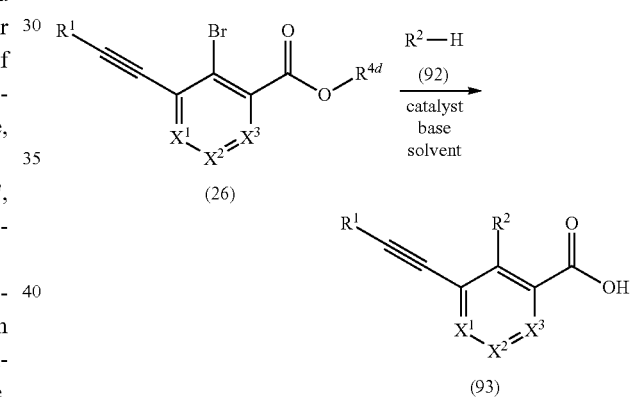

A compound of the formula (26), a known compound or compound prepared by known methods, is reacted with a compound of the formula (92), a known compound or a compound prepared by known methods, in the presence of a base such as potassium phosphate, cesium carbonate, potassium carbonate sodium carbonate, sodium tert-butoxide and the like in the presence of a copper catalyst such as copper iodide and the like, or a palladium catalyst such as palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as N, N-dimethylformamide, tetrahydrofuran, 1,4-dioxane, toluene, 1,2-dichloroethane, and the like, optionally heated, optionally heated with microwave irradiation to provide a compound of the formula (93).

The examples provided below provide representative methods for preparing exemplary compounds of the present invention. The skilled practitioner will know how to substitute the appropriate reagents, starting materials and purification methods known to those skilled in the art, in order to prepare the compounds of the present invention.

$^1$H-NMR spectra were obtained on a Varian Mercury 300-MHz NMR. Purity (%) and mass spectral data were determined with a Waters Alliance 2695 HPLC/MS (Waters Symmetry C18, 4.6×75 mm, 3.5 μm) with a 2996 diode array detector from 210-400 nm.

EXAMPLES

Examples 1-177 provide a method for preparing representative compound of formula (I). The skilled practitioner will know how to substitute the appropriate reagents, starting materials and purification methods known to those skilled in the art, in order to prepare additional compounds of the present invention. Preparative HPLC purification utilizes a gradient of 5-95% Acetonitrile in water (with 0.1% trifluoroacetic acid) over 15 minutes.

Example 1: Synthesis of 3-(3-methylsulfamoyl-phenylethynyl)-2-pyrrol-1-yl-benzoic acid

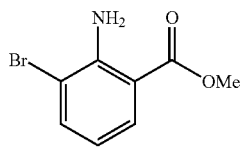 [SMILES: COC(=O)c1cccc(Br)c1N]

2-Amino-3-bromo-benzoic acid methyl ester: 2-Amino-3-bromo-benzoic acid (5 g, 23 mmol) was dissolved in methanol (30 mL), concentrated sulfuric acid (1 mL) was added dropwise and the reaction mixture was refluxed at 80° C. for 24 hours, allowed to cool to ambient temperature and then concentrated at reduced pressure. The residue was diluted by water (10 mL) and basified with saturated sodium bicarbonate solution, extracted by ethyl acetate (20 mL×3). The organic layer was dried (anhydrous magnesium sulfate), concentrated and purified by column chromatography through a silica gel cartridge (80 g) eluting with ethyl acetate/hexane (10%) to give the product as a colorless oil (5 g, 95%).

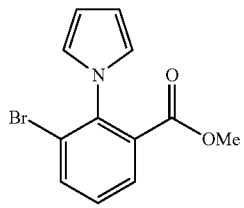 [SMILES: COC(=O)c1cccc(Br)c1-n1cccc1]

3-Bromo-2-pyrrol-1-yl-benzoic acid methyl ester. 2,5-Dimethoxy-tetrahydrofuran (1.7 g, 13 mmol) and 4-chloropyridine HCl salt (2 g, 13 mmol) were mixed in anhydrous 1,4-dioxane (30 mL) and stirred at room temperature for 15 minutes. To the solution was added 2-amino-3-bromo-benzoic acid methyl ester (3 g, 13 mmol) and the reaction mixture was refluxed at 120° C. for 2 hours. After cooling to ambient temperature, the crude mixture was filtered through celite and washed with ethyl acetate. The filtrate was concentrated and purified by column chromatography through a silica gel cartridge (80 g) eluting with ethyl acetate/hexane (10%-20%) to give the product as a white solid (3.2 g, 87%).

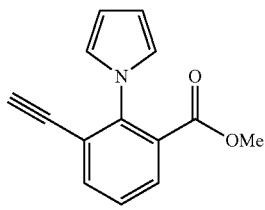 [SMILES: C#Cc1cccc(C(=O)OC)c1-n1cccc1]

3-Ethynyl-2-pyrrol-1-yl-benzoic acid methyl ester. To a pressure flask was loaded a mixture of 3-bromo-2-pyrrol-1-yl-benzoic acid methyl ester (4 g, 14.2 mmol), Pd(PPh$_3$)$_2$Cl$_2$ (501 mg, 0.71 mmol) and CuI (270 mg, 1.42 mmol) in triethylamine (40 mL), the mixture was degassed with N$_2$ for 10 minutes, trimethylsilylacetylene (10 mL) was added and the mixture was further degassed for 3 minutes. The flask was sealed with a PTFE plug and heated at 86° C. for 17 hour. After cooling to ambient temperature, the crude mixture was filtered through celite and washed with dichloromethane. The filtrate was concentrated and purified by column chromatography through a silica gel cartridge (80 g) eluting with ethyl acetate/hexane (5%-20%) to give a solid intermediate. The solid intermediate was dissolved in tetrahedrofuran (20 mL), tetrabutylammonium fluoride (1 N in THF, 20 mL, 20 mmol) was added and the reaction mixture was stirred for 10 minutes and concentrated. The residue was purified by column chromatography through a silica gel cartridge (80 g) eluting with ethyl acetate/hexane (10-20%) to give the product as a white solid (1.7 g, 53% for 2 steps)

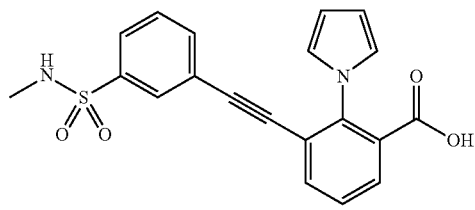 [SMILES: CNS(=O)(=O)c1cccc(C#Cc2cccc(C(=O)O)c2-n2cccc2)c1]

3-(3-Methylsulfamoyl-phenylethynyl)-2-pyrrol-1-yl-benzoic acid. A mixture of 3-ethynyl-2-pyrrol-1-yl-benzoic acid methyl ester (40 mg, 0.18 mmol), 3-bromo-N-methyl-benzenesulfonamide (90 mg, 0.36 mmol), palladium tetrakis-triphenylphosphine (21 mg, 0.018 mmol) and copper iodide (6.8 mg, 0.036 mmol), potassium carbonate (50 mg, 0.36 mmol) in 1,2-dimethoxyethane/water (1 mL/0.2 mL) was degassed with N$_2$ for 5 minutes and then heated at 60° C. for 4 hours. After cooling to ambient temperature, the crude mixture was filtered through celite and washed with dichloromethane. The filtrate was concentrated and purified by preparative thin layered chromatography eluting with ethyl acetate/hexane (30%) to give the ester intermediate. To the ester intermediate in tetrahydrofuran/methanol (1 mL/0.2 mL) was added sodium hydroxide solution (2 N in water, 0.2 mL, 0.4 mmol) and the solution was stirred at room temperature for 18 hours. 1 N hydrochloric acid aqueous solution was added dropwise until pH=1 and the reaction mixture was purified through preparative HPLC to give 19 mg (28% for 2 steps) of the pure product as a white solid. $^1$H NMR (CDCl$_3$) δ 7.87 (dd, J=7.8, 1.6 Hz, 1H), 7.82-7.72 (m, 3H), 7.49-7.30 (m, 3H), 6.88 (t, J=2.2 Hz, 2H), 6.34 (t, J=2.2 Hz, 2H), 2.6 (s, 3H). MS (ESI) m/z 380.9 (M+1)$^+$.

Example 2: Synthesis of 3-(1H-indol-3-ylethynyl)-2-pyrrol-1-yl-benzoic acid

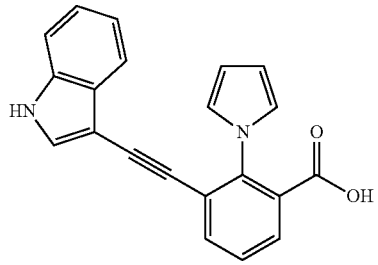 [SMILES: O=C(O)c1cccc(C#Cc2c[nH]c3ccccc23)c1-n1cccc1]

3-(1H-Indol-3-ylethynyl)-2-pyrrol-1-yl-benzoic acid was prepared by the same procedure as example 1. $^1$H NMR (CDCl$_3$) δ 7.87 (dd, J=7.8, 1.6 Hz, 1H), 7.82-7.72 (m, 3H), 7.49-7.30 (m, 3H), 6.88 (t, J=2.2 Hz, 2H), 6.34 (t, J=2.2 Hz, 2H), 2.6 (s, 3H). MS (ESI) m/z 380.9 (M+1)$^+$.

Example 3: Synthesis of 3-[2-(3-methanesulfonamidophenyl)ethynyl]-2-(1H-pyrrol-1-yl)benzoic acid

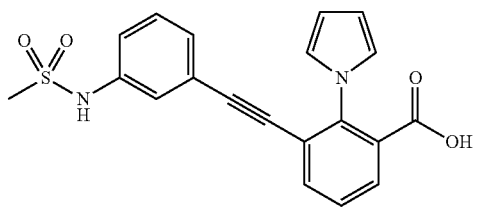 [SMILES: CS(=O)(=O)Nc1cccc(C#Cc2cccc(C(=O)O)c2-n2cccc2)c1]

3-[2-(3-methanesulfonamidophenyl)ethynyl]-2-(1H-pyrrol-1-yl)benzoic acid was prepared by the same procedure as example 1. $^1$H NMR (300 MHz, CDCl$_3$) δ=7.84 (dd, J=1.6, 7.8 Hz, 1H), 7.74 (dd, J=1.5, 7.6 Hz, 1H), 7.44 (t, J=7.8 Hz, 1H), 7.28-7.08 (m, 4H), 6.88 ((t, J=2.1 Hz, 2H), 6.33 (t, J=2.1 Hz, 2H), 2.65 (s, 3H). MS (ESI) m/z 380.9 (M+1)$^+$.

Example 4: Synthesis of 2-(1H-pyrrol-1-yl)-3-[2-(3-sulfamoylphenyl)ethynyl]benzoic acid

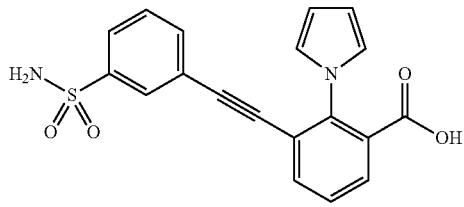 [SMILES: NS(=O)(=O)c1cccc(C#Cc2cccc(C(=O)O)c2-n2cccc2)c1]

2-(1H-pyrrol-1-yl)-3-[2-(3-sulfamoylphenyl)ethynyl] benzoic acid was prepared by the same procedure as example 1. $^1$H NMR (300 MHz, CDCl$_3$) δ=7.97-7.82 (m, 3H), 7.75 (d, J=8.8 Hz, 1H), 7.56-7.38 (m, 3H), 6.89 (t, J=2.1 Hz, 2H), 6.35 (t, J=2.1 Hz, 2H). MS (ESI) m/z 366.9 (M+1)$^+$.

Example 5: Synthesis of 3-[2-(3-carbamoylphenyl)ethynyl]-2-(1H-pyrrol-1-yl)benzoic acid

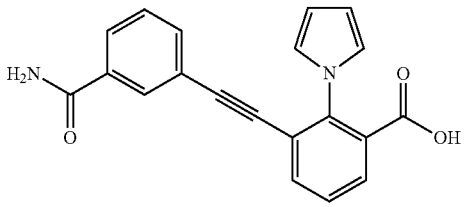 [SMILES: NC(=O)c1cccc(C#Cc2cccc(C(=O)O)c2-n2cccc2)c1]

3-[2-(3-carbamoylphenyl)ethynyl]-2-(1H-pyrrol-1-yl) benzoic acid was prepared by the same procedure as example 1. $^1$H NMR (300 MHz, CDCl$_3$) δ=7.84 (dd, J=1.6, 7.8 Hz, 1H), 7.82-7.72 (m, 3H), 7.50-7.25 (m, 3H), 6.88 ((t, J=2.1 Hz, 2H), 6.33 (t, J=2.1 Hz, 2H). MS (ESI) m/z 330.9 (M+1)$^+$.

Example 6: Synthesis of 3-(2-{imidazo[1,2-a]pyridin-6-yl}ethynyl)-2-(1H-pyrrol-1-yl)benzoic acid

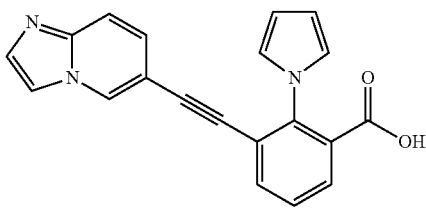 [SMILES: O=C(O)c1cccc(C#Cc2ccc3nccn3c2)c1-n1cccc1]

3-(2-{imidazo[1,2-a]pyridin-6-yl}ethynyl)-2-(1H-pyrrol-1-yl)benzoic acid was prepared by the same procedure as example 1. $^1$H NMR (300 MHz, CDCl$_3$) δ=8.24 (s, 1H), 8.05 (d, J=9.1 Hz, 1H), 7.92-7.83 (m, 2H), 7.74-7.64 (m, 2H), 7.51-7.43 (m, 2H), 6.85 (t, J=2.1 Hz, 2H), 6.33 (t, J=2.1 Hz, 2H). MS (ESI) m/z 328.0 (M+1)$^+$.

Example 7: Synthesis of 3-[2-(2-hydroxypyridin-4-yl)ethynyl]-2-(1H-pyrrol-1-yl)benzoic acid

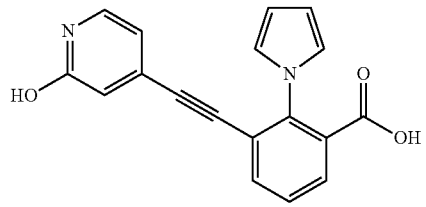 [SMILES: O=C(O)c1cccc(C#Cc2ccnc(O)c2)c1-n1cccc1]

3-[2-(2-hydroxypyridin-4-yl)ethynyl]-2-(1H-pyrrol-1-yl) benzoic acid was prepared by the same procedure as example 1. $^1$H NMR (300 MHz, CDCl$_3$) δ=8.19 (br. s., 1H), 8.03 (br. s., 1H), 7.90 (d, J=7.7 Hz, 1H), 7.75 (d, J=7.5 Hz, 1H), 7.48 (t, J=7.7 Hz, 1H), 7.31-7.28 (m, 1H), 6.86 (t, J=2.1 Hz, 2H), 6.34 (t, J=2.1 Hz, 2H). MS (ESI) m/z 305.0 (M+1)$^+$.

Example 8: Synthesis of 3-[2-(1H-indazol-6-yl)ethynyl]-2-(1H-pyrrol-1-yl)benzoic acid

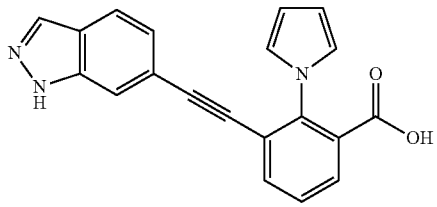 [SMILES: O=C(O)c1cccc(C#Cc2ccc3cn[nH]c3c2)c1-n1cccc1]

3-[2-(1H-indazol-6-yl)ethynyl]-2-(1H-pyrrol-1-yl)benzoic acid was prepared by the same procedure as example 1. ¹H NMR (300 MHz, CDCl₃) δ=8.02 (br. S., 1H), 7.85 (dd, J=1.8, 7.8 Hz, 1H), 7.78 (dd, J=1.5, 7.7 Hz, 1H), 7.70-7.59 (m, 3H), 7.46 (t, J=7.9 Hz, 1H), 7.12 (d, J=8.2 Hz, 1H), 6.93 (t, J=2.1 Hz, 2H), 6.37 (t, J=2.1 Hz, 2H). MS (ESI) m/z 328.0 (M+1)⁺.

Example 9: Synthesis of 3-{2-[3-(3,3-dimethyl-2-oxoazetidin-1-yl)phenyl]ethynyl}-2-(1H-pyrrol-1-yl)benzoic acid

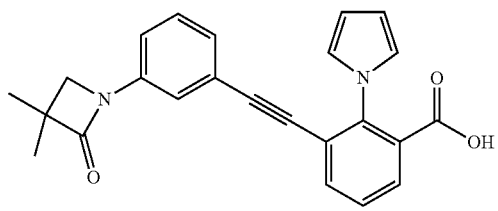 [SMILES: CC1(C)CN(c2cccc(C#Cc3cccc(C(=O)O)c3-n3cccc3)c2)C1=O]

3-{2-[3-(3,3-dimethyl-2-oxoazetidin-1-yl)phenyl]ethynyl}-2-(1H-pyrrol-1-yl)benzoic acid: To a pressure tube was added a mixture of 3-bromo-2-pyrrol-1-yl-benzoic acid methyl ester (50 mg, 0.18 mmol), 1-(3-ethynyl-phenyl)-3,3-dimethyl-azetidin-2-one (71 mg, 0.28 mmol), Pd(PPh₃)₂Cl₂ (12.6 mg, 0.018 mmol) and CuI (6.9 mg, 0.036 mmol) in triethylamine (1 mL). The mixture was degassed with N₂ for 10 minutes and then heated at 90° C. for 17 hours. After cooling to ambient temperature, the crude mixture was filtered through celite and washed with dichloromethane. The filtrate was concentrated and purified by column chromatography through preparative thin layer chromatography eluting with ethyl acetate/hexane (30%) to give a solid intermediate. To the solid intermediate in tetrahydrofuran/methanol (1 mL/0.2 mL) was added sodium hydroxide solution (2 N in water, 0.2 mL, 0.4 mmol) and the solution was stirred at room temperature for 18 hours. 1 N hydrochloric acid aqueous solution was added dropwise until pH=1 and the reaction mixture was purified through preparative HPLC to give 12 mg (17% for 2 steps) of the pure product as a yellow solid. ¹H NMR (300 MHz, CDCl₃) δ=7.85 (dd, J=1.6, 7.8 Hz, 1H), 7.74 (dd, J=1.6, 7.8 Hz, 1H), 7.53-7.35 (m, 2H), 7.34-7.22 (m, 1H), 7.15 (t, J=5.0 Hz, 1H), 7.05 (d, J=7.6 Hz, 1H), 6.89 (t, J=2.1 Hz, 2H), 6.35 (t, J=2.1 Hz, 2H), 3.44 (s, 2H), 2.56 (s, 6H). MS (ESI) m/z 385.1 (M+1)⁺.

Example 10: Synthesis of 3-(2-{3-[(2-carboxy-2,2-dimethylethyl)amino]phenyl}ethynyl)-2-(1H-pyrrol-1-yl)benzoic acid

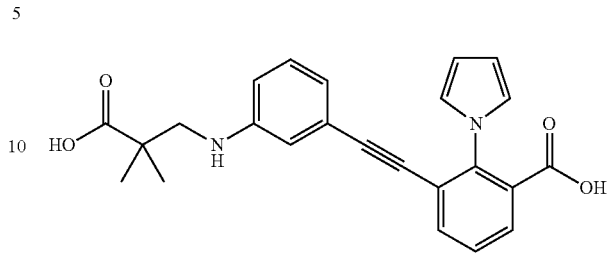

3-(2-{3-[(2-carboxy-2,2-dimethylethyl)amino]phenyl}ethynyl)-2-(1H-pyrrol-1-yl)benzoic acid was isolated as a second product in purifying example 9. ¹H NMR (300 MHz, CDCl₃) δ=7.82 (d, J=7.6 Hz, 1H), 7.72 (d, J=7.7 Hz, 1H), 7.42 (t, J=7.8 Hz, 1H), 7.08 (t, J=7.7 Hz, 1H), 6.88 (t, J=2.1 Hz, 2H), 6.75-6.58 (m, 3H), 6.33 (t, J=2.1 Hz, 2H), 3.22 (s, 2H), 1.30 (s, 6H). MS (ESI) m/z 403.1 (M+1)⁺.

Example 11: Synthesis of 3-(2-{imidazo[1,2-a]pyrazin-3-yl}ethynyl)-2-(1H-pyrrol-1-yl)benzoic acid

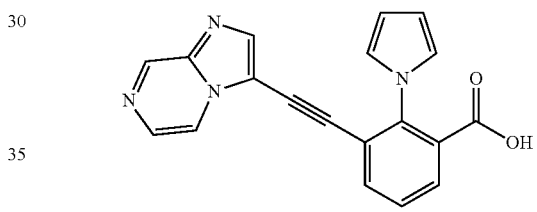

3-(2-{imidazo[1,2-a]pyrazin-3-yl})ethynyl)-2-(1H-pyrrol-1-yl)benzoic acid was prepared by the same procedure as example 1. ¹H NMR (300 MHz, DMSO) δ=13.1 (br. s., 1H), 9.15 (d, J=1.5 Hz, 1H), 8.12-8.04 (m, 2H), 7.95-7.89 (m, 2H), 7.82 (d, J=7.6 Hz, 1H), 7.61 (t, J=7.7 Hz, 1H), 6.97 (t, J=2.2 Hz, 2H), 6.30 (t, J=2.2 Hz, 2H). MS (ESI) m/z 328.9 (M+1)⁺.

Example 12: Synthesis of 3-(2-{imidazo[1,2-a]pyridin-3-yl})ethynyl)-2-(1H-pyrrol-1-yl)benzoic acid

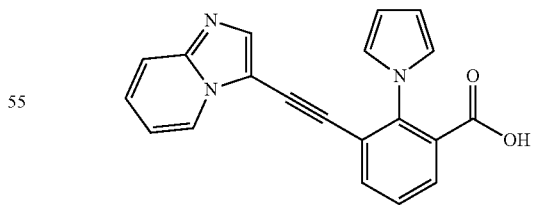

3-(2-{imidazo[1,2-a]pyridin-3-yl})ethynyl)-2-(1H-pyrrol-1-yl)benzoic acid was prepared by the same procedure as example 1. ¹H NMR (300 MHz, CDCl₃) δ=7.94 (dd, J=1.6, 7.8 Hz, 1H), 7.91-7.84 (m, 2H), 7.81 (dd, J=1.5, 7.9 Hz, 1H), 7.76-7.70 (m, 1H), 7.58-7.50 (m, 2H), 7.07 (t, J=6.9 Hz, 1H), 6.89 (t, J=2.1 Hz, 2H), 6.40 (t, J=2.1 Hz, 2H). MS (ESI) m/z 328.0 (M+1)⁺.

Example 13: Synthesis of 3-(2-{imidazo[1,2-a]pyridin-5-yl)}ethynyl)-2-(1H-pyrrol-1-yl)benzoic acid

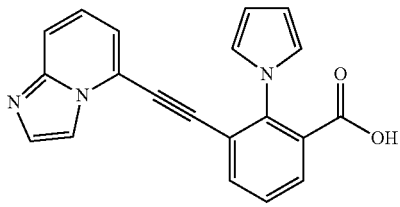 [SMILES: O=C(O)c1cccc(C#Cc2cccc3nccn23)c1-n1cccc1]

3-(2-{imidazo[1,2-a]pyridin-5-yl}ethynyl)-1-yl)benzoic acid was prepared by the same procedure as example 1. $^{1}$H NMR (300 MHz, CDCl$_3$) δ=8.14 (d, J=9.1 Hz, 1H), 8.03 (dd, J=1.5, 7.9 Hz, 1H), 7.89 (dd, J=1.6, 7.8 Hz, 1H), 7.81 (d, J=4.1 Hz, 1H), 7.66-7.56 (m, 2H), 7.38-7.30 (m, 2H), 6.89 (t, J=2.0 Hz, 2H), 6.41 (t, J=2.0 Hz, 2H). MS (ESI) m/z 328.0 (M+1)$^{+}$.

Example 14: Synthesis of 2-(1H-pyrrol-1-yl)-3-(2-{1H-pyrrolo[2,3-b]pyridin-5-yl}ethynyl)benzoic acid

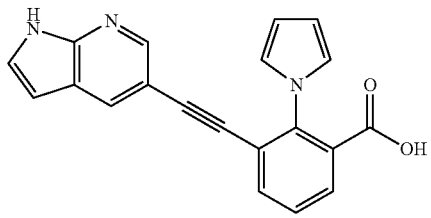 [SMILES: O=C(O)c1cccc(C#Cc2cnc3[nH]ccc3c2)c1-n1cccc1]

2-(1H-pyrrol-1-yl)-3-(2-{1H-pyrrolo[2,3-b]pyridin-5-yl}ethynyl)benzoic acid was prepared by the same procedure as example 1. $^{1}$H NMR (300 MHz, CDCl$_3$) δ=8.15 (br. s., 1H), 8.01 (s, 1H), 7.87 (s, 1H), 7.74 (dd, J=1.6, 7.6 Hz, 1H), 7.67 (dd, J=1.6, 7.9 Hz, 1H), 7.31 (t, J=7.8 Hz, 1H), 7.31-7.23 (m, 1H), 6.83 (t, J=2.2 Hz, 2H), 6.46-6.31 (m, 1H), 6.27 (t, J=2.2 Hz, 2H). MS (ESI) m/z 328.0 (M+1)$^{+}$.

Example 15: Synthesis of 3-[2-(1-methyl-1H-indol-4-yl)ethynyl]-2-(1H-pyrrol-1-yl)benzoic acid

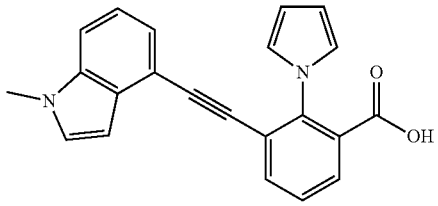 [SMILES: Cn1ccc2c(C#Cc3cccc(C(=O)O)c3-n3cccc3)cccc21]

3-[2-(1-methyl-1H-indol-4-yl)ethynyl]-2-(1H-pyrrol-1-yl)benzoic acid was prepared by the same procedure as example 1. $^{1}$H NMR (300 MHz, CDCl$_3$) δ=7.81 (dt, J=1.5, 7.8 Hz, 2H), 7.44 (t, J=7.8 Hz, 1H), 7.22-7.07 (m, 3H), 6.94 (t, J=2.2 Hz, 2H), 6.43 (d, J=3.2 Hz, 1H), 6.35 (t, J=2.2 Hz, 2H), 3.79 (s, 3H). MS (ESI) m/z 341.0 (M+1)$^{+}$.

Example 16: Synthesis of 3-[2-(1-methyl-1H-indol-5-yl)ethynyl]-2-(1H-pyrrol-1-yl)benzoic acid

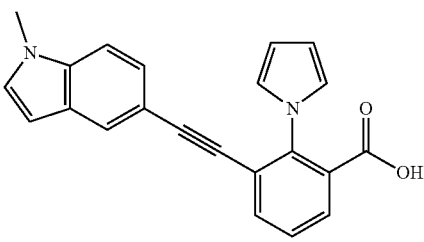 [SMILES: Cn1ccc2cc(C#Cc3cccc(C(=O)O)c3-n3cccc3)ccc21]

3-[2-(1-methyl-1H-indol-5-yl)ethynyl]-2-(1H-pyrrol-1-yl)benzoic acid was prepared by the same procedure as example 1. $^{1}$H NMR (300 MHz, CDCl$_3$) δ=7.87-7.55 (m, 3H), 7.53-7.40 (m, 1H), 7.27-7.19 (m, 2H), 7.05 (d, J=2.9 Hz, 1H), 7.00-6.85 (m, 2H), 6.46 (d, J=2.9 Hz, 1H), 6.40-6.25 (m, 2H), 3.78 (s, 3H). MS (ESI) m/z 341.0 (M+1)$^{+}$.

Example 17: Synthesis of 3-[2-(1-benzothiophen-6-yl)ethynyl]-2-(1H-pyrrol-1-yl)benzoic acid

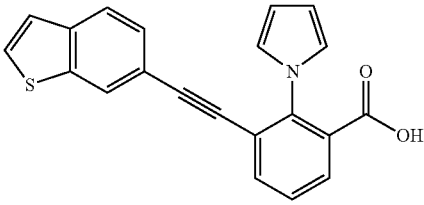 [SMILES: O=C(O)c1cccc(C#Cc2ccc3ccsc3c2)c1-n1cccc1]

3-[2-(1-benzothiophen-6-yl)ethynyl]-2-(1H-pyrrol-1-yl)benzoic acid was prepared by the same procedure as example 1. $^{1}$H NMR (300 MHz, CDCl$_3$) δ=7.90 (dd, J=1.6, 7.8 Hz, 1H), 7.82-7.75 (m, 3H), 7.52-7.41 (m, 2H), 7.32-7.28 (m, 2H), 6.91 (t, J=2.1 Hz, 2H), 6.40 (t, J=2.2 Hz, 2H). MS (ESI) m/z 344.0 (M+1)$^{+}$.

Example 18: Synthesis of 3-[2-(1H-indol-7-yl)ethynyl]-2-(1H-pyrrol-1-yl)benzoic acid

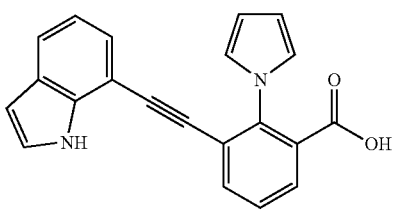 [SMILES: O=C(O)c1cccc(C#Cc2cccc3cc[nH]c23)c1-n1cccc1]

3-[2-(1H-indol-7-yl)ethynyl]-2-(1H-pyrrol-1-yl)benzoic acid was prepared by the same procedure as example 1. $^{1}$H NMR (300 MHz, CDCl$_3$) δ=8.24 (br. s., 1H), 7.89 (dd, J=1.6, 7.8 Hz, 1H), 7.83 (dd, J=1.6, 7.8 Hz, 1H), 7.62 (d, J=7.9 Hz, 1H), 7.51 (t, J=7.9 Hz, 1H), 7.35-7.26 (m, 1H), 7.18 (t, J=2.8 Hz, 1H), 7.04 (t, J=7.7 Hz, 1H), 6.97 (t, J=2.2 Hz, 2H), 6.56-6.43 (m, 3H). MS (ESI) m/z 327.0 (M+1)$^{+}$.

Example 19: Synthesis of 3-{2-[2-(hydroxymethyl)phenyl]ethynyl}-2-(1H-pyrrol-1-yl)benzoic acid

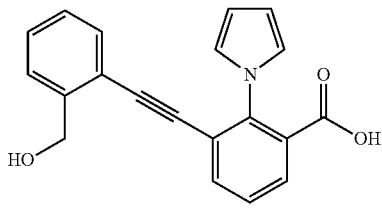 [SMILES: O=C(O)c1cccc(C#Cc2ccccc2CO)c1-n1cccc1]

3-{2-[2-(hydroxymethyl)phenyl]ethynyl}-2-(1H-pyrrol-1-yl)benzoic acid was prepared by the same procedure as example 1. $^1$H NMR (300 MHz, DMSO) δ=7.81 (dd, J=1.6, 7.8 Hz, 1H), 7.74 (dd, J=1.4, 7.6 Hz, 1H), 7.60-7.34 (m, 3H), 7.30-7.19 (m, 2H), 6.87 (t, J=2.2 Hz, 2H), 6.20 (t, J=2.2 Hz, 2H), 5.18 (t, J=5.6 Hz, 1H), 4.45 (d, J=5.0 Hz, 2H). MS (ESI) m/z 317.9 (M+1)$^+$.

Example 20: Synthesis of 3-{2-[4-(hydroxymethyl)phenyl]ethynyl}-2-(1H-pyrrol-1-yl)benzoic acid

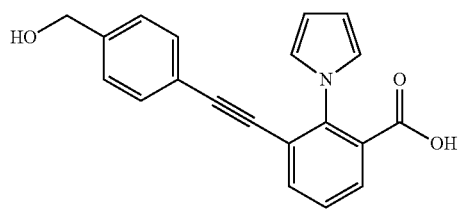 [SMILES: O=C(O)c1cccc(C#Cc2ccc(CO)cc2)c1-n1cccc1]

3-{2-[4-(hydroxymethyl)phenyl]ethynyl}-2-(1H-pyrrol-1-yl)benzoic acid was prepared by the same procedure as example 1. $^1$H NMR (300 MHz, CDCl$_3$) δ=7.82 (dd, J=1.6, 7.8 Hz, 1H), 7.73 (dd, J=1.6, 7.8 Hz, 1H), 7.42 (t, J=7.8 Hz, 1H), 7.35-7.27 (m, 4H), 6.88 (t, J=2.1 Hz, 2H), 6.33 (t, J=2.1 Hz, 2H), 4.64 (s, 2H). MS (ESI) m/z 317.9 (M+1)$^+$.

Example 21: Synthesis of 2-(2,5-dimethyl-1H-pyrrol-1-yl)-3-[2-(4-methylphenyl)ethynyl] benzoic acid

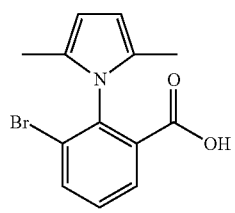 [SMILES: Cc1ccc(C)n1-c1c(Br)cccc1C(=O)O]

3-Bromo-2-(2,5-dimethyl-pyrrol-1-yl)-benzoic acid: A mixture of 2-amino-3-bromo-benzoic acid (2 g, 9.26 mmol) in hexane-2, 5-dione (20 mL) was heated at 100° C. for 3 days, allowed to cool to ambient temperature and then partitioned between water and ethyl acetate. The organic layer was dried (anhydrous magnesium sulfate), concentrated and purified by HPLC to give the product as a solid (1.6 g, 59%).

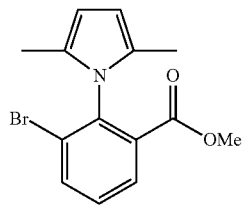 [SMILES: COC(=O)c1cccc(Br)c1-n1c(C)ccc1C]

3-Bromo-2-(2,5-dimethyl-pyrrol-1-yl)-benzoic acid methyl ester. To a solution of 3-bromo-2-(2,5-dimethyl-pyrrol-1-yl)-benzoic acid (1.4 g, 4.8 mmol) in ether (30 mL) and methanol (10 mL) at 0° C. was added trimethylsilyldiazomethane (2 M in hexane, 4.8 mL, 9.5 mmol) dropwise. After addition the reaction mixture was stirred at room temperature for 30 minutes. Acetic acid (0.2 mL) was added to quench the reaction and the solution was concentrated and purified by column chromatography through eluting with ethyl acetate/hexane (10%) to give the desired product 3-Bromo-2-(2,5-dimethyl-pyrrol-1-yl)-benzoic acid methyl ester as a solid.

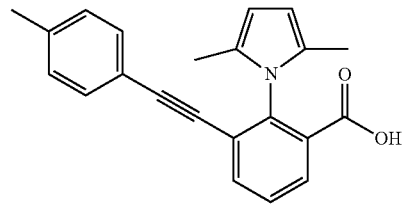 [SMILES: Cc1ccc(C#Cc2cccc(C(=O)O)c2-n2c(C)ccc2C)cc1]

2-(2,5-dimethyl-pyrrol-1-yl)-3-p-tolylethynyl-benzoic acid: To a pressure tube was loaded a mixture of 3-bromo-2-(2,5-dimethyl-pyrrol-1-yl)-benzoic acid methyl ester (40 mg, 0.13 mmol), 1-ethynyl-4-methyl-benzene (75 mg, 0.65 mmol), Pd(PPh$_3$)$_2$Cl$_2$ (9.1 mg, 0.013 mmol) and CuI (5 mg, 0.026 mmol) in triethylamine (1 mL). The mixture was degassed with N$_2$ for 10 minutes and then heated at 90° C. for 17 hours. After cooling to ambient temperature, the crude mixture was filtered through celite and washed with dichloromethane. The filtrate was concentrated and purified by column chromatography through preparative thin layer chromatography eluting with ethyl acetate/hexane (20%) to give a solid. To solid in tetrahydrofuran/methanol (1 mL/0.2 mL) was added sodium hydroxide solution (2 N in water, 0.2 mL, 0.4 mmol) and the solution was stirred at room temperature for 18 hours. 1 N hydrochloric acid aqueous solution was added dropwise until pH=1 and the reaction mixture was purified through preparative HPLC to give 6 mg (14% for 2 steps) of the pure product as a brown solid. $^1$H NMR (300 MHz, CDCl$_3$) δ=8.07 (dd, J=1.8, 7.9 Hz, 1H), 7.80 (dd, J=1.5, 7.9 Hz, 1H), 7.52 (t, J=7.8 Hz, 1H), 7.26-7.07 (m, 4H), 5.98 (s, 2H), 3.98 (s, 2H), 2.33 (s, 3H), 1.97 (s, 6H). MS (ESI) m/z 330.0 (M+1)$^+$.

Example 22: Synthesis of 2-(2,5-dimethyl-1H-pyrrol-1-yl)-3-[2-(3-hydroxyphenyl)ethynyl] benzoic acid

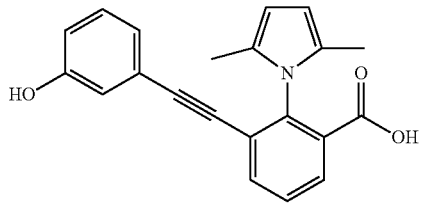 [SMILES: Cc1ccc(C)n1-c1c(C#Cc2cccc(O)c2)cccc1C(=O)O]

2-(2,5-dimethyl-1H-pyrrol-1-yl)-3-[2-(3-hydroxyphenyl)ethynyl]benzoic acid was prepared by the same procedure as example 21. $^1$H NMR (300 MHz, CDCl$_3$) δ=8.06 (dd, J=1.5, 7.6 Hz, 1H), 7.80 (dd, J=1.5, 7.6 Hz, 1H), 7.52 (t, J=7.8 Hz, 1H), 7.15 (t, J=7.9 Hz, 1H), 6.91-6.70 (m, 3H), 5.98 (s, 2H), 5.61 (br. s., 1H), 1.97 (s, 6H). MS (ESI) m/z 332.1 (M+1)$^+$.

Example 23: Synthesis of 3-[2-(2,3-dihydro-1H-indol-6-yl)ethynyl]-2-(1H-pyrrol-1-yl) benzoic acid

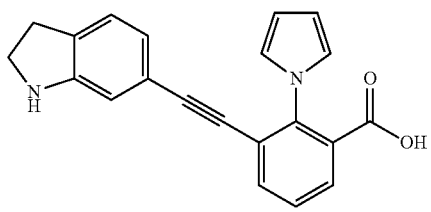

3-[2-(2,3-dihydro-1H-indol-6-yl)ethynyl]-2-(1H-pyrrol-1-yl)benzoic acid was prepared by the same procedure as example 1. MS (ESI) m/z 332.1 (M–H$_2$O)$^+$.

Example 24: Synthesis of 3-[2-(1-methyl-1H-pyrazol-4-yl)ethynyl]-2-(1H-pyrrol-1-yl)benzoic acid

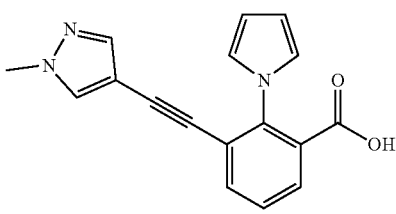 [SMILES: Cn1cc(C#Cc2cccc(C(=O)O)c2-n2cccc2)cn1]

3-[2-(1-methyl-1H-pyrazol-4-yl)ethynyl]-2-(1H-pyrrol-1-yl)benzoic acid was prepared by the same procedure as example 1. MS (ESI) m/z 292.0 (M+1)$^+$.

Example 25: Synthesis of 3-[2-(1,2-dimethyl-1H-imidazol-4-yl)ethynyl]-2-(1H-pyrrol-1-yl)benzoic acid

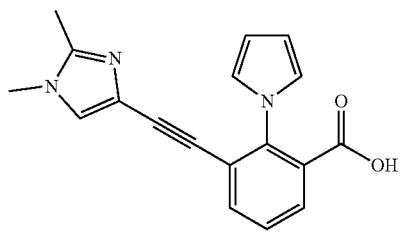 [SMILES: Cc1nc(C#Cc2cccc(C(=O)O)c2-n2cccc2)cn1C]

3-[2-(1,2-dimethyl-1H-imidazol-4-yl)ethynyl]-2-(1H-pyrrol-1-yl)benzoic acid was prepared by the same procedure as example 1. MS (ESI) m/z 306.1 (M+1)$^+$.

Example 26: Synthesis of 3-[2-(1-methyl-1H-imidazol-5-yl)ethynyl]-2-(1H-pyrrol-1-yl)benzoic acid

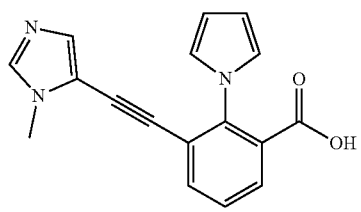 [SMILES: Cn1cncc1C#Cc1cccc(C(=O)O)c1-n1cccc1]

3-[2-(1-methyl-1H-imidazol-5-yl)ethynyl]-2-(1H-pyrrol-1-yl)benzoic acid was prepared by the same procedure as example 1. MS (ESI) m/z 292.1 (M+1)$^+$.

Example 27: Synthesis of 3-[2-(1-methyl-1H-imidazol-2-yl)ethynyl]-2-(1H-pyrrol-1-yl) benzoic acid

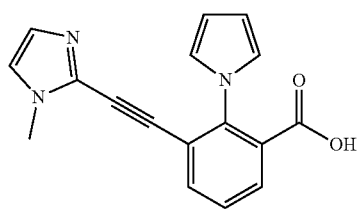 [SMILES: Cn1ccnc1C#Cc1cccc(C(=O)O)c1-n1cccc1]

3-[2-(1-methyl-1H-imidazol-2-yl)ethynyl]-2-(1H-pyrrol-1-yl)benzoic acid was prepared by the same procedure as example 1. MS (ESI) m/z 292.1 (M+1)$^+$.

Example 28: Synthesis of 2-(1H-pyrrol-1-yl)-3-[2-(1,3-thiazol-5-yl)ethynyl]benzoic acid

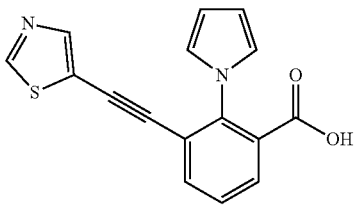 [SMILES: O=C(O)c1cccc(C#Cc2cncs2)c1-n1cccc1]

2-(1H-pyrrol-1-yl)-3-[2-(1,3-thiazol-5-yl)ethynyl]benzoic acid was prepared by the same procedure as example 1. MS (ESI) m/z 295.0 (M+1)+.

Example 29: Synthesis of 2-(1H-pyrrol-1-yl)-3-[2-(1,3-thiazol-4-yl)ethynyl]benzoic acid

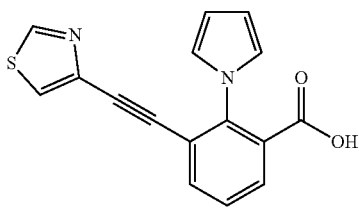 [SMILES: O=C(O)c1cccc(C#Cc2cscn2)c1-n1cccc1]

2-(1H-pyrrol-1-yl)-3-[2-(1,3-thiazol-4-yl)ethynyl]benzoic acid was prepared by the same procedure as example 1. MS (ESI) m/z 295.0 (M+1)+.

Example 30: Synthesis of 2-(1H-pyrrol-1-yl)-3-(2-{1H-pyrrolo[2,3-b]pyridin-6-yl}ethynyl) benzoic acid

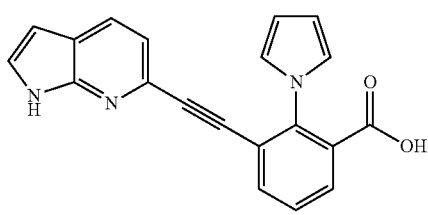

2-(1H-pyrrol-1-yl)-3-(2-{1H-pyrrolo[2,3-b]pyridin-6-yl}ethynyl)benzoic acid was prepared by the same procedure as example 1. MS (ESI) m/z 328.0 (M+1)+.

Example 31: Synthesis of 3-{2-[3-(2-hydroxypropan-2-yl)phenyl]ethynyl}-2-(1H-pyrrol-1-yl)benzoic acid

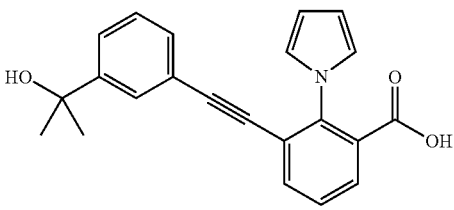 [SMILES: CC(C)(O)c1cccc(C#Cc2cccc(C(=O)O)c2-n2cccc2)c1]

3-{2-[3-(2-hydroxypropan-2-yl)phenyl]ethynyl}-2-(1H-pyrrol-1-yl)benzoic acid was prepared by the same procedure as example 1. $^1$H NMR (300 MHz, CDCl$_3$) δ=7.84 (dd, J=1.6, 7.6 Hz, 1H), 7.74 (dd, J=1.6, 7.8 Hz, 1H), 7.50-7.41 (m, 2H), 7.34-7.17 (m, 3H), 6.89 (t, J=2.1 Hz, 2H), 6.34 (t, J=2.1 Hz, 2H), 1.56 (s, 6H). MS (ESI) m/z 346.1 (M+1)+.

Example 32: Synthesis of 3-(3-hydroxy-4-methylpent-1-yn-1-yl)-2-(1H-pyrrol-1-yl)benzoic acid

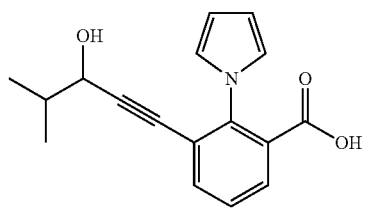 [SMILES: CC(C)C(O)C#Cc1cccc(C(=O)O)c1-n1cccc1]

3-(3-hydroxy-4-methylpent-1-yn-1-yl)-2-(1H-pyrrol-1-yl)benzoic acid was prepared by the same procedure as example 9. $^1$H NMR (300 MHz, CDCl$_3$) δ=7.87 (dd, J=1.5, 7.9 Hz, 1H), 7.67 (dd, J=1.5, 7.6 Hz, 1H), 7.42 (t, J=7.7 Hz, 1H), 6.76 (t, J=2.1 Hz, 2H), 6.28 (t, J=2.1 Hz, 2H), 4.22 (dd, J=5.7, 12.2 Hz, 1H), 2.01-1.73 (m, 1H), 0.89 (d, J=6.7 Hz, 6H). MS (ESI) m/z 266.1 (M−H$_2$O)+.

Example 33: Synthesis of 3-(3-hydroxy-3-phenylprop-1-yn-1-yl)-2-(1H-pyrrol-1-yl)benzoic acid

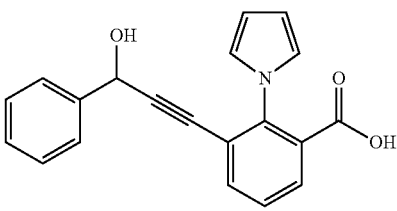 [SMILES: O=C(O)c1cccc(C#CC(O)c2ccccc2)c1-n1cccc1]

3-(3-hydroxy-3-phenylprop-1-yn-1-yl)-2-(1H-pyrrol-1-yl)benzoic acid was prepared by the same procedure as example 9. $^1$H NMR (300 MHz, CDCl$_3$) δ=7.84 (d, J=7.5 Hz, 1H), 7.68 (dd, J=1.6, 7.8 Hz, 1H), 7.44-7.19 (m, 6H), 6.83 (t, J=2.2 Hz, 2H), 6.31 (t, J=2.2 Hz, 2H), 5.48 (s, 1H). MS (ESI) m/z 300.0 (M−H$_2$O)+.

Example 34: Synthesis of 2-(1H-pyrrol-1-yl)-3-(2-{1H-pyrrolo[2,3-b]pyridin-3-yl}ethynyl)benzoic acid

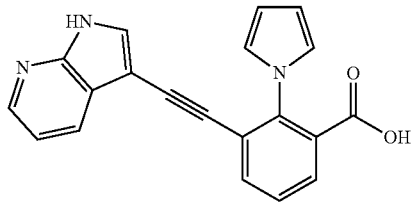 [SMILES: O=C(O)c1cccc(C#Cc2c[nH]c3ncccc23)c1-n1cccc1]

2-(1H-pyrrol-1-yl)-3-(2-{1H-pyrrolo[2,3-b]pyridin-3-yl}ethynyl)benzoic acid was prepared by the same procedure as example 1. $^1$H NMR (300 MHz, DMSO) δ=12.14 (br. s., 1H), 8.26 (d, J=3.5 Hz, 1H), 7.79-7.70 (m, 3H), 7.68 (dd, J=1.6, 7.8 Hz, 1H), 7.52 (t, J=7.8 Hz, 1H), 7.13 (dd, J=4.7, 7.9 Hz, 1H), 6.92 (t, J=2.2 Hz, 2H), 6.24 (t, J=2.2 Hz, 2H). MS (ESI) m/z 328.0 (M+H)$^+$.

Example 35: Synthesis of 3-[2-(1H-indol-4-yl)ethynyl]-2-(1H-pyrrol-1-yl)benzoic acid

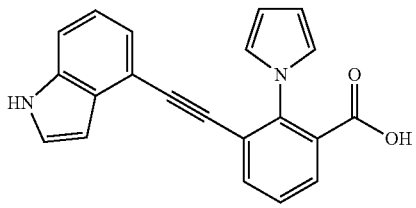 [SMILES: O=C(O)c1cccc(C#Cc2cccc3[nH]ccc23)c1-n1cccc1]

3-[2-(1H-indol-4-yl)ethynyl]-2-(1H-pyrrol-1-yl)benzoic acid was prepared by the same procedure as example 1. $^1$H NMR (300 MHz, CDCl$_3$) δ=7.85-7.79 (m, 2H), 7.44 (t, J=8.0 Hz, 1H), 7.39-7.35 (m, 1H), 7.24-7.18 (m, 2H), 7.11 (t, J=7.9 Hz, 1H), 6.95 (t, J=2.2 Hz, 2H), 6.51-6.47 (m, 1H), 6.36 (t, J=2.2 Hz, 2H). MS (ESI) m/z 327.0 (M+H)$^+$.

Example 36: Synthesis of 2-(1H-pyrrol-1-yl)-3-(2-{[1,2,4]triazolo[1,5-a]pyridin-7-yl}ethynyl)benzoic acid

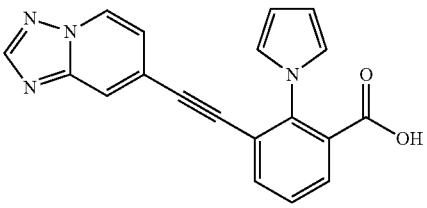 [SMILES: O=C(O)c1cccc(C#Cc2ccn3ncnc3c2)c1-n1cccc1]

2-(1H-pyrrol-1-yl)-3-(2-{[1,2,4]triazolo[1,5-a]pyridin-7-yl}ethynyl)benzoic acid was prepared by the same procedure as example 1. $^1$H NMR (300 MHz, CDCl$_3$) δ=8.51 (d, J=7.0 Hz, 1H), 8.38 (s, 1H), 7.93 (dd, J=1.6, 7.8 Hz, 1H), 7.79 (d, J=7.8 Hz, 1H), 7.75 (s, 1H), 7.49 (t, J=7.9 Hz, 1H), 6.93-6.87 (m, 3H), 6.37 (t, J=2.1 Hz, 2H). MS (ESI) m/z 329.1 (M+H)$^+$.

Example 37: Synthesis of 3-{2-[3-(dimethylsulfamoyl)phenyl]ethynyl}-2-(1H-pyrrol-1-yl)benzoic acid

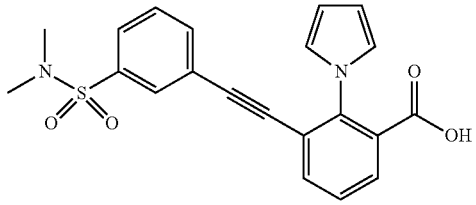 [SMILES: CN(C)S(=O)(=O)c1cccc(C#Cc2cccc(C(=O)O)c2-n2cccc2)c1]

3-{2-[3-(dimethylsulfamoyl)phenyl]ethynyl}-2-(1H-pyrrol-1-yl)benzoic acid was prepared by the same procedure as example 1. $^1$H NMR (300 MHz, CDCl$_3$) δ=7.89 (dd, J=1.6, 7.8 Hz, 1H), 7.82-7.64 (m, 3H), 7.50-7.42 (m, 3H), 6.89 (t, J=2.1 Hz, 2H), 6.34 (t, J=2.1 Hz, 2H), 2.76 (s, 6H). MS (ESI) m/z 395.1 (M+H)$^+$.

Example 38: Synthesis of 3-[2-(3-fluoro-5-hydroxyphenyl)ethynyl]-2-(1H-pyrrol-1-yl) benzoic acid

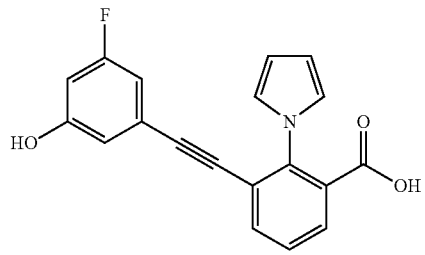 [SMILES: O=C(O)c1cccc(C#Cc2cc(O)cc(F)c2)c1-n1cccc1]

3-[2-(3-fluoro-5-hydroxyphenyl)ethynyl]-2-(1H-pyrrol-1-yl)benzoic acid was prepared by the same procedure as example 1. $^1$H NMR (300 MHz, CDCl$_3$) δ=7.84 (dd, J=1.6, 7.8 Hz, 1H), 7.72 (dd, J=1.6, 7.8 Hz, 1H), 7.43 (t, J=7.8 Hz, 1H), 6.87 (t, J=2.2 Hz, 2H), 6.64-6.47 (m, 3H), 6.33 (t, J=2.2 Hz, 2H). MS (ESI) m/z 322.0 (M+H)$^+$.

Example 39: Synthesis of 3-{2-[3-(hydroxymethyl)phenyl]ethynyl}-2-(1H-pyrrol-1-yl)benzoic acid

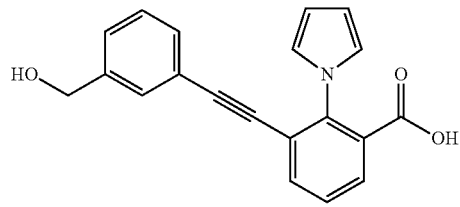 [SMILES: O=C(O)c1cccc(C#Cc2cccc(CO)c2)c1-n1cccc1]

3-{2-[3-(hydroxymethyl)phenyl]ethynyl}-2-(1H-pyrrol-1-yl)benzoic acid was prepared by the same procedure as example 1. $^1$H NMR (300 MHz, CDCl$_3$) δ=7.83 (d, J=8.0 Hz, 1H), 7.73 (d, J=7.7 Hz, 1H), 7.43 (t, J=7.9 Hz, 1H), 7.36-7.23 (m, 4H), 6.89 (t, J=2.1 Hz, 2H), 6.33 (t, J=2.1 Hz, 2H), 4.63 (s, 2H). MS (ESI) m/z 318.0 (M+H)$^+$.

Example 40: Synthesis of 3-[2-(5-hydroxypyridin-3-yl)ethynyl]-2-(1H-pyrrol-1-yl)benzoic acid

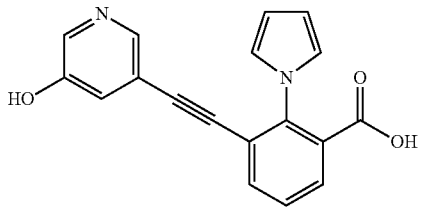 [SMILES: O=C(O)c1cccc(C#Cc2cncc(O)c2)c1-n1cccc1]

3-[2-(5-hydroxypyridin-3-yl)ethynyl]-2-(1H-pyrrol-1-yl)benzoic acid was prepared by the same procedure as example 1. $^1$H NMR (300 MHz, CDCl$_3$) δ=8.15 (s, 1H), 8.02 (s, 1H), 7.89 (dd, J=1.6, 7.8 Hz, 1H), 7.75 (dd, J=1.6, 7.8 Hz, 1H), 7.47 (t, J=7.7 Hz, 1H), 7.25-7.22 (m, 1H), 6.87 (t, J=2.2 Hz, 2H), 6.34 (t, J=2.2 Hz, 2H). MS (ESI) m/z 305.1 (M+H)$^+$.

Example 41: Synthesis of 3-[2-(5-hydroxypyridin-3-yl)ethynyl]-2-(1H-pyrrol-1-yl)benzoic acid

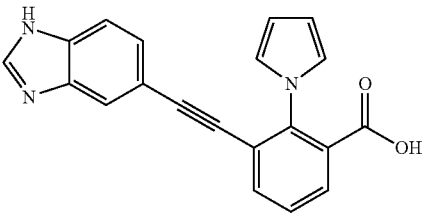 [SMILES: O=C(O)c1cccc(C#Cc2ccc3[nH]cnc3c2)c1-n1cccc1]

3-[2-(5-hydroxypyridin-3-yl)ethynyl]-2-(1H-pyrrol-1-yl)benzoic acid was prepared by the same procedure as example 1. MS (ESI) m/z 328.1 (M+H)$^+$.

Example 42: Synthesis of 3-[2-(1H-indol-5-yl)ethynyl]-2-(1H-pyrrol-1-yl)benzoic acid

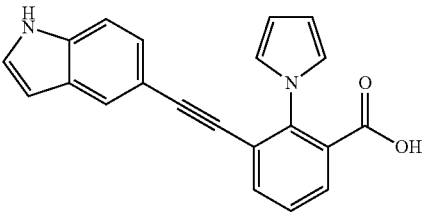 [SMILES: O=C(O)c1cccc(C#Cc2ccc3[nH]ccc3c2)c1-n1cccc1]

3-[2-(1H-indol-5-yl)ethynyl]-2-(1H-pyrrol-1-yl)benzoic acid was prepared by the same procedure as example 1. $^1$H NMR (300 MHz, CDCl$_3$) δ=8.03 (s, 1H), 7.82 (dd, J=1.6, 7.8 Hz, 1H), 7.79-7.73 (m, 2H), 7.47-7.40 (m, 2H), 7.34-7.28 (m, 1H), 6.92 (t, J=2.2 Hz, 2H), 6.37 (t, J=2.1 Hz, 2H). MS (ESI) m/z 328.1 (M+H)$^+$.

Example 43: Synthesis of 3-[2-(1H-indol-6-yl)ethynyl]-2-(1H-pyrrol-1-yl)benzoic acid

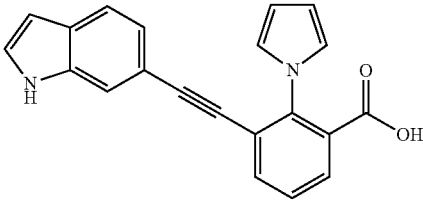 [SMILES: O=C(O)c1cccc(C#Cc2ccc3cc[nH]c3c2)c1-n1cccc1]

3-[2-(1H-indol-6-yl)ethynyl]-2-(1H-pyrrol-1-yl)benzoic acid was prepared by the same procedure as example 1. $^1$H NMR (300 MHz, DMSO) δ=11.29 (br. s., 1H), 7.79 (dd, J=1.5, 7.7 Hz, 1H), 7.69 (dd, J=1.6, 7.8 Hz, 1H), 7.51 (t, J=7.6 Hz, 2H), 7.44 (t, J=2.8 Hz, 1H), 7.37 (s, 1H), 6.95-6.90 (m, 3H), 6.46-6.42 (m, 1H), 6.24 (t, J=2.2 Hz, 2H). MS (ESI) m/z 327.0 (M+H)$^+$.

Example 44: Synthesis of 3-[2-(4-methylphenyl)ethynyl]-2-(1H-pyrrol-1-yl)benzoic acid

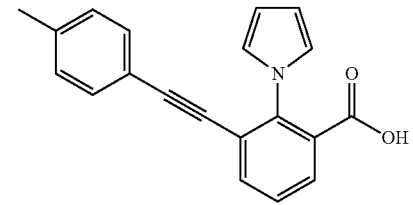 [SMILES: Cc1ccc(C#Cc2cccc(C(=O)O)c2-n2cccc2)cc1]

3-[2-(4-methylphenyl)ethynyl]-2-(1H-pyrrol-1-yl)benzoic acid was prepared by the same procedure as example 1. $^1$H NMR (300 MHz, CDCl$_3$) δ=7.88 (dd, J=1.6, 7.8 Hz, 1H), 7.77 (dd, J=1.5, 7.6 Hz, 1H), 7.47 (t, J=7.8 Hz, 1H), 7.20 (d, J=7.5 Hz, 2H), 7.10 (d, J=7.5 Hz, 2H), 6.88 (t, J=2.2 Hz, 2H), 6.37 (t, J=2.1 Hz, 2H), 2.34 (s, 3H). MS (ESI) m/z 302.0 (M+H)$^+$.

Example 45: Synthesis of 3-[2-(3,5-difluorophenyl)ethynyl]-2-(1H-pyrrol-1-yl)benzoic acid

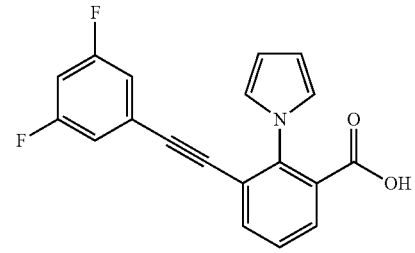 [SMILES: O=C(O)c1cccc(C#Cc2cc(F)cc(F)c2)c1-n1cccc1]

3-[2-(3,5-difluorophenyl)ethynyl]-2-(1H-pyrrol-1-yl)benzoic acid was prepared by the same procedure as example 1. $^1$H NMR (300 MHz, CDCl$_3$) δ=7.95 (d, J=8.0 Hz, 1H), 7.78 (d, J=7.7 Hz, 1H), 7.48 (t, J=7.8 Hz, 1H), 6.87-6.74 (m, 5H), 6.39 (t, J=2.1 Hz, 2H). MS (ESI) m/z 323.2 (M–H$_2$O)$^+$.

Example 46: Synthesis of 3-{2-[3-(difluoromethoxy)phenyl]ethynyl}-2-(1H-pyrrol-1-yl) benzoic acid

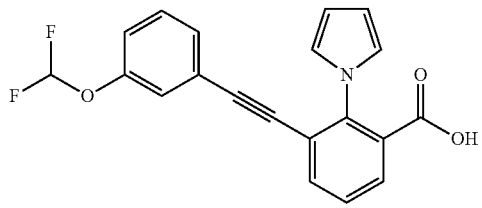 [SMILES: O=C(O)c1cccc(C#Cc2cccc(OC(F)F)c2)c1-n1cccc1]

3-{2-[3-(difluoromethoxy)phenyl]ethynyl}-2-(1H-pyrrol-1-yl)benzoic acid was prepared by the same procedure as example 1. $^1$H NMR (300 MHz, CDCl$_3$) δ=7.92 (dd, J=1.8, 7.8 Hz, 1H), 7.78 (dd, J=1.6, 7.8 Hz, 1H), 7.47 (t, J=7.8 Hz, 1H), 7.33-7.22 (m, 1H), 7.19-7.14 (m, 1H), 7.10-7.04 (m, 2H), 6.86 (t, J=2.2 Hz, 2H), 6.49 (t, J=73.6 Hz, 1H), 6.37 (t, J=2.2 Hz, 2H). MS (ESI) m/z 354.1 (M+H)$^+$.

Example 47: Synthesis of 3-ethynyl-2-(1H-pyrrol-1-yl)benzoic acid

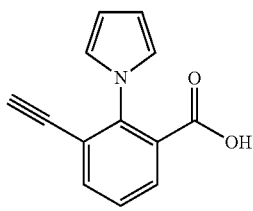 [SMILES: C#Cc1cccc(C(=O)O)c1-n1cccc1]

To 3-ethynyl-2-pyrrol-1-yl-benzoic acid methyl ester (50 mg, 0.22 mmol) in tetrahydrofuran/methanol (1 mL/0.2 mL) was added sodium hydroxide solution (2 N in water, 0.2 mL, 0.4 mmol) and the solution was stirred at room temperature for 18 hours. 1 N hydrochloric acid aqueous solution was added dropwise until pH=1 and the reaction mixture was purified through preparative HPLC to give 43 mg (92%) of the pure product as a white solid. $^1$H NMR (300 MHz, CDCl$_3$) δ=7.70-7.58 (m, 2H), 7.39 (t, J=7.8 Hz, 1H), 6.80 (t, J=2.1 Hz, 1H), 6.31 (t, J=2.1 Hz, 2H), 3.65 (s, 2H). MS (ESI) m/z 212.0 (M+H)$^+$.

Example 48: Synthesis of 3-(3-amino-3-methylbut-1-yn-1-yl)-2-(1H-pyrrol-1-yl)benzoic acid

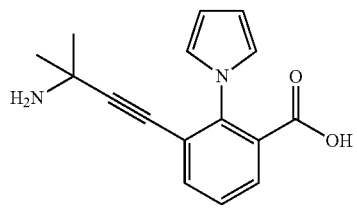 [SMILES: CC(C)(N)C#Cc1cccc(C(=O)O)c1-n1cccc1]

3-(3-amino-3-methylbut-1-yn-1-yl)-2-(1H-pyrrol-1-yl) benzoic acid was prepared by the same procedure as example 9. $^1$H NMR (300 MHz, DMSO) δ=8.49 (br. s., 2H), 7.76 (dd, J=1.8, 7.6 Hz, 1H), 7.66 (dd, J=1.8, 7.6 Hz, 1H), 7.52 (t, J=7.6 Hz, 1H), 6.82 (t, J=2.2 Hz, 2H), 6.17 (t, J=2.2 Hz, 2H), 1.41 (s, 6H). MS (ESI) m/z 269.0 (M+H)$^+$.

Example 49: Synthesis of 3-(3,3-dimethylbut-1-yn-1-yl)-2-(1H-pyrrol-1-yl)benzoic acid

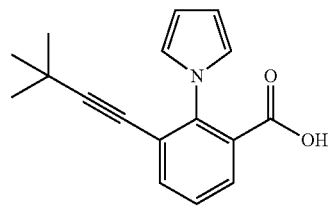 [SMILES: CC(C)(C)C#Cc1cccc(C(=O)O)c1-n1cccc1]

3-(3,3-dimethylbut-1-yn-1-yl)-2-(1H-pyrrol-1-yl)benzoic acid was prepared by the same procedure as example 9. $^1$H NMR (300 MHz, CDCl$_3$) δ=7.78 (dd, J=1.2, 7.6 Hz, 1H), 7.61 (dd, J=1.2, 7.6 Hz, 1H), 7.35 (t, J=7.8 Hz, 1H), 6.76 (t, J=1.9 Hz, 2H), 6.26 (t, J=1.9 Hz, 2H), 1.14 (s, 9H). MS (ESI) m/z 268.2 (M+H)$^+$.

Example 50: Synthesis of 2-(2,5-dimethyl-1H-pyrrol-1-yl)-3-(2-phenylethynyl)benzoic acid

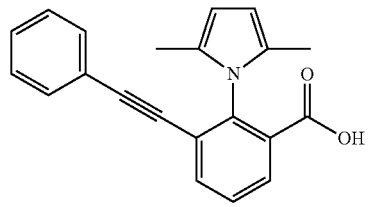 [SMILES: Cc1ccc(C)n1-c1c(C#Cc2ccccc2)cccc1C(=O)O]

2-(2,5-dimethyl-1H-pyrrol-1-yl)-3-(2-phenylethynyl) benzoic acid was prepared by the same procedure as example 21. $^1$H NMR (300 MHz, CDCl$_3$) δ=8.04 (dd, J=1.6, 7.8 Hz, 1H), 7.81 (d, J=7.6 Hz, 1H), 7.52 (t, J=7.9 Hz, 1H), 7.36-7.21 (m, 5H), 5.97 (s, 2H), 1.97 (s, 6H). MS (ESI) m/z 316.0 (M+H)$^+$.

Example 51: Synthesis of 2-(2,5-dimethyl-1H-pyrrol-1-yl)-3-(2-phenylethynyl)benzoic acid

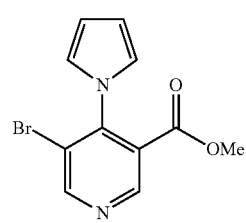 [SMILES: COC(=O)c1cncc(Br)c1-n1cccc1]

5-Bromo-4-pyrrol-1-yl-nicotinic acid methyl ester was prepared in the same manner as 3-bromo-2-pyrrol-1-yl-benzoic acid methyl ester.

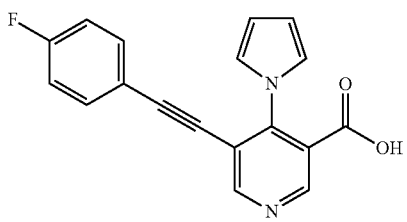 [SMILES: O=C(O)c1cncc(C#Cc2ccc(F)cc2)c1-n1cccc1]

2-(2,5-dimethyl-1H-pyrrol-1-yl)-3-(2-phenylethynyl)benzoic acid was prepared by the same procedure as example 9 starting from 5-bromo-4-pyrrol-1-yl-nicotinic acid methyl ester. MS (ESI) m/z 307.0 (M+H)+.

Example 52: Synthesis of 5-(2-phenylethynyl)-4-(1H-pyrrol-1-yl)pyridine-3-carboxylic acid

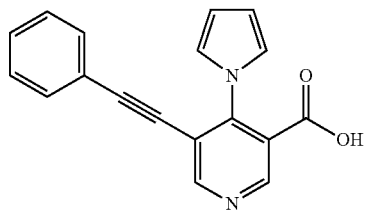 [SMILES: O=C(O)c1cncc(C#Cc2ccccc2)c1-n1cccc1]

5-(2-phenylethynyl)-4-(1H-pyrrol-1-yl)pyridine-3-carboxylic acid was prepared by the same procedure as example 51. MS (ESI) m/z 289.0 (M+H)+.

Example 53: Synthesis of 3-[2-(1-aminocyclohexyl)ethynyl]-2-(1H-pyrrol-1-yl)benzoic acid trifluoroacetic acid

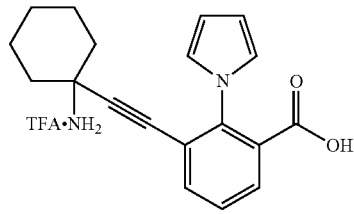

3-[2-(1-aminocyclohexyl)ethynyl]-2-(1H-pyrrol-1-yl)benzoic acid trifluoroacetic acid was prepared by the same procedure as example 9. ¹H NMR (300 MHz, CDCl₃) δ=7.87 (dd, J=1.5, 7.9 Hz, 1H), 7.68 (dd, J=1.6, 7.8 Hz, 1H), 7.42 (t, J=7.8 Hz, 1H), 6.77 (t, J=2.2 Hz, 2H), 6.25 (t, J=2.2 Hz, 2H), 3.22 (br. s., 2H), 2.00-1.95 (m, 2H), 1.79-1.51 (m, 5H), 1.48-1.05 (m, 3H). MS (ESI) m/z 292.1 (M−H₂O)+.

Example 54: Synthesis of 3-[2-(1-hydroxycyclohexyl)ethynyl]-2-(1H-pyrrol-1-yl)benzoic acid

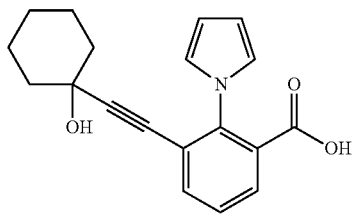 [SMILES: O=C(O)c1cccc(C#CC2(O)CCCCC2)c1-n1cccc1]

3-[2-(1-hydroxycyclohexyl)ethynyl]-2-(1H-pyrrol-1-yl)benzoic acid was prepared by the same procedure as example 9. ¹H NMR (300 MHz, CDCl₃) δ=7.78 (d, J=7.7 Hz, 1H), 7.61 (d, J=7.6 Hz, 1H), 7.36 (t, J=7.8 Hz, 1H), 6.76 (t, J=2.0 Hz, 2H), 6.23 (t, J=2.0 Hz, 2H), 1.84-1.71 (m, 2H), 1.62-1.10 (m, 8H). MS (ESI) m/z 292.1 (M−H₂O)+.

Example 55: Synthesis of 3-(4-ethyl-3-hydroxyoct-1-yn-1-yl)-2-(1H-pyrrol-1-yl)benzoic acid

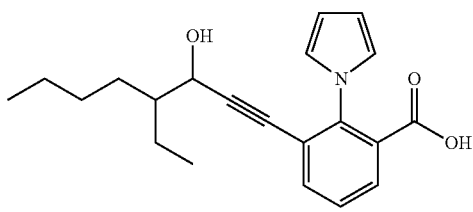 [SMILES: CCCCC(CC)C(O)C#Cc1cccc(C(=O)O)c1-n1cccc1]

3-(4-ethyl-3-hydroxyoct-1-yn-1-yl)-2-(1H-pyrrol-1-yl)benzoic acid was prepared by the same procedure as example 9. MS (ESI) m/z 322.2 (M−H₂O)+.

Example 56: Synthesis of 3-(2-{imidazo[1,2-a]pyrazin-6-yl}ethynyl)-2-(1H-pyrrol-1-yl)benzoic acid

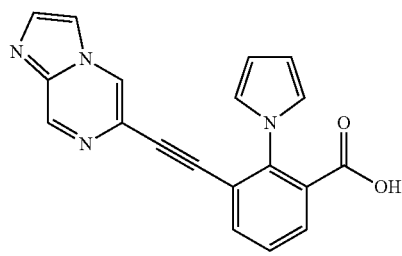 [SMILES: O=C(O)c1cccc(C#Cc2cn3ccnc3cn2)c1-n1cccc1]

3-(2-{imidazo[1,2-a]pyrazin-6-yl})ethynyl)-2-(1H-pyrrol-1-yl)benzoic acid was prepared by the same procedure as example 9. ¹H NMR (300 MHz, DMSO) δ=9.03 (s, 1H), 8.64 (s, 1H), 8.19 (s, 1H), 7.93-7.75 (m, 2H), 7.57 (dd, J=1.6, 7.8 Hz, 1H), 7.56 (t, J=7.8 Hz, 1H), 6.92 (t, J=2.2 Hz, 2H), 6.24 (t, J=2.2 Hz, 2H). MS (ESI) m/z 328.9 (M+H)+.

Example 57: Synthesis of 3-[2-(3-hydroxyphenyl)ethynyl]-2-(1H-pyrrol-1-yl)benzoic acid

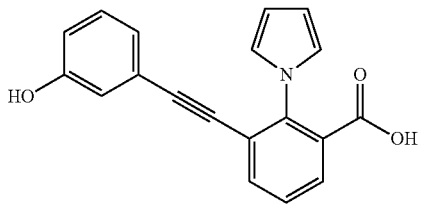 [SMILES: O=C(O)c1cccc(C#Cc2cccc(O)c2)c1-n1cccc1]

3-[2-(3-hydroxyphenyl)ethynyl]-2-(1H-pyrrol-1-yl)benzoic acid was prepared by the same procedure as example 9. $^1$H NMR (300 MHz, CDCl$_3$) δ=7.79 (dd, J=1.6, 7.8 Hz, 1H), 7.66 (dd, J=1.6, 7.8 Hz, 1H), 7.39 (t, J=7.8 Hz, 1H), 7.11 (t, J=7.0 Hz, 1H), 6.90-6.71 (m, 5H), 6.30 (t, J=2.2 Hz, 2H), MS (ESI) m/z 304.1 (M+H)$^+$.

Example 58: Synthesis of 5-chloro-3-[2-(4-fluorophenyl)ethynyl]-2-(1H-pyrrol-1-yl)benzoic acid

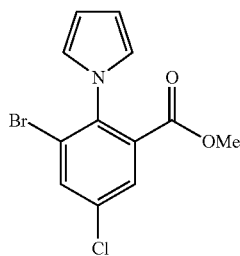 [SMILES: COC(=O)c1cc(Cl)cc(Br)c1-n1cccc1]

3-Bromo-5-chloro-2-pyrrol-1-yl-benzoic acid methyl ester was prepared in the same manner as 3-bromo-2-pyrrol-1-yl-benzoic acid methyl ester.

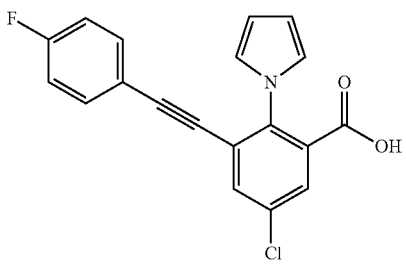 [SMILES: O=C(O)c1cc(Cl)cc(C#Cc2ccc(F)cc2)c1-n1cccc1]

5-chloro-3-[2-(4-fluorophenyl)ethynyl]-2-(1H-pyrrol-1-yl)benzoic acid was prepared by the same procedure as example 9 starting from 3-bromo-5-chloro-2-pyrrol-1-yl-benzoic acid methyl ester. $^1$H NMR (300 MHz, CDCl$_3$) δ=7.85 (d, J=3.6 Hz, 1H), 7.73 (d, J=2.4 Hz, 1H), 7.33-7.23 (m, 2H), 7.04-6.95 (m, 2H), 6.82 (t, J=2.0 Hz, 2H), 6.36 (t, J=2.0 Hz, 2H). MS (ESI) m/z 340.1 (M+H)$^+$.

Example 59: Synthesis of 5-chloro-3-(2-phenylethynyl)-2-(1H-pyrrol-1-yl)benzoic acid

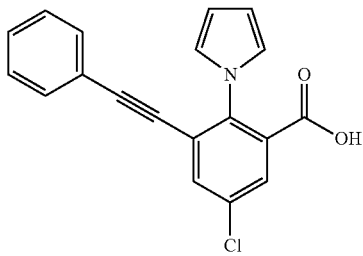

5-Chloro-3-(2-phenylethynyl)-2-(1H-pyrrol-1-yl)benzoic acid was prepared by the same procedure as example 58. $^1$H NMR (300 MHz, CDCl$_3$) δ=7.83 (d, J=2.3 Hz, 1H), 7.74 (d, J=2.3 Hz, 1H), 7.35-7.25 (m, 5H), 6.82 (t, J=2.0 Hz, 2H), 6.35 (t, J=1.8 Hz, 2H). MS (ESI) m/z 322.1 (M+H)$^+$.

Example 60: Synthesis of 5-fluoro-3-[2-(4-fluorophenyl)ethynyl]-2-(1H-pyrrol-1-yl)benzoic acid

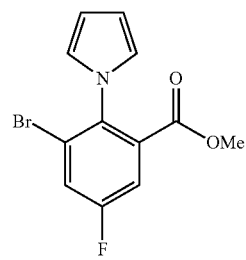 [SMILES: COC(=O)c1cc(F)cc(Br)c1-n1cccc1]

3-Bromo-5-fluoro-2-pyrrol-1-yl-benzoic acid methyl ester was prepared in the same manner as 3-bromo-2-pyrrol-1-yl-benzoic acid methyl ester.

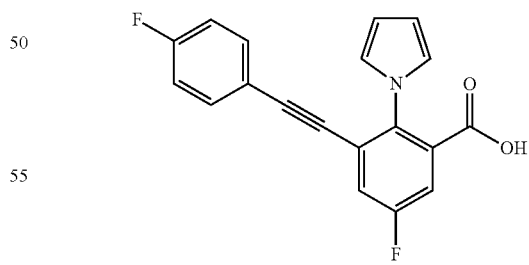

5-Fluoro-3-[2-(4-fluorophenyl)ethynyl]-2-(1H-pyrrol-1-yl)benzoic acid was prepared by the same procedure as example 9 starting from 3-bromo-5-fluoro-2-pyrrol-1-yl-benzoic acid methyl ester. $^1$H NMR (300 MHz, CDCl$_3$) δ=7.59 (dd, J=2.9, 8.2 Hz, 1H), 7.45 (dd, J=2.6, 7.9 Hz, 1H), 7.31-7.24 (m, 2H), 7.02-6.94 (m, 2H), 6.82 (t, J=2.0 Hz, 2H), 6.35 (t, J=2.0 Hz, 2H). MS (ESI) m/z 324.0 (M+H)$^+$.

Example 61: Synthesis of 5-fluoro-3-(2-phenylethynyl)-2-(1H-pyrrol-1-yl)benzoic acid

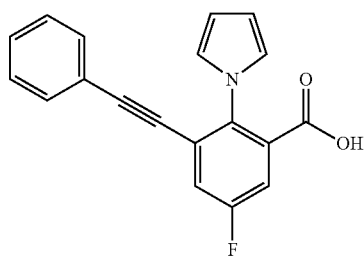 [SMILES: O=C(O)c1cc(F)cc(C#Cc2ccccc2)c1-n1cccc1]

5-fluoro-3-(2-phenylethynyl)-2-(1H-pyrrol-1-yl)benzoic acid was prepared by the same procedure as example 60. $^1$H NMR (300 MHz, CDCl$_3$) δ=7.58 (dd, J=3.1, 8.1 Hz, 1H), 7.46 (dd, J=2.9, 8.2 Hz, 1H), 7.36-7.25 (m, 5H), 6.81 (t, J=2.2 Hz, 2H), 6.35 (t, J=2.1 Hz, 2H).

Example 62: Synthesis of 3-(2-cyclopropylethynyl)-2-(1H-pyrrol-1-yl)benzoic acid

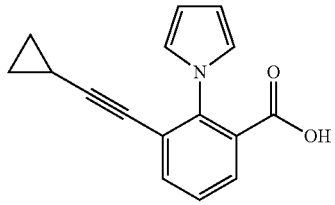 [SMILES: O=C(O)c1cccc(C#CC2CC2)c1-n1cccc1]

3-(2-cyclopropylethynyl)-2-(1H-pyrrol-1-yl)benzoic acid was prepared by the same procedure as example 9. $^1$H NMR (300 MHz, CDCl$_3$) δ=7.77 (dd, J=1.6, 7.8 Hz, 1H), 7.61 (dd, J=1.6, 7.8 Hz, 1H), 7.34 (t, J=7.8 Hz, 1H), 6.74 (t, J=2.2 Hz, 2H), 6.26 (t, J=2.2 Hz, 2H), 1.31-1.22 (m, 1H), 0.83-0.69 (m, 2H), 0.69-0.60 (m, 2H). MS (ESI) m/z 234.0 (M−H$_2$O)$^+$.

Example 63: Synthesis of 3-(3-hydroxy-3-methylbut-1-yn-1-yl)-2-(1H-pyrrol-1-yl)benzoic acid

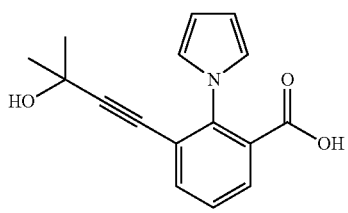 [SMILES: CC(C)(O)C#Cc1cccc(C(=O)O)c1-n1cccc1]

3-(3-hydroxy-3-methylbut-1-yn-1-yl)-2-(1H-pyrrol-1-yl)benzoic acid was prepared by the same procedure as example 9. $^1$H NMR (300 MHz, CDCl$_3$) δ=7.77 (d, J=7.7 Hz, 1H), 7.57 (dd, J=1.6, 7.8 Hz, 1H), 7.34 (t, J=7.8 Hz, 1H), 6.75 (t, J=2.2 Hz, 2H), 6.24 (t, J=2.2 Hz, 2H), 1.39 (s, 6H). MS (ESI) m/z 252.1 (M−H$_2$O)$^+$.

Example 64: Synthesis of 3-[3-(dimethylamino)prop-1-yn-1-yl]-2-(1H-pyrrol-1-yl)benzoic acid

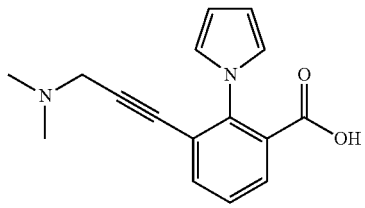 [SMILES: CN(C)CC#Cc1cccc(C(=O)O)c1-n1cccc1]

3-[3-(dimethylamino)prop-1-yn-1-yl]-2-(1H-pyrrol-1-yl)benzoic acid was prepared by the same procedure as example 9. $^1$H NMR (300 MHz, CDCl$_3$) δ=7.95 (dd, J=1.6, 7.8 Hz, 1H), 7.70 (dd, J=1.6, 7.8 Hz, 1H), 7.49 (t, J=7.8 Hz, 1H), 6.78 (t, J=2.2 Hz, 2H), 6.26 (t, J=2.1 Hz, 2H), 4.01 (s, 2H), 2.61 (s, 6H). MS (ESI) m/z 269.1 (M+H)$^+$.

Example 65: Synthesis of 3-(4-phenylbut-1-yn-1-yl)-2-(1H-pyrrol-1-yl)benzoic acid

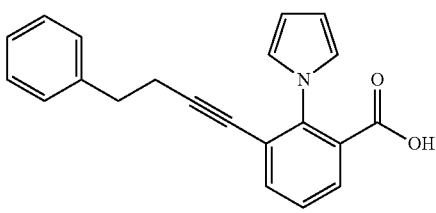 [SMILES: O=C(O)c1cccc(C#CCCc2ccccc2)c1-n1cccc1]

3-(4-phenylbut-1-yn-1-yl)-2-(1H-pyrrol-1-yl)benzoic acid was prepared by the same procedure as example 9. $^1$H NMR (300 MHz, CDCl$_3$) δ=7.78 (dd, J=1.6, 7.8 Hz, 1H), 7.60 (dd, J=1.6, 7.8 Hz, 1H), 7.37-7.09 (m, 6H), 6.76 (t, J=2.2 Hz, 2H), 6.28 (t, J=2.1 Hz, 2H), 2.76 (t, J=7.5 Hz, 2H), 2.55 (t, J=7.3 Hz, 2H). MS (ESI) m/z 316.1 (M+H)$^+$.

Example 66: Synthesis of 3-(5-hydroxypent-1-yn-1-yl)-2-(1H-pyrrol-1-yl)benzoic acid

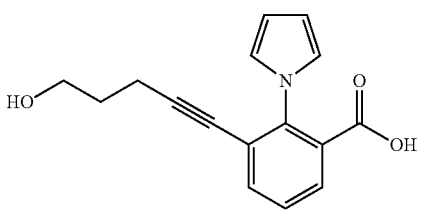 [SMILES: O=C(O)c1cccc(C#CCCCO)c1-n1cccc1]

3-(5-hydroxypent-1-yn-1-yl)-2-(1H-pyrrol-1-yl)benzoic acid was prepared by the same procedure as example 9. $^1$H NMR (300 MHz, CDCl$_3$) δ=7.77 (d, J=7.8 Hz, 1H), 7.61 (d, J=7.8 Hz, 1H), 7.29 (t, J=7.8 Hz, 1H), 6.78 (t, J=2.2 Hz, 2H), 6.30 (t, J=2.2 Hz, 2H), 3.53 (t, J=9.5 Hz, 2H), 2.40 (t, J=9.7 Hz, 2H), 1.71-1.62 (m, 2H). MS (ESI) m/z 270.1 (M+H)$^+$.

Example 67: Synthesis of 3-[2-(4-methoxyphenyl) ethynyl]-2-(1H-pyrrol-1-yl)benzoic acid

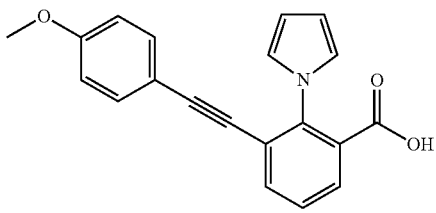 [SMILES: COc1ccc(C#Cc2cccc(C(=O)O)c2-n2cccc2)cc1]

3-[2-(4-methoxyphenyl)ethynyl]-2-(1H-pyrrol-1-yl)benzoic acid was prepared by the same procedure as example 9. $^1$H NMR (300 MHz, CDCl$_3$) δ=7.86 (dd, J=1.6, 7.8 Hz, 1H), 7.75 (dd, J=1.5, 7.9 Hz, 1H), 7.43 (t, J=7.9 Hz, 1H), 7.29-7.23 (m, 2H), 6.89-6.80 (m, 4H), 6.36 (t, J=2.2 Hz, 2H), 3.80 (s, 3H). MS (ESI) m/z 318.1 (M+H)$^+$.

Example 68: Synthesis of 3-[2-(pyridin-4-yl)ethynyl]-2-(1H-pyrrol-1-yl)benzoic acid

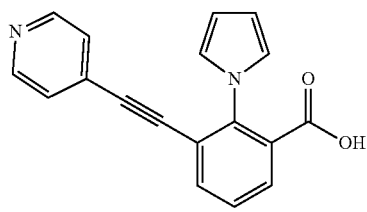 [SMILES: O=C(O)c1cccc(C#Cc2ccncc2)c1-n1cccc1]

3-[2-(pyridin-4-yl)ethynyl]-2-(1H-pyrrol-1-yl)benzoic acid was prepared by the same procedure as example 9. $^1$H NMR (300 MHz, CDCl$_3$) δ=8.63 (d, J=6.5 Hz, 2H), 7.97 (dd, J=1.6, 7.8 Hz, 1H), 7.79 (dd, J=1.6, 7.8 Hz, 1H), 7.51 (t, J=7.8 Hz, 1H), 7.44-7.40 (m, 2H), 6.78 (t, J=2.2 Hz, 2H), 6.30 (t, J=2.2 Hz, 2H). MS (ESI) m/z 289.1 (M+H)$^+$.

Example 69: Synthesis of 3-[2-(pyridin-3-yl)ethynyl]-2-(1H-pyrrol-1-yl)benzoic acid

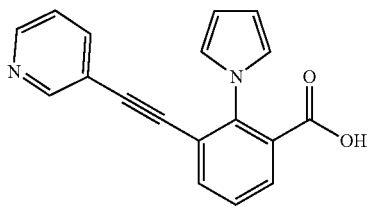 [SMILES: O=C(O)c1cccc(C#Cc2cccnc2)c1-n1cccc1]

3-[2-(pyridin-3-yl)ethynyl]-2-(1H-pyrrol-1-yl)benzoic acid was prepared by the same procedure as example 9. $^1$H NMR (300 MHz, CDCl$_3$) δ=$^1$H NMR (300 MHz, CDCl$_3$) δ=8.80-8.55 (m, 2H), 7.99-7.87 (m, 2H), 7.80-7.74 (m, 1H), 7.65-7.55 (m, 1H), 7.51 (t, J=7.8 Hz, 1H), 6.86 (t, J=2.2 Hz, 2H), 6.35 (t, J=2.2 Hz, 2H). MS (ESI) m/z 289.1 (M+H)$^+$.

Example 70: Synthesis of 3-[2-(3-methoxyphenyl) ethynyl]-2-(1H-pyrrol-1-yl)benzoic acid

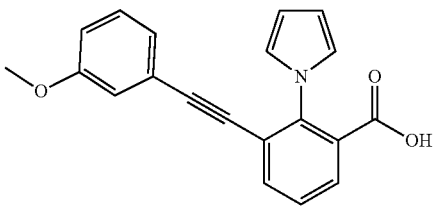 [SMILES: COc1cccc(C#Cc2cccc(C(=O)O)c2-n2cccc2)c1]

3-[2-(3-methoxyphenyl)ethynyl]-2-(1H-pyrrol-1-yl)benzoic acid was prepared by the same procedure as example 9. $^1$H NMR (300 MHz, CDCl$_3$) δ=7.90 (dd, J=1.7, 7.8 Hz, 1H), 7.78 (dd, J=1.6, 7.8 Hz, 1H), 7.46 (t, J=7.9 Hz, 1H), 7.20 (t, J=7.9 Hz, 1H), 6.95-6.82 (m, 5H), 6.37 (t, J=2.2 Hz, 2H), 3.80 (s, 3H). MS (ESI) m/z 318.1 (M+H)$^+$.

Example 71: Synthesis of 3-[2-(4-fluorophenyl) ethynyl]-2-(1H-pyrrol-1-yl)benzoic acid

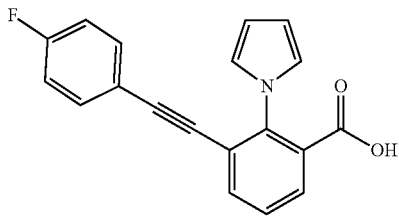 [SMILES: O=C(O)c1cccc(C#Cc2ccc(F)cc2)c1-n1cccc1]

3-[2-(4-fluorophenyl)ethynyl]-2-(1H-pyrrol-1-yl)benzoic acid was prepared by the same procedure as example 9. $^1$H NMR (300 MHz, CDCl$_3$) δ=7.88 (dd, J=1.5, 7.9 Hz, 1H), 7.75 (dd, J=1.6, 7.7 Hz, 1H), 7.44 (t, J=7.8 Hz, 1H), 7.32-7.26 (m, 2H), 7.02-6.94 (m, 2H), 6.87 (t, J=2.2 Hz, 2H), 6.25 (t, J=2.2 Hz, 2H). MS (ESI) m/z 306.0 (M+H)$^+$.

Example 72: Synthesis of 3-(2-phenylethynyl)-2-(1H-pyrrol-1-yl)benzoic acid

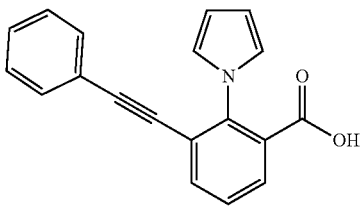 [SMILES: O=C(O)c1cccc(C#Cc2ccccc2)c1-n1cccc1]

3-(2-phenylethynyl)-2-(1H-pyrrol-1-yl)benzoic acid was prepared by the same procedure as example 9. $^1$H NMR (300 MHz, CDCl$_3$) δ=7.86 (dd, J=1.5, 7.9 Hz, 1H), 7.77 (dd, J=1.6, 7.8 Hz, 1H), 7.42 (t, J=7.9 Hz, 1H), 7.35-7.26 (m, 5H), 6.87 (t, J=2.1 Hz, 2H), 6.36 (t, J=2.1 Hz, 2H). MS (ESI) m/z 288.0 (M+H)$^+$.

Example 73: 3-{3-[benzyl(methyl)amino]prop-1-yn-1-yl}-2-(1H-pyrrol-1-yl)benzoic acid

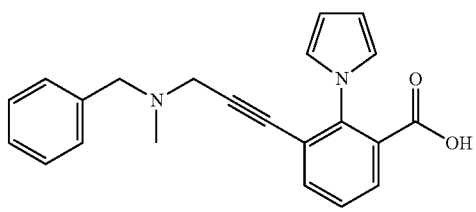 [SMILES: CN(CC#Cc1cccc(C(=O)O)c1-n1cccc1)Cc1ccccc1]

3-{3-[benzyl(methyl)amino]prop-1-yn-1-yl}-2-(1H-pyrrol-1-yl)benzoic acid was prepared by the same procedure as example 9. $^1$H NMR (300 MHz, CD$_3$OD) δ=7.82-7.6 (m, 2H), 7.58-7.45 (m, 4H), 7.42-7.38 (m, 1H), 6.90 (d, J=3.4 Hz, 2H), 6.82-6.55 (m, 1H), 6.28-6.22 (m, 2H), 4.42-4.21 (m, 2H), 4.08 (m, 2H), 2.75-2.67 (m, 3H). MS (ES$^+$)=345.0 (MH)$^+$.

Example 74: 3-[3-(1H-imidazol-1-yl)prop-1-yn-1-yl]-2-(1H-pyrrol-1-yl)benzoic acid

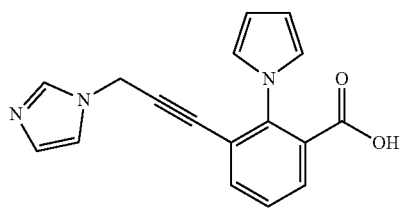 [SMILES: O=C(O)c1cccc(C#CCn2ccnc2)c1-n1cccc1]

3-[3-(1H-imidazol-1-yl)prop-1-yn-1-yl]-2-(1H-pyrrol-1-yl)benzoic acid was prepared by the same procedure as example 9. $^1$H NMR (300 MHz, CD$_3$OD) δ=8.89 (br. s., 1H), 8.79-8.63 (m, 1H), 8.60-8.44 (m, 1H), 8.37-8.22 (m, 1H), 8.16-8.07 (m, 1H), 7.91-7.76 (m, 1H), 7.61-7.48 (m, 1H), 7.36 (d, J=7.6 Hz, 1H), 7.00 (br. s., 1H), 6.51 (d, J=12.0 Hz, 1H), 4.64 (br. s., 2H). MS (ES$^+$)=291.9 (M)$^+$.

Example 75: Synthesis of 3-[2-(1,3-thiazol-4-yl)ethynyl]benzoic acid

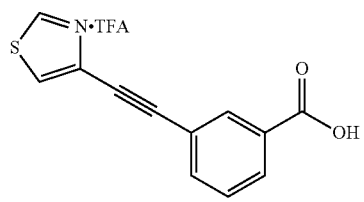

3-[2-(1,3-thiazol-4-yl)ethynyl]benzoic acid. A mixture of 3-ethynyl-1-yl-benzoic acid methyl ester (40 mg, 0.25 mmol), 4-bromo-thiazole (82 mg, 0.5 mmol), palladium tetrakis-triphenylphosphine (29 mg, 0.025 mmol) and copper iodide (9.5 mg, 0.05 mmol), potassium carbonate (69 mg, 0.5 mmol) in 1,2-dimethoxyethane/water (1 mL/0.3 mL) was degassed with N$_2$ for 5 minutes and then heated at 60° C. for 4 hours. After cooling to ambient temperature, the crude mixture was filtered through celite and washed with dichloromethane. The filtrate was concentrated and purified by preparative thin layered chromatography eluting with ethyl acetate/hexane (30%) to give the ester intermediate. To this intermediate in tetrahydrofuran/methanol (1 mL/0.2 mL) was added sodium hydroxide solution (2 N in water, 0.2 mL, 0.4 mmol) and the solution was stirred at room temperature for 18 hours. 1 N hydrochloric acid aqueous solution was added dropwise until pH=1 and the reaction mixture was purified through preparative HPLC to give 18 mg (22% for 2 steps) of the pure product as a white solid. $^1$H NMR (300 MHz, DMSO) δ=13.2 (br. s., 1H), 9.18 (d, J=2.1 Hz, 1H), 8.19 (d, J=1.8 Hz, 1H), 8.05 (t, J=1.5 Hz, 1H), 7.98 (td, J=1.4, 7.8 Hz, 1H), 7.81 (td, J=1.4, 7.8 Hz, 1H), 7.57 (t, J=7.8 Hz, 1H). LCMS (ESI) m/z 230.0 (M+1)$^+$.

Example 76: Synthesis of 3-(2-{1H-pyrrolo[2,3-b]pyridin-3-yl}ethynyl)benzoic acid

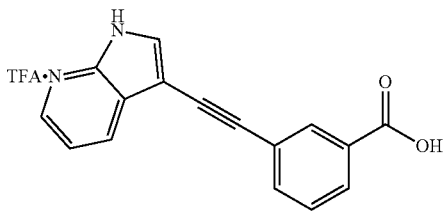

3-(2-{1H-pyrrolo[2,3-b]pyridin-3-yl}) ethynyl)benzoic acid was prepared by the same procedure as example 75. $^1$H NMR (300 MHz, DMSO) δ=12.20 (br. s., 1H), 8.31 (dd, J=1.5, 4.7 Hz, 1H), 8.13 (dd, J=1.5, 7.9 Hz, 1H), 8.05 (d, J=2.4 Hz, 1H), 7.97-7.95 (m, 1H), 7.91 (d, J=7.7 Hz, 1H), 7.78 (d, J=7.6 Hz, 1H), 7.54 (t, J=7.8 Hz, 1H), 7.20 (dd, J=4.8, 7.8 Hz, 1H). LCMS (ESI) m/z 263.0 (M+1)$^+$.

Example 77: Synthesis of 3-[2-(1H-indol-5-yl)ethynyl]benzoic acid

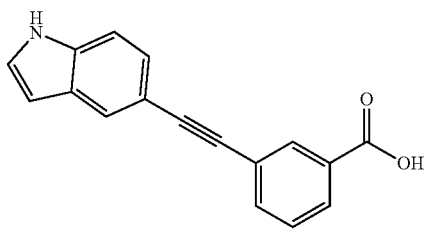 [SMILES: O=C(O)c1cccc(C#Cc2ccc3[nH]ccc3c2)c1]

3-[2-(1H-indol-5-yl)ethynyl]benzoic acid was prepared by the same procedure as example 75. $^1$H NMR (300 MHz, CDCl$_3$) δ=9.30 (br. s., 1H), 8.23 (t, J=1.8 Hz, 1H), 7.98 (td, J=1.5, 7.9 Hz, 1H), 7.87 (d, J=0.9 Hz, 1H), 7.72 (td, J=1.3, 7.9 Hz, 1H), 7.47-7.23 (m, 4H), 6.59-6.50 (m, 1H). LCMS (ESI) m/z 262.0 (M+1)$^+$.

Example 78: Synthesis of 2-amino-3-(2-{1H-pyrrolo[2,3-b]pyridin-3-yl}ethynyl)benzoic acid

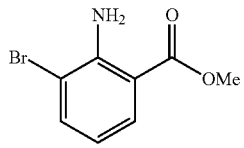

2-Amino-3-bromo-benzoic acid methyl ester: 2-Amino-3-bromo-benzoic acid (5 g, 23 mmol) was dissolved in methanol (30 mL), concentrated sulfuric acid (1 mL) was added dropwise and the reaction mixture was refluxed at 80° C. for 24 hours, allowed to cool to ambient temperature and then concentrated at reduced pressure. The residue was diluted by water (10 mL) and basified with saturated sodium bicarbonate solution, extracted by ethyl acetate (20 mL×3). The organic layer was dried (anhydrous magnesium sulfate), concentrated and purified by column chromatography through a silica gel cartridge (80 g) eluting with ethyl acetate/hexane (10%) to give the product as a colorless oil (5 g, 95%).

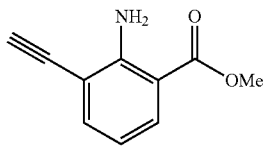

2-Amino-3-ethynyl-benzoic acid methyl ester: To a pressure flask was loaded a mixture of 2-amino-3-bromo-benzoic acid methyl ester (2 g, 8.7 mmol), Pd(PPh$_3$)$_2$Cl$_2$ (610 mg, 0.87 mmol) and CuI (331 mg, 1.74 mmol) in triethyl amine (20 mL), the mixture was degassed with N$_2$ for 10 minutes, trimethylsilylacetylene (4 mL) was added, and the mixture was further degassed for 3 minutes. The flask was sealed with a PFTE plug and heated at 90° C. for 5 hours. After cooling to ambient temperature, the crude mixture was filtered through celite and washed with dichloromethane and the filtrate was concentrated and purified by column chromatography through a silica gel cartridge (80 g) eluting with hexane to give a solid intermediate. The solid intermediate was dissolved in tetrahedrofuran (15 mL), tetrabutyl ammonium fluoride (1 N in THF, 14 mL, 14 mmol) was added and the reaction mixture was stirred for 10 minutes and concentrated. The residue was purified by column chromatography through a silica gel cartridge (80 g) eluting with ethyl acetate/hexane (0-20%) to give the product as a white solid (1.4 g, 86% for 2 steps).

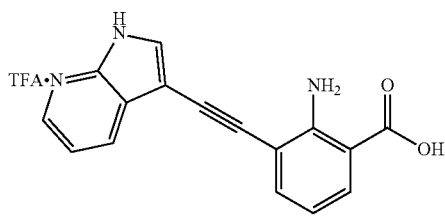

2-amino-3-(2-{1H-pyrrolo[2,3-b]pyridin-3-yl}ethynyl)benzoic acid was prepared by the same procedure as example 75 starting with 2-amino-3-ethynyl-benzoic acid methyl ester. $^1$H NMR (300 MHz, CDCl$_3$) δ=7.98-7.76 (m, 1H), 7.68-7.52 (m, 1H), 7.44 (d, J=8.5 Hz, 1H), 7.35-7.30 (m, 3H), 7.25-7.14 (m, 1H), 6.77-6.48 (m, 2H).

Example 79: Synthesis of 2-amino-3-[2-(1H-indol-4-yl)ethynyl]benzoic acid

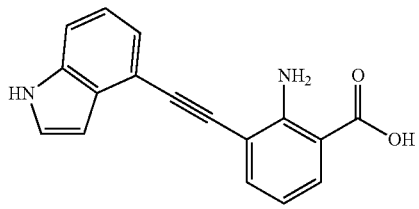 [SMILES: Nc1c(C#Cc2cccc3[nH]ccc23)cccc1C(=O)O]

2-amino-3-[2-(1H-indol-4-yl)ethynyl]benzoic acid was prepared by the same procedure as example 78. $^1$H NMR (300 MHz, CDCl$_3$) δ=7.94 (td, J=1.7, 7.4 Hz, 2H), 7.60 (dd, J=1.6, 7.5 Hz, 1H), 7.53 (dd, J=1.6, 7.6 Hz, 1H), 7.44 (d, J=8.2 Hz, 1H), 7.35-7.29 (m, 1H), 7.17 (t, J=8.0 Hz, 1H), 6.76-6.52 (m, 3H). LCMS (ESI) m/z 278.0 (M+1)$^+$.

Example 80: Synthesis of 2-amino-3-[2-(1H-indol-6-yl)ethynyl]benzoic acid

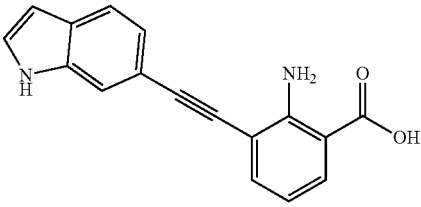 [SMILES: Nc1c(C#Cc2ccc3cc[nH]c3c2)cccc1C(=O)O]

2-amino-3-[2-(1H-indol-6-yl)ethynyl]benzoic acid was prepared by the same procedure as example 78. $^1$H NMR (300 MHz, CDCl$_3$) δ=7.91 (dd, J=1.6, 8.1 Hz, 1H), 7.72-7.44 (m, 3H), 7.41-7.17 (m, 4H), 6.64 (t, J=7.8 Hz, 1H), 6.55 (d, J=3.4 Hz, 1H). LCMS (ESI) m/z 278.0 (M+1)$^+$.

Example 81: Synthesis of 2-amino-3-[2-(1H-indol-5-yl)ethynyl]benzoic acid

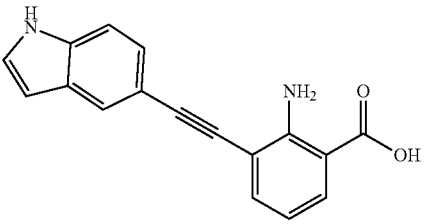 [SMILES: Nc1c(C#Cc2ccc3[nH]ccc3c2)cccc1C(=O)O]

2-amino-3-[2-(1H-indol-5-yl)ethynyl]benzoic acid was prepared by the same procedure as example 78. LCMS (ESI) m/z 277.1 (M+1)$^+$.

Example 82: Synthesis of 2-amino-3-{2-[3-(hydroxymethyl)phenyl]ethynyl}benzoic acid

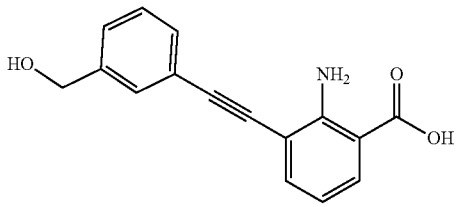 [SMILES: Nc1c(C#Cc2cccc(CO)c2)cccc1C(=O)O]

2-amino-3-{2-[3-(hydroxymethyl)phenyl]ethynyl}benzoic acid was prepared by the same procedure as example 78. LCMS (ESI) m/z 250.1 (M–H$_2$O)$^+$.

Example 83: Synthesis of 2-amino-3-[2-(3-hydroxyphenyl)ethynyl]benzoic acid

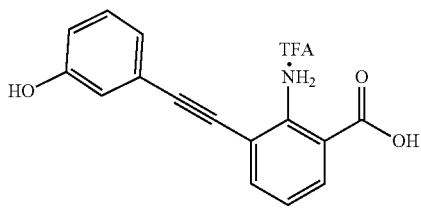 [SMILES: Nc1c(C#Cc2cccc(O)c2)cccc1C(=O)O]

2-amino-3-[2-(3-hydroxyphenyl)ethynyl]benzoic acid: To a sealed tube was loaded a mixture of 2-amino-3-bromobenzoic acid methyl ester (50 mg, 0.22 mmol), Pd(PPh$_3$)$_2$Cl$_2$ (15.4 mg, 0.022 mmol) and CuI (4.2 mg, 0.022 mmol) in triethyl amine (1 mL). The mixture was degassed with N$_2$ for 10 minutes, 3-ethynyl-phenol (103 mg, 0.87 mmol) was added and the mixture degassed with N$_2$ for 5 minutes. The reaction mixture was heated at 90° C. for 5 hours. After cooling to ambient temperature, the crude mixture was filtered through celite and washed with dichloromethane. The filtrate was concentrated and purified by preparative thin layer chromatography eluting with ethyl acetate/hexane (30%) to give a solid intermediate. To the solid intermediate in tetrahydrofuran/methanol (1 mL/0.2 mL) was added sodium hydroxide solution (2 N in water, 0.2 mL, 0.4 mmol) and the solution was stirred at room temperature for 18 hours. 1 N hydrochloric acid aqueous solution was added dropwise until pH=1 and the reaction mixture was purified through preparative HPLC to give 11 mg (14% for 2 steps) of the pure product as a white solid. LCMS (ESI) m/z 254.1 (M+1)$^+$.

Example 84: Synthesis of 2-amino-3-(2-phenylethynyl)benzoic acid

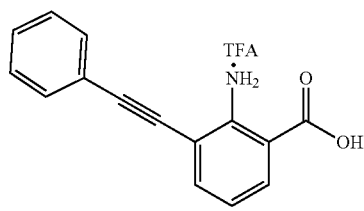 [SMILES: Nc1c(C#Cc2ccccc2)cccc1C(=O)O]

2-amino-3-(2-phenylethynyl)benzoic acid was prepared by the same procedure as example 83. $^1$H NMR (300 MHz, CDCl$_3$) δ=7.93 (dd, J=1.6, 8.1 Hz, 1H), 7.58-7.50 (m, 4H), 7.39-7.34 (m, 4H), 6.64 (t, J=7.6 Hz, 1H). LCMS (ESI) m/z 220.2 (M–H$_2$O)$^+$.

Example 85: Synthesis of 2-fluoro-3-(2-phenylethynyl)benzoic acid

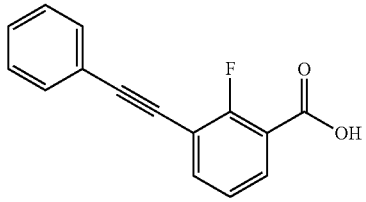 [SMILES: O=C(O)c1cccc(C#Cc2ccccc2)c1F]

2-fluoro-3-(2-phenylethynyl)benzoic acid was prepared by the same procedure as example 83 starting with 2-fluoro-3-bromobenzoic acid methyl ester. $^1$H NMR (300 MHz, CDCl$_3$) δ 7.98 (m, 1H), 7.75 (m, 1H), 7.57 (m, 2H), 7.48-7.32 (m, 4H). MS m/z (M+) 240.7.

Example 86: Synthesis of 2-fluoro-3-(2-{1H-pyrrolo[2,3-b]pyridin-3-yl}ethynyl)benzoic acid

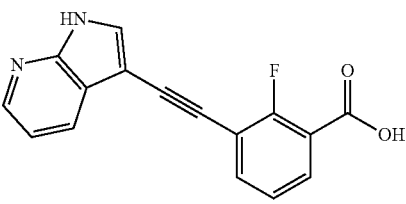 [SMILES: O=C(O)c1cccc(C#Cc2c[nH]c3ncccc23)c1F]

2-fluoro-3-(2-{1H-pyrrolo[2,3-b]pyridin-3-yl}ethynyl)benzoic acid was prepared by the same procedure as example 78 starting with 2-fluoro-3-bromobenzoic acid methyl ester. $^1$H NMR (300 MHz, CD$_3$OD) δ 8.34 (bs, 1H), 8.25 (dd, J=7.9, 1.3 Hz, 1H), 7.98-7.83 (m, 1H), 7.80-7.71 (m, 2H), 7.35-7.31 (m, 1H), 7.28 (t, J=7.7 Hz, 1H). MS m/z (M+H) 281.0.

Example 87: Synthesis of 2-fluoro-3-(2-{imidazo[1,2-a]pyrazin-3-yl}ethynyl)benzoic acid

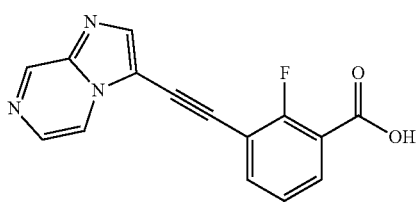 [SMILES: O=C(O)c1cccc(C#Cc2cnc3cnccn23)c1F]

2-fluoro-3-(2-{imidazo[1,2-a]pyrazin-3-yl}ethynyl)benzoic acid was prepared by the same procedure as example 86. $^1$H NMR (300 MHz, DMSO) δ 9.21 (d, J=1.5 Hz, 1H), 8.66 (dd, J=4.6, 1.5 Hz, 1H), 8.28 (s, 1H), 8.14 (d, J=4.5 Hz, 1H), 8.06-7.97 (m, 1H), 7.97-7.89 (m, 1H), 7.41 (t, J=7.8 Hz, 1H). MS m/z (M+H) 282.0

Example 88: Synthesis of 2-fluoro-3-{2-[2-(hydroxymethyl)phenyl]ethynyl}benzoic acid

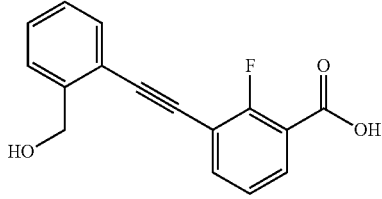 [SMILES: O=C(O)c1cccc(C#Cc2ccccc2CO)c1F]

2-fluoro-3-{2-[2-(hydroxymethyl)phenyl]ethynyl}benzoic acid was prepared by the same procedure as example 86. $^1$H NMR (300 MHz, CDCl$_3$) δ 7.94-7.85 (m, 1H), 7.71-7.61 (m, 1H), 7.58-7.47 (m, 2H), 7.43-7.34 (m, 1H), 7.32-7.25 (m, 1H), 7.23-7.14 (m, 1H), 4.89 (d, J=20.9 Hz, 2H). MS m/z (M+) 270.7

Example 89: Synthesis of 2-fluoro-3-[2-(1,3-thiazol-4-yl)ethynyl]benzoic acid

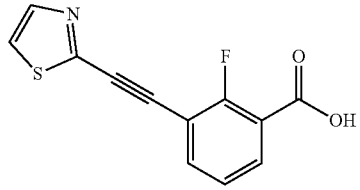 [SMILES: O=C(O)c1cccc(C#Cc2nccs2)c1F]

2-fluoro-3-[2-(1,3-thiazol-4-yl)ethynyl]benzoic acid was prepared by the same procedure as example 86. $^1$H NMR (300 MHz, DMSO) δ 13.49 (s, 1H), 9.20 (d, J=1.9 Hz, 1H), 8.23 (d, J=1.9 Hz, 1H), 8.05-7.52 (m, 2H), 7.36 (t, J=7.8 Hz, 1H). MS m/z (M+H) 248.0

Example 90: Synthesis of 3-[2-(pyridin-2-yl)ethynyl]benzoic acid

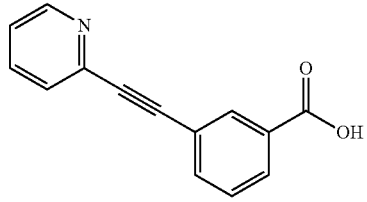 [SMILES: O=C(O)c1cccc(C#Cc2ccccn2)c1]

3-[2-(pyridin-2-yl)ethynyl]benzoic acid was prepared by the same procedure as example 78 starting with 3-bromobenzoic acid methyl ester. $^1$H NMR (300 MHz, CDCl$_3$) δ 8.65 (s, 1H), 8.29 (s, 1H), 8.04 (d, J=7.9 Hz, 1H), 7.78 (d, J=7.4 Hz, 1H), 7.71 (dd, J=7.7, 6.0 Hz, 1H), 7.55 (d, J=7.8 Hz, 1H), 7.46 (t, J=7.8 Hz, 1H), 7.28 (d, J=10.1 Hz, 1H). MS m/z (M+H) 224.0

Example 91: Synthesis of 3-[2-(pyridin-3-yl)ethynyl]benzoic acid

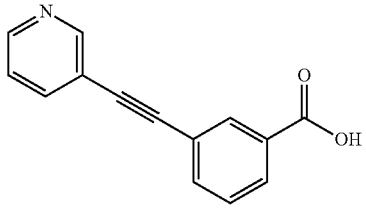 [SMILES: O=C(O)c1cccc(C#Cc2cccnc2)c1]

3-[2-(pyridin-3-yl)ethynyl]benzoic acid was prepared by the same procedure as example 90. $^1$H NMR (300 MHz, CDCl$_3$) δ 8.79 (s, 1H), 8.57 (d, J=3.3 Hz, 1H), 8.23 (s, 1H), 8.04 (d, J=7.9 Hz, 1H), 7.83 (d, J=7.8 Hz, 1H), 7.72 (d, J=7.7 Hz, 1H), 7.46 (t, J=7.9 Hz, 1H), 7.31 (dd, J=7.4, 4.6 Hz, 2H). MS m/z (M+H) 224.1

Example 92: Synthesis of 3-(2-phenylethynyl)benzoic acid

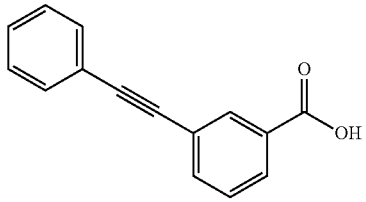 [SMILES: O=C(O)c1cccc(C#Cc2ccccc2)c1]

3-(2-phenylethynyl)benzoic acid was prepared by the same procedure as example 90. $^1$H NMR (300 MHz, CDCl$_3$) δ 8.21 (s, 1H), 8.00 (d, J=8.2 Hz, 1H), 7.69 (s, 2H), 7.54 (d, J=3.5 Hz, 2H), 7.45 (d, J=7.7 Hz, 1H), 7.35 (d, J=2.6 Hz, 2H). MS m/z (M+H) 223.1

Example 93: Synthesis of 3-[2-(pyridin-4-yl)ethynyl]benzoic acid

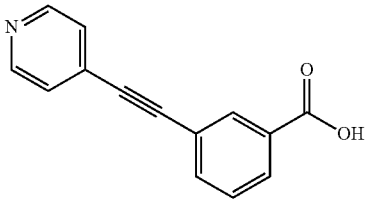 [SMILES: O=C(O)c1cccc(C#Cc2ccncc2)c1]

3-[2-(pyridin-4-yl)ethynyl]benzoic acid was prepared by the same procedure as example 90. $^1$H NMR (300 MHz, CDCl$_3$) δ 8.63 (d, J=5.2 Hz, 1H), 8.24 (s, 1H), 8.06 (d, J=7.9 Hz, 1H), 7.73 (d, J=7.5 Hz, 1H), 7.47 (t, J=8.0 Hz, 1H), 7.45-7.34 (m, 2H), 7.26 (m, 1H). MS m/z (M+H) 224.0

Example 94: Synthesis of 3-[2-(4-methoxyphenyl)ethynyl]benzoic acid

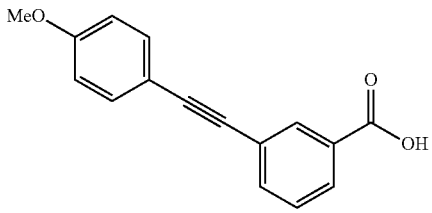 [SMILES: COc1ccc(C#Cc2cccc(C(=O)O)c2)cc1]

3-[2-(4-methoxyphenyl)ethynyl]benzoic acid was prepared by the same procedure as example 90. $^1$H NMR (300 MHz, CDCl$_3$) δ 8.19 (s, 1H), 7.97 (d, J=7.8 Hz, 1H), 7.68 (d, J=7.6 Hz, 1H), 7.48 (d, J=8.9 Hz, 2H), 7.42 (t, J=7.7 Hz, 1H), 6.89 (d, J=8.9 Hz, 2H). MS m/z (M+H) 253.0

Example 95: Synthesis of 2-{4-[(dimethylamino)methyl]phenyl}-3-(2-phenylethynyl)benzoic acid trifluoroacetic acid salt

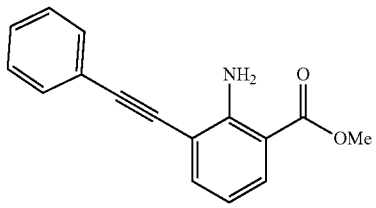 [SMILES: COC(=O)c1cccc(C#Cc2ccccc2)c1N]

2-Amino-3-phenylethynyl-benzoic acid methyl ester: To a sealed flask was loaded a mixture of 2-amino-3-bromo-benzoic acid methyl ester (4 g, 17.4 mmol), Pd(PPh$_3$)$_2$Cl$_2$ (618 mg, 0.88 mmol) and copper iodide (335 mg, 1.76 mmol) in triethyl amine (80 mL). The mixture was degassed with N$_2$ for 10 minutes, phenylacetylene (7.2 g, 70.5 mmol) was added and the mixture was degassed with N$_2$ for 5 minutes. The reaction mixture was heated at 90° C. for 17 hours. After cooling to ambient temperature, the crude mixture was filtered through celite and washed with dichloromethane. The filtrate was concentrated and purified by column chromatography through a silica gel cartridge (80 g) eluting with ethyl acetate/hexane (0-30%) to give 4.3 g (98%) of the product as a white solid.

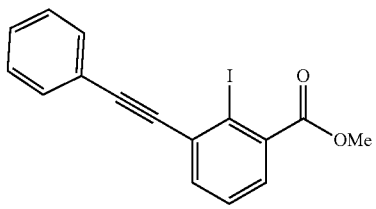 [SMILES: COC(=O)c1cccc(C#Cc2ccccc2)c1I]

2-Iodo-3-phenylethynyl-benzoic acid methyl ester: A solution of 2-amino-3-phenylethynyl-benzoic acid methyl ester (1 g, 3.98 mmol) in 1,4-dioxane was treated with concentrated hydrochloric acid (7.8 mL) slowly and stirred for 10 minutes. At 0° C. sodium nitrite (304 mg, 4.4 mmol) in water (5 mL) was added and the reaction mixture was stirred at 0° C. for 1 hour. Potassium iodide (6.8 g, 4.1 mmol) in water (5.5 mL) was added at 0° C. and the solution was stirred at room temperature for 17 hours. Saturated sodium bicarbonate was added until bubbling ceased and the solution was extracted with dichloromethane (15 mL×3), the organic extracts were combined, dried (anhydrous sodium sulfate), concentrated and purified by column chromatography through a silica gel cartridge (40 g) eluting with ethyl acetate/hexane (0-20%) to give the product as a white solid (340 mg, 30%).

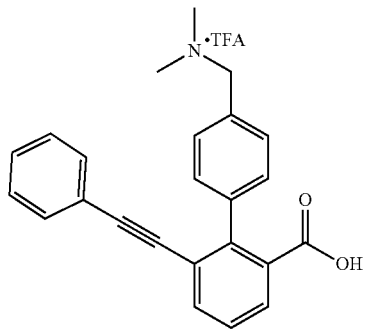 [SMILES: CN(C)Cc1ccc(-c2c(C#Cc3ccccc3)cccc2C(=O)O)cc1]

2-{4-[(dimethylamino)methyl]phenyl}-3-(2-phenylethynyl)benzoic acid trifluoroacetic acid salt. A mixture of 2-iodo-3-phenylethynyl-benzoic acid methyl ester (25 mg, 0.069 mmol), dimethyl-[4-(4,4,5,5-tetramethyl-[1,3,2]dioxaborolan-2-yl)-benzyl]-amine (26 mg, 0.1 mmol), 1,1'-bis(diphenylphosphino)ferrocene-palladium(II)dichloride (6.1 mg, 0.007 mmol) and potassium carbonate (23 mg, 0.17 mmol) in 1,4-dioxane (0.8 mL) and water (0.2 mL) was degassed with N$_2$ for 10 minutes and heated at 90° C. for 17 hours. After cooling down the reaction mixture was partitioned between water and ethyl acetate, the organic layer was dried (sodium sulfate), filtered, concentrated and purified through preparative thin layer chromatography to give a solid intermediate. To this solid intermediate in tetrahydrofuran/methanol (1 mL/0.2 mL) was added sodium hydroxide solution (2 N in water, 0.2 mL, 0.4 mmol) and the solution was stirred at room temperature for 18 hours. 1 N hydrochloric acid aqueous solution was added dropwise until pH=1 and the reaction mixture was purified through preparative HPLC to give 13 mg (42% for 2 steps) of the pure product as a white solid. $^1$H NMR (300 MHz, CDCl$_3$) δ=7.97 (d, J=7.6 Hz, 1H), 7.77 (d, J=7.9 Hz, 1H), 7.57-7.38 (m, 3H), 7.37-7.09 (m, 7H), 4.03 (s, 2H), 2.67 (s, 6H). LCMS (ESI) m/z 356.1 (M+1)$^+$.

Example 96: Synthesis of 3-(2-phenylethynyl)-2-(1,2,3,6-tetrahydropyridin-4-yl)benzoic acid trifluoroacetic acid salt

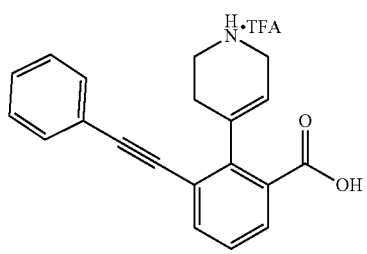 [SMILES: O=C(O)c1cccc(C#Cc2ccccc2)c1C1=CCNCC1]

3-(2-phenylethynyl)-2-(1,2,3,6-tetrahydropyridin-4-yl) benzoic acid trifluoroacetic acid salt was prepared by the same procedure as example 95. LCMS (ESI) m/z 304.1 (M+1)⁺.

Example 97:
3-(2-phenylethynyl)-2-(pyridin-4-yl)benzoic acid trifluoroacetic acid salt

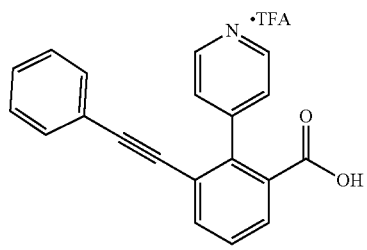 [SMILES: O=C(O)c1cccc(C#Cc2ccccc2)c1-c1ccncc1]

3-(2-phenylethynyl)-2-(pyridin-4-yl)benzoic acid trifluoroacetic acid salt was prepared by the same procedure as example 95. ¹H NMR (300 MHz, CDCl₃) δ=8.74 (d, J=6.7 Hz, 2H), 8.19 (dd, J=1.2, 7.9 Hz, 1H), 7.85 (dd, J=1.3, 7.8 Hz, 1H), 7.77 (d, J=6.5 Hz, 2H), 7.61 (t, J=7.9 Hz, 1H), 7.31-7.23 (m, 3H), 7.09 (dd, J=1.6, 8.1 Hz, 2H). LCMS (ESI) m/z 300.1 (M+1)⁺.

Example 98: Synthesis of 2-(4-methanesulfonylphenyl)-3-(2-phenylethynyl)benzoic acid

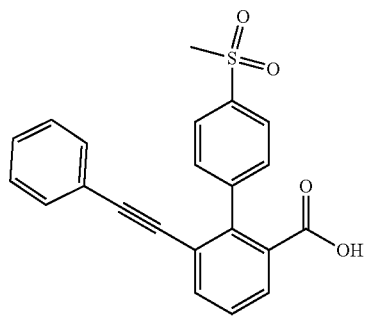 [SMILES: CS(=O)(=O)c1ccc(-c2c(C#Cc3ccccc3)cccc2C(=O)O)cc1]

2-(4-methanesulfonylphenyl)-3-(2-phenylethynyl)benzoic acid was prepared by the same procedure as example 95. ¹H NMR (300 MHz, CDCl₃) δ=8.04-7.99 (m, 3H), 7.82 (dd, J=1.2, 7.6 Hz, 1H), 7.58-7.48 (m, 3H), 7.29-7.22 (m, 3H), 7.09-7.04 (m, 2H), 3.11 (s, 3H). LCMS (ESI) m/z 377.0 (M+1)⁺.

Example 99: Synthesis of 3-(2-phenylethynyl)-2-(1H-pyrazol-4-yl)benzoic acid

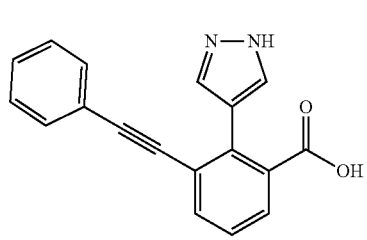 [SMILES: O=C(O)c1cccc(C#Cc2ccccc2)c1-c1cn[nH]c1]

3-Phenylethynyl-2-(1H-pyrazol-4-yl)-benzoic acid was prepared by the same procedure as example 95. ¹H NMR (300 MHz, CDCl₃) δ=8.03 (s, 2H), 7.91 (d, J=8.0 Hz, 1H), 7.81 (dd, J=1.3, 7.8 Hz, 1H), 7.48 (t, J=7.8 Hz, 1H), 7.35-7.27 (m, 5H). LCMS (ESI) m/z 289.1 (M+1)⁺.

Example 100: Synthesis of 3-(2-phenylethynyl)-2-(pyrimidin-5-yl)benzoic acid

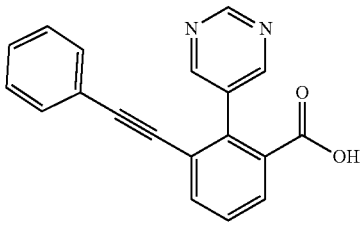 [SMILES: O=C(O)c1cccc(C#Cc2ccccc2)c1-c1cncnc1]

3-(2-phenylethynyl)-2-(pyrimidin-5-yl)benzoic acid was prepared by the same procedure as example 95. ¹H NMR (300 MHz, CDCl₃) δ=9.18 (s, 1H), 8.74 (s, 2H), 8.06 (dd, J=1.5, 7.9 Hz, 1H), 7.81 (dd, J=1.3, 7.8 Hz, 1H), 7.51 (t, J=7.8 Hz, 1H), 7.28-7.15 (m, 5H). LCMS (ESI) m/z 301.1 (M+1)⁺.

Example 101: Synthesis of 2-(1-methyl-1H-pyrazol-4-yl)-3-(2-phenylethynyl)benzoic acid

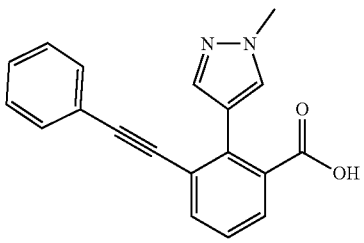 [SMILES: Cn1cc(-c2c(C#Cc3ccccc3)cccc2C(=O)O)cn1]

2-(1-methyl-1H-pyrazol-4-yl)-3-(2-phenylethynyl)benzoic acid was prepared by the same procedure as example 95. ¹H NMR (300 MHz, CDCl₃) δ=8.87 (br. s., 1H), 7.93-7.89 (m, 1H), 7.89 (s, 1H), 7.80 (dd, J=1.3, 7.8 Hz, 1H), 7.70 (s, 1H), 7.44 (t, J=7.8 Hz, 1H), 7.36-7.26 (m, 5H), 4.08 (s, 3H). LCMS (ESI) m/z 303.0 (M+1)⁺.

Example 102: Synthesis of 3-(2-phenylethynyl)-2-(2-phenylpyrrolidin-1-yl)benzoic acid

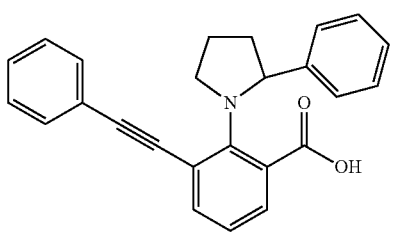 [SMILES: O=C(O)c1cccc(C#Cc2ccccc2)c1N1CCCC1c1ccccc1]

A solution of methyl 2-fluoro-3-bromobenzoate (6.41 mmol) and phenylacetylene (7.76 mmol) in tetrahydrofuran/ triethylamine (32 mL/32 mL) was degassed using a N₂ gas balloon for 15 minutes in a sealed round bottom flask. To this solution was added Bis(triphenylphosphine)palladium (II) dichloride (450 mg, 0.64 mmol) and copper iodide (60 mg), sealed and heated to 80° C. for 16 hours. The reaction mixture was then cooled to ambient temperature, filtered through celite using ethyl acetate (50 mL). The filtrate was then concentrated under reduced pressure and purified through silica gel cartridge eluting with ethyl acetate/hexanes to give the product as a brown liquid in 70% yield. To a stirring solution of 2-fluoro-3-phenylethynyl-benzoic acid methyl ester (60 mg, 0.236 mmol) in dimethyl sulfoxide (2 mL) was added 2-phenylpyrrolidine (0. 27 mmol), potassium carbonate (0.1 g, 0.7 mmol), and catalytic tetra butyl ammonium iodide. This solution was heated to 140° C. for 24 hours. The reaction mixture was then cooled to ambient temperature diluted with ethyl acetate (10 mL) washed with water (2×4 mL). The organic layers were washed with 1N hydrochloric acid (2 mL), water (2 mL), brine (2 mL) dried (sodium sulfate), filtered and concentrated under reduced pressure. The resulting crude product was then dissolved in tetrahydrofuran/methanol (1/1 mL) and added 2N sodium hydroxide solution (0.3 mL) and stirred for 24 hours at ambient temperature. This solution was then concentrated and neutralized to pH 4 using 1 N hydrochloric acid solution. The aqueous layer was then extracted using ethyl acetate (2×5 mL) and washed with water (2 mL) and brine (3 mL). The organic layers were combined, dried (sodium sulfate), filtered and concentrated under reduced pressure. The resulting crude product was then purified using reversed phase HPLC. ¹H NMR (300 MHz, CDCl₃) δ 8.14 (d, J=7.7 Hz, 1H), 7.76 (d, J=7.7 Hz, 1H), 7.59 (dd, J=6.6, 3.1 Hz, 2H), 7.46 (q, J=3.7 Hz, 3H), 7.35 (t, J=7.7 Hz, 1H), 7.23 (bs, 5H), 5.52 (t, J=7.8 Hz, 1H), 4.05-3.86 (m, 1H), 3.75 (s, 1H), 2.61-2.28 (m, 4H). MS m/z (M+H) 368.1

Example 103: Synthesis of 2-(3-(dimethylamino) pyrrolidin-1-yl)-3-(phenylethynyl)benzoic acid

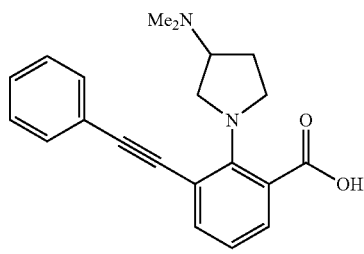 [SMILES: CN(C)C1CCN(c2c(C#Cc3ccccc3)cccc2C(=O)O)C1]

2-(3-(dimethylamino)pyrrolidin-1-yl)-3-(phenylethynyl) benzoic acid was prepared by the same procedure as example 102. ¹H NMR (300 MHz, CDCl₃) δ 8.32 (dd, J=7.9, 1.7 Hz, 1H), 7.81 (dd, J=7.7, 1.7 Hz, 1H), 7.59-7.52 (m, 2H), 7.51-7.41 (m, 4H), 3.82-3.80 (m, 1H), 3.11-2.90 (m, 2H), 2.82 (s, 6H), 2.76-2.45 (m, 2H), 1.75-1.55 (m, 1H), 1.39 (dq, J=14.7, 7.3 Hz, 1H). MS m/z (M+H) 335.2

Example 104: Synthesis of 1-(2-carboxy-6-(phenylethynyl)phenyl)pyrrolidine-3-carboxylic acid

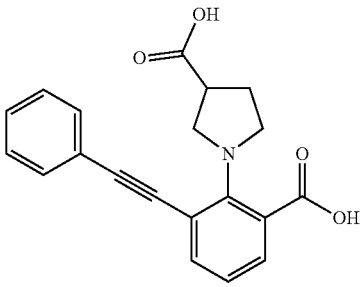 [SMILES: O=C(O)c1cccc(C#Cc2ccccc2)c1N1CCC(C(=O)O)C1]

1-(2-carboxy-6-(phenylethynyl)phenyl)pyrrolidine-3-carboxylic acid was prepared by the same procedure as example 102. ¹H NMR (300 MHz, CDCl₃) δ 8.31 (d, J=6.9 Hz, 1H), 7.80-7.70 (m, 1H), 7.74 (ddd, J=8.5, 7.9, 4.7 Hz, 1H), 7.53 (dd, J=6.7, 3.1 Hz, 1H), 7.48-7.33 (m, 3H), 7.09 (td, J=7.9, 0.9 Hz, 1H), 3.91 (m, 1H) 3.73 (bs, 1H), 3.21-2.91 (m, 2H), 2.53 (m, 1H), 1.63 (bs, 1H), 1.40 (dd, J=14.7, 7.1 Hz, 1H). MS m/z (M+H) 336.4

Example 105: Synthesis of (S)-2-(3-hydroxypyrrolidin-1-yl)-3-(phenylethynyl)benzoic acid

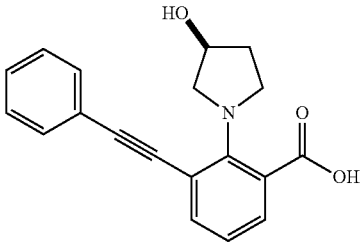 [SMILES: O=C(O)c1cccc(C#Cc2ccccc2)c1N1CC[C@H](O)C1]

(S)-2-(3-hydroxypyrrolidin-1-yl)-3-(phenylethynyl) benzoic acid was prepared by the same procedure as example 102. ¹H NMR (300 MHz, CDCl₃) δ 8.32 (d, J=7.9 Hz, 1H), 7.75 (d, J=7.6 Hz, 1H), 7.50 (dd, J=13.1, 9.4 Hz, 2H), 7.45-7.35 (m, 4H), 4.82 (s, 1H), 3.92 (d, J=12.1 Hz, 1H), 3.87-3.69 (m, 3H), 3.49 (d, J=9.1 Hz, 1H), 2.46 (s, 1H), 2.25 (s, 1H). MS m/z (M+H) 308.2

Example 106: Synthesis of 3-(phenylethynyl)-2-(pyrrolidin-1-yl) benzoic acid

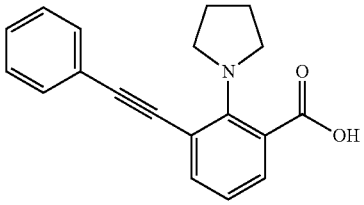 [SMILES: O=C(O)c1cccc(C#Cc2ccccc2)c1N1CCCC1]

3-(phenylethynyl)-2-(pyrrolidin-1-yl) benzoic acid was prepared by the same procedure as example 102. ¹H NMR (300 MHz, CD₃OD) δ 8.25 (dd, J=7.9, 1.6 Hz, 1H), 7.88 (dd, J=7.7, 1.5 Hz, 1H), 7.68-7.51 (m, 3H), 7.47-7.33 (m, 3H), 3.85-3.75 (m, 4H), 2.49-2.19 (m, 4H). MS m/z (M+H) 292.1

Example 107: Synthesis of 3-(phenylethynyl)-2-(piperazin-1-yl)benzoic acid

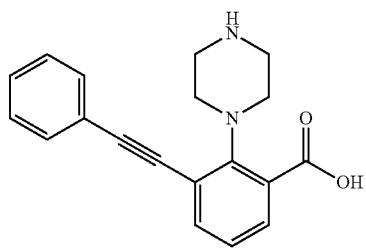 [SMILES: O=C(O)c1cccc(C#Cc2ccccc2)c1N1CCNCC1]

3-(phenylethynyl)-2-(piperazin-1-yl) benzoic acid acid was prepared by the same procedure as example 102. $^1$H NMR (300 MHz, CD$_3$OD) δ 7.70 (dd, J=3.4, 1.6 Hz, 1H), 7.67 (dd, J=3.6, 1.6 Hz, 1H), 7.63-7.58 (m, 2H), 7.45-7.40 (m, 3H), 7.27 (td, J=7.7, 3.3 Hz, 1H), 3.67-3.55 (m, 4H), 3.35 (dd, J=8.8, 4.2 Hz, 4H). MS m/z (M+H) 307.2

Example 108: Synthesis of 2-(benzylamino)-3-(phenylethynyl benzoic acid

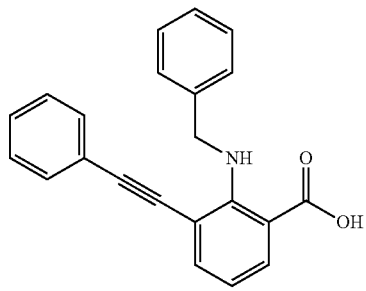 [SMILES: O=C(O)c1cccc(C#Cc2ccccc2)c1NCc1ccccc1]

2-(benzylamino)-3-(phenylethynyl) benzoic acid was prepared by the same procedure as example 102. $^1$H NMR (300 MHz, CDCl$_3$) δ 8.25 (d, J=7.3 Hz, 1H), 7.83 (d, J=7.3 Hz, 1H), 7.64-7.28 (m, 9H), 7.31-7.17 (m, 2H), 4.12 (s, 2H). MS m/z (M+H) 328.6

Example 109: Synthesis of 2-(4-phenyl-1H-1,2,3-triazol-1-yl)-3-(2-phenylethynyl)benzoic acid

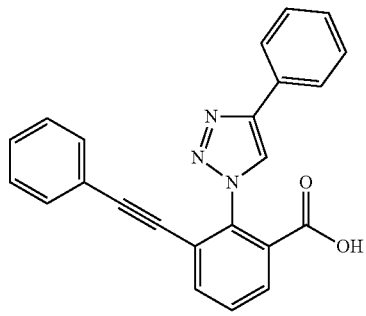 [SMILES: O=C(O)c1cccc(C#Cc2ccccc2)c1-n1cc(-c2ccccc2)nn1]

To a stirring solution of methyl 2-amino-3-bromobenzoate (0.23 g, 1 mmol) in water/1,4-dioxane (3.5/0.5 mL) at 0° C. was added concentrated hydrochloric acid (0.2 mL, 2.4 mmol) dropwise followed by a solution of sodium nitrite (0.07 g, 1 mmol) in water (1 mL) dropwise. This solution was stirred for 1 hour at 0° C. after which a solution of sodium azide (0.07 g, 1 mmol) in water (1 mL) was added. The resultant mixture was allowed to warm to ambient temperature and stirred for 3 hours. After 3 hours, the reaction mixture was extracted with dichloromethane (2×10 mL). The organic layers were combined, dried (sodium sulfate), filtered and concentrated under reduced pressure. The resulting crude product was used as is in the next reaction. To a stirring solution of methyl 2-azido-3-bromobenzoate (0.07 g, 0.27 mmol) in tert-butanol:water (1:1 mL) was added alkyne (0.27 mmol), 1M sodium ascorbate solution in water (0.1 mL) and copper sulfate (~5 mg). This solution was stirred for 24 hours at ambient temperature. After 24 hours the reaction mixture was extracted with ethyl acetate (2×10 mL). The organic layers were washed with water (5 mL), brine (5 mL) and dried (sodium sulfate), filtered and concentrated under reduced pressure. The resulting crude product was purified through silica gel cartridge eluting with ethyl acetate/hexanes to give the product as a pale yellow solid in 45% overall yield.

A solution of 3-bromo-2-(4-phenyl-[1,2,3]triazol-1-yl)-benzoic acid methyl ester (0.11 mmol) and phenylacetylene (0.11 mmol) in tetrahydrofuran:triethylamine (1:1 mL) was deaerated using a N$_2$ gas balloon for 2 minutes. To this solution was added Bis(triphenylphosphine)palladium(II) dichloride (10 mg, 0.011 mmol) and copper iodide (5 mg) and heated to 80° C. for 16 hours. The reaction mixture was then cooled to ambient temperature, filtered through celite using ethyl acetate (5 mL). The resultant solution was the concentrated under reduced pressure and purified via either short silica gel cartridge or preparative thin layer chromatography eluting with ethyl acetate/hexanes. This product was then dissolved in tetrahydrofuran/methanol (1/1 mL) and 2N sodium hydroxide solution (0.3 mL) was added and the solution was stirred for 24 hours at ambient temperature. This solution was then concentrated and neutralized to pH 4 using 1 N hydrochloric acid solution. The aqueous layer was then extracted using ethyl acetate (2×5 mL) and washed with brine (3 mL). The organic layers were combined, dried (sodium sulfate), filtered and concentrated under reduced pressure. The resulting crude product was then purified using reversed phase HPLC. $^1$H NMR (300 MHz, CD$_3$OD) δ 8.74 (s, 1H), 8.10 (dd, J=7.8, 1.5 Hz, 1H), 7.93 (dtd, J=5.0, 3.0, 1.8 Hz, 3H), 7.74 (t, J=7.8 Hz, 1H), 7.53-7.42 (m, 2H), 7.41-7.32 (m, 1H), 7.27 (tdd, J=10.1, 3.7, 1.9 Hz, 1H), 7.22-7.17 (m, 4H). MS m/z (M+H) 366.0.

Example 110: Synthesis of 2-(4-(3-methoxyphenyl)-1H-1,2,3-triazol-1-yl)-3-(phenylethynyl) benzoic acid

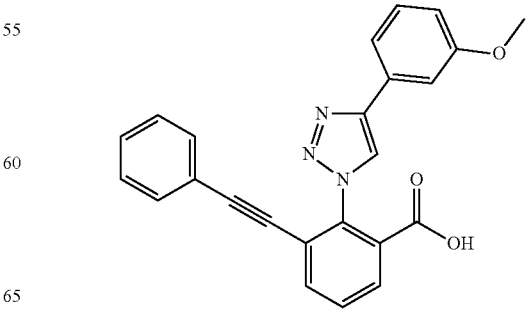

2-(4-(3-methoxyphenyl)-1H-1,2,3-triazol-1-yl)-3-(phenylethynyl)benzoic acid was prepared by the same procedure as example 102. ¹H NMR (300 MHz, CD₃OD) δ 8.75 (s, 1H), 8.10 (dd, J=7.8, 1.5 Hz, 1H), 7.94 (dd, J=7.8, 1.5 Hz, 1H), 7.74 (t, J=7.8 Hz, 1H), 7.49 (dt, J=2.5, 1.5 Hz, 2H), 7.37 (dd, J=8.2, 7.6 Hz, 1H), 7.28 (tdd, J=5.0, 4.5, 3.1 Hz, 1H), 7.23-7.18 (m, 4H), 6.95 (ddd, J=8.2, 2.5, 1.1 Hz, 1H), 3.82 (d, J=20.1 Hz, 3H). MS m/z (M+H) 396.1

Example 111: Synthesis of 3-(phenylethynyl)-2-(4-(pyridin-3-yl)-1H-1,2,3-triazol-1-yl) benzoic acid

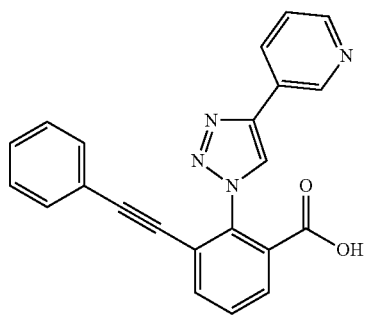 [SMILES: O=C(O)c1cccc(C#Cc2ccccc2)c1-n1cc(-c2cccnc2)nn1]

3-(phenylethynyl)-2-(4-(pyridin-3-yl)-1H-1,2,3-triazol-1-yl)benzoic acid was prepared by the same procedure as example 102. ¹H NMR (300 MHz, CD₃OD) δ 9.37 (d, J=1.9 Hz, 1H), 9.07 (s, 1H), 9.00-8.88 (m, 1H), 8.76 (d, J=4.3 Hz, 1H), 8.16 (dd, J=7.9, 1.5 Hz, 1H), 8.06-8.01 (m, 1H), 7.99 (dd, J=7.9, 1.5 Hz, 1H), 7.79 (t, J=7.8 Hz, 1H), 7.34-7.26 (m, 1H), 7.26-7.17 (m, 4H). MS m/z (M+H) 367.1

Example 112: Synthesis of 2-(4-(3-hydroxypropyl)-1H-1,2,3-triazol-1-yl)-3-(phenylethynyl) benzoic acid

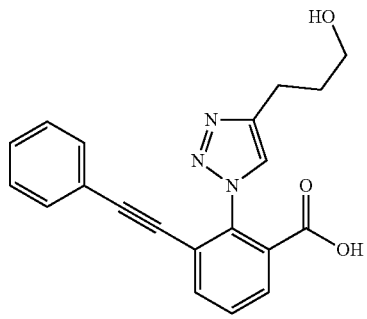 [SMILES: O=C(O)c1cccc(C#Cc2ccccc2)c1-n1cc(CCCO)nn1]

2-(4-(3-hydroxypropyl)-1H-1,2,3-triazol-1-yl)-3-(phenylethynyl)benzoic acid was prepared by the same procedure as example 102. ¹H NMR (300 MHz, CD₃OD) δ 8.09 (s, 1H), 8.08-8.01 (m, 1H), 7.90 (dd, J=7.8, 1.5 Hz, 1H), 7.70 (t, J=7.8 Hz, 1H), 7.39-7.21 (m, 5H), 3.60 (t, J=6.4 Hz, 2H), 2.92 (dd, J=17.8, 10.3 Hz, 2H), 1.94 (dq, J=9.8, 6.4 Hz, 2H). MS m/z (M+H) 348.1

Example 113: Synthesis of N-(Dimethylsulfamoyl)-3-(2-phenylethynyl)-2-(1H-pyrrol-1-yl) benzamide

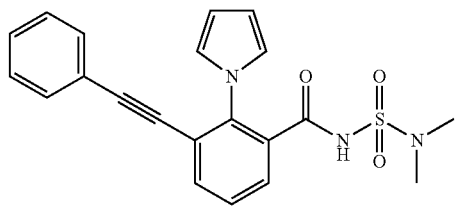 [SMILES: CN(C)S(=O)(=O)NC(=O)c1cccc(C#Cc2ccccc2)c1-n1cccc1]

To a solution of 3-phenylethynyl-2-pyrrol-1-yl-benzoic acid (50 mg, 0.17 mmol) in N,N-dimethylformamide (0.25 mL) was added N,N-dimethylsulfamide (43 mg, 0.35 mmol), 1-ethyl-3-(3-dimethylaminopropyl)carbodiimide hydrochloride (67 mg, 0.35 mmol), and hydroxyl-benzotriazole hydrate (43 mg, 0.35 mmol). After 16 hours, the reaction mixture was diluted with ethyl acetate (40 mL) and washed with dilute hydrochloric acid (30 mL, 0.1N), saturated aqueous sodium hydrogen carbonate (30 mL) and saturated aqueous sodium chloride (25 mL). The organic layer was concentrated at reduce pressure. The resulting oil was purified by column chromatography through a silica gel cartridge (4 g) eluting with ethyl acetate/hexane (1/4 to 1/2) to give the product as a white foam. ¹H NMR (300 MHz, CDCl₃) δ=7.95 (dd, J=1.6, 7.8 Hz, 1H), 7.79 (d, J=7.6 Hz, 1H), 7.54 (t, J=7.8 Hz, 1H), 7.36-7.23 (m, 5H), 6.92 (t, J=2.2 Hz, 2H), 6.54 (t, J=2.2 Hz, 2H), 2.90 (s, 6H). MS (ES⁺)=394 (MH)⁺.

Example 114: Synthesis of N-(Dimethylsulfamoyl)-3-[2-(4-fluorophenyl)ethynyl]-2-(1H-pyrrol-1-yl) benzamide

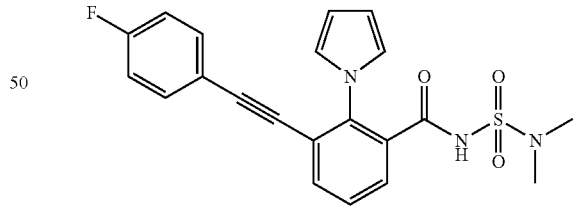

N-(Dimethylsulfamoyl)-3-[2-(4-fluorophenyl)ethynyl]-2-(1H-pyrrol-1-yl) was prepared by the same procedure as example 113. ¹H NMR (300 MHz, CDCl₃) δ=7.95 (dd, J=1.6, 7.8 Hz, 1H), 7.77 (dd, J=1.5, 7.6 Hz, 1H), 7.54 (t, J=7.8 Hz, 1H), 7.39 (br s, 1H), 7.31-7.20 (m, 1H), 7.02-6.90 (m, 1H), 6.91 (t, J=2.2 Hz, 2H), 6.54 (t, J=2.2 Hz, 2H), 2.90 (s, 6H). MS (ES⁺)=412 (MH)⁺.

Example 115: Synthesis of N-(morpholine-4-sulfonyl)-3-(2-phenylethynyl)-2-(1H-pyrrol-1-yl)benzamide

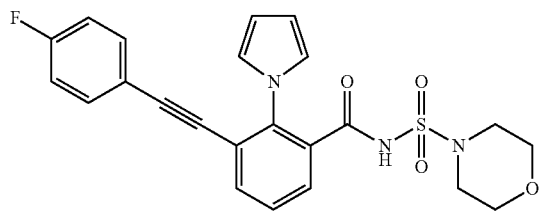 [SMILES: O=C(NS(=O)(=O)N1CCOCC1)c1cccc(C#Cc2ccc(F)cc2)c1-n1cccc1]

N-(morpholine-4-sulfonyl)-3-(2-phenylethynyl)-2-(1H-pyrrol-1-yl)benzamide was prepared by the same procedure as example 113. $^1$H NMR (300 MHz, CDCl$_3$) δ 7.92 (dt, J=15.9, 8.0 Hz, 1H), 7.87-7.74 (m, 1H), 7.54 (t, J=7.8 Hz, 1H), 7.46 (bs, 1H), 7.36-7.22 (m, 5H), 7.00-6.85 (m, 2H), 6.59-6.48 (m, 2H), 3.70 (m, 4H), 3.49-3.05 (m, 4H). MS m/z (M+H) 436.4.

Example 116: Synthesis of N-[(1,1-dioxo-4-thiomorpholin-4-yl)sulfonyl]-3-(2-phenylethynyl)-2-(1H-pyrrol-1-yl)benzamide

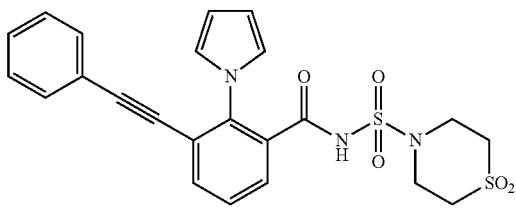 [SMILES: O=C(NS(=O)(=O)N1CCS(=O)(=O)CC1)c1cccc(C#Cc2ccccc2)c1-n1cccc1]

N-[(1,1-dioxo-4-thiomorpholin-4-yl)sulfonyl]-3-(2-phenylethynyl)-2-(1H-pyrrol-1-yl)benzamide was prepared by the same procedure as example 113. $^1$H NMR (300 MHz, CDCl$_3$) δ 7.94 (dd, J=7.9, 1.6 Hz, 1H), 7.83 (dd, J=7.8, 1.6 Hz, 1H), 7.57 (t, J=7.8 Hz, 1H), 7.52 (bs, 1H), 7.36-7.22 (m, 5H), 7.00-6.85 (m, 2H), 6.56 (t, J=2.1 Hz, 2H), 3.96-3.79 (m, 4H), 3.25-2.96 (m, 4H). MS m/z (M+H) 484.7

Example 117: Synthesis of 3-[2-(4-fluorophenyl)ethynyl]-N-methanesulfonyl-2-(1H-pyrrol-1-yl)benzamide

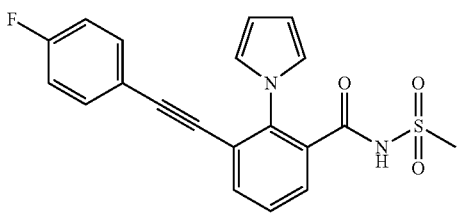 [SMILES: CS(=O)(=O)NC(=O)c1cccc(C#Cc2ccc(F)cc2)c1-n1cccc1]

3-[2-(4-fluorophenyl)ethynyl]-N-methanesulfonyl-2-(1H-pyrrol-1-yl)benzamide was prepared by the same procedure as example 113. $^1$H NMR (300 MHz, CD$_3$OD) δ 7.64 (dd, J=7.6, 1.6 Hz, 1H), 7.54 (dd, J=7.7, 1.6 Hz, 1H), 7.43 (t, J=7.7 Hz, 1H), 7.36-7.26 (m, 2H), 7.10-7.00 (m, 2H), 6.96-6.89 (m, 2H), 6.29-6.22 (m, 2H), 2.86 (s, 3H). MS m/z (M+H) 383.0

Example 118: Synthesis of 3-(phenylethynyl)-2-(1H-pyrrol-1-yl)-N-sulfamoylbenzamide

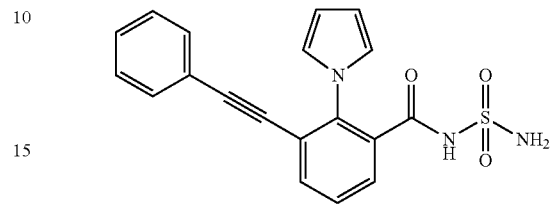

3-(phenylethynyl)-2-(1H-pyrrol-1-yl)-N-sulfamoyl benzamide was prepared by the same procedure as example 113. $^1$H NMR (300 MHz, CDCl$_3$) δ 7.91 (dd, J=7.8, 1.6 Hz, 1H), 7.82 (dd, J=7.8, 1.6 Hz, 1H), 7.60-7.52 (m, 1H), 7.50 (bs, 1H), 7.37-7.26 (m, 5H), 6.97-6.91 (m, 2H), 6.60-6.52 (m, 3H), 5.12 (bs, 2H). MS m/z (M+H) 366.3

Example 119: Synthesis of 2-(4-methoxyphenyl)-3-(2-phenylethynyl)benzoic acid

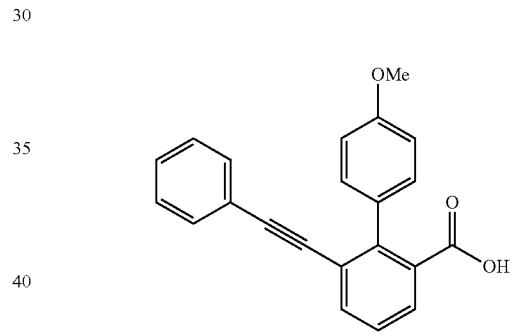

To a stirring solution of 2-bromo-3-iodobenzoic acid (1 g, 3.1 mmol) in dimethyl sulfoxide (5 mL) was added potassium carbonate (2.1 g, 15 mmol) followed by iodomethane (0.7 g, 4.6 mmol) and stirred for 12 hours at ambient temperature. The reaction mixture was then diluted with ethyl acetate (40 mL) washed with water (2×10 mL). The organic layer were washed brine (10 mL) dried (sodium sulfate), filtered and concentrated under reduced pressure. The resultant crude product was purified through silica gel cartridge eluting with ethyl acetate/hexanes to give methyl 2-bromo-3-iodobenzoate as a pale yellow liquid in 90% overall yield.

A solution of methyl 2-bromo-3-iodobenzoate (1 g, 2.9 mmol) and phenylacetylene (4.4 mmol) in tetrahydrofuran:triethylamine (20:20 mL) was deaerated using a N$_2$ gas balloon for 15 minutes in a round bottom flask. To this solution was added Bis(triphenylphosphine)palladium(II) dichloride (210 mg, 0.3 mmol) and copper iodide (30 mg) and stirred for 16 hours at ambient temperature. The reaction mixture was then filtered through celite using ethyl acetate (50 mL). The resultant solution was the concentrated under reduced pressure and purified through silica gel cartridge eluting with ethyl acetate/hexanes to give the product as a brown solid. To a stirring solution of this product (0.05 g, 0.16 mmol) in 1,4-dioxane/water (1/1 mL) was added 4-methoxyphenylboronic acid (0.32 mmol), [1,1′-Bis(diphenylphosphino)ferrocene] dichloropalladium(II), complex with dichloromethane (15 mg, 0.02 mmol) and potassium carbonate (45 mg, 0.32 mmol) and heated to 80° C. for 16 hours. The resultant mixture was allowed to cool to ambient temperature and was diluted with ethyl acetate (5 mL). The aqueous layer was extracted with ethyl acetate (2×2 mL) and the combined organic layers were washed with water (2 mL), brine (2 mL), dried (sodium sulfate), filtered and concentrated under reduced pressure. The resultant crude product was purified either through a small silica gel cartridge or preparative thin layer chromatography eluting with ethyl acetate/hexanes. The product so obtained was then dissolved in tetrahydrofuran/methanol (1/1 mL) and added 2N sodium hydroxide solution (0.3 mL) and stirred for 24 hours at ambient temperature. This solution was then concentrated and neutralized to pH 4 using 1 N hydrochloric acid solution. The aqueous layer was then extracted using ethyl acetate (2×5 mL) and washed with water (2 mL) and brine (3 mL). The organic layers were combined, dried (sodium sulfate), filtered and concentrated under reduced pressure. The resulting crude product was then purified using reversed phase HPLC. $^1$H NMR (300 MHz, CDCl$_3$) δ 7.74 (dd, J=7.7, 5.2 Hz, 2H), 7.38 (dd, J=9.7, 5.8 Hz, 1H), 7.33 (dt, J=5.0, 2.8 Hz, 1H), 7.24 (m, 6H), 7.05-6.82 (m, 2H), 3.62 (s, 3H). MS m/z (M−H$_2$O) 312.0

Example 120: Synthesis of 2-(3-methoxyphenyl)-3-(2-phenylethynyl)benzoic acid

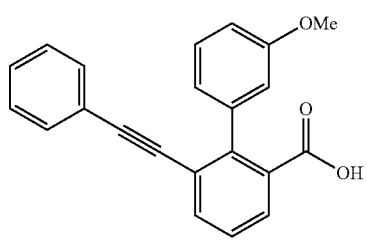 [SMILES: COc1cccc(-c2c(C#Cc3ccccc3)cccc2C(=O)O)c1]

2-(3-methoxyphenyl)-3-(2-phenylethynyl)benzoic acid was prepared by the same procedure as example 119. $^1$H NMR (300 MHz, CDCl$_3$) δ 7.75 (dd, J=9.3, 7.8 Hz, 2H), 7.39 (dd, J=12.3, 4.4 Hz, 1H), 7.36-7.29 (m, 1H), 7.28-7.22 (m, 3H), 7.22-7.15 (m, 2H), 6.99-6.90 (m, 3H), 3.61 (s, 3H). MS m/z (M−H$_2$O) 312.1

Example 121: Synthesis of 2-(2-methoxyphenyl)-3-(2-phenylethynyl)benzoic acid

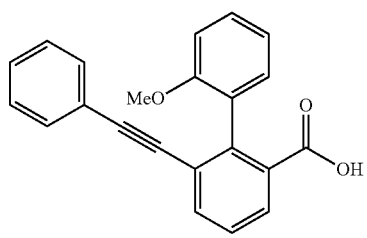 [SMILES: COc1ccccc1-c1c(C#Cc2ccccc2)cccc1C(=O)O]

2-(2-methoxyphenyl)-3-(2-phenylethynyl)benzoic acid was prepared by the same procedure as example 119. $^1$H NMR (300 MHz, CDCl$_3$) δ 7.94-7.81 (m, 1H), 7.81-7.67 (m, 1H), 7.47-7.32 (m, 2H), 7.28 (dt, J=5.5, 2.7 Hz, 1H), 7.25-7.15 (m, 3H), 7.16-7.10 (m, 2H), 7.05 (td, J=7.4, 1.0 Hz, 1H), 6.96 (dt, J=7.9, 4.0 Hz, 1H), 3.64 (s, 3H). MS m/z (M−H$_2$O) 312.1

Example 122: Synthesis of 3-(2-phenylethynyl)-2-(quinolin-3-yl)benzoic acid

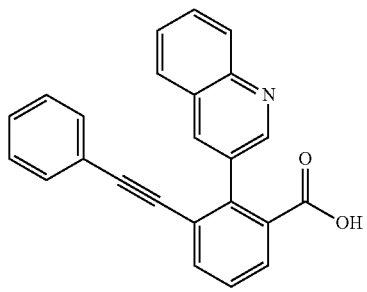 [SMILES: O=C(O)c1cccc(C#Cc2ccccc2)c1-c1cnc2ccccc2c1]

3-(2-phenylethynyl)-2-(quinolin-3-yl)benzoic acid was prepared by the same procedure as example 119. $^1$H NMR (300 MHz, CDCl$_3$) δ 8.92 (bs, 1H), 8.24-8.15 (m, 2H), 7.97 (dd, J=7.8, 1.3 Hz, 1H), 7.91-7.81 (m, 2H), 7.77 (t, J=7.7 Hz, 1H), 7.59 (t, J=6.9 Hz, 1H), 7.52 (t, J=7.8 Hz, 1H), 7.24-7.06 (m, 3H), 7.06-6.98 (m, 2H). MS m/z (M+H) 350.1

Example 123: Synthesis of 2-cyclopropyl-3-(2-phenylethynyl)benzoic acid

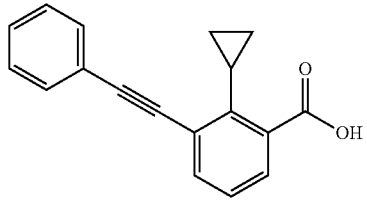 [SMILES: O=C(O)c1cccc(C#Cc2ccccc2)c1C1CC1]

2-cyclopropyl-3-(2-phenylethynyl)benzoic acid was prepared by the same procedure as example 119. $^1$H NMR (300 MHz, CDCl$_3$) δ 7.67-7.44 (m, 4H), 7.44-7.31 (m, 3H), 7.30-7.15 (m, 1H), 2.34-2.10 (m, 1H), 1.15-0.84 (m, 2H), 0.79-0.50 (m, 2H). MS m/z (M+H) 263.1

Example 124: Synthesis of 2-phenyl-3-(2-phenylethynyl)benzoic acid

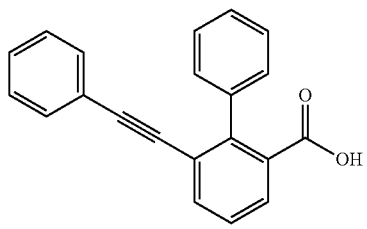 [SMILES: O=C(O)c1cccc(C#Cc2ccccc2)c1-c1ccccc1]

2-phenyl-3-(2-phenylethynyl)benzoic acid was prepared by the same procedure as example 119. ¹H NMR (300 MHz, CDCl₃) δ 7.86-7.76 (m, 1H), 7.77-7.66 (m, 1H), 7.52-7.27 (m, 6H), 7.30-7.18 (m, 3H), 7.18-7.02 (m, 2H). MS m/z (M+Na) 321.0.

Example 125: Synthesis of 2-(4-methylphenyl)-3-(2-phenylethynyl)benzoic acid

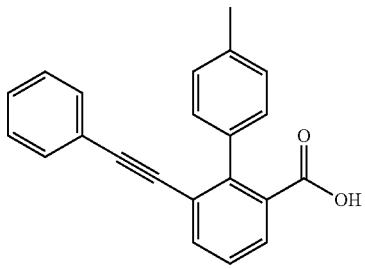 [SMILES: Cc1ccc(-c2c(C#Cc3ccccc3)cccc2C(=O)O)cc1]

2-(4-methylphenyl)-3-(2-phenylethynyl)benzoic acid was prepared by the same procedure as example 119. ¹H NMR (300 MHz, CDCl₃) δ 7.75 (ddd, J=10.5, 7.8, 1.4 Hz, 2H), 7.51-7.30 (m, 1H), 7.33-7.25 (m, 6H), 7.20-7.15 (m, 3H), 2.43 (s, 3H). MS m/z (M+Na) 335.1.

Example 126: Synthesis of 2-(6-methoxypyridin-3-yl)-3-(2-phenylethynyl)benzoic acid

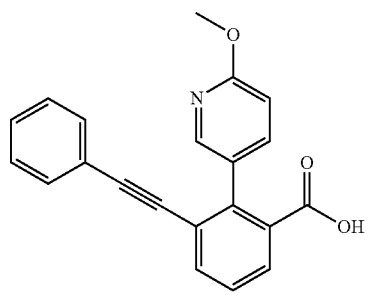 [SMILES: COc1ccc(-c2c(C#Cc3ccccc3)cccc2C(=O)O)cn1]

2-(6-methoxypyridin-3-yl)-3-(2-phenylethynyl)benzoic acid was prepared by the same procedure as example 119. ¹H NMR (300 MHz, CDCl₃) δ 8.13 (dd, J=2.5, 0.7 Hz, 1H), 7.84 (dd, J=7.8, 1.4 Hz, 1H), 7.79-7.73 (m, 1H), 7.65 (dd, J=8.5, 2.5 Hz, 1H), 7.42 (t, J=7.8 Hz, 1H), 7.32-7.20 (m, 5H), 6.83 (ddd, J=8.6, 2.0, 0.7 Hz, 1H), 3.68 (s, 3H). MS m/z (M+H) 330.0

Example 127: Synthesis of 2-[6-(dimethylamino)pyridin-3-yl]-3-(2-phenylethynyl)benzoic acid

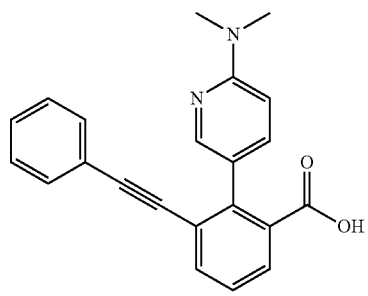 [SMILES: CN(C)c1ccc(-c2c(C#Cc3ccccc3)cccc2C(=O)O)cn1]

2-[6-(dimethylamino)pyridin-3-yl]-3-(2-phenylethynyl)benzoic acid was prepared by the same procedure as example 119. ¹H NMR (300 MHz, CDCl₃) δ 8.17 (dd, J=2.5, 0.7 Hz, 1H), 7.75 (ddd, J=9.2, 7.8, 1.4 Hz, 2H), 7.60-7.53 (m, 1H), 7.41-7.32 (m, 1H), 7.32-7.21 (m, 5H), 6.58 (dd, J=8.8, 0.7 Hz, 1H), 3.13 (s, 6H). MS m/z (M+H) 343.1

Example 128: Synthesis of 2-[3-(hydroxymethyl)phenyl]-3-(2-phenylethynyl)benzoic acid

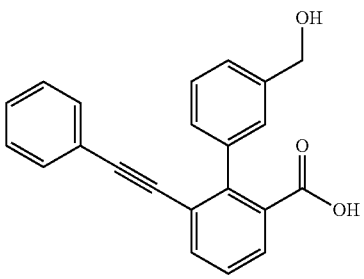 [SMILES: O=C(O)c1cccc(C#Cc2ccccc2)c1-c1cccc(CO)c1]

2-[3-(hydroxymethyl)phenyl]-3-(2-phenylethynyl)benzoic acid was prepared by the same procedure as example 119. ¹H NMR (300 MHz, CDCl₃) δ 7.85 (dd, J=7.8, 1.4 Hz, 1H), 7.75 (dd, J=7.8, 1.4 Hz, 1H), 7.48-7.33 (m, 5H), 7.25 (dd, J=5.0, 2.0 Hz, 3H), 7.15 (dd, J=6.5, 3.3 Hz, 2H), 4.67 (s, 2H). MS m/z (M+H) 329.0.

Example 129: Synthesis of 2-(1H-indol-6-yl)-3-(2-phenylethynyl)benzoic acid

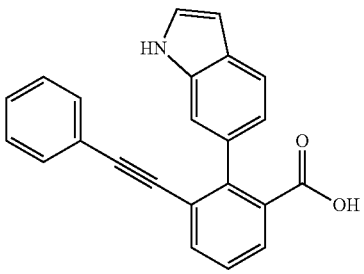 [SMILES: O=C(O)c1cccc(C#Cc2ccccc2)c1-c1ccc2cc[nH]c2c1]

2-(1H-indol-6-yl)-3-(2-phenylethynyl)benzoic acid was prepared by the same procedure as example 119. ¹H NMR (300 MHz, DMSO) δ 11.18 (s, 1H), 7.74 (dd, J=7.7, 1.3 Hz, 1H), 7.70-7.63 (m, 1H), 7.57 (d, J=8.1 Hz, 1H), 7.45 (t, J=7.7 Hz, 1H), 7.39 (dd, J=7.2, 4.7 Hz, 2H), 7.27 (dd, J=9.4, 3.2 Hz, 3H), 7.12 (dd, J=7.6, 1.9 Hz, 2H), 7.02 (dd, J=8.1, 1.5 Hz, 1H), 6.46 (s, 1H). MS m/z (M+H) 338.0

Example 130: Synthesis of 2-[4-(hydroxymethyl)phenyl]-3-(2-phenylethynyl)benzoic acid

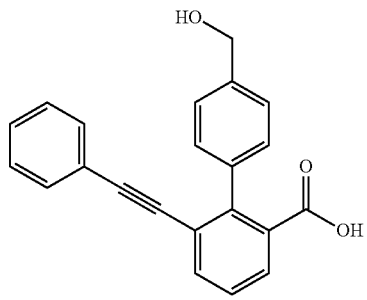 [SMILES: O=C(O)c1cccc(C#Cc2ccccc2)c1-c1ccc(CO)cc1]

2-[4-(hydroxymethyl)phenyl]-3-(2-phenylethynyl)benzoic acid was prepared by the same procedure as example 119. $^1$H NMR (300 MHz, CDCl$_3$) δ 7.83-7.77 (m, 1H), 7.74 (dd, J=7.8, 0.7 Hz, 1H), 7.42 (t, J=7.4 Hz, 1H), 7.39-7.33 (m, 5H), 7.28-7.19 (m, 3H), 7.19-7.09 (m, 2H), 4.77 (s, 2H). MS m/z (M+H) 329.0

Example 131: Synthesis of 2-(1-benzofuran-5-yl)-3-(2-phenylethynyl)benzoic acid

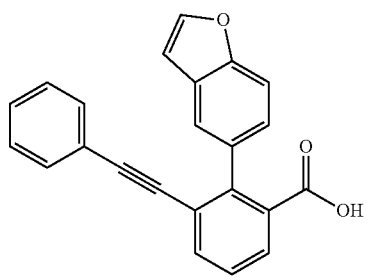 [SMILES: O=C(O)c1cccc(C#Cc2ccccc2)c1-c1ccc2occc2c1]

2-(1-benzofuran-5-yl)-3-(2-phenylethynyl)benzoic acid was prepared by the same procedure as example 119. $^1$H NMR (300 MHz, CD$_3$OD) δ 7.81-7.76 (m, 2H), 7.74 (dd, J=7.8, 1.4 Hz, 1H), 7.61 (d, J=1.8 Hz, 1H), 7.55 (d, J=8.5 Hz, 1H), 7.46 (dd, J=9.8, 5.8 Hz, 1H), 7.34-7.26 (m, 1H), 7.25-7.13 (m, 3H), 7.07-6.96 (m, 2H), 6.88 (dd, J=2.2, 0.9 Hz, 1H). MS m/z (M+H) 339.0

Example 132: Synthesis of 2-(1-benzothiophen-5-yl)-3-(2-phenylethynyl)benzoic acid

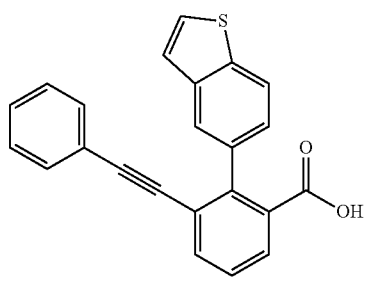 [SMILES: O=C(O)c1cccc(C#Cc2ccccc2)c1-c1ccc2sccc2c1]

2-(1-benzothiophen-5-yl)-3-(2-phenylethynyl)benzoic acid was prepared by the same procedure as example 119. $^1$H NMR (300 MHz, CD$_3$OD) δ 7.95 (d, J=8.3 Hz, 1H), 7.86-7.79 (m, 2H), 7.75 (dd, J=7.8, 1.3 Hz, 1H), 7.60 (d, J=5.5 Hz, 1H), 7.48 (t, J=7.8 Hz, 1H), 7.41 (dd, J=5.5, 0.7 Hz, 1H), 7.35 (dd, J=8.3, 1.6 Hz, 1H), 7.26-7.08 (m, 3H), 7.01-6.90 (m, 2H). MS m/z (M−H$_2$O) 337.0

Example 133: Synthesis of 2-(1-methyl-1H-indol-5-yl)-3-(2-phenylethynyl)benzoic

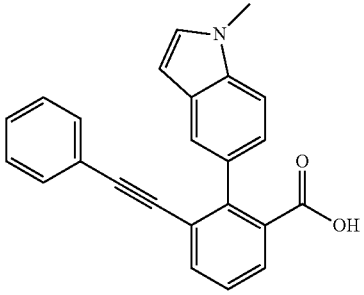 [SMILES: Cn1ccc2cc(-c3c(C#Cc4ccccc4)cccc3C(=O)O)ccc21]

2-(1-methyl-1H-indol-5-yl)-3-(2-phenylethynyl)benzoic acid was prepared by the same procedure as example 119. $^1$H NMR (300 MHz, CD$_3$OD) δ 7.72 (dd, J=3.9, 1.4 Hz, 1H), 7.70 (dd, J=4.1, 1.4 Hz, 1H), 7.60 (d, J=1.1 Hz, 1H), 7.45-7.37 (m, 3H), 7.26-7.11 (m, 5H), 7.06 (dt, J=8.2, 2.1 Hz, 2H), 3.85 (s, 3H). MS m/z (M+H) 352.0

Example 134: Synthesis of 2-(3-methanesulfonamidophenyl)-3-(2-phenylethynyl)benzoic acid

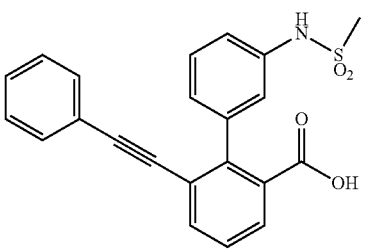 [SMILES: CS(=O)(=O)Nc1cccc(-c2c(C#Cc3ccccc3)cccc2C(=O)O)c1]

2-(3-methanesulfonamidophenyl)-3-(2-phenylethynyl)benzoic acid was prepared by the same procedure as example 119. $^1$H NMR (300 MHz, CD$_3$OD) δ 7.84 (dd, J=7.8, 1.3 Hz, 1H), 7.75 (dd, J=7.8, 1.3 Hz, 1H), 7.48 (t, J=7.8 Hz, 1H), 7.41 (t, J=7.8 Hz, 1H), 7.33-7.23 (m, 5H), 7.20-7.09 (m, 3H), 2.83 (s, 3H). MS m/z (M−H$_2$O) 373.9

Example 135: Synthesis of 2-(naphthalen-2-yl)-3-(2-phenylethynyl)benzoic acid

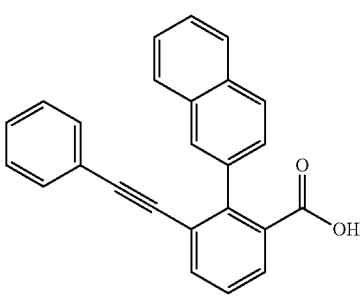 [SMILES: O=C(O)c1cccc(C#Cc2ccccc2)c1-c1ccc2ccccc2c1]

2-(naphthalen-2-yl)-3-(2-phenylethynyl)benzoic acid was prepared by the same procedure as example 119. ¹H NMR (300 MHz, CDCl₃) δ 8.11-7.70 (m, 6H), 7.68-7.39 (m, 4H), 7.22-7.01 (m, 3H), 7.00-6.85 (m, 2H). MS m/z (M+H) 349.1.

Example 136: Synthesis of 2-(1-methyl-1H-indol-6-yl)-3-(2-phenylethynyl)benzoic acid

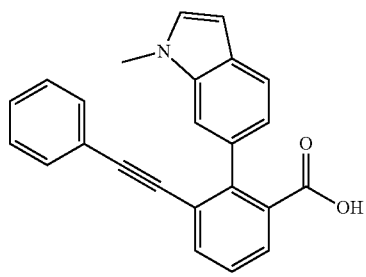 [SMILES: Cn1ccc2ccc(-c3c(C#Cc4ccccc4)cccc3C(=O)O)cc21]

2-(1-methyl-1H-indol-6-yl)-3-(2-phenylethynyl)benzoic acid was prepared by the same procedure as example 119. ¹H NMR (300 MHz, CDCl₃) δ 7.87 (dd, J=7.8, 1.4 Hz, 1H), 7.77 (dd, J=7.7, 1.4 Hz, 1H), 7.66 (dd, J=8.1, 0.6 Hz, 1H), 7.44-7.36 (m, 2H), 7.23-7.11 (m, 4H), 7.09 (d, J=3.1 Hz, 1H), 7.05-6.99 (m, 2H), 6.53 (dd, J=3.1, 0.8 Hz, 1H), 3.74 (d, J=6.5 Hz, 3H). MS m/z (M+H) 352.0

Example 137: Synthesis of 2-{2-[(2-hydroxyethyl)sulfamoyl]phenyl}-3-(2-phenylethynyl) benzoic acid

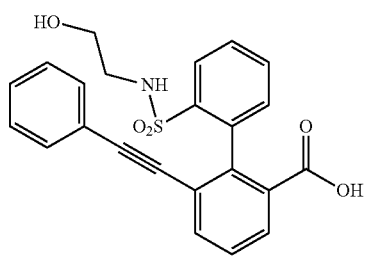 [SMILES: O=C(O)c1cccc(C#Cc2ccccc2)c1-c1ccccc1S(=O)(=O)NCCO]

2-{2-[(2-hydroxyethyl)sulfamoyl]phenyl}-3-(2-phenylethynyl)benzoic acid was prepared by the same procedure as example 119. ¹H NMR (300 MHz, CD₃OD) δ 7.91 (ddd, J=7.6, 5.6, 1.4 Hz, 2H), 7.85-7.75 (m, 2H), 7.64 (td, J=7.6, 0.5 Hz, 1H), 7.60-7.56 (m, 1H), 7.53 (t, J=7.8 Hz, 1H), 7.32-7.18 (m, 3H), 7.14 (ddd, J=4.3, 3.8, 2.5 Hz, 2H), 3.44 (t, J=5.9 Hz, 2H), 2.89 (t, J=5.9 Hz, 2H). MS m/z (M+H) 422.2

Example 138: Synthesis of 2-[4-(cyclopropylcarbamoyl)phenyl]-3-(2-phenylethynyl)benzoic acid

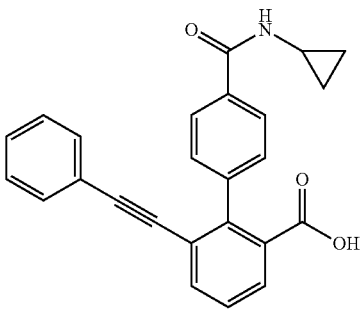 [SMILES: O=C(NC1CC1)c1ccc(-c2c(C#Cc3ccccc3)cccc2C(=O)O)cc1]

2-[4-(cyclopropylcarbamoyl)phenyl]-3-(2-phenylethynyl)benzoic acid was prepared by the same procedure as example 119. ¹H NMR (300 MHz, CD₃OD) δ 7.86 (ddd, J=5.7, 3.5, 1.6 Hz, 3H), 7.76 (dd, J=7.8, 1.3 Hz, 1H), 7.49 (t, J=7.8 Hz, 1H), 7.45-7.39 (m, 2H), 7.32-7.16 (m, 3H), 7.16-7.02 (m, 2H), 2.88 (ddd, J=11.1, 7.3, 3.9 Hz, 1H), 0.89-0.76 (m, 2H), 0.71-0.60 (m, 2H). MS m/z (M+H) 382.4

Example 139: Synthesis of 2-(1-methyl-1H-indazol-6-yl)-3-(2-phenylethynyl)benzoic acid

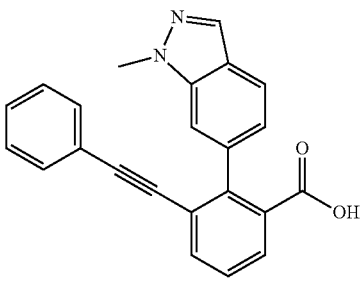 [SMILES: Cn1ncc2ccc(-c3c(C#Cc4ccccc4)cccc3C(=O)O)cc21]

2-(1-methyl-1H-indazol-6-yl)-3-(2-phenylethynyl)benzoic acid was prepared by the same procedure as example 119. ¹H NMR (300 MHz, CDCl₃) δ 8.04 (d, J=0.8 Hz, 1H), 7.84 (dt, J=7.8, 4.1 Hz, 1H), 7.77 (dd, J=7.9, 1.3 Hz, 2H), 7.49-7.38 (m, 2H), 7.24-7.10 (m, 4H), 7.04-6.93 (m, 2H), 3.56 (s, 3H). MS m/z (M+) 352.6

Example 140: Synthesis of 3-((3-hydroxyphenyl)ethynyl)-2-(quinolin-3-yl)benzoic acid

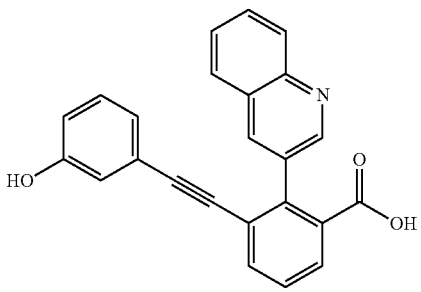 [SMILES: O=C(O)c1cccc(C#Cc2cccc(O)c2)c1-c1cnc2ccccc2c1]

To a stirring solution of 2-amino-3-bromobenzoic acid (1 g, 4.65 mmol) in water/1,4-dioxane (20 mL/2 mL) at 0° C. was added concentrated hydrochloric acid (1 mL, 11.2 mmol) dropwise followed by a solution of sodium nitrite (0.32 g, 4.65 mmol) in 10 mL water dropwise. This solution was stirred for 1 hour at 0° C. after which a solution of potassium iodide (6.9 g, 42 mmol) in 12 mL water was added. The resultant mixture was allowed to warm to ambient temperature and stirred for 12 hours. After 12 hours the reaction mixture was extracted with ethyl acetate (2×50 mL). The organic layers were combined, washed with sodium thiosulfate (2×10 mL), water (10 mL), brine (10 mL), dried (sodium sulfate), filtered and concentrated under reduced pressure. This crude mixture was dissolved in dimethyl sulfoxide (5 mL) and potassium carbonate (2.1 g, 15 mmol) was added followed by iodomethane (0.8 g, 5.6 mmol) and stirred for 12 hours at ambient temperature. The reaction mixture was then diluted with ethyl acetate (40 mL) washed with water (2×10 mL). The organic layer were washed brine (10 mL) dried (sodium sulfate), filtered and concentrated under reduced pressure. The resultant crude product was purified through silica gel cartridge eluting with ethyl acetate/hexanes to give methyl 2-iodo-3-bromobenzoate as a pale yellow liquid in 85% overall yield.

To a stirring solution of methyl 2-iodo-3-bromobenzoate (1 g, 3.3 mmol) in 1,4-dioxane/water (10 mL/10 mL) was added quinolin-3-yl boronic acid (5 mmol), [1,1'-Bis(diphenylphosphino)ferrocene] dichloropalladium(II), complex with dichloromethane (0.24 g, 0.33 mmol) and potassium carbonate (0.9 g, 6.6 mmol) and heated to 40° C. for 16 hours. The resultant mixture was allowed to cool to ambient temperature and was diluted with ethyl acetate (50 mL). The aqueous layer was extracted with ethyl acetate (2×20 mL) and the combined organic layers were washed with water (10 mL), brine (10 mL), dried (sodium sulfate), filtered and concentrated under reduced pressure. The resultant crude product was purified through silica gel cartridge eluting with ethyl acetate/hexanes to give the product. A solution of 3-bromo-2-quinolin-3-yl-benzoic acid methyl ester (0.11 mmol) and 3-hydroxyphenylacetylene (0.11 mmol) in N,N-dimethylformamide/triethylamine (1 mL/1 mL) was degassed using a $N_2$ gas balloon for 2 minutes. To this solution was added Bis(triphenylphosphine)palladium(II) dichloride (10 mg, 0.011 mmol) and copper iodide (5 mg) and heated to 100° C. for 16 hours. The reaction mixture was then cooled to ambient temperature, filtered through celite using ethyl acetate (10 mL). The resultant solution were washed with 1N hydrochloric acid (2 mL), water (2×2 mL), brine (2 mL), dried (sodium sulfate), filtered and concentrated under reduced pressure. The resultant crude product was purified through either a short silica gel cartridge. The product so obtained was then dissolved in tetrahydrofuran/methanol (1 mL/1 mL) and added 2N sodium hydroxide solution (0.3 mL) and stirred for 24 hours at ambient temperature. This solution was then concentrated and neutralized to pH 4 using 1 N hydrochloric acid solution. The aqueous layer was then extracted using ethyl acetate (2×5 mL) and washed with water (2 mL) and brine (3 mL). The organic layers were combined, dried (sodium sulfate), filtered and concentrated under reduced pressure. The resulting crude product was then purified using reversed phase HPLC. $^1$H NMR (300 MHz, CD$_3$OD) δ 9.20 (d, J=1.8 Hz, 1H), 8.92 (s, 1H), 8.34-8.12 (m, 3H), 8.09 (t, J=7.8 Hz, 1H), 8.02-7.82 (m, 3H), 7.68 (t, J=7.9 Hz, 1H), 6.95 (t, J=8.0 Hz, 1H), 6.68 (d, J=9.8 Hz, 1H), 6.48-6.27 (m, 2H). MS m/z (M+H) 366.0

Example 141: Synthesis of 3-(5-hydroxypent-1-ynyl)-2-(quinolin-3-yl)benzoic acid

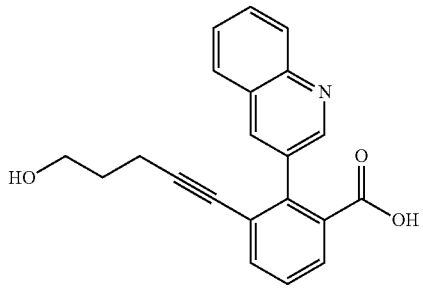 [SMILES: O=C(O)c1cccc(C#CCCCO)c1-c1cnc2ccccc2c1]

3-(5-hydroxypent-1-ynyl)-2-(quinolin-7-yl)benzoic acid was prepared by the same procedure as example 140. $^1$H NMR (300 MHz, CD$_3$OD) δ 9.23 (bs, 1H), 8.97 (dd, J=4.8, 1.7 Hz, 1H), 8.29 (td, J=8.5, 3.7 Hz, 2H), 8.22-8.09 (m, 2H), 7.95 (dt, J=7.4, 6.0 Hz, 1H), 7.83 (ddd, J=7.6, 6.1, 1.3 Hz, 1H), 7.62 (td, J=7.9, 2.8 Hz, 1H), 4.14-3.56 (m, 2H), 3.20 (t, J=6.2 Hz, 1H), 2.29-2.19 (m, 2H), 1.61 (m, 1H), 1.45-1.08 (m, 1H). MS m/z (M+H) 332.1

Example 142: Synthesis of 3-((4-methoxyphenyl)ethynyl)-2-(quinolin-3-yl)benzoic acid

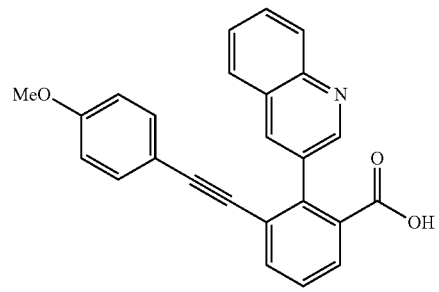 [SMILES: COc1ccc(C#Cc2cccc(C(=O)O)c2-c2cnc3ccccc3c2)cc1]

3-((4-methoxyphenyl)ethynyl)-2-(quinolin-7-yl)benzoic acid was prepared by the same procedure as example 140. $^1$H NMR (300 MHz, DMSO) δ 8.81 (d, J=2.2 Hz, 1H), 8.34 (d, J=2.2 Hz, 1H), 8.05 (t, J=9.3 Hz, 2H), 7.92 (dd, J=7.8, 1.3 Hz, 1H), 7.84 (dd, J=7.8, 1.3 Hz, 1H), 7.79 (ddd, J=8.4, 6.9, 1.5 Hz, 1H), 7.67-7.56 (m, 2H), 7.01-6.87 (m, 2H), 6.85-6.60 (m, 2H), 3.68 (s, 3H). MS m/z (M+H) 380.2

Example 143: Synthesis of 3-(imidazo[1,2-a]pyrazin-3-ylethynyl)-2-(quinolin-3-yl)benzoic acid

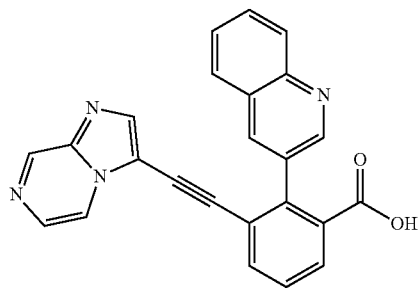 [SMILES: O=C(O)c1cccc(C#Cc2cnc3cnccn23)c1-c1cnc2ccccc2c1]

3-(imidazo[1,2-a]pyrazin-3-ylethynyl)-2-(quinolin-3-yl)benzoic acid was prepared by the same procedure as example 140. ¹H NMR (300 MHz, DMSO) δ 9.04 (d, J=1.5 Hz, 1H), 8.92 (d, J=2.2 Hz, 1H), 8.50 (d, J=2.2 Hz, 1H), 8.20-8.08 (m, 1H), 8.08-7.97 (m, 3H), 7.91-7.82 (m, 1H), 7.77-7.67 (m, 2H), 7.41 (d, J=4.5 Hz, 1H), 7.14 (dd, J=4.5, 1.5 Hz, 1H). MS m/z (M+) 390.9

Example 144: Synthesis of 3-[(1E)-3-methoxyprop-1-en-1-yl]-2-(1H-pyrrol-1-yl)benzoic acid

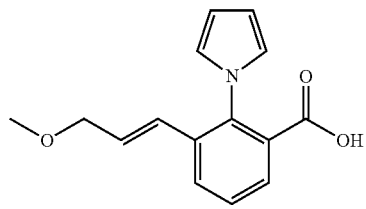 [SMILES: COC/C=C/c1cccc(C(=O)O)c1-n1cccc1]

3-[(1E)-3-methoxyprop-1-en-1-yl]-2-(1H-pyrrol-1-yl)benzoic acid: A mixture of 3-bromo-2-pyrrol-1-yl-benzoic acid methyl ester (60 mg, 0.214 mmol), 2-(3-methoxypropenyl)-4,4,5,5-tetramethyl-[1,3,2]dioxaborolane (85 mg, 0.428 mmol), 1,1'-bis(diphenylphosphino)ferrocene-palladium(II)dichloride (16 mg, 0.0214 mmol) and potassium carbonate (59 mg, 0.428 mmol) in 1,4-dioxane (0.8 mL) and water (0.8 mL) was degassed with N₂ for 10 minutes and heated at 90° C. for 17 hours. After cooling down the reaction mixture was partitioned between water and ethyl acetate, the organic layer was dried (sodium sulfate), filtered, concentrated and purified through preparative thin layer chromatography to give a solid intermediate. To this solid intermediate in dimethylsulfoxide (0.5 mL) was added sodium hydroxide solution (10% in water, 0.5 mL) and the solution was heated at 100° C. for 24 hours. 1 N hydrochloric acid aqueous solution was added dropwise until pH=1 and the reaction mixture was purified through preparative HPLC to give the product as a white solid. ¹H NMR (300 MHz, CDCl₃) δ=7.85-7.76 (m, 2H), 7.43 (t, J=7.8 Hz, 1H), 6.67 (t, J=2.2 Hz, 2H), 6.36-6.17 (m, 3H), 6.04 (d, J=16.1 Hz, 1H), 3.97 (dd, J=1.3, 6.0 Hz, 2H), 3.30 (s, 3H). LCMS (ESI) m/z 258.0 (M+1)⁺.

Example 145: Synthesis of 3-[(E)-2-phenylethenyl]-2-(1H-pyrrol-1-yl)benzoic acid

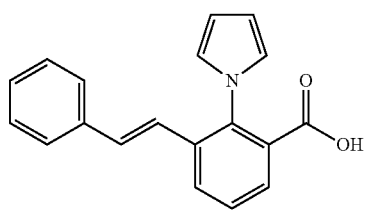 [SMILES: O=C(O)c1cccc(/C=C/c2ccccc2)c1-n1cccc1]

3-[(E)-2-phenylethenyl]-2-(1H-pyrrol-1-yl)benzoic acid was prepared by the same procedure as example 144. ¹H NMR (300 MHz, CDCl₃) δ=7.95 (dd, J=1.2, 8.2 Hz, 1H), 7.86 (dd, J=1.5, 7.6 Hz, 1H), 7.50 (t, J=7.8 Hz, 1H), 7.34-7.23 (m, 5H), 7.05 (d, J=16.5 Hz, 1H), 6.76 (t, J=2.1 Hz, 2H), 6.47 (d, J=16.4 Hz, 1H), 6.37 (t, J=2.2 Hz, 2H). LCMS (ESI) m/z 290.0 (M+1)⁺.

Example 146: Synthesis of 3-[(E)-2-(4-fluorophenyl)ethenyl]-2-(1H-pyrrol-1-yl)benzoic acid

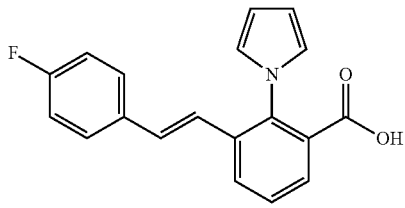 [SMILES: O=C(O)c1cccc(/C=C/c2ccc(F)cc2)c1-n1cccc1]

3-[(E)-2-(4-fluorophenyl)ethenyl]-2-(1H-pyrrol-1-yl)benzoic acid was prepared by the same procedure as example 144. ¹H NMR (300 MHz, CDCl₃) δ=7.95-7.83 (m, 2H), 7.49 (t, J=7.8 Hz, 1H), 7.32-7.24 (m, 3H), 7.04-6.94 (m, 2H), 6.75 (t, J=3.2 Hz, 2H), 6.40-6.33 (m, 3H). LCMS (ESI) m/z 308.0 (M+1)⁺.

Example 147: Synthesis of 3-(2-phenylethyl)-2-(1H-pyrrol-1-yl)benzoic acid

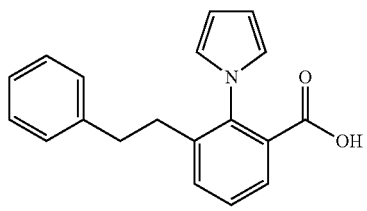 [SMILES: O=C(O)c1cccc(CCc2ccccc2)c1-n1cccc1]

A solution of Example 146 (50 mg, 0.173 mmol) and 10% Pd—C (20 mg) in methanol (3 mL) and chloroform (1 mL) was shaked under hydrogen at 40 psi for 4 hours in Parr-Shaker. The solution was filtered through celite and the filtrate was concentrated. The residue was purified through preparative HPLC to give the product as a white solid. ¹H NMR (300 MHz, CDCl₃) δ=7.80 (dd, J=1.7, 7.3 Hz, 1H), 7.49-7.37 (m, 2H), 7.25-7.12 (m, 3H), 7.01-6.95 (m, 2H), 6.63 (t, J=2.2 Hz, 2H), 6.26 (t, J=2.1 Hz, 2H), 2.75-2.60 (m, 4H). LC/MS (ESI) m/z 274.1 (M–H₂O)⁺.

Example 148: Synthesis of 3-(2-phenylethyl)-2-(pyrrolidin-1-yl)benzoic acid

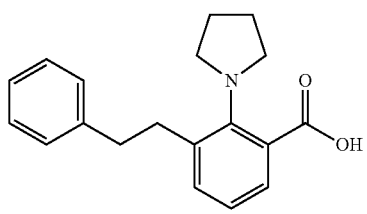 [SMILES: O=C(O)c1cccc(CCc2ccccc2)c1N1CCCC1]

3-(2-Phenylethyl)-2-(pyrrolidin-1-yl)benzoic acid was isolated as another product in synthesizing Example 147. ¹H NMR (300 MHz, CDCl₃) δ=12.09 (br. s., 1H), 8.25 (dd, J=1.8, 7.6 Hz, 1H), 7.61 (dd, J=1.6, 7.8 Hz, 1H), 7.48 (t, J=7.8 Hz, 1H), 7.35-7.12 (m, 3H), 7.16-7.12 (m, 2H), 3.40-2.85 (m, 8H), 2.23-2.10 (m, 4H). LCMS (ESI) m/z 296.1 (M+H)⁺.

Example 149: Synthesis of 3-[2-(4-fluorophenyl)ethyl]-2-(1H-pyrrol-1-yl)benzoic acid

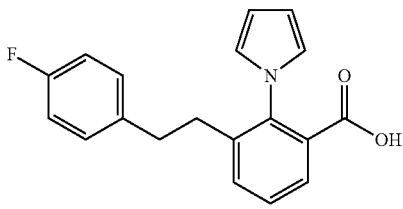 [SMILES: O=C(O)c1cccc(CCc2ccc(F)cc2)c1-n1cccc1]

3-[2-(4-fluorophenyl)ethyl]-2-(1H-pyrrol-1-yl)benzoic acid was prepared by the same procedure as example 147. LCMS (ESI) m/z 310.1 (M+H)$^+$.

Example 150: Synthesis of 2-(1H-1,3-benzodiazol-6-yl)-3-(2-phenylethynyl)benzoic acid

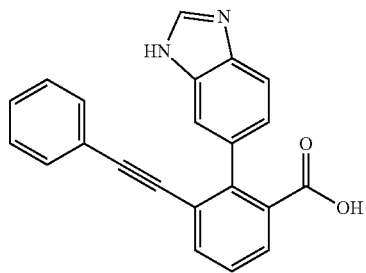 [SMILES: O=C(O)c1cccc(C#Cc2ccccc2)c1-c1ccc2nc[nH]c2c1]

2-(1H-1,3-benzodiazol-6-yl)-3-(2-phenylethynyl)benzoic acid was prepared by the same procedure as example 119. $^1$H NMR (300 MHz, DMSO) δ 9.37 (s, 1H), 7.89 (d, J=8.5 Hz, 1H), 7.85 (d, J=7.9 Hz, 2H), 7.80 (s, 1H), 7.58 (dd, J=8.0, 7.5 Hz, 1H), 7.51 (dd, J=8.5, 1.5 Hz, 1H), 7.37-7.23 (m, 3H), 7.14-7.04 (m, 2H). MS m/z (M+H) 339.0

Example 151: Synthesis of 2-(quinolin-3-yl)-3-[2-(1,3-thiazol-4-yl)ethynyl]benzoic acid

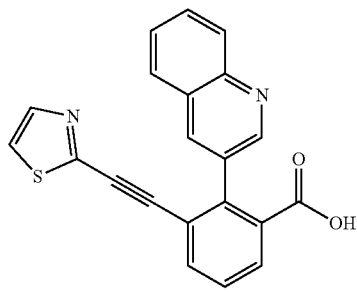 [SMILES: O=C(O)c1cccc(C#Cc2nccs2)c1-c1cnc2ccccc2c1]

2-(quinolin-3-yl)-3-[2-(1,3-thiazol-4-yl)ethynyl]benzoic acid was prepared by the same procedure as example 140. $^1$H NMR (300 MHz, DMSO) δ 9.02 (d, J=1.9 Hz, 1H), 8.96 (d, J=2.2 Hz, 1H), 8.52 (s, 1H), 8.11 (d, J=8.5 Hz, 2H), 8.02 (dd, J=7.8, 1.3 Hz, 1H), 7.97 (dd, J=7.8, 1.3 Hz, 1H), 7.86 (t, J=7.1 Hz, 1H), 7.74-7.64 (m, 2H), 7.63 (d, J=1.9 Hz, 1H). MS m/z (M+) 356.9

Example 152: Synthesis of 3-Phenylethynyl-2-pyrrol-1-yl-benzenesulfonamide

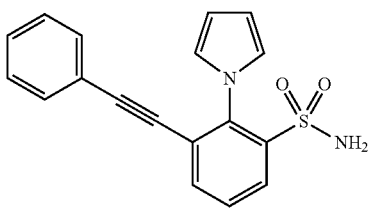 [SMILES: NS(=O)(=O)c1cccc(C#Cc2ccccc2)c1-n1cccc1]

2-Amino-3-bromo-benzenesulfonamide: To a solution of chlorosulfonyl isocyanate (3.78 g, 26.7 mmol) in nitroethane (20 mL) at 50° C. was added 2-bromoaniline (4.0 g, 23.3 mmol) in nitroethane (30 mL). After 5 minutes aluminum chloride (4.0 g, 30.2 mmol) was added in three portions and the mixture was heated to reflux at 110° C. for 30 minutes. The reaction mixture was cooled to ambient temperature and poured onto ice (100 g) and the resulting suspension in water was stirred for 10 minutes. The resulting slurry was filtered and rinsed with water (50 mL) and diethyl ether (50 mL) to give a gray green solid (2.77 g). This solid was added to sulfuric acid (50%, 30 mL) at 145° C. in three portions allowing foaming to subside between additions. The mixture was heated for an additional 30 minutes and cooled to ambient temperature. The mixture was then poured over ice (100 g) and neutralized with aqueous sodium hydroxide (6N) to pH 7 to give a white slurry. This mixture was extracted with isopropyl acetate (3×50 mL). The combined organic extracts were dried with sodium sulfate, filtered and concentrated to a white solid. $^1$H NMR (DMSO-d$_6$) δ 7.63-7.50 (m, 2H), 7.48 (br s, 2H), 6.61 (J=7.9 Hz, 1H), 5.85 (br s, 2H). MS (ES$^+$)=251 (MH)$^+$.

3-Bromo-2-pyrrol-1-yl-benzenesulfonamide: To a slurry of 2,5-dimethoxytetrahydrofuran (950 mg, 7.2 mmol) and 4-chloropyridine hydrochloride (1.08 g, 7.2 mmol) in 1,4-dioxane (50 mL) was added 2-amino-3-bromo-benzenesulfonamide (1.5 g, 6.0 mmol) and the mixture was heated to reflux for 2 hours. The reaction mixture was allowed to cool to ambient temperature and was poured into water (200 mL). The resulting slurry was vigorously stirred for 2 hours and filtered. The filtrated was extracted with ethyl acetate (3×50 mL). The combined organic extracts were dried with magnesium sulfate, filtered and concentrated at reduced pressure. The resulting oil was purified by column chromatography through a silica gel cartridge (4 g) eluting with ethyl acetate/hexane (1:9 to 1:2) to give the product as a white solid. $^1$H NMR $^1$H NMR (300 MHz, DMSO) δ=8.02-7.98 (m, 2H), 7.59 (t, J=7.9 Hz, 1H), 7.97 (br s, 2H), 6.72 (t, J=2.1 Hz, 2H), 6.20 (t, J=2.1 Hz, 2H). MS (ES$^+$)=301 (MH)$^+$.

3-Phenylethynyl-2-pyrrol-1-yl-benzenesulfonamide

To a degassed solution of 3-bromo-2-pyrrol-1-yl-benzenesulfonamide (170 mg, 0.56 mmol) in triethylamine (1.7 mL), phenylacetylene (115 mg, 124 μL, 1.13 mmol) and copper (I) iodide (5.4 mg, 0.028 mmol) in a sealed tube was added bis(triphenylphosphine)palladium(II) dichloride (40 mg, 0.056 mmol). The tube was sealed and heated at 90° C. for 16 hours. The reaction mixture was cooled to ambient temperature and concentrated at reduced pressure. The resulting mixture was purified by column chromatography through a silica gel cartridge (12 g) eluting with ethyl acetate/hexane (1:9 to 1:2) to give the product as a light yellow solid. ¹H NMR (300 MHz, DMSO) δ=8.02 (dd, J=1.5, 7.9 Hz, 1H), 7.87 (dd, J=1.5, 7.6 Hz, 1H), 7.67 (t, J=7.9 Hz, 1H), 7.36 (m, 3H), 7.31-7.19 (m, 2H), 7.01 (br s, 2H), 6.86 (t, J=2.1 Hz, 2H), 6.26 (t, J=2.1 Hz, 2H). MS (ES⁺)=323 (MH)⁺.

Example 153: Synthesis of N-Acetyl-3-phenylethynyl-2-pyrrol-1-yl-benzenesulfonamide

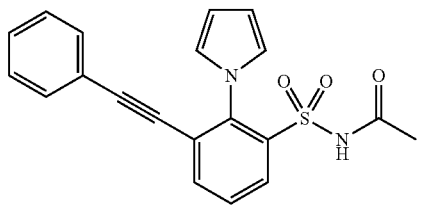 [SMILES: CC(=O)NS(=O)(=O)c1cccc(C#Cc2ccccc2)c1-n1cccc1]

N-Acetyl-3-bromo-2-pyrrol-1-yl-benzenesulfonamide: To a slurry of acetic acid (9.6 mg, 0.16 mmol), 1-ethyl-3-(3-dimethylaminopropyl)carbodiimide hydrochloride (31 mg, 0.16 mmol), and 4-dimethylaminopyridine (20 mg, 0.16 mmol) in N,N-dimethylformamide (0.20 mL) was added 3-bromo-2-pyrrol-1-yl-benzenesulfonamide (40 mg, 0.13 mmol). The resulting mixture was stirred at ambient temperature for 16 hours. The reaction mixture was then diluted with aqueous hydrochloric acid (0.1N, 10 mL) and extracted with ethyl acetate (2×15 mL). The combined organic extracts were dried with magnesium sulfate, filtered and concentrated at reduced pressure to give the product in quantitative yield, which was used in the next step without purification.

N-Acetyl-3-phenylethynyl-2-pyrrol-1-yl-benzenesulfonamide: To a degassed solution of N-Acetyl-3-bromo-2-pyrrol-1-yl-benzenesulfonamide (40 mg, 0.117 mmol) in triethylamine (0.40 mL), phenylacetylene (24 mg, 26 µL, 0.23 mmol) and copper (I) iodide (1.1 mg, 0.0058 mmol) in a sealed tube was added bis(triphenylphosphine)palladium (II) dichloride (8.2 mg, 0.00117 mmol). The tube was sealed and heated at 90° C. for 48 hours. The reaction mixture was cooled to ambient temperature and concentrated at reduced pressure. The resulting mixture was purified by column chromatography through a silica gel cartridge (4 g) eluting with ethyl acetate/hexane (1:4 to 1:2) to give the product as a white foam. ¹H NMR (300 MHz, DMSO) δ=11.74 (br s, 1H), 8.10 (dd, J=1.5, 7.9 Hz, 1H), 7.94 (dd, J=1.5, 7.6 Hz, 1H), 7.72 (t, J=7.9 Hz, 1H), 7.44-7.19 (m, 5H), 6.82 (t, J=2.2 Hz, 2H), 6.30 (t, J=2.1 Hz, 2H), 1.84 (s, 3H). MS (ES⁺)=365 (MH)⁺.

Example 154: Synthesis of 2-(dimethyl-1,2-oxazol-4-yl)-3-(2-phenylethynyl)benzoic acid

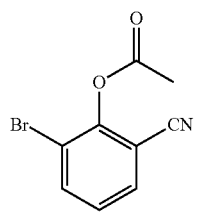

Acetic acid 2-bromo-6-cyano-phenyl ester: At 0° C. to a solution of 2-bromo-6-cyano-phenol (2 g, 10.1 mmol) and triethylamine (2.25 mL, 16.2 mmol) in dichloromethane (30 mL) was slowly added acetyl chloride (1 M in dichloromethane, 13.1 mL, 13.1 mmol). The reaction mixture was stirred at room temperature for 30 minutes, washed with water, dried (anhydrous sodium sulfate), concentrated and purified by column chromatography through a silica gel cartridge (40 g) eluting with ethyl acetate/hexane (0-20%) to give the product as a white solid.

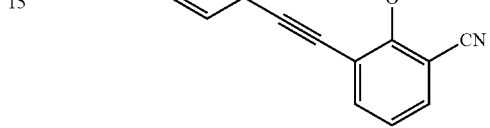

Acetic acid 2-cyano-6-phenylethynyl-phenyl ester: To a sealed flask was loaded a mixture of acetic acid 2-bromo-6-cyano-phenyl ester (1.6 g, 6.67 mmol), bis(triphenylphosphine)palladium(II) dichloride (468 mg, 0.667 mmol), copper iodide (127 mg, 0.667 mmol) and N,N-diisopropylethylamine (1.74 mL, 10 mmol). The mixture was degassed with N₂ for 10 minutes, phenylacetylene (1 g, 10 mmol) was added and the mixture was degassed with N₂ for 5 minutes. The reaction mixture was heated at 90° C. for 3 hours. After cooling to ambient temperature, the crude mixture was filtered through celite and washed with dichloromethane. The filtrate was concentrated and purified by column chromatography through a silica gel cartridge (40 g) eluting with ethyl acetate/hexane (0-20%) to give the product as a white solid.

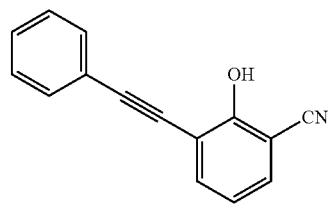 [SMILES: N#Cc1cccc(C#Cc2ccccc2)c1O]

2-Hydroxy-3-phenylethynyl-benzonitrile: To a solution of acetic acid 2-cyano-6-phenylethynyl-phenyl ester (1.9 g, 8.68 mmol) in tetrahydrofuran (3 mL) was added ammonium hydroxide (3 mL). The reaction mixture was stirred at room temperature for 30 minutes, acidified with 4 N hydrochloric acid in water and extracted with ethyl acetate (15 mL×3). The combined organic extracts were dried (anhydrous sodium sulfate), concentrated and vacuum dry to give the product as a white solid.

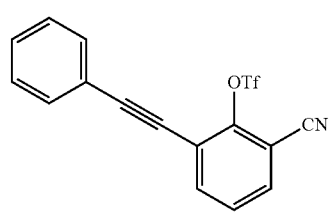 [SMILES: N#Cc1cccc(C#Cc2ccccc2)c1OS(=O)(=O)C(F)(F)F]

Trifluoro-methanesulfonic acid 2-cyano-6-phenylethynyl-phenyl ester: To a solution of 2-hydroxy-3-phenylethynyl-benzonitrile (800 mg, 3.64 mmol) in dichloromethane (20 mL) cooled at −70° C. was added triethylamine (0.76 mL, 5.46 mmol) followed by trifluoromethanesulfonic anhydride (0.67 mL, 4 mmol). The reaction mixture was allowed to be slowly warmed up to room temperature and stirred at room temperature for 30 minutes. Dichloromethane (20 mL) was added and the solution was washed with water, dried (anhydrous sodium sulfate), concentrated and purified by column chromatography through a silica gel cartridge (40 g) eluting with ethyl acetate/hexane (0-20%) to give the product as a white solid.

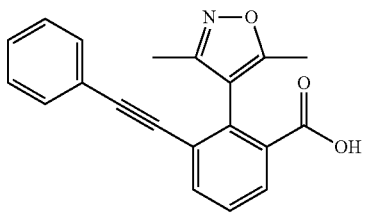 [SMILES: Cc1noc(C)c1-c1c(C#Cc2ccccc2)cccc1C(=O)O]

2-(Dimethyl-1,2-oxazol-4-yl)-3-(2-phenylethynyl)benzoic acid: A mixture of trifluoro-methanesulfonic acid 2-cyano-6-phenylethynyl-phenyl ester (50 mg, 0.143 mmol), 3,5-dimethyl-4-(4,4,5,5-tetramethyl-[1,3,2]dioxaborolan-2-yl)-isoxazole (48 mg, 0.215 mmol), 1,1'-bis(diphenylphosphino)ferrocene-palladium(II)dichloride (10.5 mg, 0.014 mmol) and potassium carbonate (39.5 mg, 0.286 mmol) in 1,4-dioxane (0.5 mL) and water (0.5 mL) was degassed with $N_2$ for 10 minutes and heated at 90° C. for 17 hours. After cooling down the reaction mixture was partitioned between water and ethyl acetate, the organic layer was dried (sodium sulfate), filtered, concentrated and purified through preparative thin layer chromatography to give a solid intermediate. To this intermediate in dimethylsulfoxide (0.5 mL) was added sodium hydroxide solution (10% in water, 0.5 mL) and the solution was heated at 100° C. for 24 hours. 1 N hydrochloric acid aqueous solution was added dropwise until pH=1 and the reaction mixture was purified through preparative HPLC to give the product as a white solid. $^1$H NMR (300 MHz, CDCl$_3$) δ=8.06-7.98 (m, 1H), 7.81 (d, J=7.6 Hz, 1H), 7.50 (t, J=7.8 Hz, 1H), 7.32-7.24 (m, 5H), 2.24 (s, 3H), 2.13 (s, 3H). LCMS (ESI) m/z 318.0 (M+1)$^+$.

Example 155: Synthesis of 2-(benzyloxy)-3-(2-phenylethynyl)benzoic acid

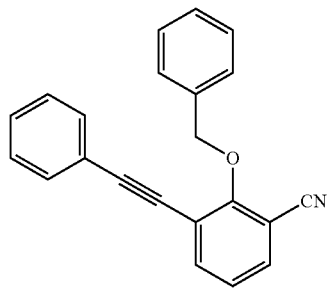 [SMILES: N#Cc1cccc(C#Cc2ccccc2)c1OCc1ccccc1]

2-Benzyloxy-3-phenylethynyl-benzonitrile: To a solution of 2-hydroxy-3-phenylethynyl-benzonitrile (50 mg, 0.227 mmol), benzyl alcohol (37 mg, 0.34 mmol) and triphenylphosphine (71.4 mg, 0.272 mmol) in tetrahydrofuran (1.5 mL) was added diisopropyl azodicarboxylate (0.055 mL, 0.272 mmol) and the reaction mixture was stirred at room temperature for 17 hours. The solution was concentrated and the residue was purified by column chromatography through a silica gel cartridge (12 g) eluting with ethyl acetate/hexane (0-20%) to give the product as a white solid.

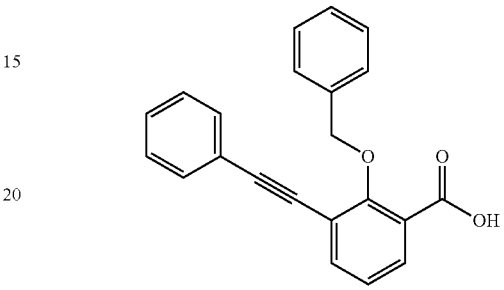

2-(benzyloxy)-3-(2-phenylethynyl)benzoic acid: To 2-benzyloxy-3-phenylethynyl-benzonitrile (40 mg, 0.129 mmol) in dimethylsulfoxide (0.5 mL) was added sodium hydroxide solution (10% in water, 0.5 mL) and the solution was heated at 100° C. for 24 h. 1 N hydrochloric acid aqueous solution was added dropwise until pH=1 and the reaction mixture was purified through preparative HPLC to give the pure product as a white solid. $^1$H NMR (300 MHz, CDCl$_3$) δ=8.06 (d, J=6.7 Hz, 1H), 7.77 (d, J=7.6 Hz, 1H), 7.55-7.44 (m, 4H), 7.43-7.23 (m, 7H), 5.45 (s, 2H). LCMS (ESI) m/z 329.0 (M+1)$^+$.

Example 156: Synthesis of 2-[3-(methoxycarbonyl)-1H-indol-6-yl]-3-(2-phenylethynyl) benzoic acid

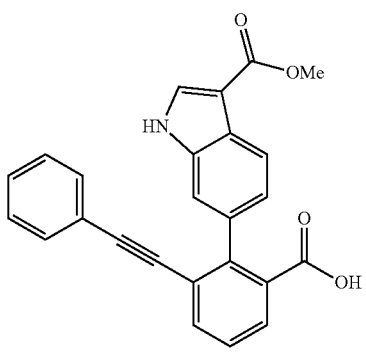 [SMILES: COC(=O)c1c[nH]c2cc(-c3c(C#Cc4ccccc4)cccc3C(=O)O)ccc12]

2-[3-(methoxycarbonyl)-1H-indol-6-yl]-3-(2-phenylethynyl)benzoic acid was prepared by the same procedure as example 119. $^1$H NMR (300 MHz, DMSO) δ 12.00 (s, 1H), 8.13 (d, J=3.0 Hz, 1H), 8.00 (d, J=8.2 Hz, 1H), 7.77 (dd, J=7.7, 1.4 Hz, 1H), 7.71 (dd, J=7.8, 1.4 Hz, 1H), 7.54-7.39 (m, 2H), 7.33-7.21 (m, 3H), 7.18 (dd, J=8.2, 1.5 Hz, 1H), 7.12-7.05 (m, 2H), 3.81 (s, 3H). MS m/z (M+H) 396.0.

Example 157: Synthesis of 3-[3-(benzylamino)prop-1-yn-1-yl]-2-phenylbenzoic acid

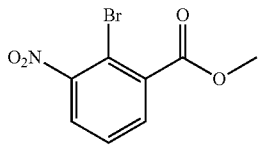

Methyl 2-bromo-3-nitrobenzoate: To a stirring solution of 2-bromo-3-nitrobenzoic acid (500 mg, 2.04 mmol) in methanol (5 mL) was added concentrated sulfuric acid (0.5 mL). The resulting solution was heated at 80° C. for 18 hours. The reaction mixture was cooled to ambient temperature and concentrated at reduced pressure. The residue was diluted with ethyl acetate (50 mL) and washed with 1N aqueous sodium hydroxide solution (50 mL) and brine, dried (magnesium sulfate), filtered and concentrated at reduced pressure to give the desired product as a colorless oil which was used in the next step without further purification.

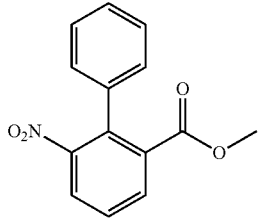 [SMILES: COC(=O)c1cccc([N+](=O)[O-])c1-c1ccccc1]

Methyl 2-phenyl-3-nitrobenzoate: To a mixture of methyl 2-bromo-3-nitrobenzoate (2.6 g, 10 mmol), phenyl boronic acid (1.46 g, 12 mmol) and palladium acetate (171 mg, 0.7 mmol) in acetone (12 mL) was added 2N aqueous potassium carbonate (12 mL). The reaction mixture was heated at 65° C. for 4 hours, cooled to ambient temperature and partitioned between ethyl acetate (200 mL) and water (100 mL). The organic layer was dried (magnesium sulfate), concentrated and purified by column chromatography through a silica gel cartridge (80 g) eluting with ethyl acetate/hexane (0 to 5%) to achieve the product as a solid. $^1$H NMR (300 MHz, CDCl$_3$) δ=7.99 (dd, J=1.2, 7.9 Hz, 1H), 7.88 (dd, J=1.3, 8.1 Hz, 1H), 7.56 (t, J=7.9 Hz, 1H), 7.44-7.35 (m, 3H), 7.27-7.19 (m, 2H), 3.57 (s, 3H).

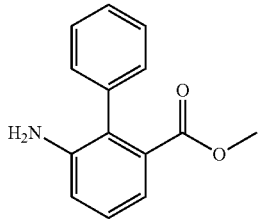

Methyl 2-phenyl-3-aminobenzoate: To a stirring solution of methyl 2-phenyl-3-nitrobenzoate (1.09 g, 4.24 mmol) in a mixture of acetic acid (4 mL) and methanol (10 mL) was added zinc powder (1.38 g, 21.2 mmol) in three portions. The resulting mixture was stirred at ambient temperature for 18 hours. The mixture was neutralized by 6N aqueous sodium hydroxide solution, extracted with ethyl acetate (3×100 mL). The organic layer was washed with brine, dried (magnesium sulfate) and concentrated at reduced pressure to give the product as a yellow solid which was used in the next step without further purification.

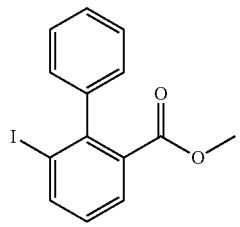 [SMILES: COC(=O)c1cccc(I)c1-c1ccccc1]

Methyl 2-phenyl-3-iodobenzoate: To a solution of methyl 2-phenyl-3-aminobenzoate (2.29 g, 10 mmol) in 1,4-dioxane (30 mL) and water (20 mL) at 0° C. was added concentrated hydrochloric acid (3.0 mL). After 25 minutes, aqueous sodium nitrate solution (760 mg, 7.4 mmol, 10 mL water) was added and the resulting mixture was stirred for 1 hour. Potassium iodide solution (14.9 g, 90 mmol, 10 mL water) was added via addition funnel. The resulting mixture was allowed to warm to ambient temperature and stirred for 18 hours. The reaction mixture was diluted with ethyl acetate (200 mL) and washed with sodium hydroxide solution (100 mL, 2N), followed by saturated aqueous sodium thiosulfate solution (50 mL). The organic layer was dried (magnesium sulfate), concentrated and purified by column chromatography through a silica gel cartridge (80 g) eluting with ethyl acetate/hexane (0 to 5%) to provide the product as a red oil (2.33 g, 68%, 70% pure)$^1$H NMR (300 MHz, CDCl$_3$) δ=8.08 (dd, J=1.2, 7.9 Hz, 1H), 7.81 (dd, J=1.3, 7.8 Hz, 1H), 7.44-7.29 (m, 3H), 7.18-7.07 (m, 2H), 3.54-3.51 (m, 3H). MS (ES$^+$)=177 (M−31)$^+$

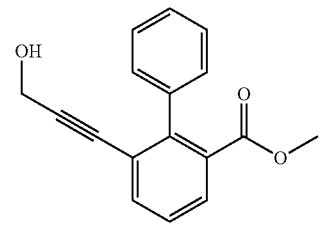 [SMILES: COC(=O)c1cccc(C#CCO)c1-c1ccccc1]

Methyl 2-phenyl-3-(3-hydroxyprop-1-ynyl)benzoate: To a sealed flask was added methyl 2-phenyl-3-iodobenzoate (734 mg, 2.17 mmol), triethylamine (3 mL) and N,N-dimethylformamide (7 mL). The mixture was degased for 30 minutes, followed by addition of bis(triphenylphosphine)palladium(II) dichloride (151 mg, 0.22 mmol), copper(I) iodide (21 mg, 0.11 mmol) and propargyl alcohol (0.26 mL, 4.34 mmol). The flask was sealed and heated at 45° C. for 18 hours. After cooling to ambient temperature, the mixture was poured into water (150 ml), extracted with ethyl acetate (3×100 mL). The organic layer was dried (magnesium sulfate), concentrated and purified by column chromatography through a silica gel cartridge (40 g) eluting with ethyl acetate/hexane (10% to 20%) to provide the product as a red oil. $^1$H NMR (300 MHz, CDCl$_3$) δ=7.78 (dd, J=1.5, 7.9 Hz, 1H), 7.63 (dd, J=1.3, 7.8 Hz, 1H), 7.41-7.26 (m, 5H), 4.20 (d, J=5.0 Hz, 2H), 3.56 (s, 3H).

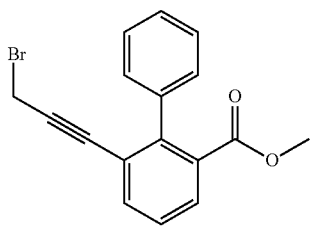 [SMILES: COC(=O)c1cccc(C#CCBr)c1-c1ccccc1]

Methyl 2-phenyl-3-(3-bromoprop-1-ynyl)benzoate: To a solution of methyl 2-phenyl-3-(3-hydroxyprop-1-ynyl)benzoate (100 mg, 0.376 mmol) in dichloromethane (1 mL), carbon tetrabromide (157 mg, 0.564 mmol) was added and the reaction mixture was cooled to 0° C., the solution of triphenyl phosphine (128 mg, 0.583 mmol) in dichloromethane (0.5 mL) was added drop wisely. The mixture warmed to ambient temperature and stirred for 3 hours. Ethanol (0.2 mL) was added. After 25 minutes, the mixture was concentrated and purified by column chromatography through a silica gel cartridge (4 g) eluting with ethyl acetate/hexane (0 to 5%) to achieve the product as a colored oil.

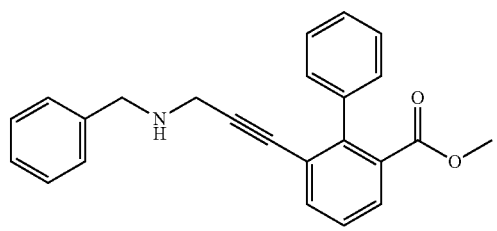 [SMILES: COC(=O)c1cccc(C#CCNCc2ccccc2)c1-c1ccccc1]

3-[3-(benzylamino)prop-1-yn-1-yl]-2-phenylbenzoic acid methyl ester: To a mixture of benzylamine (24 mg, 0.226 mmol) and cesium carbonate (92 mg, 0.282 mmol) in acetonitrile (1 mL) was added methyl 2-phenyl-3-(3-bromoprop-1-ynyl)benzoate (37 mg, 0.113 mmol) and the mixture was stirred at ambient temperature for 18 hours. The reaction mixture was filtered, concentrated and purified by column chromatography through a silica gel cartridge (4 g) eluting with ethyl acetate/hexane (0 to 10%) to achieve the product as a solid. MS (ES$^+$)=356 (MH$^+$).

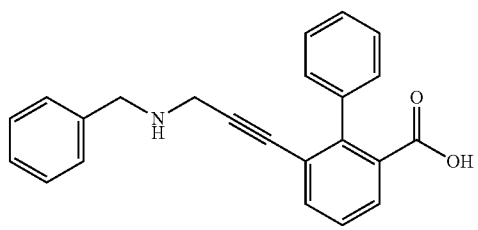 [SMILES: O=C(O)c1cccc(C#CCNCc2ccccc2)c1-c1ccccc1]

3-[3-(benzylamino)prop-1-yn-1-yl]-2-phenylbenzoic acid: To a mixture of 3-[3-(benzylamino)prop-1-yn-1-yl]-2-phenylbenzoic acid methyl ester (29 mg, 0.082 mmol) in tetrahydrofuran (0.2 mL), methanol (0.2 mL) and water (0.2 mL) was added lithium hydroxide (10 mg, 0.4 mmol) and stirred for 18 hrs. The mixture was neutralized with hydrochloric acid (2N) to pH=4 and concentrated at reduced pressure. The crude product was purified by preparative HPLC to give the product as a yellow solid. $^1$H NMR (300 MHz, DMSO-d$_6$) δ=7.84 (ddd, J=1.3, 7.8, 9.4 Hz, 2H), 7.60 (t, J=7.7 Hz, 1H), 7.53-7.33 (m, 10H), 4.02 (s, 2H), 3.86 (s, 2H). MS (ES$^+$)=342 (MH$^+$).

Example 158: Synthesis of 3-(3-{[3-(1H-imidazol-1-yl)propyl]amino}prop-1-yn-1-yl)-2-phenylbenzoic acid

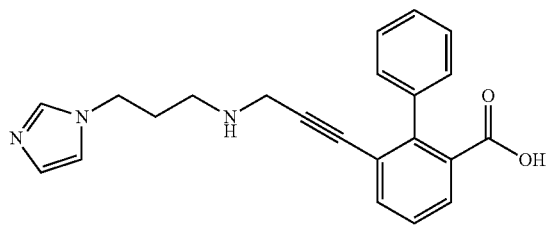 [SMILES: O=C(O)c1cccc(C#CCNCCCn2ccnc2)c1-c1ccccc1]

3-(3-{[3-(1H-imidazol-1-yl)propyl]amino}prop-1-yn-1-yl)-2-phenylbenzoic acid was prepared by the same procedure as example 157. $^1$H NMR (300 MHz, DMSO-d$_6$) δ=8.98 (s, 1H), 7.79-7.64 (m, 4H), 7.51 (t, J=7.7 Hz, 1H), 7.43-7.33 (m, 3H), 7.27-7.24 (m, 2H), 4.19 (t, J=6.9 Hz, 2H), 3.99 (s, 2H), 2.66 (d, J=7.6 Hz, 2H), 2.04 (d, J=7.3 Hz, 2H). MS (ES$^+$)=359.99 (MH$^+$).

Example 159: Synthesis of 2-phenyl-3-[3-(4-phenylpiperazin-1-yl)prop-1-yn-1-yl]benzoic acid

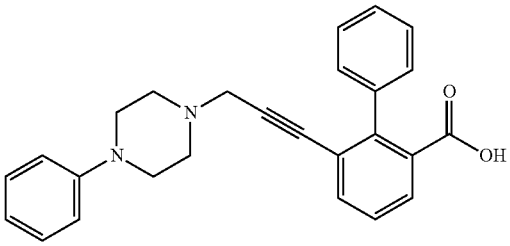 [SMILES: O=C(O)c1cccc(C#CCN2CCN(c3ccccc3)CC2)c1-c1ccccc1]

2-phenyl-3-[3-(4-phenylpiperazin-1-yl)prop-1-yn-1-yl]benzoic acid was prepared by the same procedure as example 157. $^1$H NMR (300 MHz, DMSO-d$_6$) δ=7.79 (dd, J=1.2, 7.6 Hz, 1H), 7.75 (dd, J=1.3, 7.8 Hz, 1H), 7.54-7.24 (m, 8H), 6.99 (d, J=8.5 Hz, 2H), 6.87 (t, J=7.1 Hz, 1H), 4.18 (br. s., 2H), 3.15-2.70 (br. S., 8H). MS (ES$^+$)=397.10 (MH$^+$).

Example 160: Synthesis of 2-phenyl-3-[3-(pyrrolidin-1-yl)prop-1-yn-1-yl]benzoic acid

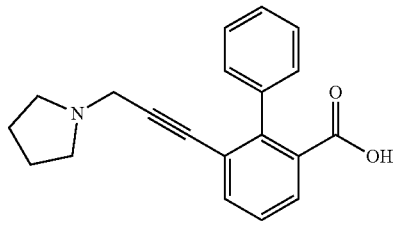 [SMILES: O=C(O)c1cccc(C#CCN2CCCC2)c1-c1ccccc1]

2-phenyl-3-[3-(pyrrolidin-1-yl)prop-1-yn-1-yl]benzoic acid was prepared by the same procedure as example 157.

¹H NMR (300 MHz, DMSO-d₆) δ=7.78 (dd, J=1.5, 7.6 Hz, 1H), 7.74 (dd, J=1.3, 7.8 Hz, 1H), 7.51 (t, J=7.8 Hz, 1H), 7.45-7.35 (m, 3H), 7.30-7.24 (m, 2H), 4.20 (s, 2H), 3.44-3.2 (br. S., 2H), 2.99-2.83 (m, 2H), 1.78 (br. s., 4H). MS (ES⁺)=306.06 (MH⁺).

Example 161: Synthesis of 3-(3-hydroxyprop-1-yn-1-yl)-2-phenylbenzoic acid

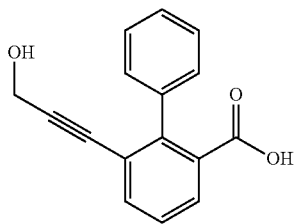 [SMILES: O=C(O)c1cccc(C#CCO)c1-c1ccccc1]

3-(3-hydroxyprop-1-yn-1-yl)-2-phenylbenzoic acid was prepared by the same procedure as example 157. ¹H NMR (300 MHz, DMSO-d₆) δ=12.75 (br. s., 1H), 7.70-7.60 (m, 2H), 7.47-7.21 (m, 6H), 5.14 (br. s., 1H), 4.04 (br. s., 2H).

Example 162: Synthesis of 3-{2-[3-(Aminomethyl)phenyl]ethynyl)}-2-(1H-pyrrol-1-yl) benzoic acid

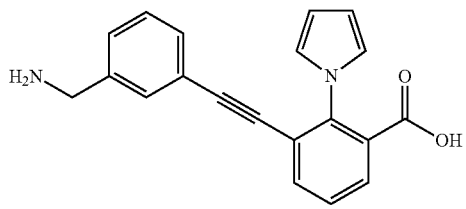 [SMILES: NCc1cccc(C#Cc2cccc(C(=O)O)c2-n2cccc2)c1]

3-{2-[3-(aminomethyl)phenyl]ethynyl}-2-(1H-pyrrol-1-yl)benzoic acid was prepared by the same procedure as example 157. ¹H NMR (300 MHz, CD₃OD) δ 7.76 (ddd, J=8.0, 6.6, 1.6 Hz, 2H), 7.50 (t, J=7.8 Hz, 1H), 7.45-7.40 (m, 3H), 7.37 (d, J=5.4 Hz, 1H), 6.93-6.73 (m, 2H), 6.35-6.08 (m, 2H), 4.09 (s, 2H). MS m/z (M+) 317.1

Example 163: Synthesis of 3-{2-[3-(3,5-difluorobenzenesulfonamidomethyl)phenyl] ethynyl}-2-(1H-pyrrol-1-yl)benzoic acid

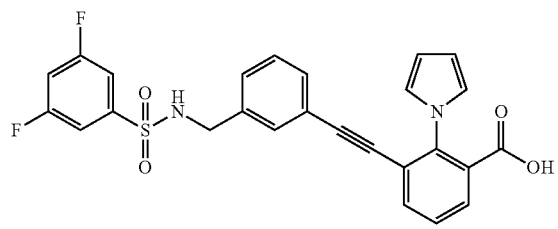 [SMILES: O=C(O)c1cccc(C#Cc2cccc(CNS(=O)(=O)c3cc(F)cc(F)c3)c2)c1-n1cccc1]

To a stirring solution of methyl 3-{2-[3-(aminomethyl)phenyl]ethynyl}-2-(1H-pyrrol-1-yl)benzoate (0.1 mmol) in dichloromethane (2 mL) was added 3,5-difluoro-benzenesulfonyl chloride (0.15 mmol), triethylamine (0.1 g), and catalytic 4-dimethylaminopyridine at 0° C. and stirred for 16 hours. The reaction mixture was then quenched with water (1 mL). The organic layers were washed with water (1 mL), brine (1 mL) dried (sodium sulfate), filtered and concentrated under reduced pressure. The resulting crude product was then dissolved in tetrahydrofuran:methanol (1:1 mL) and added 2N sodium hydroxide solution (0.3 mL) and stirred for 24 hours at ambient temperature. This solution was then concentrated and neutralized to pH 4 using 1 N HCl solution. The aqueous layer was then extracted using ethyl acetate (2×5 mL) and washed with water (2 mL) and brine (3 mL). The organic layers were combined, dried (sodium sulfate), filtered and concentrated under reduced pressure. The resulting crude product was then purified using reverse phase HPLC. ¹H NMR (300 MHz, CD₃OD) δ 8.21-8.04 (m, 1H), 7.88 (d, J=6.4 Hz, 1H), 7.83-7.70 (m, 1H), 7.54-7.45 (m, 2H), 7.33 (dd, J=6.4, 1.8 Hz, 2H), 7.26-7.06 (m, 3H), 6.86-6.79 (m, 2H), 6.66-6.56 (m, 1H), 6.32-6.26 (m, 2H), 4.12 (d, J=2.5 Hz, 2H). MS m/z (M+) 493.1

Example 164: Synthesis of 3-{2-[4-(1,2-dimethyl-1H-imidazole-5-sulfonamidomethyl) phenyl]ethynyl}-2-(1H-pyrrol-1-yl)benzoic acid

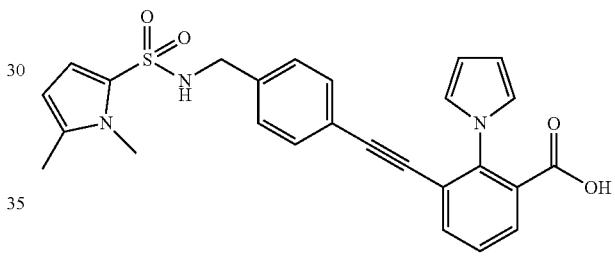

3-{2-[4-(1,2-dimethyl-1H-imidazole-5-sulfonamidomethyl)phenyl]ethynyl}-2-(1H-pyrrol-1-yl)benzoic acid was prepared by the same procedure as example 163. ¹H NMR (300 MHz, CD₃OD) δ 7.76 (ddd, J=7.9, 6.3, 1.6 Hz, 1H), 7.69-7.56 (m, 2H), 7.58-7.52 (m, 1H), 7.52-7.43 (m, 2H), 7.25-7.15 (m, 3H), 6.90-6.80 (m, 2H), 6.33-6.19 (m, 2H), 4.20 (d, J=8.8 Hz, 2H), 3.57 (s, 3H), 2.39 (s, 3H). MS m/z (M+) 475.1

Example 165: Synthesis of 3-{2-[3-(cyclopropanesulfonamidomethyl)phenyl]ethynyl}-2-(1H-pyrrol-1-yl)benzoic acid

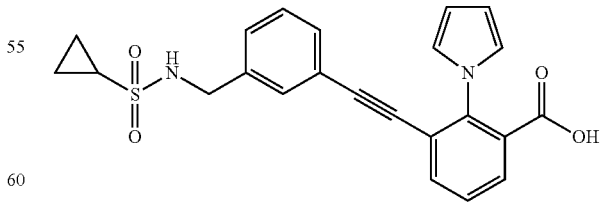

3-{2-[3-(cyclopropanesulfonamidomethyl)phenyl]ethynyl}-2-(1H-pyrrol-1-yl)benzoic acid was prepared by the same procedure as example 163. ¹H NMR (300 MHz, CD₃OD) δ 7.76 (d, J=7.8 Hz, 1H), 7.49 (dd, J=10.3, 5.3 Hz, 1H), 7.38 (d, J=6.0 Hz, 1H), 7.30 (dd, J=20.9, 13.4 Hz, 2H), 6.89-6.77 (m, 2H), 6.31-6.21 (m, 2H), 4.25 (s, 2H), 2.42 (d, J=4.9 Hz, 1H), 1.10-0.74 (m, 4H). MS m/z (M+) 421.1

Example 166: Synthesis of 2-(3-methoxyphenyl)-3-(2-{1H-pyrrolo[2,3-b]pyridin-3-yl} ethynyl)benzoic acid

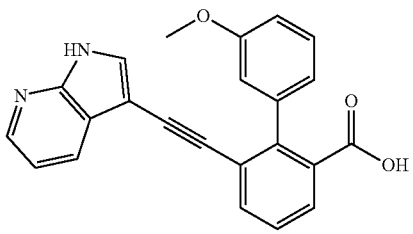 [SMILES: COc1cccc(-c2c(C#Cc3c[nH]c4ncccc34)cccc2C(=O)O)c1]

2-Bromo-3-ethynyl-benzoic acid methyl ester: A solution of 2-bromo-3-iodobenzoate (1 g, 2.9 mmol) and trimethylsilylacetylene (14.5 mmol) in tetrahydrofuran:triethylamine (20 ml:20 mL) was degassed using a nitrogen gas balloon for 5 minutes in a round bottom flask. To this solution was added Bis(triphenylphosphine)palladium(II) dichloride (210 mg, 0.3 mmol) and copper iodide (30 mg) and the reaction was stirred for 16 hours at ambient temperature. The reaction mixture was then filtered through celite using ethyl acetate (50 mL). The resultant solution was the concentrated under reduced pressure and purified through silica gel cartridge eluting with ethyl acetate/hexanes to give the product as a brown solid in 76% yield. To a stirring solution of the brown (0.6 g) in methanol (20 mL) was added solid potassium carbonate (20 mg) and the reaction was stirred for 16 hours at ambient temperature. The resultant mixture was concentrated and was diluted with ethyl acetate (10 mL) and washed with water (2×5 mL), brine (2 mL), dried (sodium sulfate), filtered and concentrated under reduced pressure. The resultant crude product was purified through a small silica gel cartridge eluting with ethyl acetate/hexanes (1:9) to provide 2-bromo-3-ethynyl-benzoic acid methyl ester.

ExTo a stirring solution of 2-bromo-3-ethynyl-benzoic acid methyl ester (0.5 g, 2.1 mmol) was added 3-iodo-1-(toluene-4-sulfonyl)-1H-pyrrolo[2,3-b]pyridine (1 g, 2.3 mmol) in tetrahydrofuran:triethylamine (20:20 mL) and the reaction was degassed using a nitrogen gas balloon for 15 minutes in a round bottom flask. To this solution was added Bis(triphenylphosphine) palladium(II) dichloride (150 mg, 0.21 mmol) and copper iodide (30 mg) and the reaction was stirred for 16 hours at ambient temperature. The reaction mixture was then filtered through celite using ethyl acetate (50 mL). The resultant solution was the concentrated under reduced pressure and purified through silica gel cartridge eluting with ethyl acetate/hnes to give the product as a brown solid in 54% yield.

To a stirring solution of above brown solid (0.05 g, 0.1 mmol) in dimethoxyethane:water (5:0.1 mL) was added 3-methoxyphenylboronic acid (0.12 mmol), Tetrakis(triphenylphosphine) palladium(0) (12 mg, 0.01 mmol) and potassium carbonate (35 mg, 0.25 mmol) in a sealed vial and the reaction was heated to 130° C. for 10 minutes. The resultant mixture was allowed to cool to ambient temperature and was diluted with ethyl acetate (20 mL) and washed with water (2×5 mL), brine (2 mL), dried (sodium sulfate), filtered and concentrated under reduced pressure. The resultant crude product was then dissolved in tetrahydrofuran:methanol (1:1 mL), 2N sodium hydroxide solution (0.3 mL) was added, and stirred for 24 hours at ambient temperature. This solution was then concentrated and neutralized to pH 4 using 1 N hydrochloric acid solution. The aqueous layer was then extracted using ethyl acetate (2×5 mL) and washed with water (2 mL) and brine (3 mL). The organic layers were combined, dried (sodium sulfate), filtered and concentrated under reduced pressure. The resulting crude product was then purified using reversed phase HPLC to provide 3-{2-[3-(cyclopropanesulfonamidomethyl)phenyl]ethynyl}-2-(1H-pyrrol-1-yl)benzoic acid. $^1$H NMR (300 MHz, DMSO) δ 12.08 (s, 1H), 8.24 (dd, J=4.7, 1.6 Hz, 1H), 7.74-7.68 (m, 2H), 7.66 (dd, J=7.8, 1.4 Hz, 1H), 7.47 (t, J=7.7 Hz, 1H), 7.41-7.31 (m, 2H), 7.07 (dd, J=7.9, 4.7 Hz, 1H), 7.01 (dd, J=7.4, 2.6 Hz, 1H), 6.92 (dd, J=8.9, 1.5 Hz, 2H), 3.73 (s, 3H). MS m/z (M+H) 369.0

Example 167: Synthesis of 2-(1-methyl-1H-indazol-6-yl)-3-(2-{1H-pyrrolo[2,3-b]pyridin-3-yl}ethynyl) benzoic acid

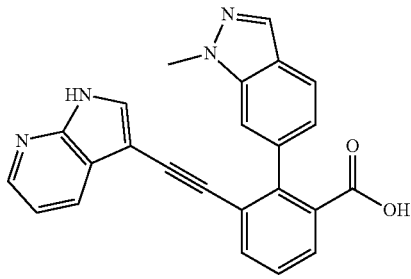 [SMILES: Cn1ncc2ccc(-c3c(C#Cc4c[nH]c5ncccc45)cccc3C(=O)O)cc21]

2-(1-methyl-1H-indazol-6-yl)-3-(2-{1H-pyrrolo[2,3-b]pyridin-3-yl}ethynyl)benzoic acid was prepared by the same procedure as example 166. $^1$H NMR (300 MHz, DMSO) δ 12.04 (s, 1H), 8.16 (dd, J=4.4, 1.9 Hz, 1H), 8.13 (d, J=1.0 Hz, 1H), 7.81-7.75 (m, 2H), 7.74 (q, J=1.4 Hz, 1H), 7.65 (d, J=1.1 Hz, 1H), 7.63 (d, J=2.7 Hz, 1H), 7.56-7.45 (m, 1H), 7.10 (dd, J=8.3, 1.3 Hz, 1H), 6.81-6.67 (m, 2H), 3.98 (s, 3H). MS m/z (M+) 392.9

Example 168: Synthesis of 2-(2-methyl-1,3-benzothiazol-5-yl)-3-(2-{1H-pyrrolo[2,3-b]pyridin-3-yl}ethynyl)benzoic acid

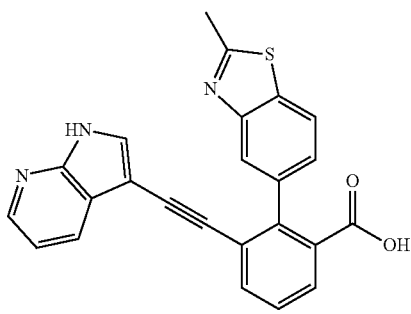 [SMILES: Cc1nc2cc(-c3c(C#Cc4c[nH]c5ncccc45)cccc3C(=O)O)ccc2s1]

2-(2-methyl-1,3-benzothiazol-5-yl)-3-(2-{1H-pyrrolo[2,3-b]pyridin-3-yl}ethynyl)benzoic acid was prepared by the same procedure as example 166. $^1$H NMR (300 MHz, DMSO) δ 12.05 (s, 1H), 8.17 (s, 1H), 8.08 (d, J=8.2 Hz, 1H), 7.89 (s, 1H), 7.75 (d, J=9.6 Hz, 2H), 7.67 (s, 1H), 7.53 (d, J=7.8 Hz, 1H), 7.34 (d, J=8.1 Hz, 1H), 6.83 (s, 2H), 2.77 (s, 3H). MS m/z (M+) 409.7

Example 169: Synthesis of 2-(3-methoxyphenyl)-3-[2-(1,3-thiazol-4-yl)ethynyl]benzoic acid

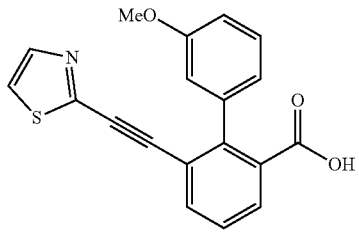 [SMILES: COc1cccc(-c2c(C#Cc3nccs3)cccc2C(=O)O)c1]

2-(3-methoxyphenyl)-3-[2-(1,3-thiazol-4-yl)ethynyl]benzoic acid was prepared by the same procedure as example 166. $^1$H NMR (300 MHz, DMSO) δ 9.10 (d, J=1.9 Hz, 1H), 7.84-7.70 (m, 3H), 7.52 (t, J=7.7 Hz, 1H), 7.34 (m, 1H), 7.00-6.87 (m, 3H), 3.76 (s, 3H). MS m/z (M+) 335.9

Example 170: Synthesis of 2-(1-methyl-1H-indazol-6-yl)-3-[2-(1,3-thiazol-4-yl)ethynyl] benzoic acid

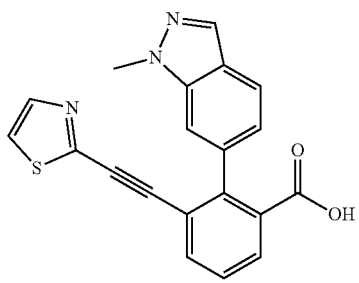 [SMILES: Cn1ncc2ccc(-c3c(C#Cc4nccs4)cccc3C(=O)O)cc21]

2-(1-methyl-1H-indazol-6-yl)-3-[2-(1,3-thiazol-4-yl)ethynyl]benzoic acid was prepared by the same procedure as example 169. $^1$H NMR (300 MHz, DMSO) δ 9.04 (d, J=1.9 Hz, 1H), 8.75 (s, 1H), 8.06 (d, J=0.8 Hz, 1H), 7.84 (dt, J=7.8, 4.1 Hz, 1H), 7.77 (dd, J=7.9, 1.3 Hz, 2H), 7.46-7.28 (m, 2H), 7.27-7.18 (m, 2H), 3.91 (s, 3H). MS m/z (M+) 359.4

Example 171: Synthesis of 2-(1-methyl-1H-indol-5-yl)-3-[2-(1,3-thiazol-4-yl)ethynyl]benzoic acid

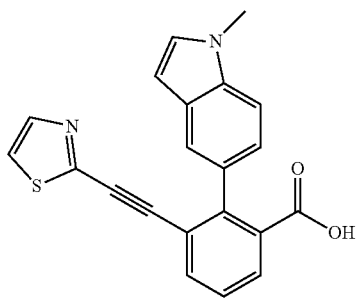 [SMILES: Cn1ccc2cc(-c3c(C#Cc4nccs4)cccc3C(=O)O)ccc21]

2-(1-methyl-1H-indol-5-yl)-3-[2-(1,3-thiazol-4-yl)ethynyl]benzoic acid was prepared by the same procedure as example 169. $^1$H NMR (300 MHz, DMSO) δ 9.06 (d, J=2.0 Hz, 1H), 7.78 (dd, J=7.7, 1.4 Hz, 1H), 7.74-7.65 (m, 2H), 7.55-7.52 (m, 1H), 7.48 (t, J=7.7 Hz, 2H), 7.35 (d, J=3.1 Hz, 1H), 7.18 (dd, J=8.4, 1.7 Hz, 1H), 6.46 (dd, J=3.1, 0.8 Hz, 1H), 3.82 (s, 3H). MS m/z (M+) 358.9

Example 172: Synthesis of 2-(pyridin-4-yl)-3-[2-(1,3-thiazol-4-yl)ethynyl]benzoic acid

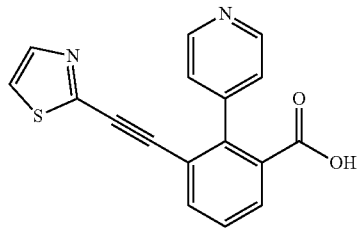 [SMILES: O=C(O)c1cccc(C#Cc2nccs2)c1-c1ccncc1]

2-(pyridin-4-yl)-3-[2-(1,3-thiazol-4-yl)ethynyl]benzoic acid was prepared by the same procedure as example 169. $^1$H NMR (300 MHz, DMSO) δ 9.10 (d, J=1.9 Hz, 1H), 8.85 (s, 1H), 8.03 (dd, J=7.8, 1.2 Hz, 1H), 7.95 (dd, J=7.8, 1.3 Hz, 1H), 7.81 (dd, J=5.7, 3.9 Hz, 4H), 7.68 (t, J=7.8 Hz, 1H). MS m/z (M+) 306.9

Example 173: Synthesis of 2-(2-methyl-1,3-benzothiazol-5-yl)-3-[2-(1,3-thiazol-4-yl)ethynyl]benzoic acid

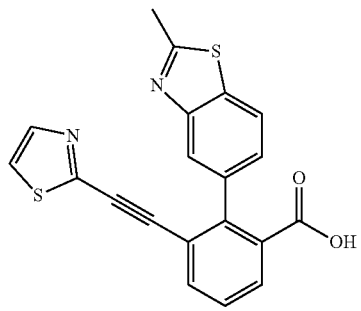 [SMILES: Cc1nc2cc(-c3c(C#Cc4nccs4)cccc3C(=O)O)ccc2s1]

2-(2-methyl-1,3-benzothiazol-5-yl)-3-[2-(1,3-thiazol-4-yl)ethynyl]benzoic acid was prepared by the same procedure as example 169. $^1$H NMR (300 MHz, CD$_3$OD) δ 8.90 (d, J=2.0 Hz, 1H), 7.98 (dd, J=8.3, 0.6 Hz, 1H), 7.93-7.86 (m, 2H), 7.84 (dd, J=7.8, 1.3 Hz, 1H), 7.54 (t, J=7.8 Hz, 1H), 7.43 (dd, J=8.3, 1.7 Hz, 1H), 7.36 (d, J=2.0 Hz, 1H), 2.85 (s, 3H). MS m/z (M+) 376.8

Example 174: Synthesis of 2-(1H-indol-3-yl)-3-[2-(pyridin-4-yl)ethynyl]benzoic acid

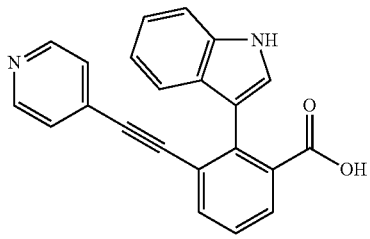 [SMILES: O=C(O)c1cccc(C#Cc2ccncc2)c1-c1c[nH]c2ccccc12]

2-(1H-indol-3-yl)-3-[2-(pyridin-4-yl)ethynyl]benzoic acid was prepared by the same procedure as example 166. $^1$H NMR (300 MHz, DMSO-d$_6$) δ=11.34 (br. s., 1H), 8.47 (br. s., 2H), 7.82 (dd, J=1.3, 7.8 Hz, 1H), 7.74 (d, J=7.5 Hz, 1H), 7.51-7.43 (m, 3H), 7.33 (d, J=7.9 Hz, 1H), 7.12 (t, J=7.6 Hz, 1H), 7.02-6.90 (m, 3H). MS (ES$^+$)=338.93 (MH$^+$).

Example 175: Synthesis of 2-[4-(dimethylamino)phenyl]-3-[2-(pyridin-4-yl)ethynyl]benzoic acid

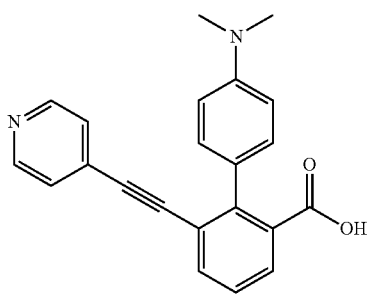 [SMILES: CN(C)c1ccc(-c2c(C#Cc3ccncc3)cccc2C(=O)O)cc1]

2-[4-(dimethylamino)phenyl]-3-[2-(pyridin-4-yl)ethynyl]benzoic acid was prepared by the same procedure as example 174. $^1$H NMR (300 MHz, DMSO-d6) δ=8.67 (br. s., 2H), 7.88-7.71 (m, 2H), 7.53-7.33 (m, 3H), 7.31-7.16 (m, 2H), 6.86 (d, J=8.8 Hz, 2H), 2.97 (s, 6H). MS (ES$^+$)=343.01 (MH$^+$).

Example 176: Synthesis of 2-(4-methyl-3,4-dihydro-2H-1,4-benzoxazin-7-yl)-3-[2-(pyridin-4-yl)ethynyl]benzoic acid

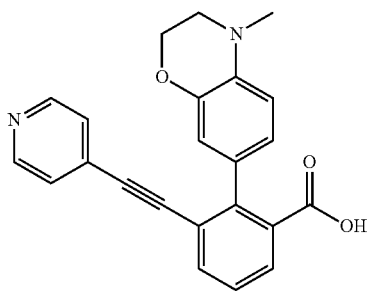 [SMILES: CN1CCOc2cc(-c3c(C#Cc4ccncc4)cccc3C(=O)O)ccc21]

2-(4-methyl-3,4-dihydro-2H-1,4-benzoxazin-7-yl)-3-[2-(pyridin-4-yl)ethynyl]benzoic acid was prepared by the same procedure as example 174. MS (ES$^+$)=371.00 (MH$^+$).

Example 177: Synthesis of 2-phenyl-3-[2-(pyridin-4-yl)ethynyl]benzoic acid

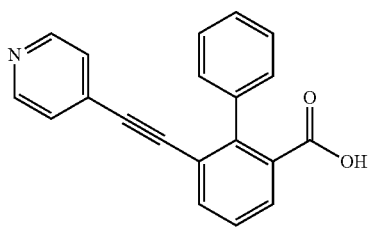 [SMILES: O=C(O)c1cccc(C#Cc2ccncc2)c1-c1ccccc1]

2-phenyl-3-[2-(pyridin-4-yl)ethynyl]benzoic acid was prepared by the same procedure as example 174. $^1$H NMR (300 MHz, DMSO-d6) δ=8.59 (d, J=5.9 Hz, 2H), 7.87-7.81 (m, 2H), 7.55 (t, J=7.8 Hz, 1H), 7.48-7.32 (m, 5H), 7.18 (d, J=5.2 Hz, 2H). MS (ES$^+$)=300.01 (MH$^+$).

Example 178: Synthesis of 6-(3-carboxy-phenylethynyl)-1H-indole-4-carboxylic acid

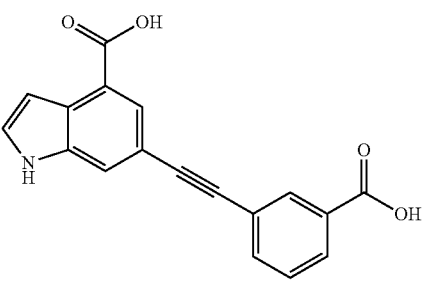 [SMILES: O=C(O)c1cccc(C#Cc2cc(C(=O)O)c3cc[nH]c3c2)c1]

6-(3-carboxy-phenylethynyl)-1H-indole-4-carboxylic acid was prepared by the same procedure as example 90. $^1$H NMR (300 MHz, DMSO) δ=11.64 (s, J=3.5, 3.5 Hz, 1H), 8.07 (d, J=2.3 Hz, 1H), 7.94 (td, J=1.7, 8.2 Hz, 1H), 7.86-7.80 (m, 3H), 7.63 (t, J=2.8 Hz, 1H), 7.56 (t, J=7.7 Hz, 1H), 6.99-6.96 (m, 1H). MS (ESI) m/z 287.9 (M−H$_2$O+1)$^+$. 1192

Example 179: Synthesis of 3-(4-carbamoyl-1H-indol-6-ylethynyl)-benzoic acid

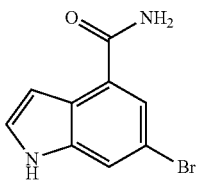 [SMILES: NC(=O)c1cc(Br)cc2[nH]ccc12]

6-Bromo-1H-indole-4-carboxylic acid amide: A solution of 6-bromo-1H-indole-4-carboxylic acid methyl ester (600 mg, 2.36 mmol) in ammonium hydroxide (10 mL) in a sealed flask was heated at 110° C. for 18 hours. After cooling to ambient temperature, the precipitates were filtered, washed with water and air dried to give 240 mg of the desired product (43%) as a white solid.

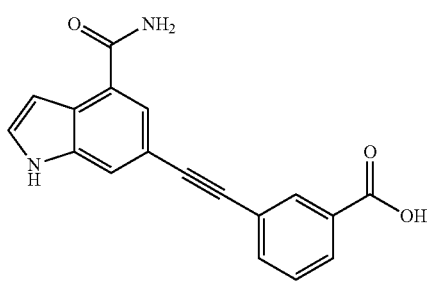 [SMILES: NC(=O)c1cc(C#Cc2cccc(C(=O)O)c2)cc2[nH]ccc12]

3-(4-Carbamoyl-1H-indol-6-ylethynyl)-benzoic acid was prepared by the same procedure as example 90. ¹H NMR (300 MHz, CD$_3$OD) δ=11.05 (br. s., 1H), 8.15 (t, J=1.5 Hz, 1H), 7.99 (td, J=1.4, 7.9 Hz, 1H), 7.78-7.72 (m, 2H), 7.68 (s, 1H), 7.53-7.47 (m, 2H), 6.95-6.92 (m, 1H). MS (ESI) m/z 305.0 (M+1)$^+$.

Example 180: Synthesis of 3-(3-carbamoyl-phenylethynyl)-benzoic acid

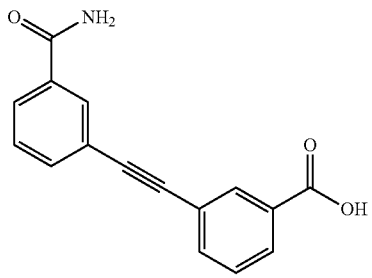 [SMILES: NC(=O)c1cccc(C#Cc2cccc(C(=O)O)c2)c1]

3-(3-Carbamoyl-phenylethynyl)-benzoic acid was prepared by the same procedure as example 90. 1H NMR (300 MHz, DMSO) δ=13.25 (br. s., 1H), 8.11-8.05 (m, 3H), 7.98 (td, J=1.5, 11.0 Hz, 2H), 7.95-7.88 (m, 1H), 7.80 (d, J=7.5 Hz, 1H), 7.73 (td, J=1.4, 7.8 Hz, 1H), 7.60-7.46 (m, 2H). MS (ESI) m/z 266.1 (M+1)$^+$.

Example 181: Synthesis of 3-(1-benzenesulfonyl-1H-indol-3-ylethynyl)-benzoic acid

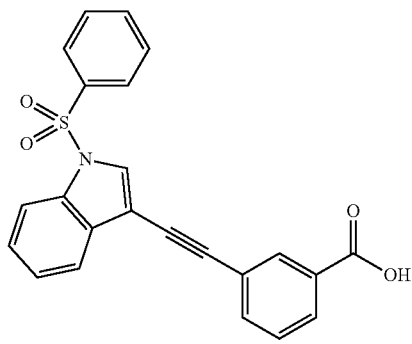 [SMILES: O=C(O)c1cccc(C#Cc2cn(S(=O)(=O)c3ccccc3)c3ccccc23)c1]

3-(1-Benzenesulfonyl-1H-indol-3-ylethynyl)-benzoic acid was prepared by the same procedure as example 90. ¹H NMR (300 MHz, CDCl$_3$) δ=9.75 (br. s., 1H), 8.24 (s, 1H), 7.98 (d, J=7.9 Hz, 1H), 7.82 (d, J=6.7 Hz, 1H), 7.74 (d, J=7.6 Hz, 1H), 7.68-7.56 (m, 2H), 7.53-7.40 (m, 5H), 7.30-7.19 (m, 3H).

Example 182: Synthesis of 3-(1H-indol-3-ylethynyl)-benzoic acid

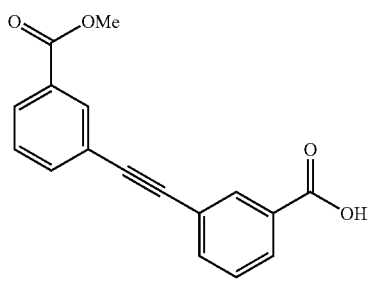 [SMILES: COC(=O)c1cccc(C#Cc2cccc(C(=O)O)c2)c1]

3-(1H-Indol-3-ylethynyl)-benzoic acid was prepared by the same procedure as example 90. 1H NMR (300 MHz, CD$_3$OD) δ=8.32 (s, 1H), 8.22 (d, J=7.2 Hz, 1H), 8.07-7.98 (m, 1H), 7.90 (d, J=7.8 Hz, 1H), 7.59 (d, J=7.9 Hz, 1H), 7.48-7.38 (m, 2H), 7.26-7.16 (m, 2H).

Example 183: Synthesis of 3-(3-carboxy-phenylethynyl)-benzoic acid methyl ester 3-(3-Methoxycarbonyl-phenylethynyl)-benzoic acid tert-butyl ester was prepared by the same procedure as example 90 and was used without further purification.

3-(3-Carboxy-phenylethynyl)-benzoic acid methyl ester: To a solution of 3-(3-methoxycarbonyl-phenylethynyl)-benzoic acid tert-butyl ester (690 mg, 2.05 mmol) in dichloromethane (5 mL) was added trifluoroacetic acid (5 mL). The solution was stirred at room temperature for 1 hour, concentrated and dried over vacuum to give 570 mg of the product (99%) as a white solid. ¹H NMR (300 MHz, CDCl$_3$) δ=8.24 (d, J=7.0 Hz, 2H), 8.04 (t, J=6.8 Hz, 2H), 7.73 (t, J=4.0 Hz, 2H), 7.46 (t, J=7.8 Hz, 2H), 3.96 (s, 3H). MS (ESI) m/z 281.0 (M+1)$^+$.

Example 184: Synthesis of 3-(3-carbamoyl-5-methoxy-phenylethynyl)-benzoic acid

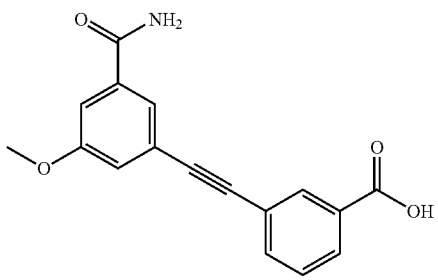 [SMILES: COc1cc(C#Cc2cccc(C(=O)O)c2)cc(C(N)=O)c1]

3-(3-Carbamoyl-5-methoxy-phenylethynyl)-benzoic acid was prepared by the same procedure as example 90. $^1$H NMR (300 MHz, CD$_3$OD) δ=8.15-8.12 (m, 1H), 8.04-8.00 (m, 1H), 7.76-7.72 (m, 1H), 7.64 (s, 1H), 7.54-7.45 (m, 2H), 7.35-7.25 (m, 1H), 3.88 (s, 3H). MS (ESI) m/z 296.1 (M+1)$^+$.

Example 185: Synthesis of 3'-hydroxy-4'-methoxy-6-pyridin-4-ylethynyl-biphenyl-2-carboxylic acid

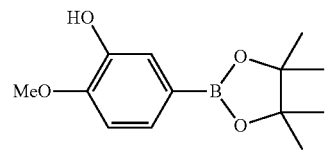 [SMILES: COc1ccc(B2OC(C)(C)C(C)(C)O2)cc1O]

2-Methoxy-5-(4,4,5,5-tetramethyl-[1,3,2]dioxaborolan-2-yl)-phenol: A mixture of 5-bromo-2-methoxy-phenol (300 mg, 1.48 mmol), bis(pinacolato)diboron (488 mg, 1.92 mmol), [1,1'-Bis(diphenylphosphino)ferrocene]palladium (II) dichloride (60 mg, 0.074 mmol) and potassium acetate (278 mg, 3 mmol) in dimethylformamide (4 mL) was heated at 90° C. for 18 hours. After cooling to room temperature, the reaction mixture was partitioned between dichlomethane (50 mL) and water (30 mL). The organic layer was dried (sodium sulfate), filtered, concentrated and purified through silica gel cartridge eluting with ethyl acetate/hexanes to give the product as a white solid in 86% yield.

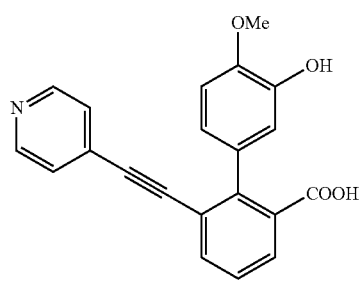 [SMILES: COc1ccc(-c2c(C#Cc3ccncc3)cccc2C(=O)O)cc1O]

3'-Hydroxy-4'-methoxy-6-pyridin-4-ylethynyl-biphenyl-2-carboxylic acid was prepared from 2-methoxy-5-(4,4,5,5-tetramethyl-[1,3,2]dioxaborolan-2-yl)-phenol by the same procedure as example 119. $^1$H NMR (300 MHz, CD$_3$OD) δ=8.45 (br. s., 2H), 7.75 (t, J=7.9 Hz, 2H), 7.43 (t, J=7.8 Hz, 1H), 7.26-7.15 (m, 2H), 7.00-6.87 (m, 2H), 6.79 (dd, J=1.8, 8.2 Hz, 1H), 3.90 (s, 3H). MS (ESI) m/z 346.13 (M+1)$^+$.

Example 186: Synthesis of 5'-hydroxy-3'-methoxy-6-pyridin-4-ylethynyl-biphenyl-2-carboxylic acid

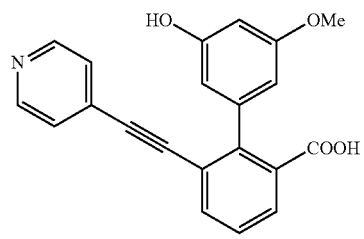 [SMILES: COc1cc(O)cc(-c2c(C#Cc3ccncc3)cccc2C(=O)O)c1]

5'-Hydroxy-3'-methoxy-6-pyridin-4-ylethynyl-biphenyl-2-carboxylic acid was prepared by the same procedure as example 119. $^1$H NMR (300 MHz, CD$_3$OD) δ=8.46 (br. s., 2H), 7.79 (dd, J=1.2, 7.6 Hz, 1H), 7.75 (dd, J=1.2, 7.9 Hz, 1H), 7.47 (t, J=7.8 Hz, 1H), 7.20 (d, J=5.3 Hz, 2H), 6.47-6.38 (m, 3H), 3.75 (s, 3H). MS (ESI) m/z 346.1 (M+1)$^+$.

Example 187: Synthesis of 2-(1H-pyrazol-3-yl)-3-pyridin-4-ylethynyl-benzoic acid

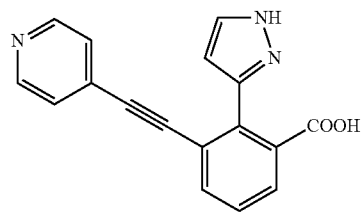 [SMILES: O=C(O)c1cccc(C#Cc2ccncc2)c1-c1cc[nH]n1]

2-(1H-Pyrazol-3-yl)-3-pyridin-4-ylethynyl-benzoic acid was prepared by the same procedure as example 119. $^1$H NMR (300 MHz, DMSO) δ=8.82-8.73 (m, 2H), 8.58-8.53 (m, 2H), 8.34 (d, J=7.3 Hz, 1H), 8.07 (d, J=7.3 Hz, 1H), 7.91 (d, J=2.1 Hz, 1H), 7.61 (t, J=7.9 Hz, 1H), 7.41 (s, 1H), 6.94 (d, J=1.7 Hz, 1H). MS (ESI) m/z 290.1 (M+1)$^+$.

Example 188: Synthesis of 2-(1H-pyrazol-4-yl)-3-pyridin-4-ylethynyl-benzoic acid

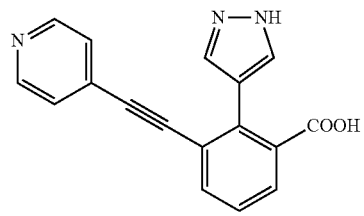 [SMILES: O=C(O)c1cccc(C#Cc2ccncc2)c1-c1cn[nH]c1]

2-(1H-Pyrazol-4-yl)-3-pyridin-4-ylethynyl-benzoic acid was prepared by the same procedure as example 119. $^1$H NMR (300 MHz, DMSO) δ=7.82-7.76 (m, 4H), 7.68-7.64 (m, 1H), 7.50-7.42 (m, 3H). MS (ESI) m/z 290.1 (M+1)$^+$.

Example 189: Synthesis of 2-(3,5-dimethyl-isoxazol-4-yl)-3-pyridin-4-ylethynyl-benzoic acid

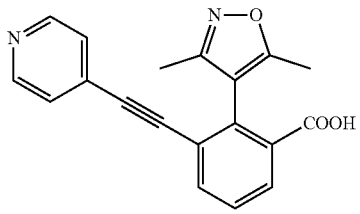 [SMILES: Cc1noc(C)c1-c1c(C#Cc2ccncc2)cccc1C(=O)O]

2-(3,5-Dimethyl-isoxazol-4-yl)-3-pyridin-4-ylethynyl-benzoic acid was prepared by the same procedure as example 119. $^1$H NMR (300 MHz, CD$_3$OD) δ=8.78 (br. s., 2H), 8.16 (d, J=7.9 Hz, 1H), 7.99 (dd, J=1.2, 7.9 Hz, 1H), 7.79-7.63 (m, 3H), 2.23 (s, 3H), 2.09 (s, 3H). MS (ESI) m/z 319.1 (M+1)$^+$.

Example 190: Synthesis of 3-phenylethynyl-2-(1,3,5-trimethyl-1H-pyrazol-4-yl)-benzoic acid

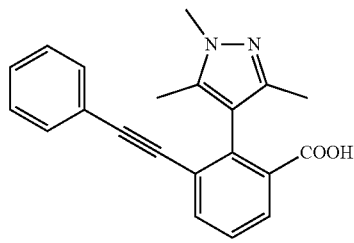 [SMILES: Cc1nn(C)c(C)c1-c1c(C#Cc2ccccc2)cccc1C(=O)O]

3-Phenylethynyl-2-(1,3,5-trimethyl-1H-pyrazol-4-yl)-benzoic acid was prepared by the same procedure as example 119. $^1$H NMR (300 MHz, CD$_3$OD) δ=7.94 (d, J=8.1 Hz, 1H), 7.80 (d, J=7.4 Hz, 1H), 7.53 (t, J=7.8 Hz, 1H), 7.38-7.20 (m, 5H), 3.87 (s, 3H), 2.12 (s, 3H), 2.11 (s, 3H). MS (ESI) m/z 331.1 (M+1)$^+$.

Example 191: Synthesis of 2-(2,5-dimethyl-pyrrol-1-yl)-3-(3-hydroxy-3-methyl-but-1-ynyl)-benzoic acid

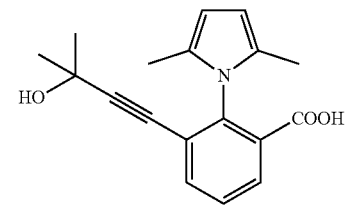 [SMILES: Cc1ccc(C)n1-c1c(C#CC(C)(C)O)cccc1C(=O)O]

2-(2,5-Dimethyl-pyrrol-1-yl)-3-(3-hydroxy-3-methyl-but-1-ynyl)-benzoic acid was prepared by the same procedure as example 21. $^1$H NMR (300 MHz, CDCl$_3$) δ=8.01 (dd, J=1.6, 7.8 Hz, 1H), 7.64 (dd, J=1.6, 7.8 Hz, 1H), 7.48 (t, J=7.7 Hz, 1H), 5.90 (s, 2H), 1.92 (s, 6H), 1.38 (s, 6H). MS (ESI) m/z 280.1 (M-H$_2$O+1)$^+$.

Example 192: Synthesis of 2-(2,5-dimethyl-pyrrol-1-yl)-3-pyridin-4-ylethynyl-benzoic acid

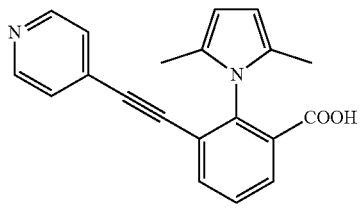 [SMILES: Cc1ccc(C)n1-c1c(C#Cc2ccncc2)cccc1C(=O)O]

2-(2,5-Dimethyl-pyrrol-1-yl)-3-pyridin-4-ylethynyl-benzoic acid was prepared by the same procedure as example 21. $^1$H NMR (300 MHz, CD$_3$OD) δ=8.69 (br. s., 2H), 8.05 (dd, J=1.5, 7.9 Hz, 1H), 7.93 (dd, J=1.5, 7.9 Hz, 1H), 7.71-7.57 (m, 3H), 5.89 (s, 2H), 1.93 (s, 6H). MS (ESI) m/z 317.1 (M+1)$^+$.

Example 193: Synthesis of 3-(3-carbamoyl-phenylethynyl)-2-(2,5-dimethyl-pyrrol-1-yl)-benzoic acid

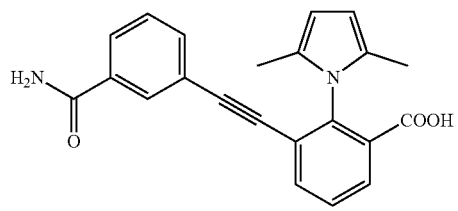 [SMILES: Cc1ccc(C)n1-c1c(C#Cc2cccc(C(N)=O)c2)cccc1C(=O)O]

3-(3-Carbamoyl-phenylethynyl)-2-(2,5-dimethyl-pyrrol-1-yl)-benzoic acid was prepared by the same procedure as example 21. $^1$H NMR (300 MHz, CD$_3$OD) δ=7.99-7.77 (m, 4H), 7.63-7.50 (m, 1H), 7.48-7.32 (m, 2H), 5.85 (s, 2H), 1.94 (s, 6H). MS (ESI) m/z 359.0 (M+1)$^+$.

Example 194: Synthesis of 3-(3-carboxy-phenylethynyl)-2-(2,5-dimethyl-pyrrol-1-yl)-benzoic acid

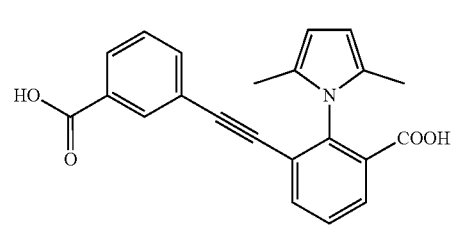 [SMILES: Cc1ccc(C)n1-c1c(C#Cc2cccc(C(=O)O)c2)cccc1C(=O)O]

3-(3-Carboxy-phenylethynyl)-2-(2,5-dimethyl-pyrrol-1-yl)-benzoic acid was prepared by the same procedure as example 21. $^1$H NMR (300 MHz, CD$_3$OD) δ=7.98-7.78 (m, 4H), 7.64-7.50 (m, 1H), 7.50-7.33 (m, 2H), 5.85 (s, 2H), 1.94 (s, 6H). MS (ESI) m/z 360.0 (M+1)$^+$.

Example 195: Synthesis of 2-(2,5-dimethyl-pyrrol-1-yl)-3-(3-hydroxymethyl-phenylethynyl)-benzoic acid

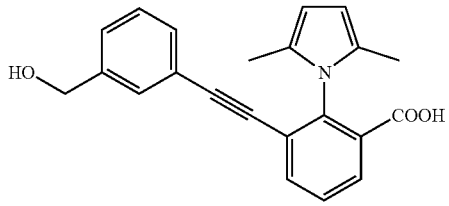 [SMILES: Cc1ccc(C)n1-c1c(C#Cc2cccc(CO)c2)cccc1C(=O)O]

2-(2,5-Dimethyl-pyrrol-1-yl)-3-(3-hydroxymethyl-phenylethynyl)-benzoic acid was prepared by the same procedure as example 21. $^1$H NMR (300 MHz, CD$_3$OD) δ=7.85 (d, J=7.6 Hz, 1H), 7.76 (d, J=7.6 Hz, 1H), 7.54 (t, J=7.6 Hz, 1H), 7.36-7.13 (m, 4H), 5.84 (s, 2H), 4.55 (s, 2H), 1.94 (s, 6H). MS (ESI) m/z 346.0 (M+1)$^+$.

Example 196: Synthesis of 2-(2,5-dimethyl-pyrrol-1-yl)-3-(1H-pyrrolo[2,3-b]pyridin-3-ylethynyl)-benzoic acid

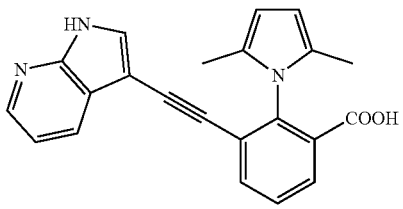 [SMILES: Cc1ccc(C)n1-c1c(C#Cc2c[nH]c3ncccc23)cccc1C(=O)O]

2-(2,5-Dimethyl-pyrrol-1-yl)-3-(1H-pyrrolo[2,3-b]pyridin-3-ylethynyl)-benzoic acid was prepared by the same procedure as example 21. $^1$H NMR (300 MHz, CD$_3$OD) δ=8.34 (br. s., 1H), 8.10 (dd, J=1.5, 7.9 Hz, 1H), 7.89-7.78 (m, 2H), 7.70 (s, 1H), 7.64-7.49 (m, 1H), 7.35 (dd, J=5.3, 7.9 Hz, 1H), 5.90 (s, 2H), 1.97 (s, 6H). MS (ESI) m/z 356.1 (M+1)$^+$.

Example 197: Synthesis of 2-(2,5-dimethyl-pyrrol-1-yl)-3-(3-hydroxy-3-phenyl-prop-1-ynyl)-benzoic acid

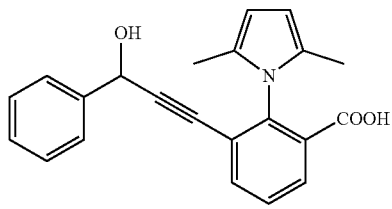 [SMILES: Cc1ccc(C)n1-c1c(C#CC(O)c2ccccc2)cccc1C(=O)O]

2-(2,5-Dimethyl-pyrrol-1-yl)-3-(3-hydroxy-3-phenyl-prop-1-ynyl)-benzoic acid was prepared by the same procedure as example 21. $^1$H NMR (300 MHz, CD$_3$OD) δ=8.08 (d, J=7.9 Hz, 1H), 7.97-7.85 (m, 2H), 7.68-7.42 (m, 3H), 7.21 (d, J=16.1 Hz, 1H), 6.85 (d, J=15.8 Hz, 1H), 5.91 (s, 2H), 3.30 (s, 1H), 1.87 (s, 6H). MS (ESI) m/z 346.0 (M+1)$^+$.

Example 198: Synthesis of 3-(3-acetylamino-phenylethynyl)-2-(2,5-dimethyl-pyrrol-1-yl)-benzoic acid

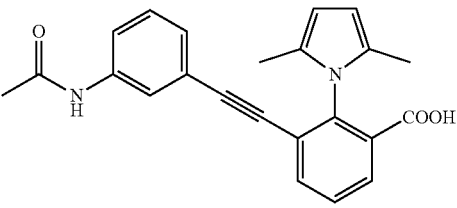 [SMILES: CC(=O)Nc1cccc(C#Cc2cccc(C(=O)O)c2-n2c(C)ccc2C)c1]

3-(3-Acetylamino-phenylethynyl)-2-(2,5-dimethyl-pyrrol-1-yl)-benzoic acid was prepared by the same procedure as example 21. $^1$H NMR (300 MHz, CD$_3$OD) δ=7.84 (d, J=5.9 Hz, 1H), 7.75 (d, J=7.9 Hz, 1H), 7.60-7.43 (m, 3H), 7.30-7.14 (m, 1H), 6.97 (d, J=7.3 Hz, 1H), 2.12 (s, 3H), 1.95 (s, 6H). MS (ESI) m/z 373.0 (M+1)$^+$.

Example 199: Synthesis of 3-cyclopropylethynyl-2-(2,5-dimethyl-pyrrol-1-yl)-benzoic acid

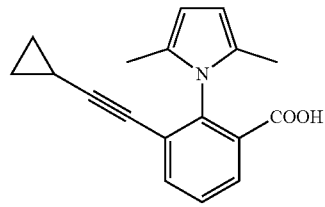 [SMILES: Cc1ccc(C)n1-c1c(C#CC2CC2)cccc1C(=O)O]

3-Cyclopropylethynyl-2-(2,5-dimethyl-pyrrol-1-yl)-benzoic acid was prepared by the same procedure as example 21. $^1$H NMR (300 MHz, CD$_3$OD) δ=7.79 (d, J=7.9 Hz, 1H), 7.60 (d, J=7.9 Hz, 1H), 7.45 (t, J=7.9 Hz, 1H), 5.72 (s, 2H), 1.85 (s, 6H), 1.36-1.13 (m, 1H), 0.75-0.63 (m, 2H), 0.62-0.37 (m, 2H). MS (ESI) m/z 280.1 (M+1)$^+$.

Example 200: Synthesis of 2-(2,5-dimethyl-pyrrol-1-yl)-3-(3-methoxy-phenylethynyl)-benzoic acid

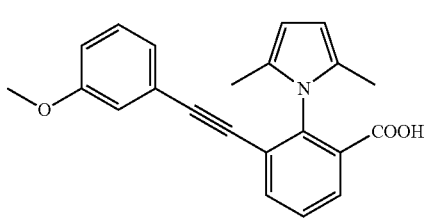 [SMILES: COc1cccc(C#Cc2cccc(C(=O)O)c2-n2c(C)ccc2C)c1]

2-(2,5-Dimethyl-pyrrol-1-yl)-3-(3-methoxy-phenylethynyl)-benzoic acid was prepared by the same procedure as example 21. $^1$H NMR (300 MHz, DMSO) δ=7.81 (d, J=7.9 Hz, 2H), 7.58 (t, J=7.6 Hz, 1H), 7.24 (t, J=8.0 Hz, 1H), 6.94 (d, J=2.6 Hz, 1H), 6.90 (d, J=2.6 Hz, 1H), 6.84-6.80 (m, 1H), 5.80 (s, 2H), 3.72 (s, 3H), 1.82 (s, 6H). MS (ESI) m/z 346.0 (M+1)$^+$.

Example 201: Synthesis of 2-(1H-indazol-6-yl)-3-phenylethynyl-benzoic acid

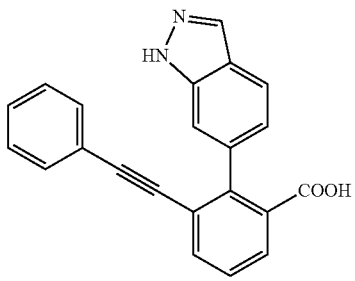 [SMILES: O=C(O)c1cccc(C#Cc2ccccc2)c1-c1ccc2cn[nH]c2c1]

2-(1H-Indazol-6-yl)-3-phenylethynyl-benzoic acid was prepared by the same procedure as example 119. ¹H NMR (300 MHz, CD$_3$OD) δ=8.10 (s, 1H), 7.85-7.74 (m, 3H), 7.55-7.45 (m, 2H), 7.25-7.13 (m, 4H), 6.96 (d, J=7.0 Hz, 2H). MS (ESI) m/z 339.0 (M+1)⁺.

Example 202: Synthesis of 2-benzo[1,3]dioxol-5-yl-3-phenylethynyl-benzoic acid

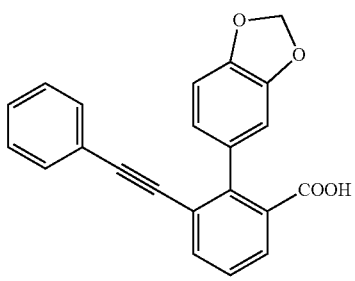 [SMILES: O=C(O)c1cccc(C#Cc2ccccc2)c1-c1ccc2c(c1)OCO2]

2-Benzo[1,3]dioxol-5-yl-3-phenylethynyl-benzoic acid was prepared by the same procedure as example 119. ¹H NMR (300 MHz, CD$_3$OD) δ=7.72 (t, J=8.5 Hz, 2H), 7.43 (t, J=7.7 Hz, 1H), 7.31-7.19 (m, 5H), 6.87 (s, 1H), 6.88 (d, J=8.2 Hz, 1H), 6.82-6.78 (m, 1H), 6.00 (s, 2H). MS (ESI) m/z 325.0 (M−H$_2$O+1)⁺.

Example 203: Synthesis of 2-isoquinolin-6-yl-3-phenylethynyl-benzoic acid

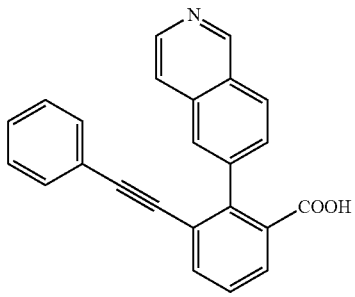 [SMILES: O=C(O)c1cccc(C#Cc2ccccc2)c1-c1ccc2cnccc2c1]

2-Isoquinolin-6-yl-3-phenylethynyl-benzoic acid was prepared by the same procedure as example 119. ¹H NMR (300 MHz, CD$_3$OD) δ=9.78 (br. s., 1H), 8.52 (d, J=8.5 Hz, 1H), 8.22-8.02 (m, 3H), 7.94 (d, J=7.3 Hz, 1H), 7.85 (br. s., 1H), 7.71 (t, J=7.8 Hz, 1H), 7.24-7.10 (m, 5H), 6.72 (d, J=7.0 Hz, 2H). MS (ESI) m/z 350.0 (M+1)⁺.

Example 204: Synthesis of 2-benzofuran-2-yl-3-phenylethynyl-benzoic acid

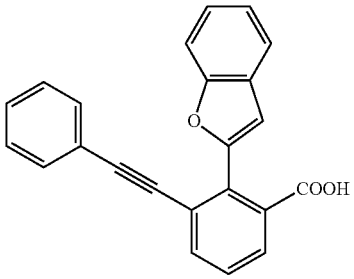 [SMILES: O=C(O)c1cccc(C#Cc2ccccc2)c1-c1cc2ccccc2o1]

2-Benzofuran-2-yl-3-phenylethynyl-benzoic acid was prepared by the same procedure as example 119. ¹H NMR (300 MHz, CD$_3$OD) δ=7.90-7.78 (m, 2H), 7.70-7.65 (m, 1H), 7.58-7.48 (m, 2H), 7.35-7.22 (m, 7H), 7.18 (s, 1H). MS (ESI) m/z 339.0 (M+1)⁺.

Example 205: Synthesis of 3-phenylethynyl-2-quinolin-8-yl-benzoic acid

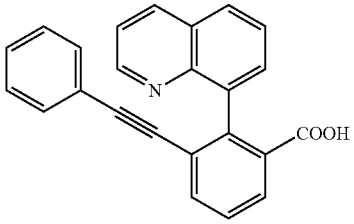 [SMILES: O=C(O)c1cccc(C#Cc2ccccc2)c1-c1cccc2cccnc12]

3-Phenylethynyl-2-quinolin-8-yl-benzoic acid was prepared by the same procedure as example 119. ¹H NMR (300 MHz, CD$_3$OD) δ=9.14 (dd, J=1.6, 8.4 Hz, 1H), 8.95 (dd, J=1.6, 5.1 Hz, 1H), 8.35 (dd, J=1.5, 8.2 Hz, 1H), 8.20 (d, J=7.9 Hz, 1H), 8.03-7.90 (m, 4H), 7.73 (t, J=7.8 Hz, 1H), 7.24-7.10 (m, 3H), 6.70 (d, J=7.5 Hz, 2H). MS (ESI) m/z 350.0 (M+1)⁺.

Example 206: Synthesis of 2-(2-amino-pyrimidin-5-yl)-3-phenylethynyl-benzoic acid

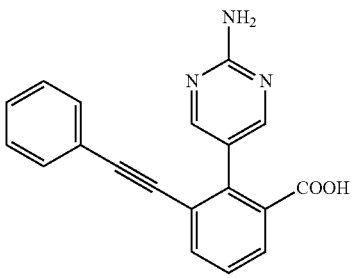 [SMILES: Nc1ncc(-c2c(C#Cc3ccccc3)cccc2C(=O)O)cn1]

2-(2-Amino-pyrimidin-5-yl)-3-phenylethynyl-benzoic acid was prepared by the same procedure as example 119. ¹H NMR (300 MHz, CD₃OD) δ=8.47 (s, 2H), 8.07 (dd, J=1.5, 7.9 Hz, 1H), 7.86 (dd, J=1.3, 7.8 Hz, 1H), 7.58 (t, J=7.8 Hz, 1H), 7.37-7.29 (m, 5H). MS (ESI) m/z 316.0 (M+1)⁺.

Example 207: Synthesis of 4'-dimethylaminomethyl-6-phenylethynyl-biphenyl-2-carboxylic acid

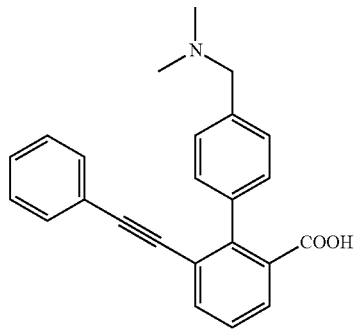 [SMILES: CN(C)Cc1ccc(-c2c(C#Cc3ccccc3)cccc2C(=O)O)cc1]

4'-Dimethylaminomethyl-6-phenylethynyl-biphenyl-2-carboxylic acid was prepared by the same procedure as example 119. ¹H NMR (300 MHz, CD₃OD) δ=7.90 (dd, J=1.2, 7.9 Hz, 1H), 7.77 (d, J=7.6 Hz, 1H), 7.58-7.44 (m, 5H), 7.34-7.09 (m, 5H), 4.39 (s, 2H), 2.85 (m, 6H). MS (ESI) m/z 356.1 (M+1)⁺.

Example 208: Synthesis of 3-(4-amino-phenylethynyl)-2-(1H-indol-6-yl)-benzoic acid

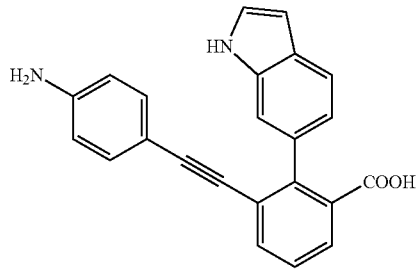 [SMILES: Nc1ccc(C#Cc2cccc(C(=O)O)c2-c2ccc3cc[nH]c3c2)cc1]

3-(4-Amino-phenylethynyl)-2-(1H-indol-6-yl)-benzoic acid was prepared by the same procedure as example 119. ¹H NMR (300 MHz, CDCl₃) δ=8.24 (d, J=8.8 Hz, 1H), 8.00 (br. s., 1H), 7.93 (d, J=7.9 Hz, 1H), 7.86-7.80 (m, 2H), 7.62 (s, 1H), 7.55 (d, J=7.6 Hz, 1H), 7.43-7.36 (m, 2H), 7.07-6.95 (m, 3H), 6.61 (dd, J=2.2, 2.9 Hz, 1H). MS (ESI) m/z 353.1 (M+1)⁺.

Example 209

Synthesis of 3-(4-carboxy-phenylethynyl)-2-(1H-indol-6-yl)-benzoic acid 2-Bromo-3-[4-(2-oxo-2-phenyl-ethoxycarbonyl)-phenylethynyl]-benzoic acid methyl ester was prepared by the same Sonogashira Coupling procedure as preparing 2-bromo-3-phenylethynyl-benzoic acid methyl ester in example 119 and was used in the next step without purification.

2-(1H-Indol-6-yl)-3-[4-(2-oxo-2-phenyl-ethoxycarbonyl)-phenylethynyl]-benzoic acid methyl ester was prepared by the same Suzuki Coupling procedure as preparing 2-(1H-indol-6-yl)-3-phenylethynyl-benzoic acid methyl ester in example 119 and was used in the next step without purification.

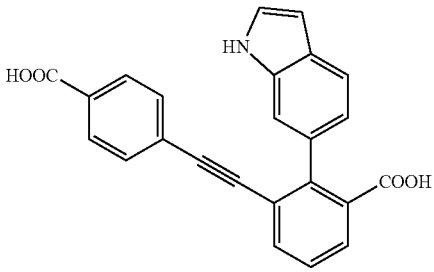 [SMILES: O=C(O)c1ccc(C#Cc2cccc(C(=O)O)c2-c2ccc3cc[nH]c3c2)cc1]

3-(4-Carboxy-phenylethynyl)-2-(1H-indol-6-yl)-benzoic acid was prepared from 22-(1H-indol-6-yl)-3-phenylethynyl-benzoic acid methyl ester by the same hydrolysis procedure as example 119. ¹H NMR (300 MHz, CDCl₃) δ=7.87-7.65 (m, 5H), 7.45-7.38 (m, 2H), 7.25 (d, J=3.2 Hz, 1H), 7.19 (dd, J=1.5, 8.2 Hz, 1H), 7.09 (d, J=8.2 Hz, 2H), 6.57 (d, J=3.3 Hz, 1H). MS (ESI) m/z 382.0 (M+1)⁺.

Example 210: Synthesis of 2-(1H-indol-6-yl)-3-(4-methoxy-phenylethynyl)-benzoic acid

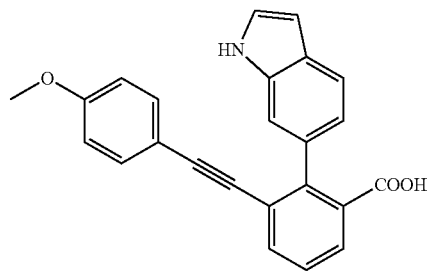 [SMILES: COc1ccc(C#Cc2cccc(C(=O)O)c2-c2ccc3cc[nH]c3c2)cc1]

2-(1H-Indol-6-yl)-3-(4-methoxy-phenylethynyl)-benzoic acid was prepared by the same procedure as example 119. ¹H NMR (300 MHz, CD₃OD) δ=7.69 (d, J=7.9 Hz, 2H), 7.59 (d, J=8.2 Hz, 1H), 7.45-7.27 (m, 2H), 7.28 (d, J=3.2 Hz, 1H), 7.05 (dd, J=1.4, 8.2 Hz, 1H), 6.96 (d, J=8.8 Hz, 2H), 6.73 (d, J=9.1 Hz, 2H), 6.50 (d, J=3.4 Hz, 1H), 3.73 (s, 3H). MS (ESI) m/z 368.1 (M+1)⁺.

Example 211: Synthesis of 3-(4-carbamoyl-phenylethynyl)-2-(1H-indol-6-yl)-benzoic acid

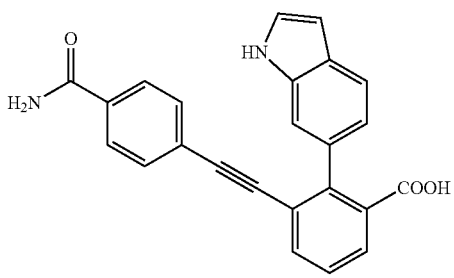 [SMILES: NC(=O)c1ccc(C#Cc2cccc(C(=O)O)c2-c2ccc3cc[nH]c3c2)cc1]

3-(4-Carbamoyl-phenylethynyl)-2-(1H-indol-6-yl)-benzoic acid was prepared by the same procedure as example 119. ¹H NMR (300 MHz, DMSO) δ=11.21 (br. s., 1H), 8.01 (s, 1H), 7.82-7.70 (m, 4H), 7.62-7.40 (m, 5H), 7.18 (d, J=8.2 Hz, 2H), 7.05 (d, J=7.0 Hz, 1H), 6.51 (s, 1H). MS (ESI) m/z 381.1 (M+1)⁺.

Example 212: Synthesis of 2-(1H-indol-6-yl)-3-[4-(piperazine-1-carbonyl)-phenylethynyl]-benzoic acid

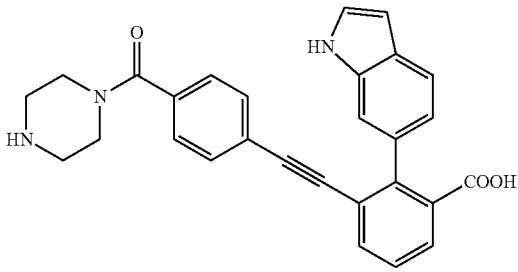 [SMILES: O=C(O)c1cccc(C#Cc2ccc(C(=O)N3CCNCC3)cc2)c1-c1ccc2cc[nH]c2c1]

2-(1H-Indol-6-yl)-3-[4-(piperazine-1-carbonyl)-phenylethynyl]-benzoic acid was prepared by the same procedure as example 119. ¹H NMR (300 MHz, CD₃OD) δ=7.78-7.74 (m, 2H), 7.60 (d, J=8.2 Hz, 1H), 7.48-7.42 (m, 2H), 7.35-7.25 (m, 3H), 7.15-7.03 (m, 3H), 6.50 (d, J=3.1 Hz, 1H), 3.85-3.70 (m, 4H), 3.30-3.06 (m, 4H). MS (ESI) m/z 450.3 (M+1)⁺.

Example 213: Synthesis of 3-(4-acetylamino-phenylethynyl)-2-(1H-indol-6-yl)-benzoic acid

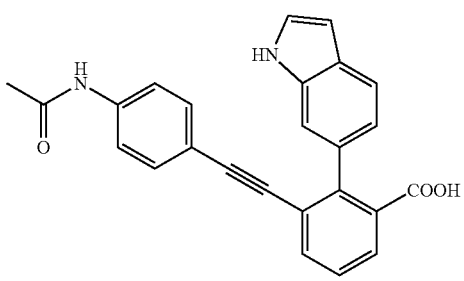 [SMILES: CC(=O)Nc1ccc(C#Cc2cccc(C(=O)O)c2-c2ccc3cc[nH]c3c2)cc1]

3-(4-acetylamino-phenylethynyl)-2-(1H-indol-6-yl)-benzoic acid was prepared by the same procedure as example 119. ¹H NMR (300 MHz, CDCl₃) δ=7.86-7.64 (m, 3H), 7.46-7.29 (m, 4H), 7.25-7.17 (m, 2H), 7.00 (d, J=8.5 Hz, 2H), 6.56 (d, J=2.4 Hz, 1H), 2.12 (s, 3H). MS (ESI) m/z 395.1 (M+1)⁺.

Example 214: Synthesis of 2-(1H-indol-6-yl)-3-{4-[(pyridine-3-carbonyl)-amino]-phenylethynyl}-benzoic acid

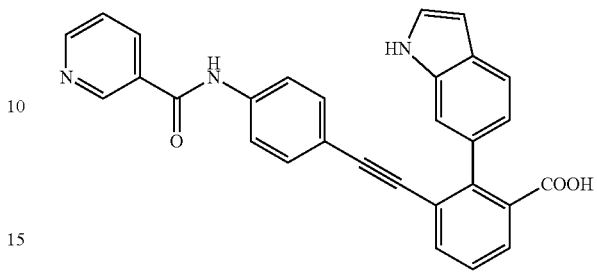

2-(1H-Indol-6-yl)-3-{4-[(pyridine-3-carbonyl)-amino]-phenylethynyl)}-benzoic acid was prepared by the same procedure as example 119. ¹H NMR (300 MHz, CDCl₃) δ=9.10 (br. s., 1H), 8.75-8.69 (m, 1H), 8.43-8.37 (m, 1H), 7.81-7.72 (m, 2H), 7.67 (d, J=8.2 Hz, 1H), 7.60-7.52 (m, 3H), 7.48-7.36 (m, 2H), 7.32-7.18 (m, 2H), 7.07 (d, J=7.9 Hz, 2H), 6.56 (dd, J=1.2, 3.2 Hz, 1H). MS (ESI) m/z 458.0 (M+1)⁺.

Example 215: Synthesis of 2-(1H-indol-6-yl)-3-(4-methanesulfonylamino-phenylethynyl)-benzoic acid

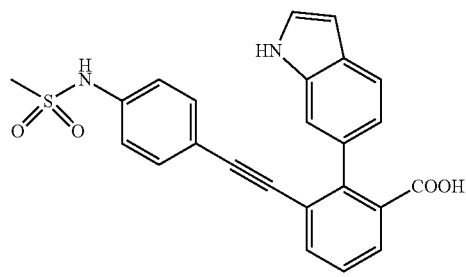 [SMILES: CS(=O)(=O)Nc1ccc(C#Cc2cccc(C(=O)O)c2-c2ccc3cc[nH]c3c2)cc1]

2-(1H-indol-6-yl)-3-(4-methanesulfonylamino-phenylethynyl)-benzoic acid was prepared by the same procedure as example 119. ¹H NMR (300 MHz, CDCl₃) δ=7.85-7.64 (m, 3H), 7.45-7.32 (m, 2H), 7.26-7.17 (m, 2H), 7.07-7.00 (m, 4H), 6.55 (dd, J=2.9 Hz, 1H), 3.46 (s, 3H). MS (ESI) m/z 431.1 (M+1)⁺.

Example 216: Synthesis of 2-(1H-indol-6-yl)-3-[4-(thiophene-2-sulfonylamino)-phenylethynyl]-benzoic acid

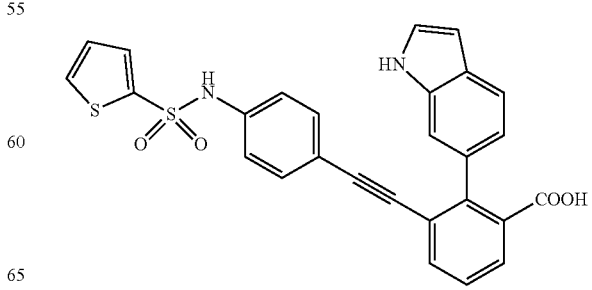

2-(1H-Indol-6-yl)-3-[4-(thiophene-2-sulfonylamino)-phenylethynyl]-benzoic acid was prepared by the same procedure as example 119. ¹H NMR (300 MHz, CDCl₃) δ=9.10 (br. s., 1H), 8.75 (br. s., 1H), 7.77 (dd, J=1.4, 7.8 Hz, 1H), 7.69 (dd, J=1.5, 7.9 Hz, 1H), 7.64 (d, J=8.2 Hz, 1H), 7.48 (dd, J=1.5, 5.0 Hz, 1H), 7.43 (dd, J=1.2, 3.8 Hz, 1H), 7.42-7.24 (m, 2H), 7.22-7.14 (m, 2H), 7.02-6.86 (m, 5H), 6.53 (dd, J=0.9, 3.2 Hz, 1H). MS (ESI) m/z 499.1 (M+1)⁺.

Example 217: Synthesis of 2-(3-(Methoxycarbonyl)-1H-indol-6-yl)-3-(thiazol-4-ylethynyl) benzoic acid

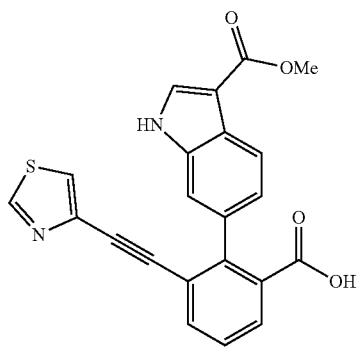 [SMILES: COC(=O)c1c[nH]c2cc(-c3c(C#Cc4cscn4)cccc3C(=O)O)ccc12]

2-(3-(Methoxycarbonyl)-1H-indol-6-yl)-3-(thiazol-4-ylethynyl) benzoic acid was prepared by the same procedure as example 119. ¹H NMR (300 MHz, DMSO) δ 11.89 (s, 1H), 9.06 (d, J=1.9 Hz, 1H), 8.04 (d, J=3.0 Hz, 1H), 8.00 (d, J=8.3 Hz, 1H), 7.81 (dd, J=7.7, 1.3 Hz, 1H), 7.73 (dd, J=7.8, 1.4 Hz, 1H), 7.69 (d, J=1.9 Hz, 1H), 7.51 (t, J=7.7 Hz, 1H), 7.48-7.44 (m, 1H), 7.18 (dd, J=8.2, 1.6 Hz, 1H), 3.82 (s, 3H). MS m/z 403.5 (M+H).

Example 218: Synthesis of 2-(1H-indol-6-yl)-3-(thiazol-4-ylethynyl)benzoic acid

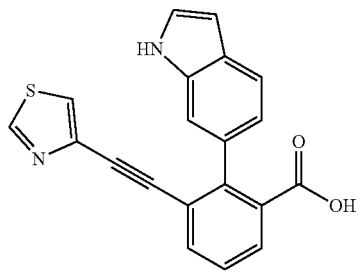 [SMILES: O=C(O)c1cccc(C#Cc2cscn2)c1-c1ccc2cc[nH]c2c1]

2-(1H-indol-6-yl)-3-(thiazol-4-ylethynyl)benzoic acid was prepared by the same procedure as example 119. ¹H NMR (300 MHz, CDCl₃) δ 8.66 (d, J=2.1 Hz, 1H), 8.41 (s, 1H), 7.76 (ddd, J=7.9, 3.7, 1.4 Hz, 2H), 7.63 (dd, J=13.0, 6.5 Hz, 1H), 7.45 (d, J=6.5 Hz, 1H), 7.38 (t, J=7.8 Hz, 1H), 7.21-7.16 (m, 1H), 7.12 (dd, J=8.1, 1.5 Hz, 1H), 6.90 (d, J=2.0 Hz, 1H), 6.56 (t, J=2.1 Hz, 1H). MS m/z 344.9 (M+H).

Example 219: Synthesis of 2-(1-methyl-1H-pyrazol-4-yl)-3-(thiazol-4-ylethynyl) benzoic acid

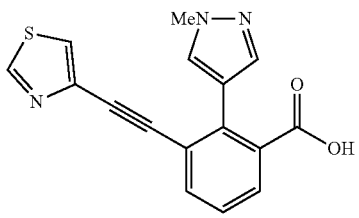 [SMILES: Cn1cc(-c2c(C#Cc3cscn3)cccc2C(=O)O)cn1]

2-(1-methyl-1H-pyrazol-4-yl)-3-(thiazol-4-ylethynyl) benzoic acid was prepared by the same procedure as example 119. ¹H NMR (300 MHz, DMSO) δ 9.16 (d, J=1.9 Hz, 1H), 8.00 (d, J=2.0 Hz, 1H), 7.93 (s, 1H), 7.74 (dd, J=7.7, 1.4 Hz, 1H), 7.61 (dd, J=7.7, 1.4 Hz, 1H), 7.57 (d, J=0.8 Hz, 1H), 7.41 (t, J=7.7 Hz, 1H), 3.89 (s, 3H). MS m/z 310.0 (M+H).

Example 220: Synthesis of 3-((3-hydroxyphenyl)ethynyl)-2-(1-methyl-1H-pyrazol-4-yl)benzoic acid

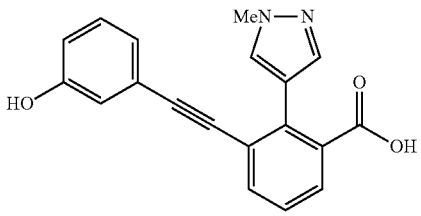 [SMILES: Cn1cc(-c2c(C#Cc3cccc(O)c3)cccc2C(=O)O)cn1]

3-((3-hydroxyphenyl)ethynyl)-2-(1-methyl-1H-pyrazol-4-yl)benzoic acid was prepared by the same procedure as example 119. ¹H NMR (300 MHz, CD₃OD) δ 7.78 (s, 1H), 7.72-7.66 (m, 2H), 7.65 (d, J=0.9 Hz, 1H), 7.38 (t, J=7.8 Hz, 1H), 7.21-7.10 (m, 1H), 6.86-6.77 (m, 2H), 6.75 (tt, J=2.5, 1.4 Hz, 1H), 3.96 (m, 3H). MS m/z 319.0 (M+H).

Example 221: Synthesis of 2-(3-chloro-1H-indol-6-yl)-3-((3-hydroxyphenyl) ethynyl)benzoic acid

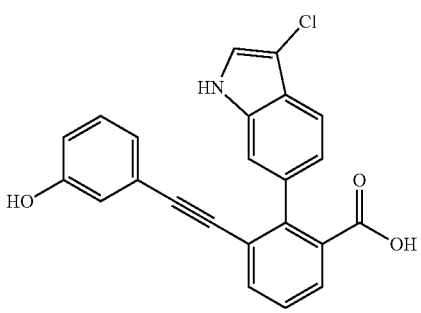 [SMILES: O=C(O)c1cccc(C#Cc2cccc(O)c2)c1-c1ccc2c(Cl)c[nH]c2c1]

2-(3-chloro-1H-indol-6-yl)-3-((3-hydroxyphenyl)ethynyl)benzoic acid was prepared by the same procedure as example 119. ¹H NMR (300 MHz, DMSO) δ 12.38 (s, 1H), 9.60 (s, 1H), 7.88-7.65 (m, 3H), 7.59-7.41 (m, 2H), 7.32 (s, 1H), 7.16 (dd, J=8.3, 1.5 Hz, 1H), 7.12-7.00 (m, 1H), 6.73 (d, J=9.7 Hz, 1H), 6.59-6.41 (m, 2H). MS m/z 371.1 (M-OH).

Example 222: Synthesis of 3-((3-hydroxyphenyl)ethynyl)-2-(1H-indazol-6-yl)benzoic acid

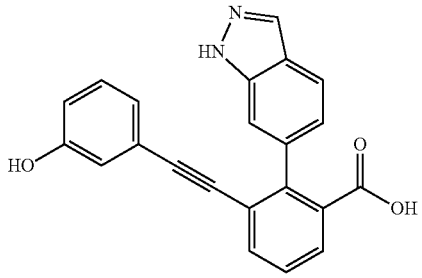 [SMILES: O=C(O)c1cccc(C#Cc2cccc(O)c2)c1-c1ccc2cn[nH]c2c1]

3-((3-hydroxyphenyl)ethynyl)-2-(1H-indazol-6-yl)benzoic acid was prepared by the same procedure as example 119. $^1$H NMR (300 MHz, DMSO) δ 8.12 (s, 1H), 7.85-7.70 (m, 4H), 7.52 (t, J=7.7 Hz, 1H), 7.45 (s, 1H), 7.16-6.99 (m, 2H), 6.78-6.65 (m, 1H), 6.53-6.44 (m, 2H). MS m/z 355.0 (M+H).

Example 223: Synthesis of 2-(3-(2-acetamidoethyl)-1H-indol-6-yl)-3-((3-hydroxyphenyl)ethynyl)benzoic acid

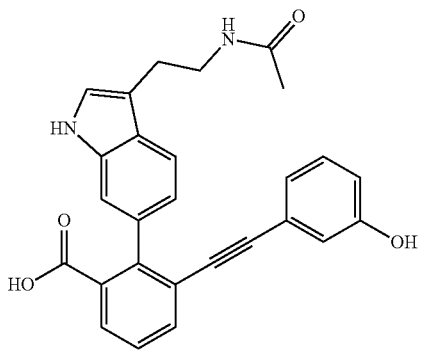 [SMILES: CC(=O)NCCc1c[nH]c2cc(-c3c(C#Cc4cccc(O)c4)cccc3C(=O)O)ccc12]

2-(3-(2-acetamidoethyl)-1H-indol-6-yl)-3-((3-hydroxyphenyl)ethynyl)benzoic acid was prepared by the same procedure as example 119. $^1$H NMR (300 MHz, DMSO) δ 10.90 (s, 1H), 7.93 (m, 1H), 7.72 (dd, J=7.7, 1.4 Hz, 1H), 7.64 (dd, J=7.7, 1.4 Hz, 1H), 7.50 (s, 1H), 7.43 (t, J=7.7 Hz, 1H), 7.36 (d, J=8.4 Hz, 1H), 7.18 (s, 1H), 7.13-6.98 (m, 2H), 6.74-6.64 (m, 1H), 6.60-6.51 (m, 2H), 3.28 (d, J=7.7 Hz, 2H), 2.86-2.72 (m, 2H), 1.77 (s, 3H). MS m/z 439.2 (M+H).

Example 224: Synthesis of 3-((3-(N,N-dimethylsulfamoyl)phenyl)ethynyl)-2-fluorobenzoic acid

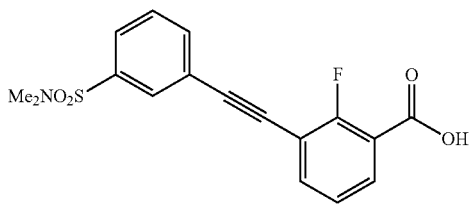

3-((3-(N,N-dimethylsulfamoyl)phenyl)ethynyl)-2-fluorobenzoic acid was prepared by the same procedure as example 85. $^1$H NMR (300 MHz, DMSO) δ 8.02-7.87 (m, 3H), 7.87-7.81 (m, 1H), 7.81-7.69 (m, 1H), 7.63 (t, J=7.9 Hz, 1H), 7.40 (t, J=7.8 Hz, 1H), 2.67 (s, 3H), 2.65 (s, 3H). MS m/z 448.0 (M+H).

Example 225: Synthesis of 2-(1H-indol-6-yl)-3-((4-(tetrahydro-2H-pyran-4-yloxy)phenyl)ethynyl)benzoic acid

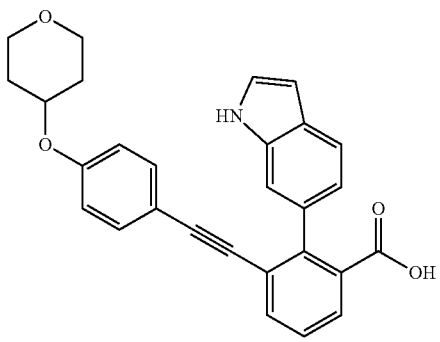 [SMILES: O=C(O)c1cccc(C#Cc2ccc(OC3CCOCC3)cc2)c1-c1ccc2cc[nH]c2c1]

2-(1H-indol-6-yl)-3-((4-(tetrahydro-2H-pyran-4-yloxy)phenyl)ethynyl)benzoic acid was prepared by the same procedure as example 119. $^1$H NMR (300 MHz, CD$_3$OD) δ 7.67 (d, J=7.7 Hz, 2H), 7.58 (dd, J=8.2, 0.7 Hz, 1H), 7.45-7.42 (m, 1H), 7.39 (dd, J=8.1, 7.4 Hz, 1H), 7.30-7.25 (m, 1H), 7.04 (dd, J=8.1, 1.5 Hz, 1H), 6.99-6.90 (m, 2H), 6.81-6.71 (m, 2H), 6.49 (dd, J=3.1, 0.9 Hz, 1H), 4.51 (dq, J=12.0, 3.8 Hz, 21H), 4.08-3.75 (m, 2H), 3.55 (ddd, J=11.7, 8.7, 3.1 Hz, 2H), 2.24-1.76 (m, 2H), 1.65 (dtd, J=12.8, 8.4, 4.0 Hz, 2H). MS m/z 438.2 (M+H).

Example 226: Synthesis of 2-(1H-indol-6-yl)-3-((4-morpholinophenyl)ethynyl)benzoic acid

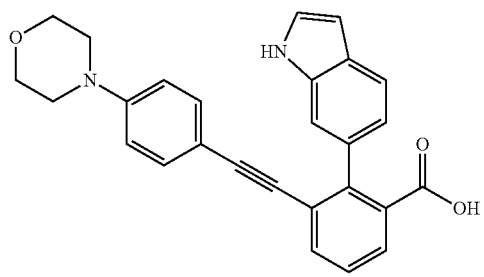 [SMILES: O=C(O)c1cccc(C#Cc2ccc(N3CCOCC3)cc2)c1-c1ccc2cc[nH]c2c1]

2-(1H-indol-6-yl)-3-((4-morpholinophenyl)ethynyl)benzoic acid was prepared by the same procedure as example 119. $^1$H NMR (300 MHz, CDCl$_3$) δ 8.20 (s, 1H), 7.69 (t, J=7.9 Hz, 3H), 7.43 (s, 1H), 7.36 (t, J=7.8 Hz, 1H), 7.26-7.21 (m, 1H), 7.15 (dd, J=8.1, 1.4 Hz, 1H), 6.95 (d, J=8.8 Hz, 2H), 6.68 (d, J=8.9 Hz, 2H), 6.60 (s, 1H), 3.92-3.71 (m, 4H), 3.20-3.02 (m, 4H). MS m/z 423.1 (M+H).

Example 227: Synthesis of 3-((3-carbamoylphenyl)ethynyl)-2-(1H-indol-6-yl)benzoic acid

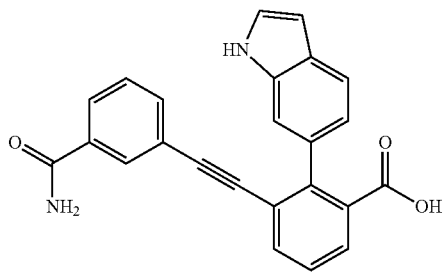 [SMILES: NC(=O)c1cccc(C#Cc2cccc(C(=O)O)c2-c2ccc3cc[nH]c3c2)c1]

3-((3-carbamoylphenyl)ethynyl)-2-(1H-indol-6-yl)benzoic acid was prepared by the same procedure as example 119. $^1$H NMR (300 MHz, DMSO) δ 13.09-12.22 (m, 1H), 11.16 (s, 1H), 7.94 (s, 1H), 7.80-7.71 (m, 2H), 7.67 (dd, J=7.7, 1.4 Hz, 1H), 7.57 (d, J=8.2 Hz, 1H), 7.47 (t, J=7.7 Hz, 1H), 7.43-7.39 (m, 1H), 7.39-7.29 (m, 2H), 7.21-7.14 (m, 1H), 7.04 (dd, J=8.1, 1.6 Hz, 1H), 6.56-6.32 (m, 1H). MS m/z 381.3 (M+H).

Example 228: Synthesis of 3-((4-Fluorophenyl)ethynyl)-2-(1H-indol-6-yl)benzoic acid

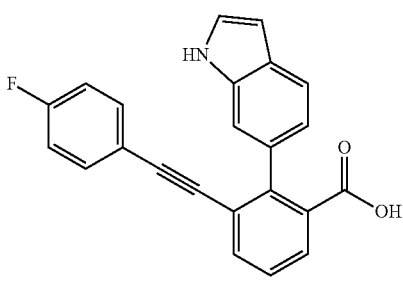 [SMILES: O=C(O)c1cccc(C#Cc2ccc(F)cc2)c1-c1ccc2cc[nH]c2c1]

3-((4-Fluorophenyl)ethynyl)-2-(1H-indol-6-yl)benzoic acid was prepared by the same procedure as example 119. $^1$H NMR (300 MHz, CD$_3$OD) δ 8.51 (s, 1H), 8.37 (s, 1H), 8.06 (dd, J=7.8, 1.3 Hz, 1H), 7.87 (dd, J=7.8, 1.3 Hz, 1H), 7.67 (d, J=3.5 Hz, 1H), 7.61 (t, J=7.8 Hz, 1H), 7.14-7.01 (m, 2H), 7.03-6.88 (m, 2H), 6.83 (d, J=3.5 Hz, 1H). MS m/z 357.1 (M+H).

Example 229: Synthesis of 3-((2,4-Difluorophenyl)ethynyl)-2-(1H-indol-6-yl)benzoic acid

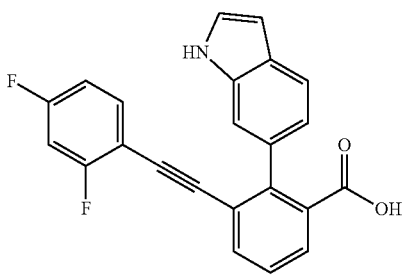 [SMILES: O=C(O)c1cccc(C#Cc2ccc(F)cc2F)c1-c1ccc2cc[nH]c2c1]

3-((2,4-Difluorophenyl)ethynyl)-2-(1H-indol-6-yl)benzoic acid was prepared by the same procedure as example 119. $^1$H NMR (300 MHz, CD$_3$OD) δ 7.73 (dq, J=7.9, 1.4 Hz, 2H), 7.56 (dt, J=7.8, 1.8 Hz, 1H), 7.47-7.39 (m, 2H), 7.29-7.22 (m, 1H), 7.03 (dd, J=8.2, 1.5 Hz, 1H), 6.97-6.82 (m, 2H), 6.78 (ddd, J=10.3, 6.0, 1.3 Hz, 1H), 6.48 (dd, J=3.1, 0.9 Hz, 1H). MS m/z 374.4 (M+H).

Example 230: Synthesis of 3-((3-Acetamidophenyl)ethynyl)-2-(1H-indol-6-yl)benzoic acid

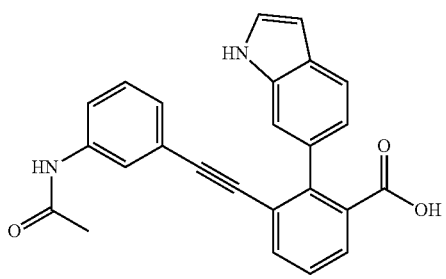 [SMILES: CC(=O)Nc1cccc(C#Cc2cccc(C(=O)O)c2-c2ccc3cc[nH]c3c2)c1]

3-((3-Acetamidophenyl)ethynyl)-2-(1H-indol-6-yl)benzoic acid was prepared by the same procedure as example 119. $^1$H NMR (300 MHz, DMSO) δ 11.17 (s, 1H), 9.96 (s, 1H), 7.77 (dd, J=7.7, 1.4 Hz, 1H), 7.67 (dd, J=7.7, 1.4 Hz, 2H), 7.63-7.55 (m, 2H), 7.45 (dd, J=13.6, 5.9 Hz, 1H), 7.38 (dd, J=3.3, 2.3 Hz, 2H), 7.18 (t, J=7.9 Hz, 1H), 7.05 (dd, J=8.1, 1.6 Hz, 1H), 6.73 (d, J=7.8 Hz, 1H), 6.50-6.35 (m, 1H), 2.05 (d, J=14.2 Hz, 3H). MS m/z 395.0 (M+H).

Example 231: Synthesis of 2-(1H-indol-6-yl)-3-((3-(nicotinamido)phenyl)ethynyl)benzoic acid

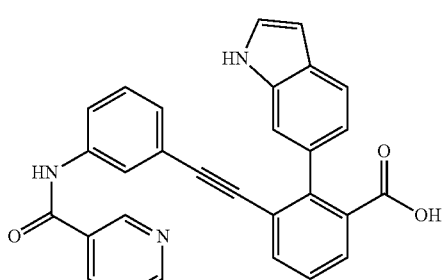

2-(1H-indol-6-yl)-3-((3-(nicotinamido)phenyl)ethynyl)benzoic acid was prepared by the same procedure as example 119. $^1$H NMR (300 MHz, DMSO) δ 11.18 (s, 1H), 10.47 (s, 1H), 9.10 (d, J=1.6 Hz, 1H), 8.79 (dd, J=4.9, 1.6 Hz, 1H), 8.41-8.13 (m, 1H), 7.79 (dd, J=7.7, 1.4 Hz, 1H), 7.75 (m, 1H), 7.68 (dd, J=7.8, 1.3 Hz, 2H), 7.62 (t, J=3.6 Hz, 1H), 7.59 (s, 1H), 7.48 (t, J=7.7 Hz, 1H), 7.41 (s, 1H), 7.39-7.35 (m, 1H), 7.28 (t, J=8.0 Hz, 1H), 7.06 (dd, J=8.1, 1.5 Hz, 1H), 6.84 (d, J=7.7 Hz, 1H), 6.46 (m, 1H). MS m/z 458.2 (M+H).

Example 232: Synthesis of 3-((3-(3-chloro-4-fluoro-phenylsulfonamido)phenyl)ethynyl)-2-(1H-indol-6-yl)benzoic acid

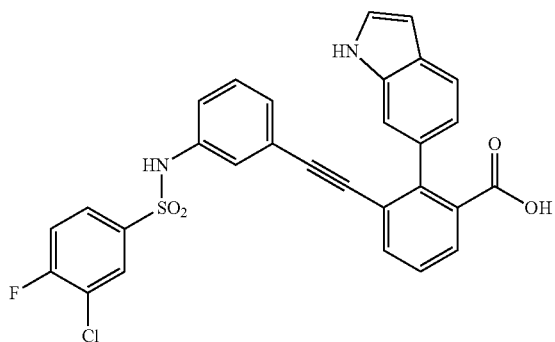 [SMILES: O=C(O)c1cccc(C#Cc2cccc(NS(=O)(=O)c3ccc(F)c(Cl)c3)c2)c1-c1ccc2cc[nH]c2c1]

3-((3-(3-chloro-4-fluorophenylsulfonamido)phenyl)ethynyl)-2-(1H-indol-6-yl)benzoic acid was prepared by the same procedure as example 119. $^1$H NMR (300 MHz, CDCl$_3$) δ 8.39 (bs, 1H), 7.76 (m, 1H), 7.71-7.60 (m, 1H), 7.42-7.34 (m, 2H), 7.24-7.14 (m, 1H), 7.12-6.96 (m, 1H), 6.97-6.83 (m, 1H), 6.80 (d, J=2.2 Hz, 1H), 6.70-6.59 (m, 2H), 6.61-6.51 (m, 2H), 6.51-6.38 (m, 2H), 6.34-6.18 (m, 1H). MS m/z 545.1 (M+H).

Example 233: Synthesis of 3-((3-aminophenyl)ethynyl)-2-(1H-indol-6-yl)benzoic acid

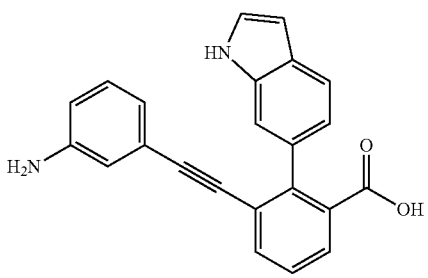 [SMILES: Nc1cccc(C#Cc2cccc(C(=O)O)c2-c2ccc3cc[nH]c3c2)c1]

3-((3-aminophenyl)ethynyl)-2-(1H-indol-6-yl)benzoic acid was prepared by the same procedure as example 119. $^1$H NMR (300 MHz, CD$_3$OD) δ 8.21 (bs, 1H), 7.73-7.46 (m, 3H), 7.35-7.28 (m, 2H), 7.13-7.08 (m, 1H), 7.02 (dd, J=8.1, 1.4 Hz, 1H), 6.86 (t, J=7.8 Hz, 1H), 6.51 (s, 1H), 6.46-6.37 (m, 2H), 5.94 (s, 1H)). MS m/z 353.5 (M+H).

Example 234: Synthesis of 2-(1H-indol-6-yl)-3-((3-(methylsulfonamido)phenyl)ethynyl)benzoic acid

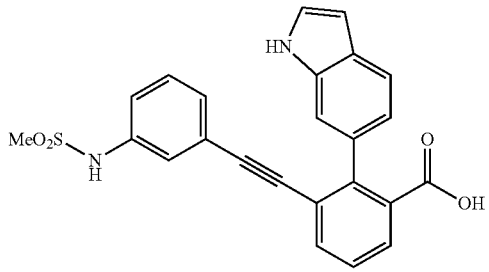 [SMILES: CS(=O)(=O)Nc1cccc(C#Cc2cccc(C(=O)O)c2-c2ccc3cc[nH]c3c2)c1]

2-(1H-indol-6-yl)-3-((3-(methylsulfonamido)phenyl)ethynyl)benzoic acid was prepared by the same procedure as example 119. $^1$H NMR (300 MHz, CD$_3$OD) δ 10.50 (s, 1H), 7.70 (ddd, J=7.9, 3.0, 1.3 Hz, 2H), 7.60 (d, J=8.2 Hz, 1H), 7.47-7.36 (m, 2H), 7.31-7.22 (m, 1H), 7.18-7.04 (m, 3H), 7.01 (d, J=1.8 Hz, 1H), 6.83-6.74 (m, 1H), 6.48 (d, J=2.3 Hz, 1H), 2.97-2.66 (m, 3H). MS m/z 431.0 (M+H).

Example 235: Synthesis of 2-(1H-indol-6-yl)-3-((3-(thiophene-2-sulfonamido)phenyl)ethynyl)benzoic acid

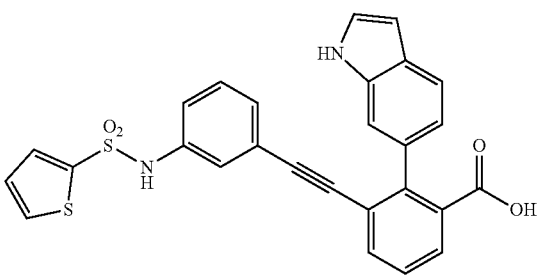 [SMILES: O=C(O)c1cccc(C#Cc2cccc(NS(=O)(=O)c3cccs3)c2)c1-c1ccc2cc[nH]c2c1]

2-(1H-indol-6-yl)-3-((3-(thiophene-2-sulfonamido)phenyl)ethynyl)benzoic acid was prepared by the same procedure as example 119. $^1$H NMR (300 MHz, Acetone) δ 10.33 (s, 1H), 9.14 (s, 1H), 7.87-7.72 (m, 3H), 7.63 (d, J=8.1 Hz, 1H), 7.54-7.43 (m, 3H), 7.42-7.33 (m, 1H), 7.23-7.10 (m, 4H), 7.05 (dd, J=5.0, 3.8 Hz, 1H), 6.85 (dd, J=4.9, 2.7 Hz, 1H), 6.53 (m, 1H). MS m/z 499.8 (M+H).

Example 236: Synthesis of 3-((3-acetamido-5-fluorophenyl)ethynyl)-2-(1H-indol-6-yl)benzoic acid

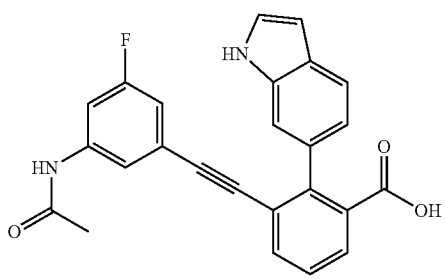 [SMILES: CC(=O)Nc1cc(F)cc(C#Cc2cccc(C(=O)O)c2-c2ccc3cc[nH]c3c2)c1]

3-((3-acetamido-5-fluorophenyl)ethynyl)-2-(1H-indol-6-yl)benzoic acid was prepared by the same procedure as example 119. $^1$H NMR (300 MHz, DMSO) δ 11.17 (s, 1H), 10.15 (s, 1H), 7.78 (d, J=7.6 Hz, 1H), 7.69 (d, J=6.5 Hz, 1H), 7.59 (d, J=8.1 Hz, 1H), 7.47 (t, J=7.8 Hz, 2H), 7.38 (m, 2H), 7.26 (s, 1H), 7.03 (d, J=8.1 Hz, 1H), 6.46 (m, 2H), 2.21 (s, 3H). MS m/z 435.1 (M+Na).

Example 237: Synthesis of 2-(indolin-6-yl)-3-(phenylethynyl)benzoic acid

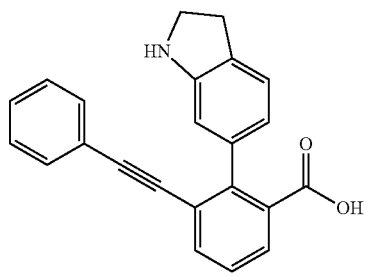 [SMILES: O=C(O)c1cccc(C#Cc2ccccc2)c1-c1ccc2c(c1)NCC2]

2-(indolin-6-yl)-3-(phenylethynyl)benzoic acid was prepared by the same procedure as example 119. $^1$H NMR (300 MHz, CDCl$_3$) δ 7.84 (dd, J=7.8, 1.3 Hz, 1H), 7.76 (dd, J=7.8, 1.3 Hz, 1H), 7.53 (d, J=7.8 Hz, 1H), 7.44 (t, J=7.8 Hz, 1H), 7.39 (s, 1H), 7.31 (d, J=8.0 Hz, 1H), 7.24 (d, J=2.5 Hz, 1H), 7.13 (dd, J=10.4, 6.7 Hz, 2H), 3.94 (d, J=7.7 Hz, 2H), 3.36 (s, 2H). MS m/z 340.1 (M+H).

Example 238: Synthesis of 3-((3-hydroxyphenyl)ethynyl)-2-(indolin-6-yl)benzoic acid

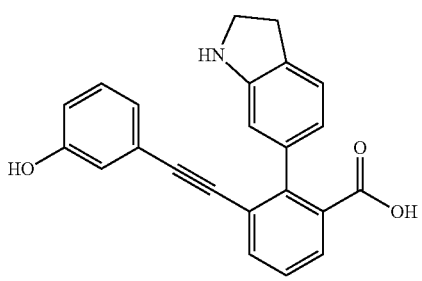 [SMILES: O=C(O)c1cccc(C#Cc2cccc(O)c2)c1-c1ccc2c(c1)NCC2]

3-((3-hydroxyphenyl)ethynyl)-2-(indolin-6-yl)benzoic acid was prepared by the same procedure as example 119. $^1$H NMR (300 MHz, CDCl$_3$) δ 7.99-7.83 (m, 1H), 7.85-7.69 (m, 1H), 7.57 (d, J=8.1 Hz, 1H), 7.51-7.39 (m, 2H), 7.32 (d, J=7.8 Hz, 1H), 7.12 (t, J=7.9 Hz, 1H), 6.88 (d, J=7.5 Hz, 1H), 6.81 (d, J=8.2 Hz, 1H), 6.12 (s, 1H), 4.23-3.73 (m, 2H), 3.40 (s, 2H). MS m/z 356.1 (M+H).

Example 239: Synthesis of 3-((6-aminopyridin-2-yl)ethynyl)-2-(1H-indol-6-yl)benzoic acid

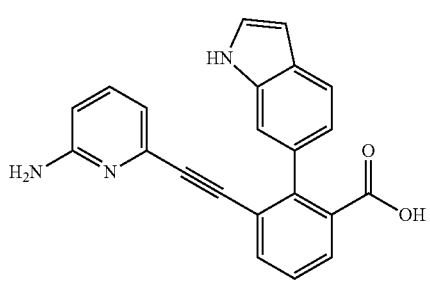 [SMILES: Nc1cccc(C#Cc2cccc(C(=O)O)c2-c2ccc3cc[nH]c3c2)n1]

3-((6-aminopyridin-2-yl)ethynyl)-2-(1H-indol-6-yl)benzoic acid was prepared by the same procedure as example 119. $^1$H NMR (300 MHz, CD$_3$OD) δ 8.65 (s, 1H), 7.74 (ddd, J=10.5, 7.7, 1.1 Hz, 2H), 7.63 (d, J=8.2 Hz, 1H), 7.43 (s, 1H), 7.34 (t, J=7.8 Hz, 1H), 7.17-7.03 (m, 3H), 6.51 (s, 1H), 6.20 (dd, J=16.1, 7.8 Hz, 1H), 4.57 (s, 2H). MS m/z 354.1 (M+H).

Example 240: Synthesis of 3-((2-aminopyridin-4-yl)ethynyl)-2-(1H-indol-6-yl)benzoic acid

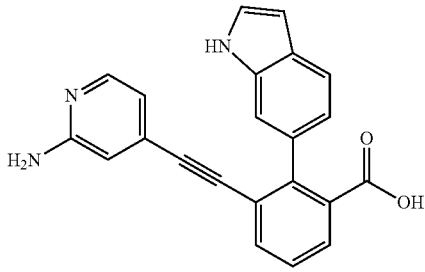 [SMILES: Nc1cc(C#Cc2cccc(C(=O)O)c2-c2ccc3cc[nH]c3c2)ccn1]

3-((2-aminopyridin-4-yl)ethynyl)-2-(1H-indol-6-yl)benzoic acid was prepared by the same procedure as example 119. $^1$H NMR (300 MHz, CD$_3$OD) δ 8.67 (s, 1H), 7.84 (d, J=5.2 Hz, 1H), 7.78 (dd, J=7.8, 1.2 Hz, 1H), 7.72-7.61 (m, 2H), 7.37 (dd, J=13.1, 5.2 Hz, 2H), 7.24-7.13 (m, 1H), 7.07 (dd, J=8.2, 1.2 Hz, 1H), 6.58 (s, 1H), 6.27 (d, J=5.2 Hz, 1H), 5.79 (s, 1H), 4.28 (s, 2H). MS m/z 354.1 (M+H).

Example 241: Synthesis of 3-((3-hydroxyphenyl)ethynyl)-2-(5-methoxypyridin-3-yl)benzoic acid

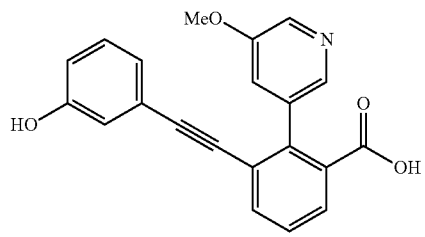 [SMILES: COc1cncc(-c2c(C#Cc3cccc(O)c3)cccc2C(=O)O)c1]

3-((3-hydroxyphenyl)ethynyl)-2-(5-methoxypyridin-3-yl)benzoic acid was prepared by the same procedure as example 119. $^1$H NMR (300 MHz, CD$_3$OD) δ 8.50 (d, J=30.3 Hz, 2H), 8.14 (dd, J=7.9, 1.1 Hz, 1H), 8.09 (s, 1H), 7.89 (dd, J=7.8, 1.1 Hz, 1H), 7.65 (t, J=7.8 Hz, 1H), 7.11 (t, J=7.9 Hz, 1H), 6.77 (dd, J=8.2, 1.6 Hz, 1H), 6.64 (d, J=7.6 Hz, 1H), 6.57 (s, 1H), 4.02 (s, 3H). MS m/z 346.3 (M+H).

Example 242: Synthesis of 2-(benzo[d][1,3]dioxol-5-yl)-3-((3-hydroxyphenyl) ethynyl)benzoic acid

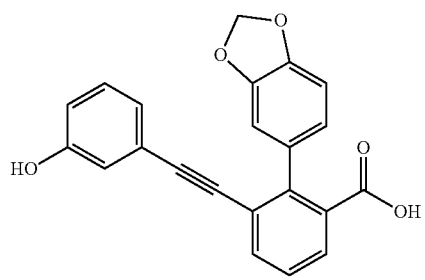 [SMILES: O=C(O)c1cccc(C#Cc2cccc(O)c2)c1-c1ccc2c(c1)OCO2]

2-(benzo[d][1,3]dioxol-5-yl)-3-((3-hydroxyphenyl)ethynyl)benzoic acid was prepared by the same procedure as example 119. ¹H NMR (300 MHz, CD₃OD) δ 7.71 (ddd, J=10.2, 7.8, 1.4 Hz, 2H), 7.42 (t, J=7.8 Hz, 1H), 7.14-7.04 (m, 1H), 6.87 (dd, J=9.1, 4.8 Hz, 2H), 6.82-6.78 (m, 1H), 6.76-6.70 (m, 1H), 6.66 (ddd, J=3.9, 2.5, 1.4 Hz, 1H), 5.99 (s, 2H). MS m/z 359.4 (M+H).

Example 243: Synthesis of 3-((3-hydroxyphenyl)ethynyl)-2-(pyrimidin-5-yl)benzoic acid

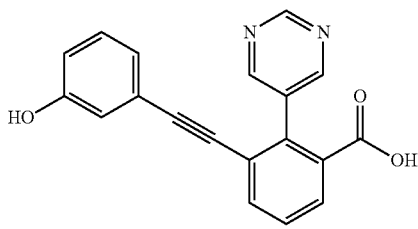 [SMILES: O=C(O)c1cccc(C#Cc2cccc(O)c2)c1-c1cncnc1]

3-((3-hydroxyphenyl)ethynyl)-2-(pyrimidin-5-yl)benzoic acid was prepared by the same procedure as example 119. ¹H NMR (300 MHz, CD₃OD) δ 9.19 (s, 1H), 8.78 (s, 2H), 8.10 (dd, J=7.9, 1.3 Hz, 1H), 7.87 (dd, J=7.8, 1.3 Hz, 1H), 7.61 (t, J=7.8 Hz, 1H), 7.09 (t, J=7.9 Hz, 2H), 6.84-6.68 (m, 1H), 6.63 (d, J=8.0 Hz, 1H), 6.57 (d, J=1.3 Hz, 1H). MS m/z 317.3 (M+H).

Example 244: Synthesis of 4'-Amino-6-((3-hydroxyphenyl)ethynyl)-5'-methoxybiphenyl-2-carboxylic acid

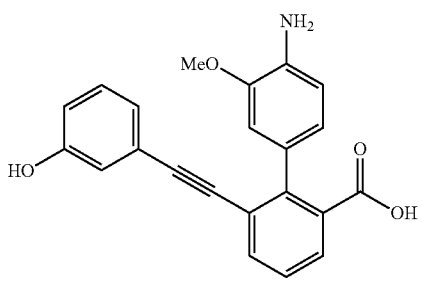 [SMILES: COc1cc(-c2c(C#Cc3cccc(O)c3)cccc2C(=O)O)ccc1N]

4'-amino-6-((3-hydroxyphenyl)ethynyl)-5'-methoxybiphenyl-2-carboxylic acid was prepared by the same procedure as example 119. ¹H NMR (300 MHz, CD₃OD) δ 7.81 (ddd, J=30.0, 7.8, 1.3 Hz, 2H), 7.50 (t, J=7.8 Hz, 1H), 7.35 (d, J=8.0 Hz, 1H), 7.19 (d, J=1.6 Hz, 1H), 7.08 (t, J=7.9 Hz, 1H), 7.00 (dd, J=8.0, 1.7 Hz, 1H), 6.74 (dd, J=8.2, 1.5 Hz, 1H), 6.60 (dd, J=13.2, 5.0 Hz, 2H), 3.88 (s, 3H). MS m/z 360.2 (M+H).

Example 245: Synthesis of 3-(4-hydroxybut-1-ynyl)-2-(1H-indol-6-yl) benzoic acid

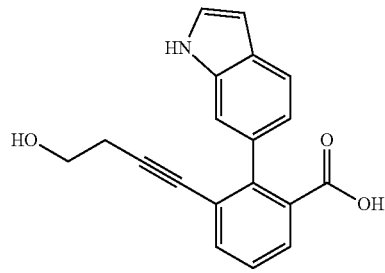 [SMILES: O=C(O)c1cccc(C#CCCO)c1-c1ccc2cc[nH]c2c1]

3-(4-hydroxybut-1-ynyl)-2-(1H-indol-6-yl) benzoic acid was prepared by the same procedure as example 119. ¹H NMR (300 MHz, CDCl₃) δ 8.54 (m, 1H), 7.73-7.64 (m, 1H), 7.65-7.49 (m, 2H), 7.29 (dd, J=16.2, 8.4 Hz, 2H), 7.18-7.05 (m, 1H), 7.01 (dd, J=8.1, 1.4 Hz, 1H), 6.54 (d, J=2.1 Hz, 1H), 3.15 (t, J=6.4 Hz, 2H), 2.22 (t, J=6.5 Hz, 2H). MS m/z 306.1 (M+H).

Example 246: Synthesis of 3-(3-amino-3-methylbut-1-ynyl)-2-(1H-indol-6-yl)benzoic acid

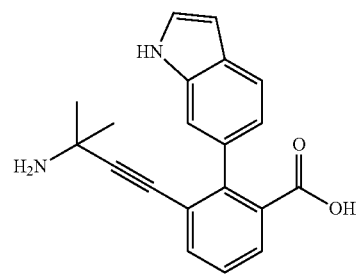 [SMILES: CC(C)(N)C#Cc1cccc(C(=O)O)c1-c1ccc2cc[nH]c2c1]

3-(3-amino-3-methylbut-1-ynyl)-2-(1H-indol-6-yl)benzoic acid was prepared by the same procedure as example 119. ¹H NMR (300 MHz, CD₃OD) δ 7.70 (ddd, J=16.2, 7.8, 1.4 Hz, 2H), 7.58 (d, J=8.1 Hz, 1H), 7.43 (dd, J=13.4, 5.7 Hz, 2H), 7.29 (d, J=3.2 Hz, 2H), 6.93 (dd, J=8.1, 1.6 Hz, 1H), 6.49 (dd, J=3.2, 0.9 Hz, 1H), 3.56 (s, 6H). MS m/z 318.1 (M+H).

Example 247: Synthesis of 3-(3-hydroxy-3-phenylprop-1-ynyl)-2-(1H-indol-6-yl)benzoic acid

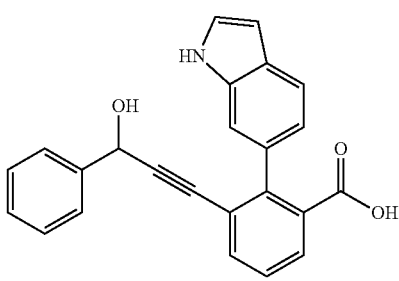 [SMILES: O=C(O)c1cccc(C#CC(O)c2ccccc2)c1-c1ccc2cc[nH]c2c1]

3-(3-hydroxy-3-phenylprop-1-ynyl)-2-(1H-indol-6-yl) benzoic acid was prepared by the same procedure as example 119. ¹H NMR (300 MHz, CD₃OD) δ 7.76-7.63 (m, 2H), 7.52 (t, J=7.2 Hz, 1H), 7.40 (dd, J=10.1, 5.4 Hz, 2H), 7.36-7.30 (m, 1H), 7.29-7.21 (m, 1H), 7.14-6.98 (m, 1H), 7.02-6.82 (m, 4H), 6.56-6.44 (m, 1H), 5.36 (s, 1H). MS m/z 368.3 (M+H).

Example 248: Synthesis of 3-(3-hydroxy-3-methyl-but-1-ynyl)-2-(1H-indol-6-yl)benzoic acid

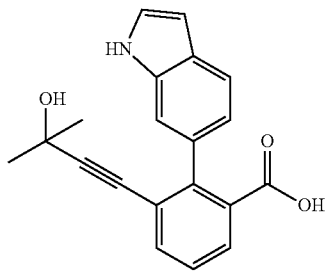 [SMILES: CC(C)(O)C#Cc1cccc(C(=O)O)c1-c1ccc2cc[nH]c2c1]

3-(3-hydroxy-3-methylbut-1-ynyl)-2-(1H-indol-6-yl)benzoic acid was prepared by the same procedure as example 119. ¹H NMR (300 MHz, CD₃OD) δ 10.48 (s, 1H), 7.71 (d, J=7.7 Hz, 1H), 7.62 (t, J=10.2 Hz, 1H), 7.47-7.35 (m, 1H), 7.30-7.19 (m, 1H), 7.20-7.04 (m, 1H), 7.01 (d, J=1.7 Hz, 1H), 6.82-6.69 (m, 1H), 6.49 (d, J=2.2 Hz, 1H), 2.98 (s, 6H). MS m/z 342.1 (M+Na).

Example 249: Synthesis of 3-((3-(hydroxymethyl)phenyl)ethynyl)-2-(1H-indol-6-yl)benzoic acid

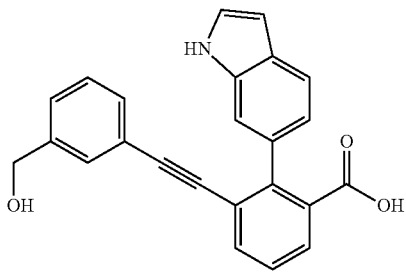 [SMILES: O=C(O)c1cccc(C#Cc2cccc(CO)c2)c1-c1ccc2cc[nH]c2c1]

3-((3-(hydroxymethyl)phenyl)ethynyl)-2-(1H-indol-6-yl)benzoic acid was prepared by the same procedure as example 119. ¹H NMR (300 MHz, CD₃OD) δ 10.53 (s, 1H), 7.76-7.64 (m, 2H), 7.59 (d, J=8.1 Hz, 1H), 7.48-7.44 (m, 1H), 7.44-7.36 (m, 1H), 7.28 (dt, J=3.0, 1.2 Hz, 1H), 7.25-7.19 (m, 1H), 7.15 (t, J=7.4 Hz, 1H), 7.04 (dt, J=3.3, 1.6 Hz, 1H), 7.00-6.83 (m, 2H), 6.57-6.42 (m, 1H), 4.77 (d, J=65.2 Hz, 2H). MS m/z 368.0 (M+H).

Example 250: Synthesis of 6-(2-carboxy-6-(phenylethynyl)phenyl)-1H-indole-2-carboxylic acid

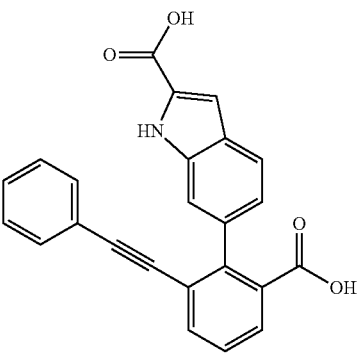 [SMILES: O=C(O)c1cc2ccc(-c3c(C#Cc4ccccc4)cccc3C(=O)O)cc2[nH]1]

6-(2-carboxy-6-(phenylethynyl)phenyl)-1H-indole-2-carboxylic acid was prepared by the same procedure as example 119. ¹H NMR (300 MHz, CD₃OD) δ 7.74 (ddd, J=7.8, 5.0, 1.4 Hz, 2H), 7.65 (dd, J=1.6, 0.8 Hz, 1H), 7.50 (dt, J=8.6, 0.8 Hz, 1H), 7.44 (t, J=7.8 Hz, 1H), 7.35-7.25 (m, 1H), 7.25-7.13 (m, 4H), 7.04 (dt, J=8.2, 2.1 Hz, 2H). MS m/z 382.0 (M+H).

Example 251: Synthesis of 2-(2-(ethoxycarbonyl)-1H-indol-6-yl)-3-(phenylethynyl) benzoic acid

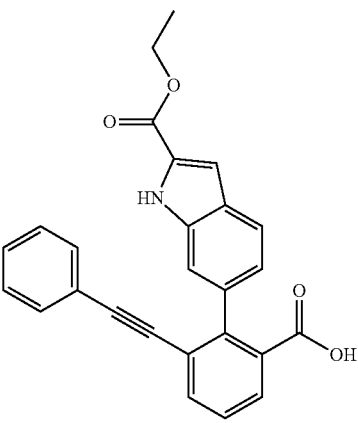 [SMILES: CCOC(=O)c1cc2ccc(-c3c(C#Cc4ccccc4)cccc3C(=O)O)cc2[nH]1]

2-(2-(ethoxycarbonyl)-1H-indol-6-yl)-3-(phenylethynyl) benzoic acid was prepared by the same procedure as example 119. ¹H NMR (300 MHz, CD₃OD) δ 7.81-7.69 (m, 2H), 7.65 (d, J=0.9 Hz, 1H), 7.50 (d, J=8.6 Hz, 1H), 7.42 (dd, J=15.2, 7.4 Hz, 1H), 7.35-7.27 (m, 1H), 7.24-7.10 (m, 4H), 7.03 (dd, J=8.0, 1.6 Hz, 2H), 4.40 (q, J=7.1 Hz, 2H), 1.42 (t, J=7.1 Hz, 3H). MS m/z 410.1 (M+H).

Example 252: Synthesis of 3-((3-carbamoyl-5-methoxyphenyl)ethynyl)-2-(1H-indol-6-yl)benzoic acid

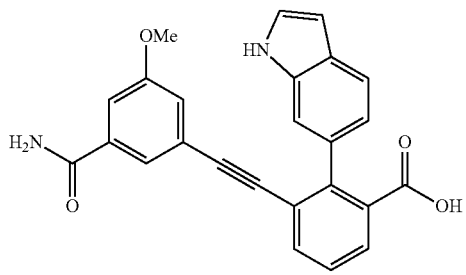 [SMILES: COc1cc(C#Cc2cccc(C(=O)O)c2-c2ccc3cc[nH]c3c2)cc(C(N)=O)c1]

3-((3-carbamoyl-5-methoxyphenyl)ethynyl)-2-(1H-indol-6-yl)benzoic acid was prepared by the same procedure as example 119. $^1$H NMR (300 MHz, CD$_3$OD) δ 7.74 (ddd, J=7.8, 4.6, 1.4 Hz, 2H), 7.62 (d, J=8.2 Hz, 1H), 7.45 (dd, J=9.9, 5.6 Hz, 2H), 7.27 (dd, J=3.6, 2.0 Hz, 2H), 7.22 (t, J=1.4 Hz, 1H), 7.05 (dd, J=8.1, 1.5 Hz, 1H), 6.51 (ddd, J=5.0, 2.8, 1.1 Hz, 2H), 3.66 (s, 3H). MS m/z 411.2 (M+H).

Example 253: Synthesis of 2-(1H-indol-5-yl)-3-(phenylethynyl)benzoic acid

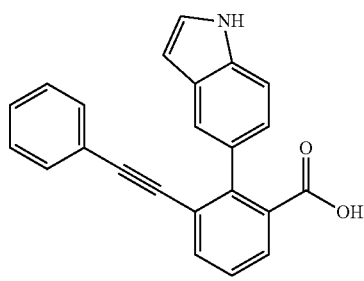 [SMILES: O=C(O)c1cccc(C#Cc2ccccc2)c1-c1ccc2[nH]ccc2c1]

2-(1H-indol-5-yl)-3-(phenylethynyl)benzoic acid was prepared by the same procedure as example 119. $^1$H NMR (300 MHz, CD$_3$OD) δ 7.71 (ddd, J=7.8, 4.8, 1.4 Hz, 2H), 7.60 (dd, J=1.7, 0.7 Hz, 1H), 7.45-7.38 (m, 2H), 7.30-7.25 (m, 1H), 7.23-7.13 (m, 4H), 7.06 (ddd, J=6.4, 3.8, 2.0 Hz, 2H), 6.49 (dd, J=3.2, 0.9 Hz, 1H). MS m/z 338.2 (M+H).

Example 254: Synthesis of 5-(2-carboxy-6-((3-hydroxyphenyl)ethynyl)phenyl)-1H-indole-2-carboxylic acid

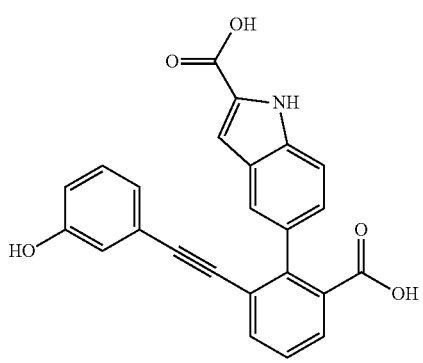 [SMILES: O=C(O)c1cc2cc(-c3c(C#Cc4cccc(O)c4)cccc3C(=O)O)ccc2[nH]1]

5-(2-carboxy-6-((3-hydroxyphenyl)ethynyl)phenyl)-1H-indole-2-carboxylic acid was prepared by the same procedure as example 119. $^1$H NMR (300 MHz, CD$_3$OD) δ 7.70 (dd, J=7.7, 1.4 Hz, 1H), 7.62 (dd, J=7.8, 1.4 Hz, 1H), 7.57-7.51 (m, 2H), 7.42 (t, J=7.7 Hz, 1H), 7.30 (dd, J=8.5, 1.7 Hz, 1H), 7.20 (d, J=0.9 Hz, 1H), 7.00 (dd, J=11.5, 4.8 Hz, 1H), 6.67 (ddd, J=8.2, 2.4, 1.2 Hz, 1H), 6.57-6.46 (m, 2H). MS m/z 398.0 (M+H).

Example 255: Synthesis of 5-(2-carboxy-6-((4-methoxyphenyl)ethynyl)phenyl)-1H-indole-2-carboxylic acid

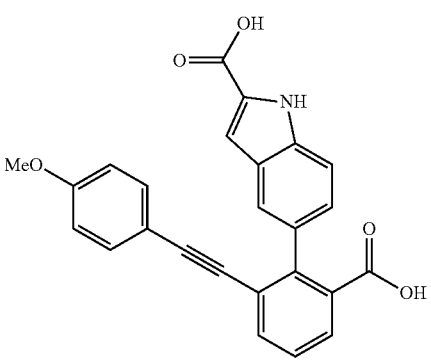 [SMILES: COc1ccc(C#Cc2cccc(C(=O)O)c2-c2ccc3[nH]c(C(=O)O)cc3c2)cc1]

5-(2-carboxy-6-((4-methoxyphenyl)ethynyl)phenyl)-1H-indole-2-carboxylic acid was prepared by the same procedure as example 119. $^1$H NMR (300 MHz, CD$_3$OD) δ 7.69-7.62 (m, 1H), 7.58 (ddd, J=4.7, 2.3, 1.1 Hz, 2H), 7.52 (dt, J=8.5, 0.8 Hz, 1H), 7.40 (t, J=7.7 Hz, 1H), 7.28 (dd, J=8.5, 1.7 Hz, 1H), 7.20 (d, J=0.9 Hz, 1H), 7.04-6.90 (m, 2H), 6.78-6.69 (m, 2H), 3.69 (s, 3H). MS m/z 412.2 (M+H).

Example 256: Synthesis of 3-((4-fluoro-3-(tetrahydro-2H-pyran-4-yloxy)phenyl) ethynyl)-2-(1H-indol-6-yl)benzoic acid

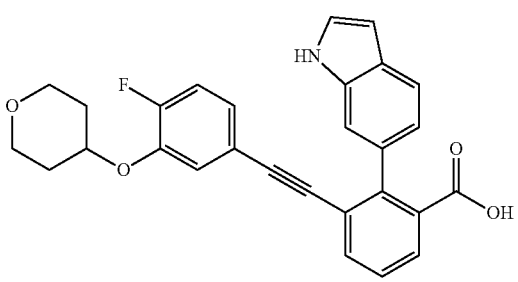 [SMILES: O=C(O)c1cccc(C#Cc2ccc(F)c(OC3CCOCC3)c2)c1-c1ccc2cc[nH]c2c1]

3-((4-fluoro-3-(tetrahydro-2H-pyran-4-yloxy)phenyl) ethynyl)-2-(1H-indol-6-yl)benzoic acid was prepared by the same procedure as example 119. $^1$H NMR (300 MHz, CD$_3$OD) δ 7.71 (ddd, J=9.2, 8.1, 1.4 Hz, 2H), 7.59 (dd, J=11.1, 10.5 Hz, 1H), 7.48-7.37 (m, 2H), 7.29 (t, J=9.2 Hz, 1H), 7.10-7.01 (m, 1H), 6.95 (dd, J=11.1, 8.4 Hz, 1H), 6.74 (ddd, J=8.4, 4.4, 2.0 Hz, 1H), 6.50 (ddd, J=9.9, 5.6, 1.4 Hz, 2H), 4.31-4.10 (m, 1H), 4.00-3.77 (m, 2H), 3.55 (ddd, J=17.7, 10.6, 6.7 Hz, 2H), 2.03-1.71 (m, 2H), 1.61 (ddd, J=21.1, 7.6, 3.7 Hz, 2H). MS m/z 456.2 (M+H).

Example 257: Synthesis of 5'-acetamido-6-(phenylethynyl)biphenyl-2-carboxylic acid

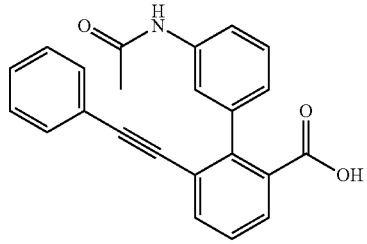 [SMILES: CC(=O)Nc1cccc(-c2c(C#Cc3ccccc3)cccc2C(=O)O)c1]

5'-acetamido-6-(phenylethynyl)biphenyl-2-carboxylic acid was prepared by the same procedure as example 119. $^1$H NMR (300 MHz, CD$_3$OD) δ 7.81 (dd, J=7.8, 1.3 Hz, 1H), 7.78-7.66 (m, 2H), 7.54 (t, J=1.9 Hz, 1H), 7.47 (t, J=7.8 Hz, 1H), 7.37 (t, J=7.9 Hz, 1H), 7.30-7.21 (m, 3H), 7.19-7.10 (m, 2H), 7.08 (d, J=7.6 Hz, 1H), 2.11 (s, 3H). MS m/z 356.2 (M+H).

Example 258: Synthesis of 3-[3-(5-amino-1H-1,3-benzodiazol-1-yl)prop-1-yn-1-yl]-2-phenylbenzoic acid trifluoroacetate salt

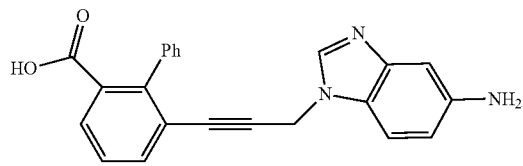 [SMILES: Nc1ccc2c(c1)ncn2CC#Cc1cccc(C(=O)O)c1-c1ccccc1]

3-[3-(5-amino-1H-1,3-benzodiazol-1-yl)prop-1-yn-1-yl]-2-phenylbenzoic acid trifluoroacetate salt was prepared by the same procedure as example 157. $^1$H NMR (300 MHz, DMSO) δ=8.72 (br. s., 1H), 7.71 (ddd, J=1.5, 7.8, 13.0 Hz, 2H), 7.46 (t, J=7.8 Hz, 1H), 7.25-7.10 (m, 6H), 6.71 (d, J=7.9 Hz, 2H), 5.31 (s, 2H), MS (ES$^+$)=367.94 (MH)$^+$.

Example 259: Synthesis of 2-(1H-indol-6-yl)-3-[2-(pyridin-4-yl)ethynyl] benzoic acid; trifluoroacetate salt

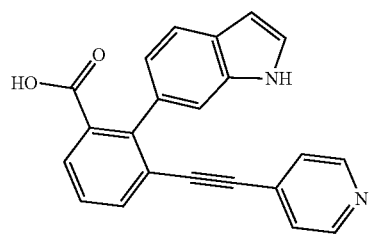 [SMILES: O=C(O)c1cccc(C#Cc2ccncc2)c1-c1ccc2cc[nH]c2c1]

2-(1H-indol-6-yl)-3-[2-(pyridin-4-yl)ethynyl] benzoic acid; trifluoroacetate salt was prepared by the same procedure as example 174. $^1$H NMR (300 MHz, DMSO) δ=11.19 (s, 1H), 8.55 (br. s., 2H), 7.82 (dd, J=1.5, 7.6 Hz, 1H), 7.74 (dd, J=1.5, 7.6 Hz, 1H), 7.64-7.45 (m, 2H), 7.44-7.36 (m, 2H), 7.17 (d, J=6.2 Hz, 2H), 7.03 (dd, J=1.8, 8.2 Hz, 1H), 6.47 (ddd, J=0.9, 2.0, 3.0 Hz, 1H). MS (ES$^+$)=339.00 (MH)$^+$.

Example 260: Synthesis of 2-(4-methylphenyl)-3-[2-(pyridin-4-yl)ethynyl]benzoic acid; trifluoroacetate salt

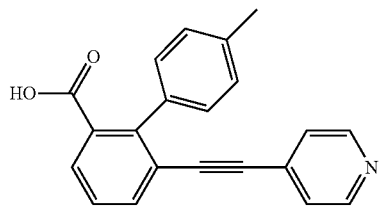 [SMILES: Cc1ccc(-c2c(C#Cc3ccncc3)cccc2C(=O)O)cc1]

2-(4-methylphenyl)-3-[2-(pyridin-4-yl)ethynyl]benzoic acid; trifluoroacetate salt was prepared by the same procedure as example 174. $^1$H NMR (300 MHz, DMSO) δ=8.59 (d, J=5.6 Hz, 2H), 7.80 (ddd, J=1.2, 7.7, 10.5 Hz, 2H), 7.52 (t, J=7.8 Hz, 1H), 7.28-7.16 (m, 6H), 2.37 (s, 3H). MS (ES$^+$)=314.00 (MH)$^+$.

Example 261: Synthesis of 3-[2-(3-hydroxyphenyl)ethynyl]-2-(4-methyl phenyl)benzoic acid

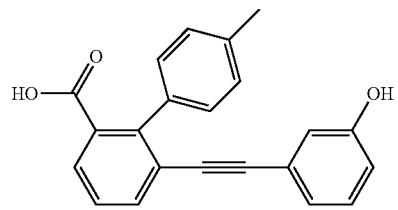 [SMILES: Cc1ccc(-c2c(C#Cc3cccc(O)c3)cccc2C(=O)O)cc1]

3-[2-(3-hydroxyphenyl)ethynyl]-2-(4-methyl phenyl) benzoic acid was prepared by the same procedure as example 166. $^1$H NMR (300 MHz, DMSO) δ=9.62 (br. s., 1H), 7.81-7.62 (m, 2H), 7.52-7.40 (m, 1H), 7.30-7.16 (m, 5H), 7.16-7.06 (m, 1H), 6.74 (ddd, J=0.9, 2.3, 8.2 Hz, 1H), 6.65-6.51 (m, 2H), 2.36 (s, 3H). MS (ES$^+$)=328.11 (MH)$^+$.

Example 262: Synthesis of 3-{3-[(1H-1,3-benzodiazol-6-yl)amino]prop-1-yn-1-yl}-2-phenylbenzoic acid; trifluoroacetate salt

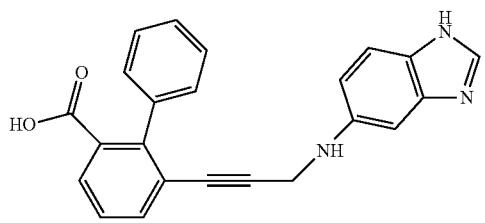 [SMILES: O=C(O)c1cccc(C#CCNc2ccc3[nH]cnc3c2)c1-c1ccccc1]

3-{3-[(1H-1,3-benzodiazol-6-yl)amino]prop-1-yn-1-yl}-2-phenylbenzoic acid; trifluoroacetate salt was prepared by the same procedure as example 157. $^1$H NMR (300 MHz, DMSO) δ=8.68 (br. s., 1H), 7.77-7.64 (m, 2H), 7.51-7.41 (m, 1H), 7.32-7.08 (m, 7H), 6.79-6.62 (m, 2H), 5.30 (s, 2H). MS (ES$^+$)=368.01 (MH)$^+$.

Example 263: Synthesis of 3-[2-(3-hydroxyphenyl) ethynyl]-2-(1-methyl-1H-indol-5-yl)benzoic acid

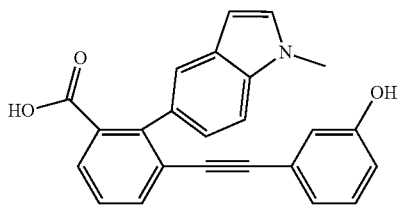 [SMILES: Cn1ccc2cc(-c3c(C#Cc4cccc(O)c4)cccc3C(=O)O)ccc21]

3-[2-(3-hydroxyphenyl)ethynyl]-2-(1-methyl-1H-indol-5-yl)benzoic acid was prepared by the same procedure as example 166. $^1$H NMR (300 MHz, DMSO) δ=9.57 (br. s., 1H), 7.76-7.69 (m, 1H), 7.65 (dd, J=1.5, 7.6 Hz, 1H), 7.56-7.49 (m, 1H), 7.49-7.40 (m, 2H), 7.34 (d, J=3.2 Hz, 1H), 7.19-7.11 (m, 1H), 7.10-6.99 (m, 1H), 6.76-6.64 (m, 1H), 6.61-6.51 (m, 2H), 6.48-6.42 (m, 1H), 3.87-3.77 (m, 3H). MS (ES$^+$)=368.08 (MH)$^+$.

Example 264: Synthesis of 3-[2-(3-hydroxyphenyl) ethynyl]-2-(4-methyl-3,4-dihydro-2H-1,4-benzoxazin-7-yl)benzoic acid; trifluoroacetate salt

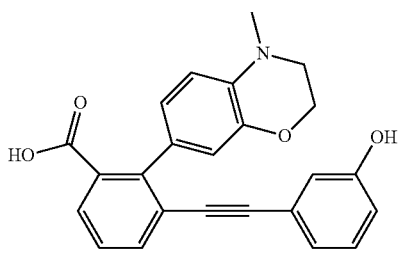 [SMILES: CN1CCOc2cc(-c3c(C#Cc4cccc(O)c4)cccc3C(=O)O)ccc21]

3-[2-(3-hydroxyphenyl)ethynyl]-2-(4-methyl-3,4-dihydro-2H-1,4-benzoxazin-7-yl)benzoic acid; trifluoroacetate salt was prepared by the same procedure as example 166. $^1$H NMR (300 MHz, DMSO) δ=7.70-7.64 (m, 1H), 7.63-7.56 (m, 1H), 7.44-7.32 (m, 1H), 7.14 (t, J=7.9 Hz, 1H), 6.80-6.63 (m, 5H), 4.25 (dd, J=3.8, 5.0 Hz, 2H), 3.33-3.21 (m, 2H), 2.87 (s, 3H). MS (ES$^+$)=386.09 (MH)$^+$.

Example 265: Synthesis of 3-[2-(3-hydroxyphenyl) ethynyl]-2-(3-methane sulfonamidophenyl) benzoic acid

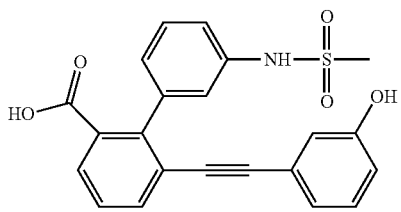 [SMILES: CS(=O)(=O)Nc1cccc(-c2c(C#Cc3cccc(O)c3)cccc2C(=O)O)c1]

3-[2-(3-hydroxyphenyl)ethynyl]-2-(3-methane sulfonamidophenyl) benzoic acid was prepared by the same procedure as example 166. $^1$H NMR (300 MHz, DMSO) δ=9.81 (s, 1H), 9.63 (br. s., 1H), 7.75 (qd, J=1.6, 7.8 Hz, 2H), 7.55-7.46 (m, 1H), 7.43-7.34 (m, 1H), 7.25-7.18 (m, 1H), 7.16-7.01 (m, 3H), 6.74 (ddd, J=1.0, 2.4, 8.3 Hz, 1H), 6.62-6.52 (m, 2H), 2.88 (s, 3H). MS (ES$^+$)=430.00 (M+Na)$^+$.

Example 266: Synthesis of 3-[2-(3-hydroxyphenyl) ethynyl]-2-(1H-indol-6-yl)benzoic acid

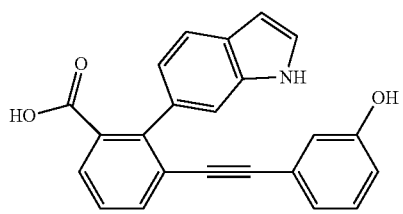 [SMILES: O=C(O)c1cccc(C#Cc2cccc(O)c2)c1-c1ccc2cc[nH]c2c1]

3-[2-(3-hydroxyphenyl)ethynyl]-2-(1H-indol-6-yl)benzoic acid was prepared by the same procedure as example 166. $^1$H NMR (300 MHz, DMSO) δ=11.15 (s, 1H), 9.57 (br. s., 1H), 7.79-7.71 (m, 1H), 7.69-7.60 (m, 1H), 7.60-7.53 (m, 1H), 7.50-7.41 (m, 1H), 7.41-7.33 (m, 2H), 7.11-6.96 (m, 2H), 6.76-6.63 (m, 2H), 6.60-6.50 (m, 2H), 6.49-6.42 (m, 1H). MS (ES$^+$)=354.01 (MH)$^+$.

Example 267: Synthesis of 2-(3-carbamoylphenyl)-3-[2-(3-hydroxyphenyl) ethynyl]benzoic acid

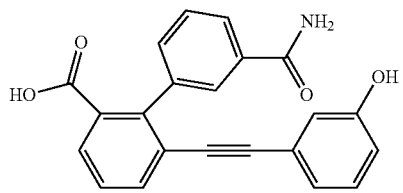 [SMILES: NC(=O)c1cccc(-c2c(C#Cc3cccc(O)c3)cccc2C(=O)O)c1]

2-(3-carbamoylphenyl)-3-[2-(3-hydroxyphenyl)ethynyl] benzoic acid was prepared by the same procedure as example 166. $^1$H NMR (300 MHz, DMSO) δ=9.58 (br. s., 1H), 7.99 (s, 1H), 7.95-7.83 (m, 3H), 7.83-7.73 (m, 2H), 7.57-7.42 (m, 3H), 7.39-7.29 (m, 1H), 7.13-7.01 (m, 1H), 6.73 (ddd, J=1.0, 2.4, 8.3 Hz, 1H), 6.59-6.48 (m, 2H). MS (ES$^+$)=380.04 (M+Na)$^+$.

Example 268: Synthesis of 2-[1-(benzenesulfonyl)-1H-indol-3-yl]-3-[2-(3-hydroxyphenyl)ethynyl] benzoic acid

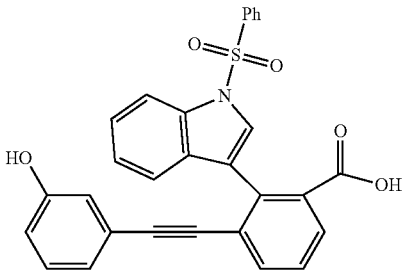 [SMILES: O=C(O)c1cccc(C#Cc2cccc(O)c2)c1-c1cn(S(=O)(=O)c2ccccc2)c2ccccc12]

2-[1-(benzenesulfonyl)-1H-indol-3-yl]-3-[2-(3-hydroxyphenyl)ethynyl] benzoic acid was prepared by the same procedure as example 166. ¹H NMR (300 MHz, DMSO) δ=9.55 (br. s., 1H), 7.97-7.86 (m, 3H), 7.85-7.77 (m, 3H), 7.61-7.46 (m, 2H), 7.42-7.29 (m, 3H), 7.26-7.18 (m, 2H), 6.92 (t, J=7.9 Hz, 1H), 6.68 (ddd, J=1.0, 2.4, 8.3 Hz, 1H), 6.29 (dd, J=1.5, 2.3 Hz, 1H), 5.94 (td, J=1.2, 7.8 Hz, 1H). MS (ES⁺)=352.99 (M−140)⁺.

Example 269: Synthesis of 2-(3-hydroxyphenyl)-3-[2-(3-hydroxyphenyl) ethynyl]benzoic acid

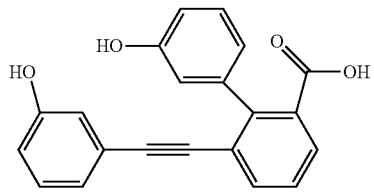 [SMILES: O=C(O)c1cccc(C#Cc2cccc(O)c2)c1-c1cccc(O)c1]

2-(3-hydroxyphenyl)-3-[2-(3-hydroxyphenyl) ethynyl] benzoic acid was prepared by the same procedure as example 166. ¹H NMR (300 MHz, DMSO) δ=9.63 (br. s., 1H), 9.42 (br. s., 1H), 7.69 (ddd, J=1.2, 7.8, 14.5 Hz, 2H), 7.52-7.37 (m, 1H), 7.27-7.16 (m, 1H), 7.17-7.06 (m, 1H), 6.82-6.68 (m, 4H), 6.68-6.54 (m, 2H), 3.95 (s, 1H). MS (ES⁺)=312.98 (MH−H₂O)⁺.

Example 270: Synthesis of 2-(1H-indol-5-yl)-3-[2-(pyridin-4-yl)ethynyl]benzoic acid; trifluoroacetate salt

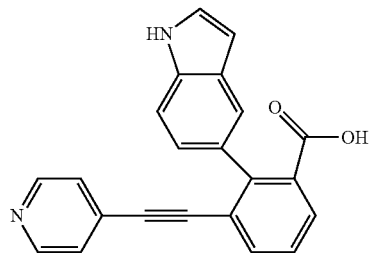 [SMILES: O=C(O)c1cccc(C#Cc2ccncc2)c1-c1ccc2[nH]ccc2c1]

2-(1H-indol-5-yl)-3-[2-(pyridin-4-yl)ethynyl]benzoic acid; trifluoroacetate salt was prepared by the same procedure as example 174. ¹H NMR (300 MHz, DMSO) δ=11.17 (s, 1H), 8.58-8.46 (m, 2H), 7.81 (dd, J=1.2, 7.9 Hz, 1H), 7.73 (dd, J=0.9, 7.9 Hz, 1H), 7.57-7.40 (m, 3H), 7.38 (t, J=2.6 Hz, 1H), 7.17 (dd, J=1.8, 4.4 Hz, 2H), 7.11 (dd, J=1.6, 8.4 Hz, 1H), 6.47 (t, J=2.2 Hz, 1H). MS (ES⁺)=339.07 (MH)⁺.

Example 271: Synthesis of 2-(3-chloro-5-hydroxyphenyl)-3-[2-(pyridin-4-yl)ethynyl] benzoic acid; trifluoroacetate salt

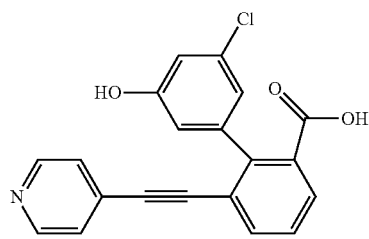

2-(3-chloro-5-hydroxyphenyl)-3-[2-(pyridin-4-yl)ethynyl] benzoic acid; trifluoroacetate salt was prepared by the same procedure as example 174. ¹H NMR (300 MHz, DMSO) δ=10.04 (br. s., 1H), 8.70-8.55 (m, 2H), 7.89-7.78 (m, 2H), 7.65-7.48 (m, 1H), 7.29-7.20 (m, 2H), 6.83 (td, J=2.0, 12.5 Hz, 2H), 6.69 (dd, J=1.5, 2.3 Hz, 1H), 6.25-6.06 (m, 1H). MS (ES⁺)=350.00 (MH)⁺.

Example 272: Synthesis of 2-(3-fluoro-5-hydroxyphenyl)-3-[2-(pyridin-4-yl)ethynyl]benzoic acid; trifluoroacetate salt

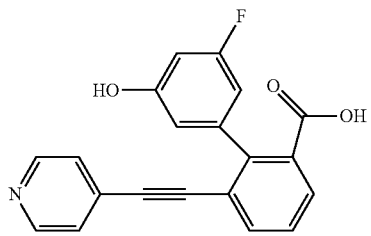 [SMILES: O=C(O)c1cccc(C#Cc2ccncc2)c1-c1cc(O)cc(Cl)c1]

2-(3-fluoro-5-hydroxyphenyl)-3-[2-(pyridin-4-yl)ethynyl]benzoic acid; trifluoroacetate salt was prepared by the same procedure as example 174. ¹H NMR (300 MHz, DMSO) δ=9.96 (br. s., 1H), 8.55 (d, J=5.9 Hz, 2H), 7.88-7.67 (m, 2H), 7.56-7.41 (m, 1H), 7.22-7.08 (m, 2H), 6.61-6.45 (m, 3H). MS (ES⁺)=334.04 (MH)⁺.

Example 273: Synthesis of 2-(3,5-dimethoxyphenyl)-3-[2-(pyridin-4-yl)ethynyl]benzoic acid; trifluoroacetate salt

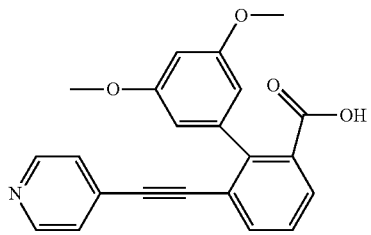 [SMILES: COc1cc(OC)cc(-c2c(C#Cc3ccncc3)cccc2C(=O)O)c1]

2-(3,5-dimethoxyphenyl)-3-[2-(pyridin-4-yl)ethynyl] benzoic acid; trifluoroacetate salt was prepared by the same procedure as example 174. ¹H NMR (300 MHz, DMSO) δ=8.61 (br. s., 2H), 7.80 (ddd, J=1.3, 7.7, 13.3 Hz, 2H), 7.53 (t, J=7.8 Hz, 1H), 7.21 (d, J=5.9 Hz, 2H), 6.61-6.52 (m, 1H), 6.49 (d, J=2.3 Hz, 2H), 3.73 (s, 6H). MS (ES⁺)=360.06 (MH)⁺.

Example 274: Synthesis of 3-[3-(4-fluorophenyl)-3-hydroxyprop-1-yn-1-yl]-2-(3-hydroxyphenyl) benzoic acid

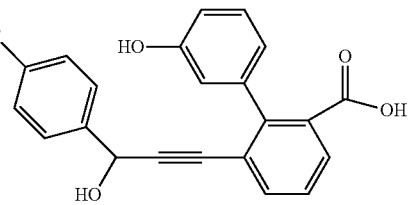

3-[3-(4-fluorophenyl)-3-hydroxyprop-1-yn-1-yl]-2-(3-hydroxyphenyl)benzoic acid was prepared by the same procedure as example 33. $^1$H NMR (300 MHz, DMSO) δ=9.18 (br. s., 1H), 7.47-7.37 (m, 2H), 7.27-7.14 (m, 1H), 6.98-6.73 (m, 5H), 6.55 (ddd, J=1.2, 2.3, 8.2 Hz, 1H), 6.44-6.34 (m, 2H), 5.19-5.09 (m, 1H).

Example 275: Synthesis of 3-[2-(3-hydroxyphenyl)ethynyl]-2-(2-phenoxyphenyl) benzoic acid

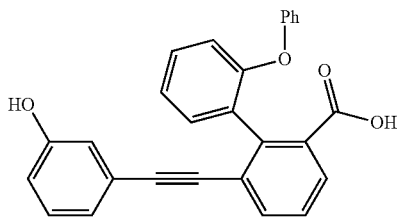 [SMILES: O=C(O)c1cccc(C#Cc2cccc(O)c2)c1-c1ccccc1Oc1ccccc1]

3-[2-(3-hydroxyphenyl)ethynyl]-2-(2-phenoxyphenyl) benzoic acid was prepared by the same procedure as example 166. $^1$H NMR (300 MHz, DMSO) δ=9.63 (br. s., 1H), 7.81 (dd, J=1.3, 7.8 Hz, 1H), 7.72 (dd, J=1.5, 7.6 Hz, 1H), 7.51-7.30 (m, 3H), 7.27-7.07 (m, 4H), 7.05-6.92 (m, 1H), 6.92-6.80 (m, 3H), 6.74 (ddd, J=1.0, 2.5, 8.2 Hz, 1H), 6.62-6.49 (m, 2H). MS (ES$^+$)=429.19 (M+Na)$^+$.

Example 276: Synthesis of 3-[2-(3-hydroxyphenyl)ethynyl]-2-(1H-indol-3-yl) benzoic acid

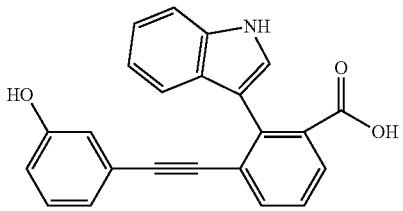 [SMILES: O=C(O)c1cccc(C#Cc2cccc(O)c2)c1-c1c[nH]c2ccccc12]

3-[2-(3-hydroxyphenyl)ethynyl]-2-(1H-indol-3-yl) benzoic acid was prepared by the same procedure as example 166. $^1$H NMR (300 MHz, DMSO) δ=11.29 (s, 1H), 9.53 (s, 1H), 7.74 (dd, J=1.3, 7.8 Hz, 1H), 7.65 (dd, J=1.5, 7.9 Hz, 1H), 7.48-7.37 (m, 3H), 7.31 (d, J=8.2 Hz, 1H), 7.16-6.91 (m, 3H), 6.69 (ddd, J=0.9, 2.6, 8.2 Hz, 1H), 6.50-6.34 (m, 2H). MS (ES$^+$)=354.08 (MH)$^+$.

Example 277: Synthesis of 2-(3,5-dimethoxyphenyl)-3-[2-(3-hydroxyphenyl) ethynyl]benzoic acid

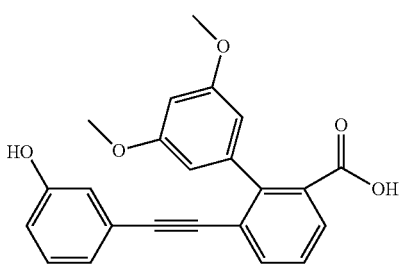 [SMILES: COc1cc(OC)cc(-c2c(C#Cc3cccc(O)c3)cccc2C(=O)O)c1]

2-(3,5-dimethoxyphenyl)-3-[2-(3-hydroxyphenyl) ethynyl]benzoic acid was prepared by the same procedure as example 166. $^1$H NMR (300 MHz, DMSO) δ=9.63 (br. s., 1H), 7.78-7.62 (m, 2H), 7.54-7.40 (m, 1H), 7.13 (t, J=7.9 Hz, 1H), 6.81-6.67 (m, 1H), 6.68-6.56 (m, 2H), 6.56-6.49 (m, 1H), 6.47 (d, J=2.3 Hz, 2H), 3.82 (s, 6H). MS (ES$^+$)=375.08 (MH)$^+$.

Example 278: Synthesis of 2-amino-3-[2-(3-carbamoylphenyl)ethynyl]benzoic acid; trifluoroacetate salt

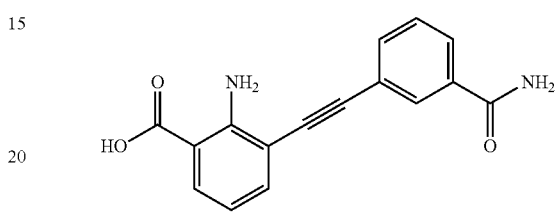

2-amino-3-[2-(3-carbamoylphenyl)ethynyl]benzoic acid; trifluoroacetate salt was prepared by the same procedure as example 78. $^1$H NMR (300 MHz, DMSO) δ=8.24-8.06 (m, 2H), 8.05-7.75 (m, 3H), 7.68-7.46 (m, 3H), 6.76-6.58 (m, 1H), 3.38 (s, 2H). MS (ES$^+$)=281.07 (MH)$^+$.

Example 279: Synthesis of 2-amino-3-[2-(3-carboxyphenyl)ethynyl]benzoic acid; trifluoroacetate salt

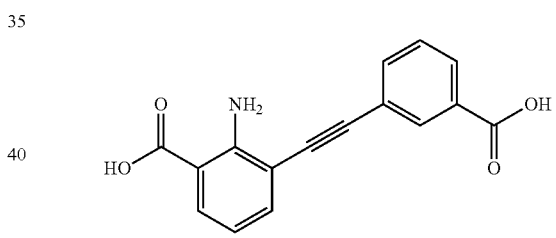

2-amino-3-[2-(3-carboxyphenyl)ethynyl]benzoic acid; trifluoroacetate salt was prepared by the same procedure as example 78. $^1$H NMR (300 MHz, DMSO) δ=13.13 (br. s., 1H), 8.18 (br. s., 1H), 7.94 (d, J=7.6 Hz, 1H), 7.83 (dd, J=7.8, 15.1 Hz, 2H), 7.64-7.45 (m, 2H), 6.59 (t, J=7.6 Hz, 1H). MS (ES$^+$)=282.09 (MH)$^+$.

Example 280: Synthesis of 5-[3-(1H-tetrazol-5-yl)-phenylethynyl]-1H-indole 5-(3-Ethynyl-phenyl)-1H-tetrazole The solution of 5-(3-Bromo-phenyl)-1H-tetrazole (2 g, 8.9 mmol) in triethylamine (20 mL) was degassed under N$_2$ for 10 min. Trimethylsilylacetylene (1 mL), bis(triphenylphosphine)palladium(II) dichloride (624 mg, 0.89 mmol) and copper iodide (339 mg, 1.78 mmol) was added and the reaction mixture was degassed under N$_2$ for 20 min and then heated at 60° C. for 18 hours. After cooling to ambient temperature, the crude mixture was filtered through celite and washed with dichloromethane. The filtrate was concentrated and purified by column chromatography through a silica gel cartridge (80 g) eluting with methanol/dichloromethane (10-20%) to give the intermediate as a white solid. To this intermediate in methanol (10 mL) was slowly added 2N NaOH (3.5 mL, 7 mmol). The reaction mixture was stirred at room temperature for 20 minutes and concentrated, diluted with water (10 mL) and acidified with 2N hydrochloric acid aqueous solution until pH=1. The precipitate was filtered and purified through preparative HPLC to give 810 mg (59% for 2 steps) of the pure product as a white solid.

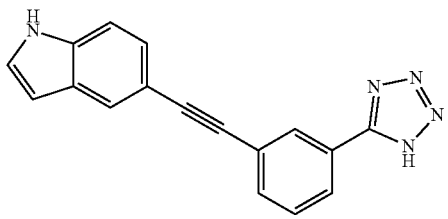 [SMILES: C(#Cc1ccc2[nH]ccc2c1)c1cccc(-c2nnn[nH]2)c1]

5-[3-(1H-Tetrazol-5-yl)-phenylethynyl]-1H-indole. A mixture of 5-(3-ethynyl-phenyl)-1H-tetrazole (34 mg, 0.2 mmol), 5-iodo-indole (97 mg, 0.4 mmol), palladium tetrakis-triphenylphosphine (23 mg, 0.02 mmol) and copper iodide (7.6 mg, 0.04 mmol), potassium carbonate (55.3 mg, 0.4 mmol) in 1,2-dimethoxyethane/water (1 mL/0.3 mL) was degassed with $N_2$ for 5 minutes and then heated at 60° C. for 3 hours. After cooling to ambient temperature, the crude mixture was filtered through celite and washed with dichloromethane. The filtrate was concentrated and purified by preparative HPLC to give 15.4 mg (27%) of the pure product as a white solid. $^1$H NMR (300 MHz, CD$_3$OD) δ=10.71 (br. s., 1H), 8.15 (d, J=2.3 Hz, 1H), 7.96 (td, J=1.5, 7.8 Hz, 1H), 7.78 (s, 1H), 7.71-7.52 (m, 3H), 7.44-7.34 (m, 1H), 7.31-7.25 (m, 2H), 6.48 (d, J=3.1 Hz, 1H). MS (ESI) m/z 285.0 (M)$^+$.

Example 281: Synthesis of 3-[3-(1H-tetrazol-5-yl)-phenylethynyl]-1H-pyrrolo[2,3-b]pyridine

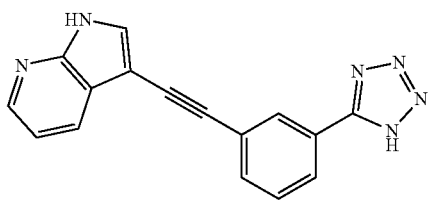 [SMILES: C(#Cc1c[nH]c2ncccc12)c1cccc(-c2nnn[nH]2)c1]

3-[3-(1H-Tetrazol-5-yl)-phenylethynyl]-1H-pyrrolo[2,3-b]pyridine was prepared by the same procedure as example 280. $^1$H NMR (300 MHz, DMSO) δ=12.23 (br. s., 1H), 8.33 (dd, J=1.5, 4.7 Hz, 1H), 8.20 (s, 1H), 8.13 (dd, J=1.6, 7.8 Hz, 1H), 8.04-7.95 (m, 2H), 7.78-7.73 (m, 1H), 7.70-7.61 (m, 1H), 7.22 (dd, J=4.7, 7.9 Hz, 1H). MS (ESI) m/z 287.1 (M+1)$^+$.

Example 282: Synthesis of 6-[3-(1H-tetrazol-5-yl)-phenylethynyl]-1H-indole

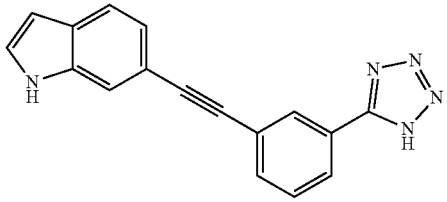 [SMILES: C(#Cc1ccc2cc[nH]c2c1)c1cccc(-c2nnn[nH]2)c1]

6-[3-(1H-Tetrazol-5-yl)-phenylethynyl]-1H-indole was prepared by the same procedure as example 280. $^1$H NMR (300 MHz, DMSO) δ=11.33 (br. s., 1H), 8.19 (d, J=2.5 Hz, 1H), 8.19 (s, 1H), 8.06-8.03 (m, 1H), 7.75 (td, J=5.0 Hz, 8.1 Hz, 1H), 7.67-7.55 (m, 3H), 7.49-7.46 (m, 1H), 7.19 (dd, J=1.3, 8.1 Hz, 1H), 6.50-6.47 (m, 1H); MS (ESI) m/z 285.1 (M)$^+$.

Example 283: Synthesis of 1-benzenesulfonyl-3-[3-(1H-tetrazol-5-yl)-phenylethynyl]-1H-indole

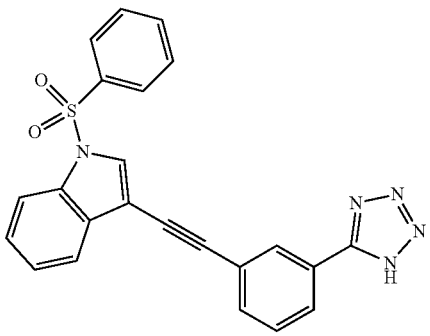 [SMILES: O=S(=O)(c1ccccc1)n1cc(C#Cc2cccc(-c3nnn[nH]3)c2)c2ccccc21]

1-Benzenesulfonyl-3-[3-(1H-tetrazol-5-yl)-phenylethynyl]-1H-indole was prepared by the same procedure as example 280. MS (ESI) m/z 426.0 (M+1)$^+$.

Example 284: Synthesis of 3-[3-(1H-tetrazol-5-yl)-phenylethynyl]-1H-indole

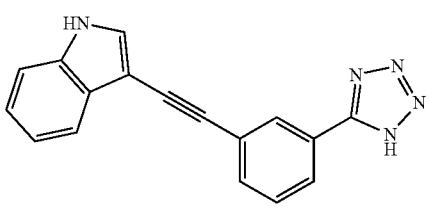 [SMILES: C(#Cc1c[nH]c2ccccc12)c1cccc(-c2nnn[nH]2)c1]

3-[3-(1H-tetrazol-5-yl)-phenylethynyl]-1H-indole. 1-Benzenesulfonyl-3-[3-(1H-tetrazol-5-yl)-phenylethynyl]-1H-indole, (30 mg, 0.07 mmol) was dissolved in tetrahydrofuran/methanol (1 mL/0.2 mL) and added sodium hydroxide solution (2 N in water, 0.1 mL, 0.2 mmol) and the solution was stirred at 60° C. for 18 hours. 1 N hydrochloric acid aqueous solution was added dropwise until pH=1 and the reaction mixture was purified through preparative HPLC to give 17 mg (84%) of the pure product as a white solid. ¹H NMR (300 MHz, DMSO) δ=11.63 (br. s., 1H), 8.18 (s, 1H), 8.03-8.01 (m, 1H), 7.83 (d, J=2.6 Hz, 1H), 7.76-7.61 (m, 3H), 7.50-7.45 (m, 1H), 7.24-7.13 (m, 2H). MS (ESI) m/z 286.0 (M+1)⁺.

Example 285: Synthesis of {2-[3-(1H-tetrazol-5-yl)-phenylethynyl]-phenyl}-methanol

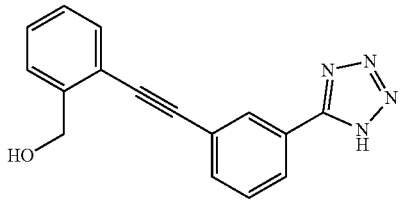 [SMILES: OCc1ccccc1C#Cc1cccc(-c2nnn[nH]2)c1]

{2-[3-(1H-Tetrazol-5-yl)-phenylethynyl]-phenyl}-methanol was prepared by the same procedure as example 280. ¹H NMR (300 MHz, CD₃OD) δ=8.21 (br. s., 1H), 8.04 (d, J=7.0 Hz, 1H), 7.77-7.69 (m, 1H), 7.65-7.51 (m, 3H), 7.42 (t, J=7.3 Hz, 1H), 7.35-7.27 (m, 1H), 4.92-4.84 (m, 2H). MS (ESI) m/z 300.0 (M+Na)⁺.

Example 286: Synthesis of 3-[3-(morpholine-4-carbonyl)-phenylethynyl]-benzoic acid

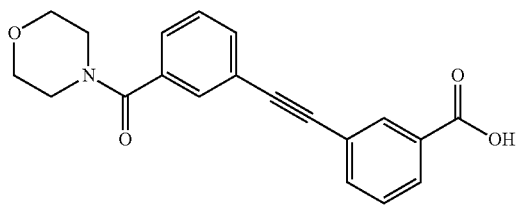 [SMILES: O=C(O)c1cccc(C#Cc2cccc(C(=O)N3CCOCC3)c2)c1]

3-[3-(Morpholine-4-carbonyl)-phenylethynyl]-benzoic acid. A mixture of 3-(3-carbamoyl-5-methoxy-phenylethynyl)-benzoic acid (40 mg, 0.14 mmol), morpholine (0.1 mL), HATU (70 mg, 0.18 mmol) and triethylamine (0.1 mmol) in tetrahydrofuran (1 mL) was stirred at room temperature for 24 hours. The reaction mixture was concentrated and purified through preparative HPLC to give the ester intermediate. To this intermediate in tetrahydrofuran/methanol (1 mL/0.2 mL) was added sodium hydroxide solution (2 N in water, 0.2 mL, 0.4 mmol) and the solution was stirred at room temperature for 18 hours. 1 N hydrochloric acid aqueous solution was added dropwise until pH=1 and the reaction mixture was purified through preparative HPLC to give 8 mg (17% for 2 steps) of the pure product as a white solid. 18 mg (22% for 2 steps) of the pure product as a white solid. ¹H NMR (300 MHz, CD₃OD) δ=8.15 (s, 1H), 8.02 (d, J=7.6 Hz, 1H), 7.75 (d, J=7.4 Hz, 1H), 7.68-7.60 (m, 2H), 7.55-7.42 (m, 3H), 3.80-3.60 (m, 6H), 3.55-3.42 (m, 2H). MS (ESI) m/z 336.1 (M+1)⁺.

Example 287: Synthesis of 3-(3-methylcarbamoyl-phenylethynyl)-benzoic acid

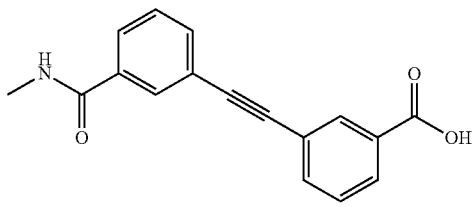 [SMILES: CNC(=O)c1cccc(C#Cc2cccc(C(=O)O)c2)c1]

3-(3-Methylcarbamoyl-phenylethynyl)-benzoic acid was prepared by the same procedure as example 286. ¹H NMR (300 MHz, CD₃OD) δ=8.15 (t, J=1.6 Hz, 1H), 8.05-7.99 (m, 2H), 7.82-7.79 (m, 1H), 7.76-7.69 (m, 2H), 7.53-7.49 (m, 2H), 2.93 (s, 3H). MS (ESI) m/z 280.1 (M+1)⁺.

Example 288: Synthesis of 3-(3-dimethylcarbamoyl-phenylethynyl)-benzoic acid

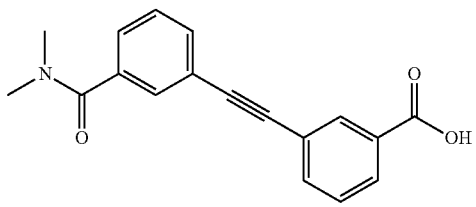 [SMILES: CN(C)C(=O)c1cccc(C#Cc2cccc(C(=O)O)c2)c1]

3-(3-Dimethylcarbamoyl-phenylethynyl)-benzoic acid was prepared by the same procedure as example 286. ¹H NMR (300 MHz, CD₃OD) δ=8.15 (t, J=1.3 Hz, 1H), 8.02 (td, J=1.5, 7.9 Hz, 1H), 7.75 (td, J=1.4, 7.8 Hz, 1H), 7.66-7.59 (m, 2H), 7.54-7.41 (m, 3H), 3.11 (s, 3H), 3.01 (s, 3H). MS (ESI) m/z 294.1 (M+1)⁺.

Example 289: Synthesis of 3-[3-(4-methyl-piperazine-1-carbonyl)-phenylethynyl]-benzoic acid

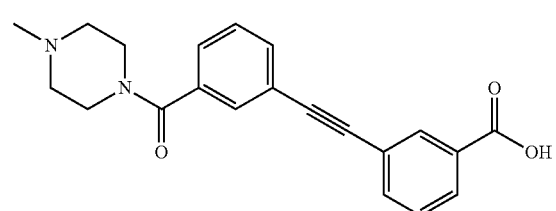

3-[3-(4-Methyl-piperazine-1-carbonyl)-phenylethynyl]-benzoic acid was prepared by the same procedure as example 286. ¹H NMR (300 MHz, CD₃OD) δ=8.14 (d, J=2.3 Hz, 1H), 8.02 (td, J=1.5, 7.9 Hz, 1H), 7.76-7.66 (m, 3H), 7.56-7.47 (m, 3H), 3.95-3.72 (m, 2H), 3.70-3.12 (m, 6H), 2.94 (s, 3H). MS (ESI) m/z 349.1 (M+1)⁺.

Example 290: Synthesis of 3-[3-(4-phenyl-piperazine-1-carbonyl)-phenylethynyl]-benzoic acid

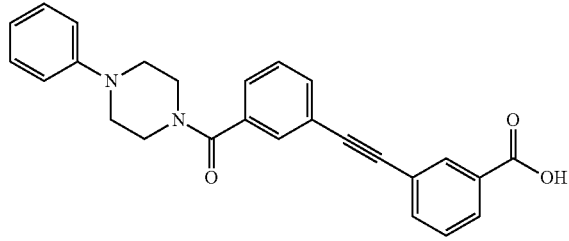 [SMILES: O=C(O)c1cccc(C#Cc2cccc(C(=O)N3CCN(c4ccccc4)CC3)c2)c1]

3-[3-(4-Phenyl-piperazine-1-carbonyl)-phenylethynyl]-benzoic acid was prepared by the same procedure as example 286. $^1$H NMR (300 MHz, CD$_3$OD) δ=8.15 (t, J=1.6 Hz, 1H), 8.02 (td, J=1.3, 7.9 Hz, 1H), 7.75 (td, J=1.5, 7.6 Hz, 1H), 7.69-7.61 (m, 2H), 7.54-7.44 (m, 3H), 7.28-7.19 (m, 2H), 7.01-6.95 (m, 2H), 6.90-6.81 (m, 1H), 3.91 (br. s., 2H), 3.69-3.53 (m, 2H), 3.30-3.10 (m, 4H). MS (ESI) m/z 411.2 (M+1)$^+$.

Example 291: Synthesis of 2-indol-1-yl-3-pyridin-4-ylethynyl-benzoic acid

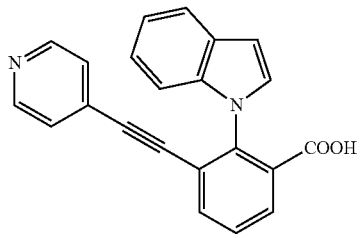 [SMILES: O=C(O)c1cccc(C#Cc2ccncc2)c1-n1ccc2ccccc21]

2-Indol-1-yl-3-pyridin-4-ylethynyl-benzoic acid. A mixture of 2-bromo-3-pyridin-4-ylethynyl-benzoic acid methyl ester (50 mg, 0.16 mmol), indole (28 mg, 0.237 mmol), potassium phosphate (70 mg, 0.332 mmol), copper iodide (3 mg, 0.016 mmol) and N,N'-dimethyl-cyclohexane-1,2-diamine (10 mg, 0.063 mmol) in toluene (1.5 mL) was degassed under N$_2$ for 10 minutes and then heated at 110° C. for 18 hours. After cooling to room temperature, the reaction mixture was filtered through celite washing with ethyl acetate (5 mL). The filtrate was concentrated and purified using reversed phase HPLC to provide the desired product as a white solid. $^1$H NMR (300 MHz, CD$_3$OD) δ=8.57 (d, J=6.2 Hz, 2H), 8.13 (dd, J=1.5, 7.9 Hz, 1H), 7.99 (d, J=7.4 Hz, 1H), 7.75-7.64 (m, 2H), 7.33 (d, J=3.5 Hz, 1H), 7.19-7.09 (m, 4H), 7.05-6.99 (m, 1H), 6.71 (d, J=3.3 Hz, 1H). MS (ESI) m/z 339.1 (M+1)$^+$.

Example 292: Synthesis of 2-imidazol-1-yl-3-pyridin-4-ylethynyl-benzoic acid

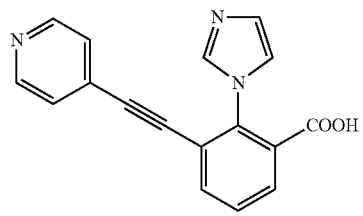 [SMILES: O=C(O)c1cccc(C#Cc2ccncc2)c1-n1ccnc1]

2-Imidazol-1-yl-3-pyridin-4-ylethynyl-benzoic acid. A mixture of 2-bromo-3-pyridin-4-ylethynyl-benzoic acid methyl ester (50 mg, 0.16 mmol), imidazole (50 mg, 0.74 mmol), copper iodide (60 mg, 0.32 mmol), cesium carbonate (82 mg, 0.25 mmol) in dimethylformamide (1.5 mL) was degassed under N$_2$ for 10 minutes and then heated at 120° C. for 18 hours. After cooling to room temperature, the reaction mixture was filtered through celite washing with ethyl acetate (5 mL). The filtrate was concentrated and purified using reversed phase HPLC to provide the desired product as a white solid. $^1$H NMR (300 MHz, CD$_3$OD) δ=9.40 (br. s., 1H), 8.38 (dd, J=1.5, 7.9 Hz, 1H), 8.14 (dd, J=1.3, 7.8 Hz, 1H), 7.96-7.78 (m, 5H), 7.74-7.64 (m, 2H). MS (ESI) m/z 290.1 (M+1)$^+$.

Example 293: Synthesis of 3-pyridin-4-ylethynyl-2-[1,2,4]triazol-1-yl-benzoic acid

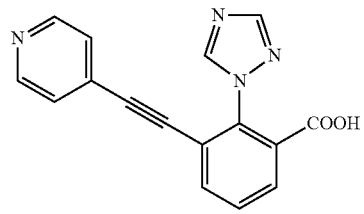 [SMILES: O=C(O)c1cccc(C#Cc2ccncc2)c1-n1cncn1]

3-Pyridin-4-ylethynyl-2-[1,2,4]triazol-1-yl-benzoic acid was prepared by the same procedure as example 293. $^1$H NMR (300 MHz, CD$_3$OD) δ=8.83 (s, 1H), 8.52 (d, J=3.8 Hz, 2H), 8.23 (s, 1H), 8.03 (d, J=7.9 Hz, 1H), 7.90 (d, J=7.6 Hz, 1H), 7.71 (t, J=7.8 Hz, 1H), 7.29 (d, J=5.6 Hz, 2H). MS (ESI) m/z 291.12 (M+1)$^+$.

Example 294: Synthesis of 2-imidazol-1-yl-3-phenylethynyl-benzoic acid

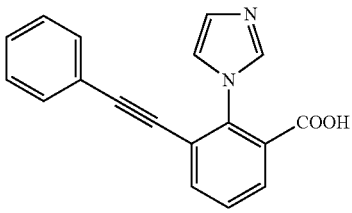 [SMILES: O=C(O)c1cccc(C#Cc2ccccc2)c1-n1ccnc1]

2-Imidazol-1-yl-3-phenylethynyl-benzoic acid was prepared by the same procedure as example 293. $^1$H NMR (300 MHz, CD$_3$OD) δ=8.02 (s, 1H), 7.97-7.68 (m, 4H), 7.64-7.58 (m, 1H), 7.34-7.22 (m, 5H). MS (ESI) m/z 289.1 (M+1)$^+$.

Example 295: Synthesis of 3-phenylethynyl-2-pyrazol-1-yl-benzoic acid

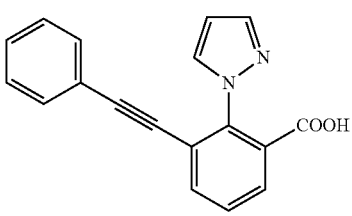 [SMILES: O=C(O)c1cccc(C#Cc2ccccc2)c1-n1cccn1]

-Phenylethynyl-2-pyrazol-1-yl-benzoic acid prepared by the same procedure as example 293. $^1$H NMR (300 MHz, CD$_3$OD) δ=7.97-7.69 (m, 4H), 7.63-7.56 (m, 1H), 7.37-7.25 (m, 5H), 6.57 (br. s., 1H). MS (ESI) m/z 289.1 (M+1)$^+$.

Example 296: Synthesis of 3-phenylethynyl-2-[1,2,4]triazol-1-yl-benzoic acid

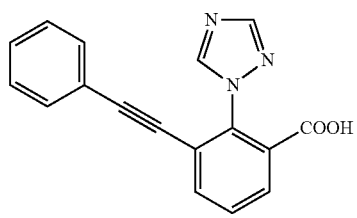 [SMILES: O=C(O)c1cccc(C#Cc2ccccc2)c1-n1cncn1]

3-Phenylethynyl-2-[1,2,4]triazol-1-yl-benzoic acid prepared by the same procedure as example 293. $^1$H NMR (300 MHz, CD$_3$OD) δ=8.84 (br. s., 1H), 8.23 (s, 1H), 8.03 (d, J=7.6 Hz, 1H), 7.88 (d, J=7.9 Hz, 1H), 7.69 (t, J=7.5 Hz, 1H), 7.40-7.23 (m, 5H). MS (ESI) m/z 290.1 (M+1)$^+$.

Example 297: Synthesis of 2-benzoimidazol-1-yl-3-phenylethynyl-benzoic acid

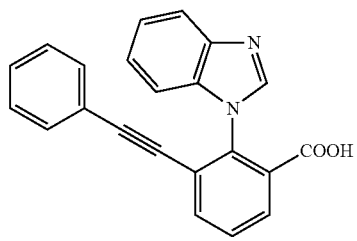 [SMILES: O=C(O)c1cccc(C#Cc2ccccc2)c1-n1cnc2ccccc21]

2-Benzoimidazol-1-yl-3-phenylethynyl-benzoic acid prepared by the same procedure as example 293. $^1$H NMR (300 MHz, CD$_3$OD) δ=8.32 (d, J=7.6 Hz, 1H), 8.15-7.95 (m, 1H), 7.95-7.80 (m, 1H), 7.71-7.52 (m, 2H), 7.48 (br. s., 1H), 7.33-7.14 (m, 5H), 6.85 (d, J=7.3 Hz, 2H). MS (ESI) m/z 339.1 (M+1)$^+$.

Example 298: Synthesis of 2-indazol-1-yl-3-phenylethynyl-benzoic acid

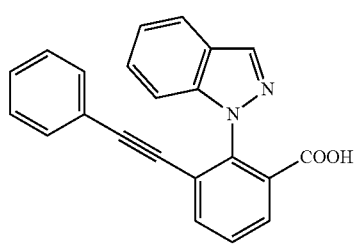 [SMILES: O=C(O)c1cccc(C#Cc2ccccc2)c1-n1ncc2ccccc21]

2-Indazol-1-yl-3-phenylethynyl-benzoic acid prepared by the same procedure as example 293. $^1$H NMR (300 MHz, CD$_3$OD) δ=8.27 (d, J=0.9 Hz, 1H), 8.03 (dd, J=1.6, 7.8 Hz, 1H), 7.93-7.85 (m, 2H), 7.67 (t, J=7.8 Hz, 1H), 7.45-7.37 (m, 1H), 7.31-7.10 (m, 5H), 6.78-6.73 (m, 2H). MS (ESI) m/z 339.1 (M+1)$^+$.

Example 299: Synthesis of 2-indol-1-yl-3-phenylethynyl-benzoic acid

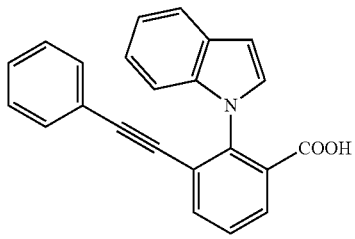 [SMILES: O=C(O)c1cccc(C#Cc2ccccc2)c1-n1ccc2ccccc21]

2-Indol-1-yl-3-phenylethynyl-benzoic acid prepared by the same procedure as example 293. $^1$H NMR (300 MHz, CD$_3$OD) δ=7.97-7.92 (m, 1H), 7.87-7.83 (m, 1H), 7.66-7.57 (m, 2H), 7.30-6.97 (m, 7H), 6.88-6.82 (m, 2H), 6.67 (d, J=3.2 Hz, 1H). MS (ESI) m/z 338.0 (M+1)$^+$.

Example 300: Synthesis of 2-benzoimidazol-1-yl-3-pyridin-4-ylethynyl-benzoic acid

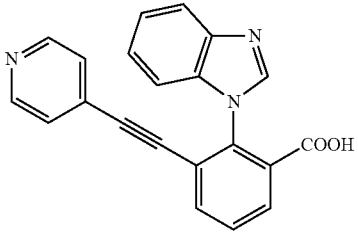 [SMILES: O=C(O)c1cccc(C#Cc2ccncc2)c1-n1cnc2ccccc21]

2-Benzoimidazol-1-yl-3-pyridin-4-ylethynyl-benzoic acid was prepared by the same procedure as example 293. $^1$H NMR (300 MHz, CD$_3$OD) δ=8.55 (d, J=6.3 Hz, 2H), 8.30 (d, J=7.4 Hz, 1H), 8.15-7.95 (m, 1H), 7.93-7.79 (m, 1H), 7.72-7.51 (m, 2H), 7.44 (br. s., 1H), 7.25 (d, J=6.1 Hz, 2H), 6.88 (d, J=7.3 Hz, 2H). MS (ESI) m/z 340.1 (M+1)$^+$.

Formulations

The present invention also relates to compositions or formulations which comprise the EBNA1 inhibitors according to the present invention. In general, the compositions of the present invention comprise an effective amount of one or more EBNA1 inhibitors and salts thereof according to the present invention which are effective and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally, intravenously (both bolus and infusion), intraperitoneally, subcutaneously, intramuscular, or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known EBNA1 inhibitors. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intravenous, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intra-nasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intra-bronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795, incorporated herein by reference.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame seed oil, benzyl alcohol, sodium chloride, tragacanth gum, or various buffers. Other adjuvants and modes of administration are well and widely known in the pharmaceutical art. The active ingredient may also be administered by injection as a composition with suitable carriers including saline, dextrose, or water, or with cyclo-dextrin (i.e. Captisol), cosolvent solubilization (i.e. propylene glycol), or micellar solubilization (i.e., Tween 80).

The sterile injectable preparation may also be a sterile injectable solution or suspension in a non-toxic parenterally acceptable diluent or solvent, for example as a solution in 1,3 butanediol. Among the acceptable vehicles and solvents that may be employed are water, Ringer's solution, isotonic sodium chloride solution. In addition, sterile, fixed oils are conventionally employed as a solvent or suspending medium. For this purpose and blan fixed oil may be employed, including synthetic mono- or diglycerides. In addition, fatty acids such as oleic acid find use in the preparation of injectables. Aqueous solutions suitable for intravenous injection (bolus or infusion) are preferably buffered and the liquid diluent first rendered isotonic. Aqueous solutions suitable for intravenous injection (bolus or infusion) are preferably sterile as prepared by standard pharmaceutical techniques well known to those skilled in the art. Pharmaceutical compositions are preferably preserved against the contaminating action of microorganisms such as fungi and bacteria by standard pharmaceutical techniques well known to those skilled in the art.

The pharmaceutical forms suitable for injection can include sterile aqueous solutions or dispersions and sterile powders for the extemporaneous preparation of sterile injectable solutions or dispersions. In some embodiments, the form can be sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered trans-dermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more EBNA1 inhibitors according to the present invention and one or more excipients; from about 0.01 mg to about 100 mg of one or more EBNA1 inhibitors according to the present invention and one or more excipients; and from about 0.1 mg to about 10 mg of one or more EBNA1 inhibitors according to the present invention; and one or more excipients. Oral dosages of the present invention, when used for the indicated effects, will range between about 0.05 to 1000 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Infused dosages, intranasal dosages and transdermal dosages will range between 0.05 to 1000 mg/day. Subcutaneous, intravenous (bolus or infusion) and intraperitoneal dosages will range between 0.05 to 1000 mg/day. Effective plasma levels of the compounds of the present invention range from 0.002 mg/mL to 50 mg/mL. Compounds of the present invention may be administered in a single daily dose, or the total daily dosage may be administered in divided doses of two, three or four times daily.

Procedures

The following procedures can be utilized in evaluating and selecting compounds as EBNA1 inhibitors.

Inhibition of 5'-biotin-oPL4624 binding to His-EBNA1 using Alpha Screen technology: Assays were performed using the DNA binding domain of EBNA1 (amino acids 459-607), which was His-tagged (His-EBNA1) and the self-complementary biotinylated (bt) oligonucleotide with the sequence 5'-bt-GGGTAGCATATGCTATCTAGATAG-CAT-ATGCTACCC-3' (bt-oPL4624). The protein was expressed in E. coli and purified according to Barwell, et al. (Barwell J A, Bochkarev A, Pfuetzner R A, Tong H, Yang D S, Frappier L, Edwards A M. (1995) Overexpression, purification, and crystallization of the DNA binding and dimerization domains of the Epstein-Barr virus nuclear antigen 1. J Biol Chem. 270: 20556-9). The bt-oPL4624 oligonucleotide was purchased from Integrated DNA Technologies, Inc (IDT). AlphaScreen donor, acceptor beads and white, opaque 384-well assay plates were purchased from PerkinElmer, Inc.

Assays contained 15 nM His-EBNA1, 0.2 nM bt-oPL4624, 5 µg/mL AlphaScreen streptavidin donor beads and nickel chelate acceptor beads, and a series of concentrations of test compound ranging from 3.2 nM to 100 µM in a total volume of 40 µL assay buffer (25 mM Tris, pH 7.2, 160 mM NaCl, 1 mM $MgCl_2$). His-EBNA1 (30 nM) and bt-oPL4624 (0.4 nM) were preincubated with 10 µg/mL nickel chelate AlphaScreen acceptor bead, or 10 µg/mL streptavidin AlphaScreen donor bead, respectively, for 30 minutes at room temperature in assay buffer. Twenty microliters of His-EBNA1/acceptor bead mix and bt-oPL4624/donor bead mix were transferred to assay plates containing 0.4 µL of 1:3 serial dilutions of test compounds previously prepared in DMSO at concentrations ranging from 0.32 µM to 10 mM. Nonspecific binding was determined with 5 µg/mL AlphaScreen acceptor bead in the absence of His-EBNA1. After 2 hr incubation at room temperature, the AlphaScreen signal was measured on the Envision plate reader (PerkinElmer, Inc.) at 680 nm excitation and 570 nm emission. Inhibition values at each concentration of test compound were determined by setting 100% equal to raw data values in the absence of EBNA1 and 0% equal to the raw data values in the presence of EBNA1. Nonlinear regression fits of the inhibition values to a one-site dose-response equation were performed using GraphPad Prism. Results from screening of representative compounds of the disclosure are described in table 6.

TABLE 6

Inhibition of 5'-biotin-oPL4624 binding to His-EBNA1 of representative compounds of the disclosure using Alpha Screen technology:

| Entry | Compound | Alpha Screen Activity |
|---|---|---|
| 1 | 3-{2-[3-(methylsulfamoyl)phenyl]ethynyl}-2-(1H-pyrrol-1-yl)benzoic acid | +++ |
| 2 | 3-[2-(1H-indol-3-yl)ethynyl]-2-(1H-pyrrol-1-yl)benzoic acid | ++++ |
| 3 | 3-[2-(3-methanesulfonamidophenyl)ethynyl]-2-(1H-pyrrol-1-yl)benzoic acid | ++++ |
| 4 | 2-(1H-pyrrol-1-yl)-3-[2-(3-sulfamoylphenyl)ethynyl]benzoic acid | ++++ |
| 5 | 3-[2-(3-carbamoylphenyl)ethynyl]-2-(1H-pyrrol-1-yl)benzoic acid | ++++ |
| 6 | 3-(2-{imidazo[1,2-a]pyridin-6-yl}ethynyl)-2-(1H-pyrrol-1-yl)benzoic acid | ++ |

TABLE 6-continued

Inhibition of 5'-biotin-oPL4624 binding to His-EBNA1 of representative compounds of the disclosure using Alpha Screen technology:

| Entry | Compound | Alpha Screen Activity |
|---|---|---|
| 7 | 3-[2-(2-hydroxypyridin-4-yl)ethynyl]-2-(1H-pyrrol-1-yl)benzoic acid | ++ |
| 8 | 3-[2-(1H-indazol-6-yl)ethynyl]-2-(1H-pyrrol-1-yl)benzoic acid | +++ |
| 9 | 3-{2-[3-(3,3-dimethyl-2-oxoazetidin-1-yl)phenyl]ethynyl}-2-(1H-pyrrol-1-yl)benzoic acid | ++++ |
| 10 | 3-(2-{3-[(2-carboxy-2,2-dimethylethyl)amino]phenyl}ethynyl)-2-(1H-pyrrol-1-yl)benzoic acid | +++ |
| 11 | 3-(2-{imidazo[1,2-a]pyrazin-3-yl}ethynyl)-2-(1H-pyrrol-1-yl)benzoic acid | ++++ |
| 12 | 3-(2-{imidazo[1,2-a]pyridin-3-yl}ethynyl)-2-(1H-pyrrol-1-yl)benzoic acid | ++++ |
| 13 | 3-(2-{imidazo[1,2-a]pyridin-5-yl}ethynyl)-2-(1H-pyrrol-1-yl)benzoic acid | ++ |
| 14 | 2-(1H-pyrrol-1-yl)-3-(2-{1H-pyrrolo[2,3-b]pyridin-5-yl}ethynyl)benzoic acid | +++ |
| 15 | 3-[2-(1-methyl-1H-indol-4-yl)ethynyl]-2-(1H-pyrrol-1-yl)benzoic acid | ++++ |
| 16 | 3-[2-(1-methyl-1H-indol-5-yl)ethynyl]-2-(1H-pyrrol-1-yl)benzoic acid | ++++ |
| 17 | 3-[2-(1-benzothiophen-6-yl)ethynyl]-2-(1H-pyrrol-1-yl)benzoic acid | +++ |
| 18 | 3-[2-(1H-indol-7-yl)ethynyl]-2-(1H-pyrrol-1-yl)benzoic acid | ++++ |
| 19 | 3-{2-[2-(hydroxymethyl)phenyl]ethynyl}-2-(1H-pyrrol-1-yl)benzoic acid | ++++ |
| 20 | 3-{2-[4-(hydroxymethyl)phenyl]ethynyl}-2-(1H-pyrrol-1-yl)benzoic acid | ++++ |
| 21 | 2-(2,5-dimethyl-1H-pyrrol-1-yl)-3-[2-(4-methylphenyl)ethynyl]benzoic acid | ++++ |
| 22 | 2-(2,5-dimethyl-1H-pyrrol-1-yl)-3-[2-(3-hydroxyphenyl)ethynyl]benzoic acid | ++++ |
| 23 | 3-[2-(2,3-dihydro-1H-indol-6-yl)ethynyl]-2-(1H-pyrrol-1-yl)benzoic acid | ++++ |
| 24 | 3-[2-(1-methyl-1H-pyrazol-4-yl)ethynyl]-2-(1H-pyrrol-1-yl)benzoic acid | +++ |
| 25 | 3-[2-(1,2-dimethyl-1H-imidazol-4-yl)ethynyl]-2-(1H-pyrrol-1-yl)benzoic acid | ++ |
| 26 | 3-[2-(1-methyl-1H-imidazol-5-yl)ethynyl]-2-(1H-pyrrol-1-yl)benzoic acid | ++ |
| 27 | 3-[2-(1-methyl-1H-imidazol-2-yl)ethynyl]-2-(1H-pyrrol-1-yl)benzoic acid | ++ |
| 28 | 2-(1H-pyrrol-1-yl)-3-[2-(1,3-thiazol-5-yl)ethynyl]benzoic acid | ++ |
| 29 | 2-(1H-pyrrol-1-yl)-3-[2-(1,3-thiazol-4-yl)ethynyl]benzoic acid | ++++ |
| 30 | 2-(1H-pyrrol-1-yl)-3-(2-{1H-pyrrolo[2,3-b]pyridin-6-yl}ethynyl)benzoic acid | +++ |
| 31 | 3-{2-[3-(2-hydroxypropan-2-yl)phenyl]ethynyl}-2-(1H-pyrrol-1-yl)benzoic acid | +++ |
| 32 | 3-(3-hydroxy-4-methylpent-1-yn-1-yl)-2-(1H-pyrrol-1-yl)benzoic acid | +++ |
| 33 | 3-(3-hydroxy-3-phenylprop-1-yn-1-yl)-2-(1H-pyrrol-1-yl)benzoic acid | ++++ |
| 34 | 2-(1H-pyrrol-1-yl)-3-(2-{1H-pyrrolo[2,3-b]pyridin-3-yl}ethynyl)benzoic acid | ++++ |
| 35 | 3-[2-(1H-indol-4-yl)ethynyl]-2-(1H-pyrrol-1-yl)benzoic acid | ++++ |
| 36 | 2-(1H-pyrrol-1-yl)-3-(2-{[1,2,4]triazolo[1,5-a]pyridin-7-yl}ethynyl)benzoic acid | ++++ |
| 37 | 3-{2-[3-(dimethylsulfamoyl)phenyl]ethynyl}-2-(1H-pyrrol-1-yl)benzoic acid | ++++ |
| 38 | 3-[2-(3-fluoro-5-hydroxyphenyl)ethynyl]-2-(1H-pyrrol-1-yl)benzoic acid | ++++ |
| 39 | 3-{2-[3-(hydroxymethyl)phenyl]ethynyl}-2-(1H-pyrrol-1-yl)benzoic acid | ++++ |
| 40 | 3-[2-(5-hydroxypyridin-3-yl)ethynyl]-2-(1H-pyrrol-1-yl)benzoic acid | ++ |
| 41 | 3-[2-(1H-1,3-benzodiazol-5-yl)ethynyl]-2-(1H-pyrrol-1-yl)benzoic acid | +++ |
| 42 | 3-[2-(1H-indol-5-yl)ethynyl]-2-(1H-pyrrol-1-yl)benzoic acid | +++ |
| 43 | 3-[2-(1H-indol-6-yl)ethynyl]-2-(1H-pyrrol-1-yl)benzoic acid | ++++ |
| 44 | 3-[2-(4-methylphenyl)ethynyl]-2-(1H-pyrrol-1-yl)benzoic acid | ++++ |
| 45 | 3-[2-(3,5-difluorophenyl)ethynyl]-2-(1H-pyrrol-1-yl)benzoic acid | +++ |
| 46 | 3-{2-[3-(difluoromethoxy)phenyl]ethynyl}-2-(1H-pyrrol-1-yl)benzoic acid | +++ |
| 47 | 3-ethynyl-2-(1H-pyrrol-1-yl)benzoic acid | ++ |
| 48 | 3-(3-amino-3-methylbut-1-yn-1-yl)-2-(1H-pyrrol-1-yl)benzoic acid | + |
| 49 | 3-(3,3-dimethylbut-1-yn-1-yl)-2-(1H-pyrrol-1-yl)benzoic acid | +++ |

TABLE 6-continued

Inhibition of 5'-biotin-oPL4624 binding to His-EBNA1 of representative compounds of the disclosure using Alpha Screen technology:

| Entry | Compound | Alpha Screen Activity |
|---|---|---|
| 50 | 2-(2,5-dimethyl-1H-pyrrol-1-yl)-3-(2-phenylethynyl)benzoic acid | ++++ |
| 51 | 5-[2-(4-fluorophenyl)ethynyl]-4-(1H-pyrrol-1-yl)pyridine-3-carboxylic acid | +++ |
| 52 | 5-(2-phenylethynyl)-4-(1H-pyrrol-1-yl)pyridine-3-carboxylic acid | ++ |
| 53 | 3-[2-(1-aminocyclohexyl)ethynyl]-2-(1H-pyrrol-1-yl)benzoic acid; trifluoroacetic acid | ++++ |
| 54 | 3-[2-(1-hydroxycyclohexyl)ethynyl]-2-(1H-pyrrol-1-yl)benzoic acid | +++ |
| 55 | 3-(4-ethyl-3-hydroxyoct-1-yn-1-yl)-2-(1H-pyrrol-1-yl)benzoic acid | ++++ |
| 56 | 3-(2-{imidazo[1,2-a]pyrazin-6-yl}ethynyl)-2-(1H-pyrrol-1-yl)benzoic acid | ++++ |
| 57 | 3-[2-(3-hydroxyphenyl)ethynyl]-2-(1H-pyrrol-1-yl)benzoic acid | ++++ |
| 58 | 5-chloro-3-[2-(4-fluorophenyl)ethynyl]-2-(1H-pyrrol-1-yl)benzoic acid | ++ |
| 59 | 5-chloro-3-(2-phenylethynyl)-2-(1H-pyrrol-1-yl)benzoic acid | ++ |
| 60 | 5-fluoro-3-[2-(4-fluorophenyl)ethynyl]-2-(1H-pyrrol-1-yl)benzoic acid | + |
| 61 | 5-fluoro-3-(2-phenylethynyl)-2-(1H-pyrrol-1-yl)benzoic acid | ++ |
| 62 | 3-(2-cyclopropylethynyl)-2-(1H-pyrrol-1-yl)benzoic acid | ++++ |
| 63 | 3-(3-hydroxy-3-methylbut-1-yn-1-yl)-2-(1H-pyrrol-1-yl)benzoic acid | ++++ |
| 64 | 3-[3-(dimethylamino)prop-1-yn-1-yl]-2-(1H-pyrrol-1-yl)benzoic acid | + |
| 65 | 3-(4-phenylbut-1-yn-1-yl)-2-(1H-pyrrol-1-yl)benzoic acid | ++++ |
| 66 | 3-(5-hydroxypent-1-yn-1-yl)-2-(1H-pyrrol-1-yl)benzoic acid | ++++ |
| 67 | 3-[2-(4-methoxyphenyl)ethynyl]-2-(1H-pyrrol-1-yl)benzoic acid | +++ |
| 68 | 3-[2-(pyridin-4-yl)ethynyl]-2-(1H-pyrrol-1-yl)benzoic acid | ++++ |
| 69 | 3-[2-(pyridin-3-yl)ethynyl]-2-(1H-pyrrol-1-yl)benzoic acid | ++ |
| 70 | 3-[2-(3-methoxyphenyl)ethynyl]-2-(1H-pyrrol-1-yl)benzoic acid | +++ |
| 71 | 3-[2-(4-fluorophenyl)ethynyl]-2-(1H-pyrrol-1-yl)benzoic acid | +++ |
| 72 | 3-(2-phenylethynyl)-2-(1H-pyrrol-1-yl)benzoic acid | ++++ |
| 73 | 3-{3-[benzyl(methyl)amino]prop-1-yn-1-yl}-2-(1H-pyrrol-1-yl)benzoic acid | ++++ |
| 74 | 3-[3-(1H-imidazol-1-yl)prop-1-yn-1-yl]-2-(1H-pyrrol-1-yl)benzoic acid | ++++ |
| 75 | 3-[2-(1,3-thiazol-4-yl)ethynyl]benzoic acid | ++ |
| 76 | 3-(2-{1H-pyrrolo[2,3-b]pyridin-3-yl}ethynyl)benzoic acid | ++ |
| 77 | 3-[2-(1H-indol-5-yl)ethynyl]benzoic acid | ++++ |
| 78 | 2-amino-3-(2-{1H-pyrrolo[2,3-b]pyridin-3-yl}ethynyl)benzoic acid | ++++ |
| 79 | 2-amino-3-[2-(1H-indol-4-yl)ethynyl]benzoic acid | ++++ |
| 80 | 2-amino-3-[2-(1H-indol-6-yl)ethynyl]benzoic acid | ++++ |
| 81 | 2-amino-3-[2-(1H-indol-5-yl)ethynyl]benzoic acid | ++++ |
| 82 | 2-amino-3-{2-[3-(hydroxymethyl)phenyl]ethynyl}benzoic acid | +++ |
| 83 | 2-amino-3-[2-(3-hydroxyphenyl)ethynyl]benzoic acid | +++ |
| 84 | 2-amino-3-(2-phenylethynyl)benzoic acid | ++ |
| 85 | 2-fluoro-3-(2-phenylethynyl)benzoic acid | +++ |
| 86 | 2-fluoro-3-(2-{1H-pyrrolo[2,3-b]pyridin-3-yl}ethynyl)benzoic acid | ++ |
| 87 | 2-fluoro-3-(2-{imidazo[1,2-a]pyrazin-3-yl}ethynyl)benzoic acid | ++++ |
| 88 | 2-fluoro-3-{2-[2-(hydroxymethyl)phenyl]ethynyl}benzoic acid | +++ |
| 89 | 2-fluoro-3-[2-(1,3-thiazol-4-yl)ethynyl]benzoic acid | +++ |
| 90 | 3-[2-(pyridin-2-yl)ethynyl]benzoic acid | + |
| 91 | 3-[2-(pyridin-3-yl)ethynyl]benzoic acid | +++ |
| 92 | 3-(2-phenylethynyl)benzoic acid | ++ |
| 93 | 3-[2-(pyridin-4-yl)ethynyl]benzoic acid | +++ |
| 94 | 3-[2-(4-methoxyphenyl)ethynyl]benzoic acid | + |
| 95 | 2-{4-[(dimethylamino)methyl]phenyl}-3-(2-phenylethynyl)benzoic acid trifluoroacetic acid salt | +++ |
| 96 | 3-(2-phenylethynyl)-2-(1,2,3,6-tetrahydropyridin-4-yl)benzoic acid trifluoroacetic acid salt | +++ |
| 97 | 3-(2-phenylethynyl)-2-(pyridin-4-yl)benzoic acid trifluoroacetic acid salt | ++ |
| 98 | 2-(4-methanesulfonylphenyl)-3-(2-phenylethynyl)benzoic acid | ++ |
| 99 | 3-(2-phenylethynyl)-2-(1H-pyrazol-4-yl)benzoic acid | +++ |
| 100 | 3-(2-phenylethynyl)-2-(pyrimidin-5-yl)benzoic acid | + |
| 101 | 2-(1-methyl-1H-pyrazol-4-yl)-3-(2-phenylethynyl)benzoic acid | +++ |
| 102 | 3-(2-phenylethynyl)-2-(2-phenylpyrrolidin-1-yl)benzoic acid | +++ |
| 103 | 2-[3-(dimethylamino)pyrrolidin-1-yl]-3-(2-phenylethynyl)benzoic acid | ++ |
| 104 | 1-[2-carboxy-6-(2-phenylethynyl)phenyl]pyrrolidine-3-carboxylic acid | ++ |
| 105 | 2-[(3S)-3-hydroxypyrrolidin-1-yl]-3-(2-phenylethynyl)benzoic acid | + |
| 106 | 3-(2-phenylethynyl)-2-(pyrrolidin-1-yl)benzoic acid | ++ |
| 107 | 3-(2-phenylethynyl)-2-(piperazin-1-yl)benzoic acid | ++ |
| 108 | 2-(benzylamino)-3-(2-phenylethynyl)benzoic acid | ++ |

TABLE 6-continued

Inhibition of 5'-biotin-oPL4624 binding to His-EBNA1 of representative compounds of the disclosure using Alpha Screen technology:

| Entry | Compound | Alpha Screen Activity |
|---|---|---|
| 109 | 2-(4-phenyl-1H-1,2,3-triazol-1-yl)-3-(2-phenylethynyl)benzoic acid | ++ |
| 110 | 2-[4-(3-methoxyphenyl)-1H-1,2,3-triazol-1-yl]-3-(2-phenylethynyl)benzoic acid | ++ |
| 111 | 3-(2-phenylethynyl)-2-[4-(pyridin-3-yl)-1H-1,2,3-triazol-1-yl] benzoic acid | ++ |
| 112 | 2-[4-(3-hydroxypropyl)-1H-1,2,3-triazol-1-yl]-3-(2-phenylethynyl)benzoic acid | ++ |
| 113 | N-(dimethylsulfamoyl)-3-(2-phenylethynyl)-2-(1H-pyrrol-1-yl)benzamide | +++ |
| 114 | N-(dimethylsulfamoyl)-3-[2-(4-fluorophenyl)ethynyl]-2-(1H-pyrrol-1-yl)benzamide | +++ |
| 115 | N-(morpholine-4-sulfonyl)-3-(2-phenylethynyl)-2-(1H-pyrrol-1-yl)benzamide | + |
| 116 | N-[(1,1-dioxo-4-thiomorpholin-4-yl)sulfonyl]-3-(2-phenylethynyl)-2-(1H-pyrrol-1-yl)benzamide | ++ |
| 117 | 3-[2-(4-fluorophenyl)ethynyl]-N-methanesulfonyl-2-(1H-pyrrol-1-yl)benzamide | ++ |
| 118 | 3-(2-phenylethynyl)-2-(1H-pyrrol-1-yl)-N-sulfamoylbenzamide | ++ |
| 119 | 2-(4-methoxyphenyl)-3-(2-phenylethynyl)benzoic acid | +++ |
| 120 | 2-(3-methoxyphenyl)-3-(2-phenylethynyl)benzoic acid | +++ |
| 121 | 2-(2-methoxyphenyl)-3-(2-phenylethynyl)benzoic acid | ++ |
| 122 | 3-(2-phenylethynyl)-2-(quinolin-3-yl)benzoic acid | ++ |
| 123 | 2-cyclopropyl-3-(2-phenylethynyl)benzoic acid | +++ |
| 124 | 2-phenyl-3-(2-phenylethynyl)benzoic acid | ++ |
| 125 | 2-(4-methylphenyl)-3-(2-phenylethynyl)benzoic acid | +++ |
| 126 | 2-(6-methoxypyridin-3-yl)-3-(2-phenylethynyl)benzoic acid | ++ |
| 127 | 2-[6-(dimethylamino)pyridin-3-yl]-3-(2-phenylethynyl)benzoic acid | ++ |
| 128 | 2-[3-(hydroxymethyl)phenyl]-3-(2-phenylethynyl)benzoic acid | ++ |
| 129 | 2-(1H-indol-6-yl)-3-(2-phenylethynyl)benzoic acid | ++++ |
| 130 | 2-[4-(hydroxymethyl)phenyl]-3-(2-phenylethynyl)benzoic acid | ++ |
| 131 | 2-(1-benzofuran-5-yl)-3-(2-phenylethynyl)benzoic acid | ++ |
| 132 | 2-(1-benzothiophen-5-yl)-3-(2-phenylethynyl)benzoic acid | ++ |
| 133 | 2-(1-methyl-1H-indol-5-yl)-3-(2-phenylethynyl)benzoic acid | +++ |
| 134 | 2-(3-methanesulfonamidophenyl)-3-(2-phenylethynyl)benzoic acid | +++ |
| 135 | 2-(naphthalen-2-yl)-3-(2-phenylethynyl)benzoic acid | +++ |
| 136 | 2-(1-methyl-1H-indol-6-yl)-3-(2-phenylethynyl)benzoic acid | +++ |
| 137 | 2-{2-[(2-hydroxyethyl)sulfamoyl]phenyl}-3-(2-phenylethynyl)benzoic acid | ++ |
| 138 | 2-[4-(cyclopropylcarbamoyl)phenyl]-3-(2-phenylethynyl)benzoic acid | ++ |
| 139 | 2-(1-methyl-1H-indazol-6-yl)-3-(2-phenylethynyl)benzoic acid | ++ |
| 140 | 3-[2-(3-hydroxyphenyl)ethynyl]-2-(quinolin-3-yl)benzoic acid | +++ |
| 141 | 3-(5-hydroxypent-1-yn-1-yl)-2-(quinolin-3-yl)benzoic acid | ++ |
| 142 | 3-[2-(4-methoxyphenyl)ethynyl]-2-(quinolin-3-yl)benzoic acid | ++ |
| 143 | 3-(2-{imidazo[1,2-a]pyrazin-3-yl}ethynyl)-2-(quinolin-3-yl)benzoic acid | +++ |
| 144 | 3-[(1E)-3-methoxyprop-1-en-1-yl]-2-(1H-pyrrol-1-yl)benzoic acid | +++ |
| 145 | 3-[(E)-2-phenylethenyl]-2-(1H-pyrrol-1-yl)benzoic acid | ++ |
| 146 | 3-[(E)-2-(4-fluorophenyl)ethenyl]-2-(1H-pyrrol-1-yl)benzoic acid | ++ |
| 147 | 3-(2-phenylethyl)-2-(1H-pyrrol-1-yl)benzoic acid | ++ |
| 148 | 3-(2-phenylethyl)-2-(pyrrolidin-1-yl)benzoic acid | ++ |
| 149 | 3-[2-(4-fluorophenyl)ethyl]-2-(1H-pyrrol-1-yl)benzoic acid | ++ |
| 150 | 2-(1H-1,3-benzodiazol-6-yl)-3-(2-phenylethynyl)benzoic acid | ++ |
| 151 | 2-(quinolin-3-yl)-3-[2-(1,3-thiazol-4-yl)ethynyl]benzoic acid | ++ |
| 152 | 3-(2-phenylethynyl)-2-(1H-pyrrol-1-yl)benzene-1-sulfonamide | +++ |
| 153 | N-[3-(2-phenylethynyl)-2-(1H-pyrrol-1-yl)benzenesulfonyl]acetamide | ++ |
| 154 | 2-(dimethyl-1,2-oxazol-4-yl)-3-(2-phenylethynyl)benzoic acid | +++ |
| 155 | 2-(benzyloxy)-3-(2-phenylethynyl)benzoic acid | ++ |
| 156 | 2-[3-(methoxycarbonyl)-1H-indol-6-yl]-3-(2-phenylethynyl)benzoic acid | +++ |
| 157 | 3-[3-(benzylamino)prop-1-yn-1-yl]-2-phenylbenzoic acid | ++ |
| 158 | 3-(3-{[3-(1H-imidazol-1-yl)propyl]amino}prop-1-yn-1-yl)-2-phenylbenzoic acid | ++ |
| 159 | 2-phenyl-3-[3-(4-phenylpiperazin-1-yl)prop-1-yn-1-yl]benzoic acid | ++ |
| 160 | 2-phenyl-3-[3-(pyrrolidin-1-yl)prop-1-yn-1-yl]benzoic acid | ++ |
| 161 | 3-(3-hydroxyprop-1-yn-1-yl)-2-phenylbenzoic acid | + |
| 162 | 3-{2-[3-(aminomethyl)phenyl]ethynyl}-2-(1H-pyrrol-1-yl)benzoic acid | +++ |
| 163 | 3-{2-[3-(3,5-difluorobenzenesulfonamidomethyl)phenyl]ethynyl}-2-(1H-pyrrol-1-yl)benzoic acid | +++ |

TABLE 6-continued

Inhibition of 5'-biotin-oPL4624 binding to His-EBNA1 of representative compounds of the disclosure using Alpha Screen technology:

| Entry | Compound | Alpha Screen Activity |
|---|---|---|
| 164 | 3-{2-[4-(1,2-dimethyl-1H-imidazole-5-sulfonamidomethyl)phenyl]ethynyl}-2-(1H-pyrrol-1-yl)benzoic acid | +++ |
| 165 | 3-{2-[3-(cyclopropanesulfonamidomethyl)phenyl]ethynyl}-2-(1H-pyrrol-1-yl)benzoic acid | ++++ |
| 166 | 2-(3-methoxyphenyl)-3-(2-{1H-pyrrolo[2,3-b]pyridin-3-yl}ethynyl)benzoic acid | ++ |
| 167 | 2-(1-methyl-1H-indazol-6-yl)-3-(2-{1H-pyrrolo[2,3-b]pyridin-3-yl}ethynyl)benzoic acid | ++ |
| 168 | 2-(2-methyl-1,3-benzothiazol-5-yl)-3-(2-{1H-pyrrolo[2,3-b]pyridin-3-yl}ethynyl)benzoic acid | ++ |
| 169 | 2-(3-methoxyphenyl)-3-[2-(1,3-thiazol-4-yl)ethynyl]benzoic acid | ++ |
| 170 | 2-(1-methyl-1H-indazol-6-yl)-3-[2-(1,3-thiazol-4-yl)ethynyl] benzoic acid | +++ |
| 171 | 2-(1-methyl-1H-indol-5-yl)-3-[2-(1,3-thiazol-4-yl)ethynyl]benzoic acid | +++ |
| 172 | 2-(pyridin-4-yl)-3-[2-(1,3-thiazol-4-yl)ethynyl]benzoic acid | ++ |
| 173 | 2-(2-methyl-1,3-benzothiazol-5-yl)-3-[2-(1,3-thiazol-4-yl)ethynyl] benzoic acid | ++ |
| 174 | 2-(1H-indol-3-yl)-3-[2-(pyridin-4-yl)ethynyl]benzoic acid | +++ |
| 175 | 2-[4-(dimethylamino)phenyl]-3-[2-(pyridin-4-yl)ethynyl]benzoic acid | ++ |
| 176 | 2-(4-methyl-3,4-dihydro-2H-1,4-benzoxazin-6-yl)-3-[2-(pyridin-4-yl)ethynyl]benzoic acid | ++ |
| 177 | 2-phenyl-3-[2-(pyridin-4-yl)ethynyl]benzoic acid | + |
| 178 | 6-(3-carboxy-phenylethynyl)-1H-indole-4-carboxylic acid | +++ |
| 179 | 3-(4-carbamoyl-1H-indol-6-ylethynyl)-benzoic acid | +++ |
| 180 | 3-(3-carbamoyl-phenylethynyl)-benzoic acid | ++++ |
| 181 | 3-(1-benzenesulfonyl-1H-indol-3-ylethynyl)-benzoic acid | ++ |
| 182 | 3-(1H-indol-3-ylethynyl)-benzoic acid | ++ |
| 183 | 3-(3-carboxy-phenylethynyl)-benzoic acid methyl ester | + |
| 184 | 3-(3-carbamoyl-5-methoxy-phenylethynyl)-benzoic acid | ++ |
| 185 | 3'-hydroxy-4'-methoxy-6-pyridin-4-ylethynyl-biphenyl-2-carboxylic acid | + |
| 186 | 5'-hydroxy-3'-methoxy-6-pyridin-4-ylethynyl-biphenyl-2-carboxylic acid | ++ |
| 187 | 2-(1H-pyrazol-3-yl)-3-pyridin-4-ylethynyl-benzoic acid | ++ |
| 188 | 2-(1H-pyrazol-4-yl)-3-pyridin-4-ylethynyl-benzoic acid | + |
| 189 | 2-(3,5-dimethyl-isoxazol-4-yl)-3-pyridin-4-ylethynyl-benzoic acid | ++ |
| 190 | 3-phenylethynyl-2-(1,3,5-trimethyl-1H-pyrazol-4-yl)-benzoic acid | + |
| 191 | 2-(2,5-dimethyl-pyrrol-1-yl)-3-(3-hydroxy-3-methyl-but-1-ynyl)-benzoic acid | ++ |
| 192 | 2-(2,5-dimethyl-pyrrol-1-yl)-3-pyridin-4-ylethynyl-benzoic acid | ++ |
| 193 | 3-(3-carbamoyl-phenylethynyl)-2-(2,5-dimethyl-pyrrol-1-yl)-benzoic acid | +++ |
| 194 | 3-(3-carboxy-phenylethynyl)-2-(2,5-dimethyl-pyrrol-1-yl)-benzoic acid | ++++ |
| 195 | 2-(2,5-dimethyl-pyrrol-1-yl)-3-(3-hydroxymethyl-phenylethynyl)-benzoic acid | ++ |
| 196 | 2-(2,5-dimethyl-pyrrol-1-yl)-3-(1H-pyrrolo[2,3-b]pyridin-3-ylethynyl)-benzoic acid | +++ |
| 197 | 2-(2,5-dimethyl-pyrrol-1-yl)-3-(3-hydroxy-3-phenyl-prop-1-ynyl)-benzoic acid | ++ |
| 198 | 3-(3-acetylamino-phenylethynyl)-2-(2,5-dimethyl-pyrrol-1-yl)-benzoic acid | ++ |
| 199 | 3-cyclopropylethynyl-2-(2,5-dimethyl-pyrrol-1-yl)-benzoic acid | +++ |
| 200 | 2-(2,5-dimethyl-pyrrol-1-yl)-3-(3-methoxy-phenylethynyl)-benzoic acid | +++ |
| 201 | 2-(1H-indazol-6-yl)-3-phenylethynyl-benzoic acid | ++ |
| 202 | 2-benzo[1,3]dioxol-5-yl-3-phenylethynyl-benzoic acid | ++ |
| 203 | 2-isoquinolin-6-yl-3-phenylethynyl-benzoic acid | ++ |
| 204 | 2-benzofuran-2-yl-3-phenylethynyl-benzoic acid | +++ |
| 205 | 3-phenylethynyl-2-quinolin-8-yl-benzoic acid | ++ |
| 206 | 2-(2-amino-pyrimidin-5-yl)-3-phenylethynyl-benzoic acid | + |
| 207 | 4'-dimethylaminomethyl-6-phenylethynyl-biphenyl-2-carboxylic acid | + |
| 208 | 3-(4-amino-phenylethynyl)-2-(1H-indol-6-yl)-benzoic acid | +++ |
| 209 | 3-(4-carboxy-phenylethynyl)-2-(1H-indol-6-yl)-benzoic acid | ++++ |
| 210 | 2-(1H-indol-6-yl)-3-(4-methoxy-phenylethynyl)-benzoic acid | +++ |
| 211 | 3-(4-carbamoyl-phenylethynyl)-2-(1H-indol-6-yl)-benzoic acid | +++ |
| 212 | 2-(1H-indol-6-yl)-3-[4-(piperazine-1-carbonyl)-phenylethynyl]-benzoic acid | +++ |

TABLE 6-continued

Inhibition of 5'-biotin-oPL4624 binding to His-EBNA1 of representative compounds of the disclosure using Alpha Screen technology:

| Entry | Compound | Alpha Screen Activity |
|---|---|---|
| 213 | 3-(4-acetylamino-phenylethynyl)-2-(1H-indol-6-yl)-benzoic acid | ++ |
| 214 | 2-(1H-indol-6-yl)-3-{4-[(pyridine-3-carbonyl)-amino]-phenylethynyl}-benzoic acid | ++++ |
| 215 | 2-(1H-indol-6-yl)-3-(4-methanesulfonylamino-phenylethynyl)-benzoic acid | +++ |
| 216 | 2-(1H-indol-6-yl)-3-[4-(thiophene-2-sulfonylamino)-phenylethynyl]-benzoic acid | +++ |
| 217 | 2-(3-(Methoxycarbonyl)-1H-indol-6-yl)-3-(thiazol-4-ylethynyl)benzoic acid | +++ |
| 218 | 2-(1H-indol-6-yl)-3-(thiazol-4-ylethynyl)benzoic acid | +++ |
| 219 | 2-(1-methyl-1H-pyrazol-4-yl)-3-(thiazol-4-ylethynyl) benzoic acid | ++ |
| 220 | 3-((3-hydroxyphenyl)ethynyl)-2-(1-methyl-1H-pyrazol-4-yl)benzoic acid | +++ |
| 221 | 2-(3-chloro-1H-indol-6-yl)-3-((3-hydroxyphenyl)ethynyl)benzoic acid | +++ |
| 222 | 3-((3-hydroxyphenyl)ethynyl)-2-(1H-indazol-6-yl)benzoic acid | +++ |
| 223 | 2-(3-(2-acetamidoethyl)-1H-indol-6-yl)-3-((3-hydroxyphenyl)ethynyl)benzoic acid | +++ |
| 224 | 3-((3-(N,N-dimethylsulfamoyl)phenyl)ethynyl)-2-fluorobenzoic acid | ++ |
| 225 | 2-(1H-indol-6-yl)-3-((4-(tetrahydro-2H-pyran-4-yloxy)phenyl)ethynyl)benzoic acid | ++++ |
| 226 | 2-(1H-indol-6-yl)-3-((4-morpholinophenyl)ethynyl)benzoic acid | ++ |
| 227 | 3-((3-carbamoylphenyl)ethynyl)-2-(1H-indol-6-yl)benzoic acid | ++ |
| 228 | 3-((4-Fluorophenyl)ethynyl)-2-(1H-indol-6-yl)benzoic acid | +++ |
| 229 | 3-((2,4-Difluorophenyl)ethynyl)-2-(1H-indol-6-yl)benzoic acid | +++ |
| 230 | 3-((3-Acetamidophenyl)ethynyl)-2-(1H-indol-6-yl)benzoic acid | ++++ |
| 231 | 2-(1H-indol-6-yl)-3-((3-(nicotinamido)phenyl)ethynyl)benzoic acid | +++ |
| 232 | 3-((3-(3-chloro-4-fluorophenylsulfonamido)phenyl)ethynyl)-2-(1H-indol-6-yl)benzoic acid | ++++ |
| 233 | 3-((3-aminophenyl)ethynyl)-2-(1H-indol-6-yl)benzoic acid | ++++ |
| 234 | 2-(1H-indol-6-yl)-3-((3-(methylsulfonamido)phenyl)ethynyl)benzoic acid | +++ |
| 235 | 2-(1H-indol-6-yl)-3-((3-(thiophene-2-sulfonamido)phenyl)ethynyl)benzoic acid | ++++ |
| 236 | 3-((3-acetamido-5-fluorophenyl)ethynyl)-2-(1H-indol-6-yl)benzoic acid | ++++ |
| 237 | 2-(indolin-6-yl)-3-(phenylethynyl)benzoic acid | ++ |
| 238 | 3-((3-hydroxyphenyl)ethynyl)-2-(indolin-6-yl)benzoic acid | +++ |
| 239 | 3-((6-aminopyridin-2-yl)ethynyl)-2-(1H-indol-6-yl)benzoic acid | +++ |
| 240 | 3-((2-aminopyridin-4-yl)ethynyl)-2-(1H-indol-6-yl)benzoic acid | +++ |
| 241 | 3-((3-hydroxyphenyl)ethynyl)-2-(5-methoxypyridin-3-yl)benzoic acid | ++ |
| 242 | 2-(benzo[d][1,3]dioxol-5-yl)-3-((3-hydroxyphenyl)ethynyl)benzoic acid | ++ |
| 243 | 3-((3-hydroxyphenyl)ethynyl)-2-(pyrimidin-5-yl)benzoic acid | ++ |
| 244 | 4'-Amino-6-((3-hydroxyphenyl)ethynyl)-5'-methoxybiphenyl-2-carboxylic acid | ++ |
| 245 | 3-(4-hydroxybut-1-ynyl)-2-(1H-indol-6-yl) benzoic acid | ++++ |
| 246 | 3-(3-amino-3-methylbut-1-ynyl)-2-(1H-indol-6-yl)benzoic acid | +++ |
| 247 | 3-(3-hydroxy-3-phenylprop-1-ynyl)-2-(1H-indol-6-yl)benzoic acid | ++++ |
| 248 | 3-(3-hydroxy-3-methylbut-1-ynyl)-2-(1H-indol-6-yl)benzoic acid | ++++ |
| 249 | 3-((3-(hydroxymethyl)phenyl)ethynyl)-2-(1H-indol-6-yl)benzoic acid | +++ |
| 250 | 6-(2-carboxy-6-(phenylethynyl)phenyl)-1H-indole-2-carboxylic acid | +++ |
| 251 | 2-(2-(ethoxycarbonyl)-1H-indol-6-yl)-3-(phenylethynyl)benzoic acid | +++ |
| 252 | 3-((3-carbamoyl-5-methoxyphenyl)ethynyl)-2-(1H-indol-6-yl)benzoic acid | +++ |
| 253 | 2-(1H-indol-5-yl)-3-(phenylethynyl)benzoic acid | +++ |
| 254 | 5-(2-carboxy-6-((3-hydroxyphenyl)ethynyl)phenyl)-1H-indole-2-carboxylic acid | ++ |
| 255 | 5-(2-carboxy-6-((4-methoxyphenyl)ethynyl)phenyl)-1H-indole-2-carboxylic acid | ++ |
| 256 | 3-((4-fluoro-3-(tetrahydro-2H-pyran-4-yloxy)phenyl)ethynyl)-2-(1H-indol-6-yl)benzoic acid | +++ |
| 257 | 5'-acetamido-6-(phenylethynyl)biphenyl-2-carboxylic acid | ++ |
| 258 | 3-[3-(5-amino-1H-1,3-benzodiazol-1-yl)prop-1-yn-1-yl]-2-phenylbenzoic acid trifluoroacetate salt | +++ |
| 259 | 2-(1H-indol-6-yl)-3-[2-(pyridin-4-yl)ethynyl] benzoic acid; trifluoroacetate salt | +++ |
| 260 | 2-(4-methylphenyl)-3-[2-(pyridin-4-yl)ethynyl]benzoic acid; trifluoroacetate salt | ++ |

TABLE 6-continued

Inhibition of 5'-biotin-oPL4624 binding to His-EBNA1 of representative compounds of the disclosure using Alpha Screen technology:

| Entry | Compound | Alpha Screen Activity |
|---|---|---|
| 261 | 3-[2-(3-hydroxyphenyl)ethynyl]-2-(4-methyl phenyl)benzoic acid | ++ |
| 262 | 3-{3-[(1H-1,3-benzodiazol-6-yl)amino]prop-1-yn-1-yl}-2-phenylbenzoic acid; trifluoroacetate salt | +++ |
| 263 | 3-[2-(3-hydroxyphenyl)ethynyl]-2-(1-methyl-1H-indol-5-yl)benzoic acid | +++ |
| 264 | 3-[2-(3-hydroxyphenyl)ethynyl]-2-(4-methyl-3,4-dihydro-2H-1,4-benzoxazin-7-yl)benzoic acid; trifluoroacetate salt | +++ |
| 265 | 3-[2-(3-hydroxyphenyl)ethynyl]-2-(3-methanesulfonamidophenyl)benzoic acid | ++ |
| 266 | 3-[2-(3-hydroxyphenyl)ethynyl]-2-(1H-indol-6-yl)benzoic acid | ++++ |
| 267 | 2-(3-carbamoylphenyl)-3-[2-(3-hydroxyphenyl)ethynyl]benzoic acid | ++ |
| 268 | 2-[1-(benzenesulfonyl)-1H-indol-3-yl]-3-[2-(3-hydroxyphenyl)ethynyl] benzoic acid | ++ |
| 269 | 2-(3-hydroxyphenyl)-3-[2-(3-hydroxyphenyl)ethynyl]benzoic acid | ++ |
| 270 | 2-(1H-indol-5-yl)-3-[2-(pyridin-4-yl)ethynyl]benzoic acid; trifluoroacetate salt | ++ |
| 271 | 2-(3-chloro-5-hydroxyphenyl)-3-[2-(pyridin-4-yl)ethynyl] benzoic acid; trifluoroacetate salt | +++ |
| 272 | 2-(3-fluoro-5-hydroxyphenyl)-3-[2-(pyridin-4-yl)ethynyl]benzoic acid; trifluoroacetate salt | ++ |
| 273 | 2-(3,5-dimethoxyphenyl)-3-[2-(pyridin-4-yl)ethynyl] benzoic acid; trifluoroacetate salt | ++ |
| 274 | 3-[3-(4-fluorophenyl)-3-hydroxyprop-1-yn-1-yl]-2-(3-hydroxyphenyl) benzoic acid | +++ |
| 275 | 3-[2-(3-hydroxyphenyl)ethynyl]-2-(2-phenoxyphenyl) benzoic acid | ++ |
| 276 | 3-[2-(3-hydroxyphenyl)ethynyl]-2-(1H-indol-3-yl) benzoic acid | ++ |
| 277 | 2-(3,5-dimethoxyphenyl)-3-[2-(3-hydroxyphenyl) ethynyl]benzoic acid | ++ |
| 278 | 2-amino-3-[2-(3-carbamoylphenyl)ethynyl]benzoic acid; trifluoroacetate salt | ++ |
| 279 | 2-amino-3-[2-(3-carboxyphenyl)ethynyl]benzoic acid; trifluoroacetate salt | ++ |
| 280 | 5-[3-(1H-tetrazol-5-yl)-phenylethynyl]-1H-indole | +++ |
| 281 | 3-[3-(1H-tetrazol-5-yl)-phenylethynyl]-1H-pyrrolo[2,3-b]pyridine | ++ |
| 282 | 6-[3-(1H-tetrazol-5-yl)-phenylethynyl]-1H-indole | +++ |
| 283 | 1-benzenesulfonyl-3-[3-(1H-tetrazol-5-yl)-phenylethynyl]-1H-indole | ++++ |
| 284 | 3-[3-(1H-tetrazol-5-yl)-phenylethynyl]-1H-indole | ++++ |
| 285 | {2-[3-(1H-tetrazol-5-yl)-phenylethynyl]-phenyl}-methanol | ++ |
| 286 | 3-[3-(morpholine-4-carbonyl)-phenylethynyl]-benzoic acid | ++ |
| 287 | 3-(3-methylcarbamoyl-phenylethynyl)-benzoic acid | ++ |
| 288 | 3-(3-dimethylcarbamoyl-phenylethynyl)-benzoic acid | + |
| 289 | 3-[3-(4-methyl-piperazine-1-carbonyl)-phenylethynyl]-benzoic acid | + |
| 290 | 3-[3-(4-phenyl-piperazine-1-carbonyl)-phenylethynyl]-benzoic acid | ++ |
| 291 | 2-indol-1-yl-3-pyridin-4-ylethynyl-benzoic acid | ++ |
| 292 | 2-imidazol-1-yl-3-pyridin-4-ylethynyl-benzoic acid | + |
| 293 | 3-pyridin-4-ylethynyl-2-[1,2,4]triazol-1-yl-benzoic acid | ++ |
| 294 | 2-imidazol-1-yl-3-phenylethynyl-benzoic acid | ++ |
| 295 | 3-phenylethynyl-2-pyrazol-1-yl-benzoic acid | + |
| 296 | 3-phenylethynyl-2-[1,2,4]triazol-1-yl-benzoic acid | ++ |
| 297 | 2-benzoimidazol-1-yl-3-phenylethynyl-benzoic acid | ++ |
| 298 | 2-indazol-1-yl-3-phenylethynyl-benzoic acid | ++ |
| 299 | 2-indol-1-yl-3-phenylethynyl-benzoic acid | +++ |
| 300 | 2-benzoimidazol-1-yl-3-pyridin-4-ylethynyl-benzoic acid | ++ |

Alpha Screen Activity: IC50 < 1 uM = ++++; 1 uM < IC50 < 10 uM = +++; 10 uM < IC50 < 100 uM = ++; 100 uM < IC50 < 1 mM = +.

Cell based luciferase assay of EBNA1 inhibition: In vivo inhibition of EBNA1 was determined for compounds of the disclosure using a cell based luciferase reporter assay. EBNA1 binding to the Family of Repeat (FR) region is essential for EBV latent infection and host-cell viability, thus providing a physiologically meaningful cell-based readout. A derivative of EBNA1, which is functionally equivalent to full-length EBNA1 and lacks the GGA repeats (90-325), was cloned into p3×FLAG-Myc-CMV™-24 (Sigma-Aldrich Co., LLC) (N803). To make the assay more sensitive by reducing the expression levels of EBNA1, the CMV promoter was excised and the TK promoter inserted upstream of EBNA1. To enhance the EBNA1-driven luciferase signal, the activation domain of herpes virus VP16 (411-490) was fused to the C-terminus of EBNA1 using SacII and BamHI restriction sites, resulting in the plasmid pTK-3×FLAG-Myc-EBNA1-VP16AD. Empty vector p3×FLAG-Myc-CMV-24 was used as a control. To create luciferase reporter plasmid, the FR region, a locus of 21 contiguous EBNA1 binding sites (7421-8042), was PCR amplified from EBV genomic DNA and cloned into the pGLuc-Basic 2 (New England Biolabs) using the KpnI and HindIII restriction sites, resulting in plasmid pGLuc2-21× FR.

For the transient transfection assay, HEK293T cells were seeded at a concentration of 4-8×10$^6$ cells in a 10 cm plate in Delbecco's Modified Eagle Medium (DMEM) (Life Technologies Corp.) supplemented with 10% Fetal Bovine Serum (FBS) (Gemini Bio-Products). After overnight incubation, the transfection was performed using Lipofectamine 2000 (Life Technologies). 3 ug of pGLuc2-21×FR and 0.6 ug of pTK-3×FLAG-Myc-EBNA1-VP16AD or p3×FLAG-Myc-CMV-24 (empty vector) were added to 0.5 ml Optimem buffer (Life Technologies Corp.). 30 ul Lipofectamine was added to a separate 0.5 ml Optimem buffer and incubated for 5 minutes. The DNA and lipofectamine mixtures were combined and incubated for 20 minutes at room temperature and added drop wise to the 10 cm plate. The cells were then incubated for 6 hours at 37° C. The cells were harvested, counted and re-suspended at a concentration of $2\times10^5$ cells/ml and distributed using a MicroFlo dispenser (BioTek) in 384-well tissue culture plate (Greiner BioOne), 40 ul (8000 cells) per well. 160 nl of solutions of compounds of the disclosure in DMSO at concentrations ranging from 50 mM to 976 uM were added to the cells (10-point 2-fold dilution series, final concentration 200 uM-390 nM) using a Janus modular Nanohead dispenser (PerkinElmer, Inc.). Compounds and transfected cells were incubated overnight at 37° C. Gaussia luciferase is secreted into the medium. The top 10 ul of cell media from the 384-well tranfected HEK293T cells is transferred to a white opaque 384-well development plate. 10 ul of substrate is added to each well and incubated for 5 minutes. Bioluminescence is then measured using the Envision Multiplate Reader (Perkin Elmer, Inc.). To normalize the activity of the compounds of the disclosure and to filter toxic compound, the remaining 30 ul of cell media (including the cells) are incubated with 6 ul resazurin, incubated for 4-6 hours at 37° C. and measured using the Envision Multiplate Reader. Data analysis and $IC_{50}$ curves are generated using Prism (GraphPad).

Cell Viability Assay: To further evaluate the cell-based efficacy of EBNA1 inhibitors, a cell cytotoxicity assay was performed. EBNA1 inhibitors should selective kill EBV-positive cell lines (Raji, LCL, C666-1) relative to EBV-negative cell lines (Bjab, DG75, HNE-1). Raji, Bjab, and DG75 were obtained from American Type Tissue Culture (ATCC), C666-1 and HNE-1 were a gift from Anne Lee (Hong Kong University) and the Lymphoblastic Cell Line (LCL) was obtained by in vitro infection of B-cells with the B95.8 strain of EBV.

To perform this assay, 40 ul of the different cell lines were seeded at a concentration of $1\times10^5$ cells in a clear 384-well plate (4000 cell/well). 160 nl of compound at concentrations ranging from 50 mM to 976 uM were added to each well (10-point, 2-fold dilution series, final concentration 200 uM-390 nM) using a Janus modular Nanohead dispenser (PerkinElmer, Inc.). Cells were incubated for 72 hours in a humidified 37° C. incubator 5% $CO_2$. The cell viability is inferred using the oxidation-reduction indicator, resazurin. 8 ul of resazurin was added to each well and after 4-6 hours incubation at 37° C., the fluorescent signal was monitored using 530-560 nm excitation wavelength and 590 nm emission wavelength using the Envision Multiplate Reader.

Data analysis and $CC_{50}$ (Cytotoxicity Concentration) curves are generated using Prism (GraphPad). A selectivity index is calculated by determining the ratio of the $CC_{50}$ from the EBV-negative cell line over the $CC_{50}$ from the EBV-positive cell line.

What is claimed is:

1. A compound of formula (IX):

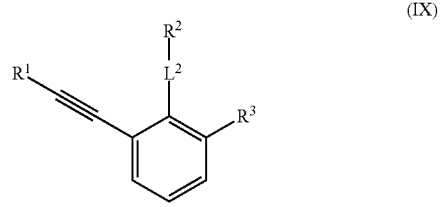

or a hydrate, solvate, or pharmaceutically acceptable salt, wherein:

$R^1$ is selected from the group consisting of optionally substituted phenyl,

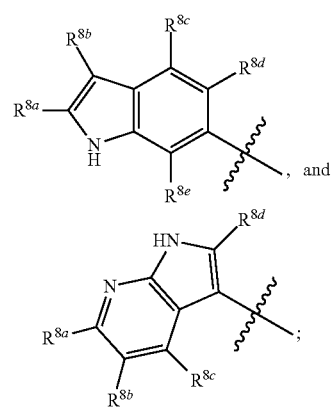

$R^2$ is selected from the group consisting of optionally substituted phenyl,

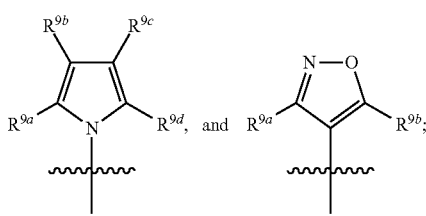

$R^3$ is $CO_2R^{4d}$;

$R^{4d}$ is selected from the group consisting of hydrogen, $C_{1-6}$ linear alkyl, and $C_{3-6}$ branched alkyl;

$R^{8a}$, $R^{8b}$, $R^{8c}$, and $R^{8d}$ are each independently selected from the group consisting of hydrogen, $C_{1-6}$ linear alkyl, and $C_{3-6}$ branched alkyl;

$R^{9a}$, $R^{9b}$, $R^{9c}$, and $R^{9d}$ are each independently selected from the group consisting of hydrogen, $C_{1-6}$ linear alkyl, and $C_{3-6}$ branched alkyl;

$L^2$ is $(CH_2)_m$; and m is 0;

wherein each phenyl is independently optionally substituted with at least one substituent independently selected from the group consisting of halogen, —CN, —OR$^{10}$, —NR$^{10}$C(=O)R$^{10}$, —S(=O)$_2$R$^{10}$, —S(=O)$_2$OR$^{10}$, —S(=O)$_2$N(R$^{10}$)$_2$, —C(=O)R$^{10}$, —C(=O)OR$^{10}$, —C(=O)N(R$^{10}$)$_2$, $C_{1-6}$ alkyl, $C_{1-6}$ haloalkyl, $C_{1-6}$ alkoxy, $C_{3-14}$ cycloalkyl, and phenyl, wherein each occurrence of R$^{10}$ is independently selected from the group consisting of hydrogen, $C_{1-6}$ alkyl, $C_{1-6}$ haloalkyl, $C_{3-6}$ cycloalkyl, and phenyl, or two R$^{10}$ units taken together with the atom(s) to which they are bound form a 3-7 membered ring.

2. The compound of claim 1, wherein $R^{4d}$ is selected from the group consisting of hydrogen, $C_{1-6}$ linear alkyl, and $C_{3-6}$ branched alkyl.

3. The compound of claim 1, wherein $R^{4d}$ is hydrogen.

4. A composition comprising at least one compound of claim 1 and at least one pharmaceutically acceptable excipient.

5. A method for treating or ameliorating a disease caused by EBNA1 activity, wherein the disease is infectious mononucleosis, chronic fatigue syndrome, multiple sclerosis, systemic lupus erythematosus, or rheumatoid arthritis, the method comprising administering to a subject a therapeutically effective amount of at least one compound of claim 1.

6. A method for treating and ameliorating a cancer caused by EBNA1 activity, the method comprising administering to a subject a therapeutically effective amount of at least one compound of claim 1.

7. The method of claim 6, wherein the cancer is nasopharyngeal carcinoma, gastric carcinomas, non-Hodgkin's lymphoma, anaplastic large-cell lymphoma, angioimmunoblastic T-cell lymphoma, hepatosplenic T-cell lymphoma, B-cell lymphoma, Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma, B-cell chronic lymphocytic leukemia, mantle cell lymphoma, mediastinal large B cell lymphoma, lymphoplasmactic lymphoma, nodal marginal zone B cell lymphoma, splenic marginal zone lymphoma, intravascular large B-cell lymphoma, primary effusion lymphoma, lyphomatoid granulomatosis, angioimmunoblastic lymphadenopathy, leiomyosarcomas, X-linked lymphoproliferative disease, post-transplant lymphoproliferative disorders, Hodgkin's lymphoma, or breast cancer.

8. A method for treating or ameliorating Epstein-Barr Virus infection, the method comprising administering to a subject a therapeutically effective amount of at least one compound of claim 1.

9. The method of claim 8, wherein the Epstein-Barr Virus infection is lytic or latent.

10. A compound selected from the group consisting of:

3-{2-[3-(methylsulfamoyl)phenyl]ethynyl}-2-(1H-pyrrol-1-yl)benzoic acid;

3-[2-(1H-indol-3-yl)ethynyl]-2-(1H-pyrrol-1-yl)benzoic acid;

3-[2-(3-methanesulfonamidophenyl)ethynyl]-2-(1H-pyrrol-1-yl)benzoic acid;

2-(1H-pyrrol-1-yl)-3-[2-(3-sulfamoylphenyl)ethynyl] benzoic acid;

3-[2-(3-carbamoylphenyl)ethynyl]-2-(1H-pyrrol-1-yl) benzoic acid;

3-(2-{imidazo[1,2-a]pyridin-6-yl}ethynyl)-2-(1H-pyrrol-1-yl)benzoic acid;

3-[2-(2-hydroxypyridin-4-yl)ethynyl]-2-(1H-pyrrol-1-yl) benzoic acid;

3-[2-(1H-indazol-6-yl)ethynyl]-2-(1H-pyrrol-1-yl)benzoic acid;

3-{2-[3-(3,3-dimethyl-2-oxoazetidin-1-yl)phenyl]ethynyl}-2-(1H-pyrrol-1-yl)benzoic acid;

3-(2-{3-[(2-carboxy-2,2-dimethylethyl)amino] phenyl}ethynyl)-2-(1H-pyrrol-1-yl)benzoic acid;

3-(2-{imidazo[1,2-a]pyrazin-3-yl}ethynyl)-2-(1H-pyrrol-1-yl)benzoic acid;

3-(2-{imidazo[1,2-a]pyridin-3-yl}ethynyl)-2-(1H-pyrrol-1-yl)benzoic acid;

3-(2-{imidazo[1,2-a]pyridin-5-yl}ethynyl)-2-(1H-pyrrol-1-yl)benzoic acid;

2-(1H-pyrrol-1-yl)-3-(2-{1H-pyrrolo[2,3-b]pyridin-5-yl}ethynyl)benzoic acid;

3-[2-(1-methyl-1H-indol-4-yl)ethynyl]-2-(1H-pyrrol-1-yl)benzoic acid;

3-[2-(1-methyl-1H-indol-5-yl)ethynyl]-2-(1H-pyrrol-1-yl)benzoic acid;

3-[2-(1-benzothiophen-6-yl)ethynyl]-2-(1H-pyrrol-1-yl) benzoic acid;

3-[2-(1H-indol-7-yl)ethynyl]-2-(1H-pyrrol-1-yl)benzoic acid;

3-{2-[2-(hydroxymethyl)phenyl]ethynyl}-2-(1H-pyrrol-1-yl)benzoic acid;

3-{2-[4-(hydroxymethyl)phenyl]ethynyl}-2-(1H-pyrrol-1-yl)benzoic acid;

2-(2,5-dimethyl-1H-pyrrol-1-yl)-3-[2-(4-methylphenyl) ethynyl]benzoic acid;

2-(2,5-dimethyl-1H-pyrrol-1-yl)-3-[2-(3-hydroxyphenyl) ethynyl]benzoic acid;

3-[2-(2,3-dihydro-1H-indol-6-yl)ethynyl]-2-(1H-pyrrol-1-yl)benzoic acid;

3-[2-(1-methyl-1H-pyrazol-4-yl)ethynyl]-2-(1H-pyrrol-1-yl)benzoic acid;

3-[2-(1,2-dimethyl-1H-imidazol-4-yl)ethynyl]-2-(1H-pyrrol-1-yl)benzoic acid;

3-[2-(1-methyl-1H-imidazol-5-yl)ethynyl]-2-(1H-pyrrol-1-yl)benzoic acid;

3-[2-(1-methyl-1H-imidazol-2-yl)ethynyl]-2-(1H-pyrrol-1-yl)benzoic acid;

2-(1H-pyrrol-1-yl)-3-[2-(1,3-thiazol-5-yl)ethynyl]benzoic acid;

2-(1H-pyrrol-1-yl)-3-[2-(1,3-thiazol-4-yl)ethynyl]benzoic acid;
2-(1H-pyrrol-1-yl)-3-(2-{1H-pyrrolo[2,3-b]pyridin-6-yl}ethynyl)benzoic acid;
3-{2-[3-(2-hydroxypropan-2-yl)phenyl]ethynyl}-2-(1H-pyrrol-1-yl)benzoic acid;
2-(1H-pyrrol-1-yl)-3-(2-{1H-pyrrolo[2,3-b]pyridin-3-yl}ethynyl)benzoic acid;
3-[2-(1H-indol-4-yl)ethynyl]-2-(1H-pyrrol-1-yl)benzoic acid;
2-(1H-pyrrol-1-yl)-3-(2-{[1,2,4]triazolo[1,5-a]pyridin-7-yl} ethynyl)benzoic acid;
3-{2-[3-(dimethylsulfamoyl)phenyl]ethynyl}-2-(1H-pyrrol-1-yl)benzoic acid;
3-[2-(3-fluoro-5-hydroxyphenyl)ethynyl]-2-(1H-pyrrol-1-yl)benzoic acid;
3-{2-[3-(hydroxymethyl)phenyl]ethynyl}-2-(1H-pyrrol-1-yl)benzoic acid;
3-[2-(5-hydroxypyridin-3-yl)ethynyl]-2-(1H-pyrrol-1-yl)benzoic acid;
3-[2-(1H-1,3-benzodiazol-5-yl)ethynyl]-2-(1H-pyrrol-1-yl)benzoic acid;
3-[2-(1H-indol-5-yl)ethynyl]-2-(1H-pyrrol-1-yl)benzoic acid;
3-[2-(1H-indol-6-yl)ethynyl]-2-(1H-pyrrol-1-yl)benzoic acid;
3-[2-(4-methylphenyl)ethynyl]-2-(1H-pyrrol-1-yl)benzoic acid;
3-[2-(3,5-difluorophenyl)ethynyl]-2-(1H-pyrrol-1-yl)benzoic acid;
3-{2-[3-(difluoromethoxy)phenyl]ethynyl}-2-(1H-pyrrol-1-yl)benzoic acid;
2-(2,5-dimethyl-1H-pyrrol-1-yl)-3-(2-phenylethynyl)benzoic acid;
3-(2-{imidazo[1,2-a]pyrazin-6-yl}ethynyl)-2-(1H-pyrrol-1-yl)benzoic acid;
3-[2-(3-hydroxyphenyl)ethynyl]-2-(1H-pyrrol-1-yl)benzoic acid;
3-[2-(4-methoxyphenyl)ethynyl]-2-(1H-pyrrol-1-yl)benzoic acid;
3-[2-(pyridin-4-yl)ethynyl]-2-(1H-pyrrol-1-yl)benzoic acid;
3-[2-(pyridin-3-yl)ethynyl]-2-(1H-pyrrol-1-yl)benzoic acid;
3-[2-(3-methoxyphenyl)ethynyl]-2-(1H-pyrrol-1-yl)benzoic acid;
3-[2-(4-fluorophenyl)ethynyl]-2-(1H-pyrrol-1-yl)benzoic acid;
3-(2-phenylethynyl)-2-(1H-pyrrol-1-yl)benzoic acid;
3-[3-(1H-imidazol-1-yl)prop-1-yn-1-yl]-2-(1H-pyrrol-1-yl)benzoic acid;
2-{4-[(dimethylamino)methyl]phenyl}-3-(2-phenylethynyl)benzoic acid;
2-(4-methanesulfonylphenyl)-3-(2-phenylethynyl)benzoic acid;
2-(4-methoxyphenyl)-3-(2-phenylethynyl)benzoic acid;
2-(3-methoxyphenyl)-3-(2-phenylethynyl)benzoic acid;
2-(2-methoxyphenyl)-3-(2-phenylethynyl)benzoic acid;
2-phenyl-3-(2-phenylethynyl)benzoic acid;
2-(4-methylphenyl)-3-(2-phenylethynyl)benzoic acid;
2-[3-(hydroxymethyl)phenyl]-3-(2-phenylethynyl)benzoic acid;
2-[4-(hydroxymethyl)phenyl]-3-(2-phenylethynyl)benzoic acid;
2-(3-methanesulfonamidophenyl)-3-(2-phenylethynyl)benzoic acid;
2-{2-[(2-hydroxyethyl)sulfamoyl]phenyl}-3-(2-phenylethynyl)benzoic acid;
2-[4-(cyclopropylcarbamoyl)phenyl]-3-(2-phenylethynyl)benzoic acid;
2-(dimethyl-1,2-oxazol-4-yl)-3-(2-phenylethynyl)benzoic acid;
3-(3-{[3-(1H-imidazol-1-yl)propyl]amino}prop-1-yn-1-yl)-2-phenylbenzoic acid;
3-{2-[3-(aminomethyl)phenyl]ethynyl}-2-(1H-pyrrol-1-yl)benzoic acid;
3-{2-[3-(3,5-difluorobenzenesulfonamidomethyl)phenyl]ethynyl}-2-(1H-pyrrol-1-yl)benzoic acid;
3-{2-[3-(cyclopropanesulfonamidomethyl)phenyl]ethynyl}-2-(1H-pyrrol-1-yl)benzoic acid;
2-(3-methoxyphenyl)-3-(2-{1H-pyrrolo [2,3-b]pyridin-3-yl}ethynyl)benzoic acid;
2-(3-methoxyphenyl)-3-[2-(1,3-thiazol-4-yl)ethynyl]benzoic acid;
2-[4-(dimethylamino)phenyl]-3-[2-(pyridin-4-yl)ethynyl]benzoic acid;
2-phenyl-3-[2-(pyridin-4-yl)ethynyl]benzoic acid;
3'-hydroxy-4'-methoxy-6-pyridin-4-ylethynyl-biphenyl-2-carboxylic acid;
5'-hydroxy-3'-methoxy-6-pyridin-4-ylethynyl-biphenyl-2-carboxylic acid;
2-(3,5-dimethyl-isoxazol-4-yl)-3-pyridin-4-ylethynyl-benzoic acid;
2-(2,5-dimethyl-pyrrol-1-yl)-3-pyridin-4-ylethynyl-benzoic acid;
3-(3-carbamoyl-phenylethynyl)-2-(2,5-dimethyl-pyrrol-1-yl)-benzoic acid;
3-(3-carboxy-phenylethynyl)-2-(2,5-dimethyl-pyrrol-1-yl)-benzoic acid;
2-(2,5-dimethyl-pyrrol-1-yl)-3-(3-hydroxymethyl-phenylethynyl)-benzoic acid;
2-(2,5-dimethyl-pyrrol-1-yl)-3-(1H-pyrrolo[2,3-b]pyridin-3-ylethynyl)-benzoic acid;
3-(3-acetylamino-phenylethynyl)-2-(2,5-dimethyl-pyrrol-1-yl)-benzoic acid;
2-(2,5-dimethyl-pyrrol-1-yl)-3-(3-methoxy-phenylethynyl)-benzoic acid;
4'-dimethylaminomethyl-6-phenylethynyl-biphenyl-2-carboxylic acid;
4'-Amino-6-((3-hydroxyphenyl)ethynyl)-5'-methoxybiphenyl-2-carboxylic acid;
5'-acetamido-6-(phenylethynyl)biphenyl-2-carboxylic acid;
2-(4-methylphenyl)-3-[2-(pyridin-4-yl)ethynyl]benzoic acid;
3-[2-(3-hydroxyphenyl)ethynyl]-2-(4-methyl phenyl) benzoic acid;
3-[2-(3-hydroxyphenyl)ethynyl]-2-(3-methanesulfonamidophenyl) benzoic acid;
2-(3-carbamoylphenyl)-3-[2-(3-hydroxyphenyl)ethynyl] benzoic acid;
2-(3-hydroxyphenyl)-3-[2-(3-hydroxyphenyl)ethynyl] benzoic acid;
2-(3-chloro-5-hydroxyphenyl)-3-[2-(pyridin-4-yl)ethynyl] benzoic acid;
2-(3-fluoro-5-hydroxyphenyl)-3-[2-(pyridin-4-yl)ethynyl]benzoic acid;
2-(3,5-dimethoxyphenyl)-3-[2-(pyridin-4-yl)ethynyl] benzoic acid;
3-[2-(3-hydroxyphenyl)ethynyl]-2-(2-phenoxyphenyl) benzoic acid;
2-(3,5-dimethoxyphenyl)-3-[2-(3-hydroxyphenyl) ethynyl]benzoic acid;

or a pharmaceutically acceptable salt, carboxylic ester, or solvate thereof.

11. The compound of claim 10, wherein the carboxylic ester is selected from the group consisting of methyl, ethyl, n-propyl, isopropyl, n-butyl, sec-butyl, iso-butyl, and tert-butyl.

12. A composition comprising at least one compound of claim 10 and at least one pharmaceutically acceptable excipient.

13. A method for treating and ameliorating a disease caused by EBNA1 activity, wherein the disease is infectious mononucleosis, chronic fatigue syndrome, multiple sclerosis, systemic lupus erythematosus, or rheumatoid arthritis, the method comprising administering to a subject a therapeutically effective amount of at least one compound of claim 10.

14. A method for treating or ameliorating a cancer caused by EBNA1 activity, the method comprising administering to a subject a therapeutically effective amount of at least one compound of claim 10.

15. The method of claim 14, wherein the cancer is nasopharyngeal carcinoma, gastric carcinomas, non-Hodgkin's lymphoma, anaplastic large-cell lymphoma, angioimmunoblastic T-cell lymphoma, hepatosplenic T-cell lymphoma, B-cell lymphoma, Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma, B-cell chronic lymphocytic leukemia, mantle cell lymphoma, mediastinal large B cell lymphoma, lymphoplasmactic lymphoma, nodal marginal zone B cell lymphoma, splenic marginal zone lymphoma, intravascular large B-cell lymphoma, primary effusion lymphoma, lyphomatoid granulomatosis, angioimmunoblastic lymphadenopathy, leiomyosarcomas, X-linked lymphoproliferative disease, post-transplant lymphoproliferative disorders, Hodgkin's lymphoma, or breast cancer.

16. A method for treating or ameliorating Epstein-Barr Virus infection, the method comprising administering to a subject a therapeutically effective amount of at least one compound of claim 10.

17. The method of claim 16, wherein the Epstein-Barr Virus infection is lytic or latent.

* * * * *